US007460961B2

(12) United States Patent
Tsao et al.

(10) Patent No.: US 7,460,961 B2
(45) Date of Patent: Dec. 2, 2008

(54) N-TRADD ACTIVE SITE AND USES THEREOF

(75) Inventors: Desiree H. H. Tsao, Belmont, MA (US); Jean-Baptiste Telliez, Waltham, MA (US); Thomas McDonagh, Acton, MA (US); Lih-Ling Lin, Concord, MA (US); Sang Hsu, Lexington, MA (US); Guang-Yi Xu, Medford, MA (US); A. Karl Malakian, Boxborough, MA (US)

(73) Assignee: Genetics Institute, LLC, Cambridge, MA (US)

( * ) Notice: Subject to any disclaimer, the term of this patent is extended or adjusted under 35 U.S.C. 154(b) by 441 days.

(21) Appl. No.: 10/894,834

(22) Filed: Jul. 20, 2004

(65) Prior Publication Data

US 2005/0002898 A1      Jan. 6, 2005

Related U.S. Application Data

(62) Division of application No. 09/821,819, filed on Mar. 29, 2001, now abandoned.

(60) Provisional application No. 60/195,370, filed on Apr. 6, 2000.

(51) Int. Cl.
*G06F 17/11* (2006.01)
*G06F 17/50* (2006.01)
*G06F 19/00* (2006.01)

(52) U.S. Cl. .................. 702/27; 702/19; 702/23
(58) Field of Classification Search .................. 702/19; 435/23, 212, 219
See application file for complete search history.

(56) References Cited

U.S. PATENT DOCUMENTS

| 5,674,734 | A |  | 10/1997 | Leder et al. |  |
| 5,834,228 | A |  | 11/1998 | Becker et al. |  |
| 5,856,116 | A |  | 1/1999 | Wilson et al. |  |
| 5,939,528 | A |  | 8/1999 | Clardy et al. |  |
| 6,322,972 | B1 | * | 11/2001 | Lin et al. | 435/6 |
| 2002/0094540 | A1 |  | 7/2002 | Tsao et al. |  |

FOREIGN PATENT DOCUMENTS

WO      WO 99/09148      2/1999

OTHER PUBLICATIONS

Arch et al. "Tumor necrosis factor receptor-associated factors (TRAFs)—a family of adapter proteins that regulates life and death" *Genes & Development* 12:2821-2830 (1988).
Baker et al. "Modulation of life and death by the TNF receptor superfamily" *Oncogene* 17:3261-3270 (1998).
Boldin et al. "Self-association of the "Death Domains" of the p55 Tumor Necrosis Factor (TNF) Receptor and Fas/APO1 Prompts Signaling for TNF and Fas/APO1 Effects" *J. of Biological Chemistry* 270(1):387-391 (1995).
Cao et al. "TRAF6 is a signal tranducer for interleukin-1" *Nature* 383:443-446 (1996).
Cheng et al. "Involvement of CRAF1, a Relative of TRAF, in CD40 Signaling" *Science* 267:1494-1498 (1995).
Chou et al. "Solution Structure of the RAIDD CARD and Model for CARD/CARD Interaction in Caspase-2 and Caspase-9 Recruitment" *Cell* 94:171-180 (1988).
Day et al. "Solution Structure and mutagenesis of the capase recruitment domain (CARD) from Apaf-1" *Cell Death and Differentiation* 6:1125-1132 (1999).
Duan et al. "RAIDD is a new 'death' adaptor molecule" *Nature* 385:86-89 (1997).
Eberstadt et al. "NMR structure and mutagenesis of the FADD (Mort1) death-effector domain" *Nature* 392:941-945 (1998).
Eck et al. "Crystallization of Trimeric Recombinant Human Tumor Necrosis Factor (Cachectin)" *J. Biol. Chem.* 263(26):12816-12819 (1988).
Farrell "Epstein-Barr virus immortalizing genes" *Trends Microbio.* 3:105-109 (1998).
Feinstein et al. "The death domain: a module shared by proteins with diverse cellular functions" *Tibs* 20:342-344 (1995).
Grell et al. "TR60 and TR80 Tumor Necrosis Factor (TNF)-Receptors Can Independently Mediate Cytolysis" *Lymphokine and Cytokine Res.* 12:143-148 (1993).
Grell "Tumor Necrosis Factor (TNF) Receptors in Cellular Signaling of Soluble and Membrane-Expressed TNF" *J. Inflamm.* 47:8-17 (1995).
Hofmann et al. "The CARD domain: a new apoptotic signaling motif" *TIBS* 22:155-156 (1997).
Hsu et al. "The TNF Receptor 1-Associated Protein TRADD Signals Cell Death and NF-κB Activation" *Cell* 81:495-504 (1995).
Hsu et al. "TNF-Dependent Recruitment of the Protein Kinase RIP to the TNF Receptor-1 Signaling Complex" *Immunity* 4:387-396 (1996).
Hsu et al. "TRADD—TRAF2 and TRADD-FADD Interactions Define Two Distinct TNF Receptor 1 Signal Transduction Pathways" *Cell* 84:299-308 (1996).
Huang et al. "NMR structure and mutagenesis of the Fas (APO-1/CD95) death domain" *Nature* 384:638-641 (1996).
Jeong et al. "The Solution Structure of FADD Death Domain" *J. Biol. Chem.* 274(23):16337-16342 (1999).

(Continued)

*Primary Examiner*—Michael Borin
(74) *Attorney, Agent, or Firm*—Lowrie, Lando & Anastasi, LLP

(57) ABSTRACT

The present invention relates to the three dimensional solution structure of the N-terminal domain of TNFR-1 associated death domain protein ("N-TRADD"), as well as the identification and characterization of a C-TRAF2 binding active site of N-TRADD. Also provided for by the present invention are methods of utilizing the three dimensional structures for the design and selection of potent and selective inhibitors of TNF signaling pathways.

47 Claims, 37 Drawing Sheets

OTHER PUBLICATIONS

Kelliher et al. "The Death Domain Kinase RIP Mediates the TNF-Induced NF—κB Signal" *Immunity* 8:297-303 (1998).

Kieser et al. "LMP1 signal transduction differs substantially from TNF receptor I signaling in the molecular functions of TRADD and TRAF2" *EMBO J.* 18(9):2511-2521 (1999).

Liepinsh et al. "NMR structure of the death domain of the p75 neurotrophin receptor" *EMBO J.* 16(16):4999-5005 (1997).

McWhirter et al. "Crystallographic analysis of CD40 recognition and signaling by human TRAF2" *Proc. Natl. Acad. Sci. USA* 96:8408-8413 (1999).

Nakano et al. "TRAF5, an Activator of NF-κB and Putative Signal Transducer for the Lymphotoxin-β Receptor" *J. of Biol. Chem.* 271(25):14661-14664 (1996).

Park et al. "Structural basis for self-association and receptor recognition of human TRAF2" *Nature* 398:533-538 (1999).

Pullen et al. "CD40-Tumor Necrosis Factor Receptor-Associated Factor (TRAF) Interactions: Regulation of CD40 Signaling through Multiple TRAF Binding Sites and TRAF Hetero-Oligomerization" *Biochemistry* 37:11836-11845 (1998).

Pullen et al. "CD40 Signaling through Tumor Necrosis Factor Receptor-associated Factors (TRAFs)" *J. Biol. Chem.* 274:14246-14254 (1999).

Qin et al. "Structural basis of procaspase-9 recruitment by the apoptotic protease-activating factor 1" *Nature* 399:549-557 (1999).

Reinhard et al. "Tumor necrosis factor α-induced activation of c-jun N-terminal kinase is mediated by TRAF2" *EMBO J.* 16:1080-1092 (1997).

Rothe et al. "Tumor Necrosis Factor Receptors-Structure and Function" *Immunol. Res.* 11:81-90 (1992).

Sato et al. "A novel member of the TRAF family of putative signal transducing protein binds to the cytosolic domain of the CD40" *FEBS Letters* 358:113-118 (1995).

Sioud et al. "Design of Nuclease Resistant Protein Kinase Cα DNA Enzymes with Potential Therapeutic Application" *J. Mol. Biol.* 296:937-947 (2000).

Smith et al. "The TNF Receptor Superfamily of Cellular and Viral Proteins: Activation, Costimulation and Death" *Cell* 76:959-962 (1994).

Song et al. "Tumor necrosis factor (TNF)-mediated kinase cascades: Bifurcation of Nuclear Factor-κB and c-jun N-terminal kinase (JNK/SAPK) pathways at TNF receptor-associated factor 2" *Proc. Natl. Acad. Sci.* 94:9792-9796 (1997).

Stanger et al. "RIP: A Novel Protein Containing a Death Domain That Interacts with Fas/APO-1 (CD95) in Yeast and Causes Cell Death" *Cell* 81:513-523 (1995).

Sukits et al. "Solution Structure of the Tumor Necrosis Factor Receptor-1 Death Domain" *J. Mol. Biol.* 310:895-906 (2001).

Tartaglia et al. "Tumor Necrosis Factor's Cytotoxic Activity Is Signaled by the p55 TNF Receptor" *Cell* 73:213-216 (1993).

Telliez et al. "Mutational Analysis and NMR studies of the Death Domain of the Tumor Necrosis Factor Receptor-1" *J. Mol. Biol.* 300:1323-1333 (2000).

Vandevoorde et al. "Induced Expression of Trimerized Intracellular Domains of the Human Tumor Necrosis Factor (TNF) p55 Receptor Elicits TNF Effects" *J. Cell Biol.* 137(7):1627-1638 (1997).

Xiao et al. "Three-Dimensional Structure of a Complex between the Death Domains of Pelle and Tube" *Cell* 99:545-555 (1999).

Yuan "Transducing signals of life and death" *Curr. Opin. Cell Biol.* 9:247-251 (1997).

Zhou et al. "Solution Structure of Apaf-1 CARD and its interaction with caspase-9 CARD: A Structural basis for specific adaptor/caspase interaction" *Proc. Natl. Acad. Sci. USA* 96:11265-11270 (1999).

\* cited by examiner

```
         1        10             20            30
         MAAGQNGHEWVGSATIEVESSLDRVVLSDAYAH
                        ━━━━━         ━━━━━━━
                          β1              α1

40         50            60          70
         PQQKVAVYRALQAALAESGGSPDVLQMLKIHRSDPQ
         ━━━━━━━━━━━━━━━━━━━━       ━━━━━
                  α2                    β2

80            90           100
         LIVQLRFCGRQPCGRFLRAYREGALRAALQRSLAAAL
         ━━       ━━━━━━━━━━━━━━━━━━━━━━━━━━
         β3                  α3

110         120           130         140
         AQHSVPLQLELRAGAERLDALLADEERCLSCILAQQPDRLRE
                  ━━━━━                ━━━━━━━━━━
                    β4                      α4

150         160
         EELAELEDALRNLKCGSGAR
         ━━━━━━━━━━━━━━━
               α5
```

| | | Atom Type | Residue | | X | Y | Z | | | |
|---|---|---|---|---|---|---|---|---|---|---|
| ATOM | 1 | CA | MET | 1 | -24.866 | 15.535 | -19.254 | 1.00 | 15.51 | SEG1 |
| ATOM | 2 | HA | MET | 1 | -25.390 | 14.593 | -19.279 | 1.00 | 15.31 | SEG1 |
| ATOM | 3 | CB | MET | 1 | -25.349 | 16.777 | -19.399 | 1.00 | 15.70 | SEG1 |
| ATOM | 4 | HB1 | MET | 1 | -26.446 | 16.343 | -19.393 | 1.00 | 15.58 | SEG1 |
| ATOM | 5 | HB2 | MET | 1 | -25.298 | 17.678 | -18.764 | 1.00 | 15.98 | SEG1 |
| ATOM | 6 | CG | MET | 1 | -26.765 | 16.422 | -17.327 | 1.00 | 15.38 | SEG1 |
| ATOM | 7 | HG1 | MET | 1 | -26.172 | 16.103 | -16.986 | 1.00 | 16.14 | SEG1 |
| ATOM | 8 | HG2 | MET | 1 | -27.432 | 15.624 | -18.121 | 1.00 | 15.63 | SEG1 |
| ATOM | 9 | SD | MET | 1 | -27.737 | 17.376 | -17.362 | 1.00 | 16.37 | SEG1 |
| ATOM | 10 | CE | MET | 1 | -28.779 | 17.948 | -18.839 | 1.00 | 15.46 | SEG1 |
| ATOM | 11 | HE1 | MET | 1 | -28.342 | 17.340 | -19.619 | 1.00 | 15.46 | SEG1 |
| ATOM | 12 | HE2 | MET | 1 | -28.851 | 18.969 | -19.180 | 1.00 | 16.49 | SEG1 |
| ATOM | 13 | HE3 | MET | 1 | -29.765 | 17.580 | -19.600 | 1.00 | 16.65 | SEG1 |
| ATOM | 14 | C | MET | 1 | -24.152 | 15.871 | -20.591 | 1.00 | 15.23 | SEG1 |
| ATOM | 15 | O | MET | 1 | -23.015 | 16.304 | -20.628 | 1.00 | 15.46 | SEG1 |
| ATOM | 16 | N | MET | 1 | -23.891 | 15.675 | -18.134 | 1.00 | 16.16 | SEG1 |
| ATOM | 17 | HT1 | MET | 1 | -23.122 | 15.001 | -18.319 | 1.00 | 16.50 | SEG1 |
| ATOM | 18 | HT2 | MET | 1 | -24.371 | 15.419 | -17.249 | 1.00 | 16.33 | SEG1 |
| ATOM | 19 | HT3 | MET | 1 | -23.495 | 16.634 | -18.051 | 1.00 | 16.24 | SEG1 |
| ATOM | 20 | N | ALA | 2 | -24.826 | 15.613 | -21.680 | 1.00 | 14.89 | SEG1 |
| ATOM | 21 | HN | ALA | 2 | -25.749 | 15.283 | -21.617 | 1.00 | 14.81 | SEG1 |
| ATOM | 22 | CA | ALA | 2 | -24.206 | 15.846 | -23.013 | 1.00 | 14.80 | SEG1 |
| ATOM | 23 | HA | ALA | 2 | -23.356 | 15.339 | -23.085 | 1.00 | 15.17 | SEG1 |
| ATOM | 24 | CB | ALA | 2 | -25.199 | 15.268 | -24.026 | 1.00 | 15.06 | SEG1 |
| ATOM | 25 | HB1 | ALA | 2 | -25.968 | 15.998 | -24.234 | 1.00 | 15.17 | SEG1 |
| ATOM | 26 | HB2 | ALA | 2 | -25.650 | 14.375 | -23.618 | 1.00 | 15.16 | SEG1 |
| ATOM | 27 | HB3 | ALA | 2 | -24.680 | 15.021 | -24.941 | 1.00 | 15.20 | SEG1 |
| ATOM | 28 | C | ALA | 2 | -24.035 | 17.355 | -23.207 | 1.00 | 14.21 | SEG1 |
| ATOM | 29 | O | ALA | 2 | -24.023 | 18.097 | -22.248 | 1.00 | 13.70 | SEG1 |
| ATOM | 30 | N | ALA | 3 | -23.920 | 17.811 | -24.431 | 1.00 | 14.43 | SEG1 |
| ATOM | 31 | HN | ALA | 3 | -23.947 | 17.183 | -25.183 | 1.00 | 14.93 | SEG1 |
| ATOM | 32 | CA | ALA | 3 | -23.761 | 19.283 | -24.704 | 1.00 | 14.09 | SEG1 |
| ATOM | 33 | HA | ALA | 3 | -23.704 | 19.448 | -25.769 | 1.00 | 14.05 | SEG1 |
| ATOM | 34 | CB | ALA | 3 | -25.032 | 19.954 | -24.154 | 1.00 | 14.73 | SEG1 |
| ATOM | 35 | HB1 | ALA | 3 | -25.756 | 19.196 | -23.921 | 1.00 | 15.01 | SEG1 |
| ATOM | 36 | HB2 | ALA | 3 | -25.435 | 20.626 | -24.899 | 1.00 | 14.84 | SEG1 |
| ATOM | 37 | HB3 | ALA | 3 | -24.797 | 20.512 | -23.260 | 1.00 | 14.95 | SEG1 |
| ATOM | 38 | C | ALA | 3 | -22.497 | 19.847 | -24.031 | 1.00 | 13.47 | SEG1 |
| ATOM | 39 | O | ALA | 3 | -21.504 | 20.099 | -24.689 | 1.00 | 13.42 | SEG1 |
| ATOM | 40 | N | GLY | 4 | -22.521 | 20.052 | -22.737 | 1.00 | 13.16 | SEG1 |
| ATOM | 41 | HN | GLY | 4 | -23.326 | 19.842 | -22.224 | 1.00 | 13.34 | SEG1 |
| ATOM | 42 | CA | GLY | 4 | -21.324 | 20.601 | -22.038 | 1.00 | 12.72 | SEG1 |
| ATOM | 43 | HA1 | GLY | 4 | -21.640 | 21.265 | -21.248 | 1.00 | 13.03 | SEG1 |
| ATOM | 44 | HA2 | GLY | 4 | -20.715 | 21.145 | -22.745 | 1.00 | 12.88 | SEG1 |
| ATOM | 45 | C | GLY | 4 | -20.510 | 19.454 | -21.438 | 1.00 | 11.83 | SEG1 |
| ATOM | 46 | O | GLY | 4 | -20.666 | 18.306 | -21.810 | 1.00 | 11.80 | SEG1 |
| ATOM | 47 | N | GLN | 5 | -19.639 | 19.764 | -20.517 | 1.00 | 11.27 | SEG1 |
| ATOM | 48 | HN | GLN | 5 | -19.534 | 20.700 | -20.246 | 1.00 | 11.46 | SEG1 |
| ATOM | 49 | CA | GLN | 5 | -18.796 | 18.703 | -19.882 | 1.00 | 10.54 | SEG1 |
| ATOM | 50 | HA | GLN | 5 | -18.209 | 18.192 | -20.629 | 1.00 | 10.74 | SEG1 |
| ATOM | 51 | CB | GLN | 5 | -17.867 | 19.456 | -18.918 | 1.00 | 10.66 | SEG1 |
| ATOM | 52 | HB1 | GLN | 5 | -17.255 | 20.149 | -19.477 | 1.00 | 10.48 | SEG1 |
| ATOM | 53 | HB2 | GLN | 5 | -17.231 | 18.747 | -18.408 | 1.00 | 10.80 | SEG1 |
| ATOM | 54 | CG | GLN | 5 | -18.696 | 20.230 | -17.982 | 1.00 | 11.16 | SEG1 |
| ATOM | 55 | HG1 | GLN | 5 | -18.846 | 19.613 | -17.008 | 1.00 | 11.36 | SEG1 |
| ATOM | 56 | HG2 | GLN | 5 | -19.655 | 20.493 | -18.302 | 1.00 | 11.17 | SEG1 |
| ATOM | 57 | CD | GLN | 5 | -17.944 | 21.499 | -17.481 | 1.00 | 11.68 | SEG1 |
| ATOM | 58 | OE1 | GLN | 5 | -17.092 | 21.465 | -16.617 | 1.00 | 11.76 | SEG1 |
| ATOM | 59 | NE2 | GLN | 5 | -18.222 | 22.527 | -18.079 | 1.00 | 12.23 | SEG1 |
| ATOM | 60 | HE21 | GLN | 5 | -18.310 | 22.655 | -18.775 | 1.00 | 12.30 | SEG1 |
| ATOM | 61 | HE22 | GLN | 5 | -17.740 | 23.443 | -17.833 | 1.00 | 12.69 | SEG1 |
| ATOM | 62 | C | GLN | 5 | -19.665 | 17.702 | -19.111 | 1.00 | 9.75 | SEG1 |
| ATOM | 63 | O | GLN | 5 | -20.496 | 18.080 | -18.306 | 1.00 | 9.62 | SEG1 |
| ATOM | 64 | N | ASN | 6 | -19.460 | 16.426 | -19.339 | 1.00 | 9.41 | SEG1 |

FIG. 2

| | | | | | | | | | |
|---|---|---|---|---|---|---|---|---|---|
| ATOM | 65 | HN | ASN | 6 | -18.775 | 15.151 | -19.981 | 1.00 | 9.70 | SEG1 |
| ATOM | 66 | CA | ASN | 6 | -20.257 | 15.396 | -19.600 | 1.00 | 8.79 | SEG1 |
| ATOM | 67 | HA | ASN | 6 | -21.287 | 15.710 | -18.535 | 1.00 | 9.04 | SEG1 |
| ATOM | 68 | CB | ASN | 6 | -20.161 | 14.093 | -19.418 | 1.00 | 9.02 | SEG1 |
| ATOM | 69 | HB1 | ASN | 6 | -20.676 | 14.225 | -20.357 | 1.00 | 8.79 | SEG1 |
| ATOM | 70 | HB2 | ASN | 6 | -20.631 | 13.293 | -18.867 | 1.00 | 9.43 | SEG1 |
| ATOM | 71 | CG | ASN | 6 | -18.700 | 13.720 | -19.695 | 1.00 | 9.37 | SEG1 |
| ATOM | 72 | OD1 | ASN | 6 | -17.847 | 13.872 | -18.845 | 1.00 | 9.72 | SEG1 |
| ATOM | 73 | ND2 | ASN | 6 | -18.379 | 13.226 | -20.863 | 1.00 | 9.56 | SEG1 |
| ATOM | 74 | HD21 | ASN | 6 | -19.069 | 13.099 | -21.547 | 1.00 | 9.44 | SEG1 |
| ATOM | 75 | HD22 | ASN | 6 | -17.450 | 12.985 | -21.056 | 1.00 | 9.96 | SEG1 |
| ATOM | 76 | C | ASN | 6 | -19.675 | 15.229 | -17.193 | 1.00 | 8.00 | SEG1 |
| ATOM | 77 | O | ASN | 6 | -18.499 | 15.450 | -16.975 | 1.00 | 7.88 | SEG1 |
| ATOM | 78 | N | GLY | 7 | -20.492 | 14.873 | -16.233 | 1.00 | 7.69 | SEG1 |
| ATOM | 79 | HN | GLY | 7 | -21.441 | 14.724 | -16.431 | 1.00 | 8.01 | SEG1 |
| ATOM | 80 | CA | GLY | 7 | -19.993 | 14.729 | -14.831 | 1.00 | 7.15 | SEG1 |
| ATOM | 81 | HA1 | GLY | 7 | -20.823 | 14.807 | -14.147 | 1.00 | 7.30 | SEG1 |
| ATOM | 82 | HA2 | GLY | 7 | -19.286 | 15.520 | -14.625 | 1.00 | 7.43 | SEG1 |
| ATOM | 83 | C | GLY | 7 | -19.305 | 13.377 | -14.636 | 1.00 | 6.36 | SEG1 |
| ATOM | 84 | O | GLY | 7 | -19.058 | 12.651 | -15.579 | 1.00 | 6.40 | SEG1 |
| ATOM | 85 | N | HIS | 8 | -18.990 | 13.040 | -13.407 | 1.00 | 5.93 | SEG1 |
| ATOM | 86 | HN | HIS | 8 | -19.199 | 13.649 | -12.668 | 1.00 | 6.17 | SEG1 |
| ATOM | 87 | CA | HIS | 8 | -18.311 | 11.740 | -13.127 | 1.00 | 5.39 | SEG1 |
| ATOM | 88 | HA | HIS | 8 | -18.677 | 10.972 | -13.791 | 1.00 | 5.57 | SEG1 |
| ATOM | 89 | CB | HIS | 8 | -16.830 | 12.005 | -13.398 | 1.00 | 5.92 | SEG1 |
| ATOM | 90 | HB1 | HIS | 8 | -16.355 | 12.352 | -12.492 | 1.00 | 6.12 | SEG1 |
| ATOM | 91 | HB2 | HIS | 8 | -16.733 | 12.757 | -14.166 | 1.00 | 6.23 | SEG1 |
| ATOM | 92 | CG | HIS | 8 | -16.170 | 10.733 | -13.851 | 1.00 | 6.32 | SEG1 |
| ATOM | 93 | ND1 | HIS | 8 | -16.762 | 9.885 | -14.773 | 1.00 | 6.76 | SEG1 |
| ATOM | 94 | HD1 | HIS | 8 | -17.627 | 10.024 | -15.215 | 1.00 | 6.84 | SEG1 |
| ATOM | 95 | CD2 | HIS | 8 | -14.976 | 10.147 | -13.515 | 1.00 | 6.77 | SEG1 |
| ATOM | 96 | HD2 | HIS | 8 | -14.259 | 10.552 | -12.816 | 1.00 | 6.87 | SEG1 |
| ATOM | 97 | CE1 | HIS | 8 | -15.933 | 8.842 | -14.956 | 1.00 | 7.39 | SEG1 |
| ATOM | 98 | HE1 | HIS | 8 | -16.140 | 8.014 | -15.617 | 1.00 | 8.01 | SEG1 |
| ATOM | 99 | NE2 | HIS | 8 | -14.828 | 8.952 | -14.213 | 1.00 | 7.43 | SEG1 |
| ATOM | 100 | C | HIS | 8 | -18.520 | 11.331 | -11.664 | 1.00 | 4.62 | SEG1 |
| ATOM | 101 | O | HIS | 8 | -18.996 | 12.104 | -10.854 | 1.00 | 4.56 | SEG1 |
| ATOM | 102 | N | GLU | 9 | -18.163 | 10.118 | -11.327 | 1.00 | 4.40 | SEG1 |
| ATOM | 103 | HN | GLU | 9 | -17.783 | 9.518 | -12.002 | 1.00 | 4.79 | SEG1 |
| ATOM | 104 | CA | GLU | 9 | -18.332 | 9.637 | -9.922 | 1.00 | 3.95 | SEG1 |
| ATOM | 105 | HA | GLU | 9 | -19.165 | 10.132 | -9.449 | 1.00 | 4.17 | SEG1 |
| ATOM | 106 | CB | GLU | 9 | -18.618 | 8.140 | -10.058 | 1.00 | 4.47 | SEG1 |
| ATOM | 107 | HB1 | GLU | 9 | -18.580 | 7.675 | -9.084 | 1.00 | 4.63 | SEG1 |
| ATOM | 108 | HB2 | GLU | 9 | -17.877 | 7.689 | -10.703 | 1.00 | 4.60 | SEG1 |
| ATOM | 109 | CG | GLU | 9 | -20.011 | 7.939 | -10.661 | 1.00 | 5.14 | SEG1 |
| ATOM | 110 | HG1 | GLU | 9 | -20.102 | 6.931 | -11.038 | 1.00 | 5.23 | SEG1 |
| ATOM | 111 | HG2 | GLU | 9 | -20.157 | 8.642 | -11.469 | 1.00 | 5.30 | SEG1 |
| ATOM | 112 | CD | GLU | 9 | -21.069 | 8.175 | -9.582 | 1.00 | 5.96 | SEG1 |
| ATOM | 113 | OE1 | GLU | 9 | -22.112 | 8.718 | -9.908 | 1.00 | 6.30 | SEG1 |
| ATOM | 114 | OE2 | GLU | 9 | -20.819 | 7.806 | -8.446 | 1.00 | 6.51 | SEG1 |
| ATOM | 115 | C | GLU | 9 | -17.043 | 9.872 | -9.127 | 1.00 | 3.32 | SEG1 |
| ATOM | 116 | O | GLU | 9 | -15.955 | 9.639 | -9.621 | 1.00 | 3.53 | SEG1 |
| ATOM | 117 | N | GLU | 10 | -17.155 | 10.329 | -7.902 | 1.00 | 2.92 | SEG1 |
| ATOM | 118 | HN | GLU | 10 | -18.042 | 10.508 | -7.525 | 1.00 | 3.15 | SEG1 |
| ATOM | 119 | CA | GLU | 10 | -15.930 | 10.572 | -7.084 | 1.00 | 2.63 | SEG1 |
| ATOM | 120 | HA | GLU | 10 | -15.122 | 10.912 | -7.713 | 1.00 | 2.97 | SEG1 |
| ATOM | 121 | CB | GLU | 10 | -16.306 | 11.667 | -6.084 | 1.00 | 3.13 | SEG1 |
| ATOM | 122 | HB1 | GLU | 10 | -15.459 | 11.879 | -5.449 | 1.00 | 3.26 | SEG1 |
| ATOM | 123 | HB2 | GLU | 10 | -17.134 | 11.333 | -5.477 | 1.00 | 3.47 | SEG1 |
| ATOM | 124 | CG | GLU | 10 | -16.703 | 12.940 | -6.840 | 1.00 | 3.83 | SEG1 |
| ATOM | 125 | HG1 | GLU | 10 | -17.631 | 12.768 | -7.365 | 1.00 | 4.16 | SEG1 |
| ATOM | 126 | HG2 | GLU | 10 | -15.930 | 13.189 | -7.552 | 1.00 | 4.02 | SEG1 |
| ATOM | 127 | CD | GLU | 10 | -16.888 | 14.107 | -5.858 | 1.00 | 4.51 | SEG1 |
| ATOM | 128 | OE1 | GLU | 10 | -16.595 | 13.936 | -4.682 | 1.00 | 5.01 | SEG1 |
| ATOM | 129 | OE2 | GLU | 10 | -17.319 | 15.159 | -6.302 | 1.00 | 4.85 | SEG1 |
| ATOM | 130 | C | GLU | 10 | -15.531 | 9.290 | -6.355 | 1.00 | 2.02 | SEG1 |
| ATOM | 131 | O | GLU | 10 | -16.296 | 8.732 | -5.591 | 1.00 | 2.17 | SEG1 |
| ATOM | 132 | N | TRP | 11 | -14.339 | 8.818 | -6.599 | 1.00 | 1.56 | SEG1 |
| ATOM | 133 | HN | TRP | 11 | -13.749 | 9.288 | -7.225 | 1.00 | 1.73 | SEG1 |
| ATOM | 134 | CA | TRP | 11 | -13.868 | 7.567 | -5.940 | 1.00 | 1.15 | SEG1 |
| ATOM | 135 | HA | TRP | 11 | -14.611 | 7.214 | -5.241 | 1.00 | 1.26 | SEG1 |
| ATOM | 136 | CB | TRP | 11 | -13.737 | 6.567 | -7.116 | 1.00 | 1.36 | SEG1 |
| ATOM | 137 | HB1 | TRP | 11 | -13.492 | 7.113 | -8.017 | 1.00 | 1.88 | SEG1 |
| ATOM | 138 | HB2 | TRP | 11 | -14.682 | 6.065 | -7.257 | 1.00 | 1.58 | SEG1 |
| ATOM | 139 | CG | TRP | 11 | -12.677 | 5.536 | -6.862 | 1.00 | 1.30 | SEG1 |
| ATOM | 140 | CD1 | TRP | 11 | -11.365 | 5.717 | -7.112 | 1.00 | 2.28 | SEG1 |
| ATOM | 141 | HD1 | TRP | 11 | -10.924 | 6.614 | -7.517 | 1.00 | 3.09 | SEG1 |

FIG. 2

| ATOM | 142 | CD2 | TRP | 11 | -12.809 | 4.189 | -6.326 | 1.00 | 0.69 | SEG1 |
|---|---|---|---|---|---|---|---|---|---|---|
| ATOM | 143 | NE1 | TRP | 11 | -10.683 | 4.571 | -6.764 | 1.00 | 2.24 | SEG1 |
| ATOM | 144 | HE1 | TRP | 11 | -9.724 | 4.445 | -6.846 | 1.00 | 2.95 | SEG1 |
| ATOM | 145 | CE2 | TRP | 11 | -11.525 | 3.600 | -6.274 | 1.00 | 1.19 | SEG1 |
| ATOM | 146 | CE3 | TRP | 11 | -13.901 | 3.430 | -5.384 | 1.00 | 1.24 | SEG1 |
| ATOM | 147 | HE3 | TRP | 11 | -14.889 | 3.854 | -5.910 | 1.00 | 1.82 | SEG1 |
| ATOM | 148 | CZ2 | TRP | 11 | -11.331 | 2.304 | -5.901 | 1.00 | 1.05 | SEG1 |
| ATOM | 149 | HZ2 | TRP | 11 | -10.339 | 1.878 | -5.771 | 1.00 | 1.59 | SEG1 |
| ATOM | 150 | CZ3 | TRP | 11 | -13.712 | 2.125 | -5.406 | 1.00 | 1.72 | SEG1 |
| ATOM | 151 | HZ3 | TRP | 11 | -14.560 | 1.550 | -5.068 | 1.00 | 2.64 | SEG1 |
| ATOM | 152 | CH2 | TRP | 11 | -12.428 | 1.563 | -5.365 | 1.00 | 1.25 | SEG1 |
| ATOM | 153 | HH2 | TRP | 11 | -12.289 | 0.559 | -4.995 | 1.00 | 1.70 | SEG1 |
| ATOM | 154 | C | TRP | 11 | -12.535 | 7.832 | -5.212 | 1.00 | 1.07 | SEG1 |
| ATOM | 155 | O | TRP | 11 | -11.569 | 8.269 | -5.807 | 1.00 | 1.43 | SEG1 |
| ATOM | 156 | N | VAL | 12 | -12.488 | 7.557 | -3.933 | 1.00 | 0.90 | SEG1 |
| ATOM | 157 | HN | VAL | 12 | -13.283 | 7.199 | -3.483 | 1.00 | 1.07 | SEG1 |
| ATOM | 158 | CA | VAL | 12 | -11.230 | 7.774 | -3.153 | 1.00 | 0.81 | SEG1 |
| ATOM | 159 | HA | VAL | 12 | -10.374 | 7.754 | -3.809 | 1.00 | 0.90 | SEG1 |
| ATOM | 160 | CB | VAL | 12 | -11.366 | 9.163 | -2.513 | 1.00 | 1.11 | SEG1 |
| ATOM | 161 | HB | VAL | 12 | -10.500 | 9.347 | -1.893 | 1.00 | 1.25 | SEG1 |
| ATOM | 162 | CG1 | VAL | 12 | -11.445 | 10.238 | -3.600 | 1.00 | 1.39 | SEG1 |
| ATOM | 163 | HG11 | VAL | 12 | -11.487 | 11.213 | -3.136 | 1.00 | 1.88 | SEG1 |
| ATOM | 164 | HG12 | VAL | 12 | -12.332 | 10.087 | -4.195 | 1.00 | 1.88 | SEG1 |
| ATOM | 165 | HG13 | VAL | 12 | -10.571 | 10.178 | -4.231 | 1.00 | 1.65 | SEG1 |
| ATOM | 166 | CG2 | VAL | 12 | -12.632 | 9.223 | -1.651 | 1.00 | 1.61 | SEG1 |
| ATOM | 167 | HG21 | VAL | 12 | -12.669 | 10.169 | -1.132 | 1.00 | 2.15 | SEG1 |
| ATOM | 168 | HG22 | VAL | 12 | -12.616 | 8.419 | -0.931 | 1.00 | 1.97 | SEG1 |
| ATOM | 169 | HG23 | VAL | 12 | -13.504 | 9.125 | -2.281 | 1.00 | 1.99 | SEG1 |
| ATOM | 170 | C | VAL | 12 | -11.095 | 6.703 | -2.063 | 1.00 | 0.82 | SEG1 |
| ATOM | 171 | O | VAL | 12 | -10.758 | 7.001 | -0.932 | 1.00 | 1.69 | SEG1 |
| ATOM | 172 | N | GLY | 13 | -11.375 | 5.466 | -2.388 | 1.00 | 0.62 | SEG1 |
| ATOM | 173 | HN | GLY | 13 | -11.660 | 5.252 | -3.302 | 1.00 | 1.15 | SEG1 |
| ATOM | 174 | CA | GLY | 13 | -11.287 | 4.378 | -1.367 | 1.00 | 0.89 | SEG1 |
| ATOM | 175 | HA1 | GLY | 13 | -11.623 | 3.451 | -1.805 | 1.00 | 1.13 | SEG1 |
| ATOM | 176 | HA2 | GLY | 13 | -11.922 | 4.626 | -0.529 | 1.00 | 1.25 | SEG1 |
| ATOM | 177 | C | GLY | 13 | -9.848 | 4.206 | -0.874 | 1.00 | 0.68 | SEG1 |
| ATOM | 178 | O | GLY | 13 | -8.900 | 4.566 | -1.544 | 1.00 | 0.70 | SEG1 |
| ATOM | 179 | N | SER | 14 | -9.692 | 3.645 | 0.299 | 1.00 | 0.57 | SEG1 |
| ATOM | 180 | HN | SER | 14 | -10.481 | 3.363 | 0.809 | 1.00 | 0.64 | SEG1 |
| ATOM | 181 | CA | SER | 14 | -8.330 | 3.421 | 0.867 | 1.00 | 0.46 | SEG1 |
| ATOM | 182 | HA | SER | 14 | -7.570 | 3.656 | 0.139 | 1.00 | 0.47 | SEG1 |
| ATOM | 183 | CB | SER | 14 | -8.235 | 4.373 | 2.057 | 1.00 | 0.63 | SEG1 |
| ATOM | 184 | HB1 | SER | 14 | -8.473 | 5.378 | 1.733 | 1.00 | 1.22 | SEG1 |
| ATOM | 185 | HB2 | SER | 14 | -7.235 | 4.356 | 2.457 | 1.00 | 1.22 | SEG1 |
| ATOM | 186 | OG | SER | 14 | -9.150 | 3.958 | 3.063 | 1.00 | 1.27 | SEG1 |
| ATOM | 187 | HG | SER | 14 | -8.910 | 4.396 | 3.882 | 1.00 | 1.63 | SEG1 |
| ATOM | 188 | C | SER | 14 | -8.206 | 1.967 | 1.331 | 1.00 | 0.35 | SEG1 |
| ATOM | 189 | O | SER | 14 | -9.198 | 1.309 | 1.587 | 1.00 | 0.36 | SEG1 |
| ATOM | 190 | N | ALA | 15 | -7.004 | 1.456 | 1.433 | 1.00 | 0.31 | SEG1 |
| ATOM | 191 | HN | ALA | 15 | -6.220 | 2.001 | 1.215 | 1.00 | 0.37 | SEG1 |
| ATOM | 192 | CA | ALA | 15 | -6.830 | 0.036 | 1.869 | 1.00 | 0.26 | SEG1 |
| ATOM | 193 | HA | ALA | 15 | -7.719 | -0.320 | 2.363 | 1.00 | 0.26 | SEG1 |
| ATOM | 194 | CB | ALA | 15 | -6.611 | -0.741 | 0.573 | 1.00 | 0.33 | SEG1 |
| ATOM | 195 | HB1 | ALA | 15 | -7.409 | -0.518 | -0.120 | 1.00 | 1.05 | SEG1 |
| ATOM | 196 | HB2 | ALA | 15 | -6.603 | -1.800 | 0.785 | 1.00 | 1.09 | SEG1 |
| ATOM | 197 | HB3 | ALA | 15 | -5.664 | -0.454 | 0.138 | 1.00 | 1.01 | SEG1 |
| ATOM | 198 | C | ALA | 15 | -5.612 | -0.112 | 2.785 | 1.00 | 0.24 | SEG1 |
| ATOM | 199 | O | ALA | 15 | -4.700 | 0.693 | 2.759 | 1.00 | 0.25 | SEG1 |
| ATOM | 200 | N | TYR | 16 | -5.590 | -1.151 | 3.584 | 1.00 | 0.24 | SEG1 |
| ATOM | 201 | HN | TYR | 16 | -6.336 | -1.788 | 3.574 | 1.00 | 0.25 | SEG1 |
| ATOM | 202 | CA | TYR | 16 | -4.431 | -1.381 | 4.498 | 1.00 | 0.24 | SEG1 |
| ATOM | 203 | HA | TYR | 16 | -3.769 | -0.529 | 4.495 | 1.00 | 0.25 | SEG1 |
| ATOM | 204 | CB | TYR | 16 | -5.045 | -1.561 | 5.886 | 1.00 | 0.28 | SEG1 |
| ATOM | 205 | HB1 | TYR | 16 | -4.302 | -1.960 | 6.560 | 1.00 | 0.30 | SEG1 |
| ATOM | 206 | HB2 | TYR | 16 | -5.880 | -2.244 | 5.825 | 1.00 | 0.29 | SEG1 |
| ATOM | 207 | CG | TYR | 16 | -5.524 | -0.224 | 6.401 | 1.00 | 0.30 | SEG1 |
| ATOM | 208 | CD1 | TYR | 16 | -6.885 | 0.100 | 6.365 | 1.00 | 1.20 | SEG1 |
| ATOM | 209 | HD1 | TYR | 16 | -7.597 | -0.607 | 5.967 | 1.00 | 2.11 | SEG1 |
| ATOM | 210 | CD2 | TYR | 16 | -4.601 | 0.693 | 6.916 | 1.00 | 0.30 | SEG1 |
| ATOM | 211 | HD2 | TYR | 16 | -3.550 | 0.442 | 6.943 | 1.00 | 2.22 | SEG1 |
| ATOM | 212 | CE1 | TYR | 16 | -7.322 | 1.340 | 6.845 | 1.00 | 1.20 | SEG1 |
| ATOM | 213 | HE1 | TYR | 16 | -8.372 | 1.591 | 6.818 | 1.00 | 2.12 | SEG1 |
| ATOM | 214 | CE2 | TYR | 16 | -5.036 | 1.933 | 7.395 | 1.00 | 1.32 | SEG1 |
| ATOM | 215 | HE2 | TYR | 16 | -4.323 | 2.639 | 7.792 | 1.00 | 2.24 | SEG1 |
| ATOM | 216 | CZ | TYR | 16 | -6.397 | 2.259 | 7.361 | 1.00 | 0.37 | SEG1 |
| ATOM | 217 | OH | TYR | 16 | -6.826 | 3.483 | 7.839 | 1.00 | 0.42 | SEG1 |
| ATOM | 218 | HH | TYR | 16 | -7.602 | 3.747 | 7.339 | 1.00 | 1.02 | SEG1 |

FIG. 2

| | | | | | | | | | | |
|---|---|---|---|---|---|---|---|---|---|---|
| ATOM | 219 | C | TYR | 16 | -3.678 | -2.645 | 4.068 | 1.00 | 0.23 | SEG1 |
| ATOM | 220 | O | TYR | 16 | -4.273 | -3.675 | 3.812 | 1.00 | 0.25 | SEG1 |
| ATOM | 221 | N | LEU | 17 | -2.377 | -2.565 | 3.979 | 1.00 | 0.23 | SEG1 |
| ATOM | 222 | HN | LEU | 17 | -1.930 | -1.721 | 4.133 | 1.00 | 0.23 | SEG1 |
| ATOM | 223 | CA | LEU | 17 | -1.570 | -3.747 | 3.551 | 1.00 | 0.23 | SEG1 |
| ATOM | 224 | HA | LEU | 17 | -2.217 | -4.569 | 3.299 | 1.00 | 0.24 | SEG1 |
| ATOM | 225 | CB | LEU | 17 | -0.815 | -3.278 | 2.306 | 1.00 | 0.25 | SEG1 |
| ATOM | 226 | HB1 | LEU | 17 | 0.169 | -3.723 | 2.294 | 1.00 | 0.26 | SEG1 |
| ATOM | 227 | HB2 | LEU | 17 | -0.724 | -2.202 | 2.326 | 1.00 | 0.25 | SEG1 |
| ATOM | 228 | CG | LEU | 17 | -1.577 | -3.703 | 1.051 | 1.00 | 0.25 | SEG1 |
| ATOM | 229 | HG | LEU | 17 | -1.713 | -4.777 | 1.063 | 1.00 | 0.26 | SEG1 |
| ATOM | 230 | CD1 | LEU | 17 | -2.943 | -3.009 | 1.014 | 1.00 | 0.25 | SEG1 |
| ATOM | 231 | HD11 | LEU | 17 | -3.272 | -2.919 | -0.010 | 1.00 | 1.04 | SEG1 |
| ATOM | 232 | HD12 | LEU | 17 | -2.859 | -2.026 | 1.453 | 1.00 | 1.04 | SEG1 |
| ATOM | 233 | HD13 | LEU | 17 | -3.659 | -3.593 | 1.573 | 1.00 | 1.03 | SEG1 |
| ATOM | 234 | CD2 | LEU | 17 | -0.775 | -3.299 | -0.188 | 1.00 | 0.28 | SEG1 |
| ATOM | 235 | HD21 | LEU | 17 | -1.452 | -3.080 | -0.999 | 1.00 | 1.03 | SEG1 |
| ATOM | 236 | HD22 | LEU | 17 | -0.120 | -4.109 | -0.473 | 1.00 | 1.07 | SEG1 |
| ATOM | 237 | HD23 | LEU | 17 | -0.187 | -2.421 | 0.037 | 1.00 | 1.01 | SEG1 |
| ATOM | 238 | C | LEU | 17 | -0.587 | -4.159 | 4.646 | 1.00 | 0.24 | SEG1 |
| ATOM | 239 | O | LEU | 17 | -0.008 | -3.327 | 5.318 | 1.00 | 0.24 | SEG1 |
| ATOM | 240 | N | PHE | 18 | -0.397 | -5.443 | 4.826 | 1.00 | 0.26 | SEG1 |
| ATOM | 241 | HN | PHE | 18 | -0.877 | -6.090 | 4.269 | 1.00 | 0.28 | SEG1 |
| ATOM | 242 | CA | PHE | 18 | 0.549 | -5.923 | 5.878 | 1.00 | 0.28 | SEG1 |
| ATOM | 243 | HA | PHE | 18 | 0.825 | -5.116 | 6.536 | 1.00 | 0.26 | SEG1 |
| ATOM | 244 | CB | PHE | 18 | -0.221 | -6.998 | 6.657 | 1.00 | 0.30 | SEG1 |
| ATOM | 245 | HB1 | PHE | 18 | 0.392 | -7.355 | 7.471 | 1.00 | 0.31 | SEG1 |
| ATOM | 246 | HB2 | PHE | 18 | -0.447 | -7.820 | 5.996 | 1.00 | 0.31 | SEG1 |
| ATOM | 247 | CG | PHE | 18 | -1.514 | -6.433 | 7.214 | 1.00 | 0.29 | SEG1 |
| ATOM | 248 | CD1 | PHE | 18 | -1.550 | -5.139 | 7.750 | 1.00 | 1.21 | SEG1 |
| ATOM | 249 | HD1 | PHE | 18 | -0.652 | -4.540 | 7.764 | 1.00 | 2.13 | SEG1 |
| ATOM | 250 | CD2 | PHE | 18 | -2.678 | -7.210 | 7.191 | 1.00 | 1.27 | SEG1 |
| ATOM | 251 | HD2 | PHE | 18 | -2.652 | -8.208 | 6.779 | 1.00 | 2.18 | SEG1 |
| ATOM | 252 | CE1 | PHE | 18 | -2.745 | -4.624 | 8.261 | 1.00 | 1.20 | SEG1 |
| ATOM | 253 | HE1 | PHE | 18 | -2.770 | -3.626 | 8.674 | 1.00 | 2.11 | SEG1 |
| ATOM | 254 | CE2 | PHE | 18 | -3.874 | -6.695 | 7.703 | 1.00 | 1.29 | SEG1 |
| ATOM | 255 | HE2 | PHE | 18 | -4.772 | -7.296 | 7.685 | 1.00 | 2.22 | SEG1 |
| ATOM | 256 | CZ | PHE | 18 | -3.907 | -5.402 | 8.238 | 1.00 | 0.32 | SEG1 |
| ATOM | 257 | HZ | PHE | 18 | -4.828 | -5.004 | 8.631 | 1.00 | 0.35 | SEG1 |
| ATOM | 258 | C | PHE | 18 | 1.787 | -6.535 | 5.226 | 1.00 | 0.30 | SEG1 |
| ATOM | 259 | O | PHE | 18 | 1.681 | -7.379 | 4.360 | 1.00 | 0.33 | SEG1 |
| ATOM | 260 | N | VAL | 19 | 2.956 | -6.123 | 5.641 | 1.00 | 0.29 | SEG1 |
| ATOM | 261 | HN | VAL | 19 | 3.013 | -5.443 | 6.346 | 1.00 | 0.27 | SEG1 |
| ATOM | 262 | CA | VAL | 19 | 4.206 | -6.689 | 5.048 | 1.00 | 0.32 | SEG1 |
| ATOM | 263 | HA | VAL | 19 | 3.970 | -7.353 | 4.230 | 1.00 | 0.35 | SEG1 |
| ATOM | 264 | CB | VAL | 19 | 4.993 | -5.478 | 4.535 | 1.00 | 0.33 | SEG1 |
| ATOM | 265 | HB | VAL | 19 | 5.223 | -4.826 | 5.367 | 1.00 | 0.31 | SEG1 |
| ATOM | 266 | CG1 | VAL | 19 | 6.300 | -5.953 | 3.891 | 1.00 | 0.37 | SEG1 |
| ATOM | 267 | HG11 | VAL | 19 | 6.080 | -6.458 | 2.962 | 1.00 | 1.07 | SEG1 |
| ATOM | 268 | HG12 | VAL | 19 | 6.804 | -6.635 | 4.560 | 1.00 | 1.07 | SEG1 |
| ATOM | 269 | HG13 | VAL | 19 | 6.936 | -5.102 | 3.696 | 1.00 | 1.08 | SEG1 |
| ATOM | 270 | CG2 | VAL | 19 | 4.157 | -4.712 | 3.500 | 1.00 | 0.36 | SEG1 |
| ATOM | 271 | HG21 | VAL | 19 | 4.520 | -4.930 | 2.507 | 1.00 | 1.03 | SEG1 |
| ATOM | 272 | HG22 | VAL | 19 | 4.240 | -3.652 | 3.687 | 1.00 | 1.07 | SEG1 |
| ATOM | 273 | HG23 | VAL | 19 | 3.121 | -5.010 | 3.578 | 1.00 | 1.13 | SEG1 |
| ATOM | 274 | C | VAL | 19 | 5.001 | -7.426 | 6.128 | 1.00 | 0.32 | SEG1 |
| ATOM | 275 | O | VAL | 19 | 5.376 | -6.844 | 7.131 | 1.00 | 0.31 | SEG1 |
| ATOM | 276 | N | GLU | 20 | 5.260 | -8.698 | 5.937 | 1.00 | 0.36 | SEG1 |
| ATOM | 277 | HN | GLU | 20 | 4.945 | -9.149 | 5.122 | 1.00 | 0.38 | SEG1 |
| ATOM | 278 | CA | GLU | 20 | 6.035 | -9.459 | 6.969 | 1.00 | 0.38 | SEG1 |
| ATOM | 279 | HA | GLU | 20 | 6.640 | -8.784 | 7.553 | 1.00 | 0.38 | SEG1 |
| ATOM | 280 | CB | GLU | 20 | 4.968 | -10.101 | 7.858 | 1.00 | 0.41 | SEG1 |
| ATOM | 281 | HB1 | GLU | 20 | 4.576 | -10.981 | 7.372 | 1.00 | 0.96 | SEG1 |
| ATOM | 282 | HB2 | GLU | 20 | 4.167 | -9.393 | 8.025 | 1.00 | 0.89 | SEG1 |
| ATOM | 283 | CG | GLU | 20 | 5.581 | -10.495 | 9.206 | 1.00 | 1.26 | SEG1 |
| ATOM | 284 | HG1 | GLU | 20 | 5.966 | -9.612 | 9.693 | 1.00 | 1.79 | SEG1 |
| ATOM | 285 | HG2 | GLU | 20 | 6.387 | -11.193 | 9.045 | 1.00 | 1.83 | SEG1 |
| ATOM | 286 | CD | GLU | 20 | 4.515 | -11.141 | 10.106 | 1.00 | 1.26 | SEG1 |
| ATOM | 287 | OE1 | GLU | 20 | 4.890 | -11.676 | 11.136 | 1.00 | 1.44 | SEG1 |
| ATOM | 288 | OE2 | GLU | 20 | 3.343 | -11.084 | 9.758 | 1.00 | 1.82 | SEG1 |
| ATOM | 289 | C | GLU | 20 | 6.920 | -10.527 | 6.305 | 1.00 | 0.41 | SEG1 |
| ATOM | 290 | O | GLU | 20 | 6.590 | -11.059 | 5.254 | 1.00 | 0.48 | SEG1 |
| ATOM | 291 | N | SER | 21 | 8.045 | -10.834 | 6.906 | 1.00 | 0.42 | SEG1 |
| ATOM | 292 | HN | SER | 21 | 8.286 | -10.383 | 7.743 | 1.00 | 0.44 | SEG1 |
| ATOM | 293 | CA | SER | 21 | 8.971 | -11.860 | 6.324 | 1.00 | 0.48 | SEG1 |
| ATOM | 294 | HA | SER | 21 | 8.796 | -11.968 | 5.265 | 1.00 | 0.50 | SEG1 |
| ATOM | 295 | CB | SER | 21 | 10.372 | -11.292 | 6.554 | 1.00 | 0.52 | SEG1 |

| | | | | | | | | | |
|---|---|---|---|---|---|---|---|---|---|
| ATOM | 296 | HB1 | SER | 21 | 10.474 | -10.360 | 5.014 | 1.00 | 0.55 | SEG1 |
| ATOM | 297 | HB2 | SER | 21 | 11.109 | -11.992 | 6.197 | 1.00 | 0.54 | SEG1 |
| ATOM | 298 | OG | SER | 21 | 10.572 | -11.073 | 7.945 | 1.00 | 0.62 | SEG1 |
| ATOM | 299 | HG | SER | 21 | 10.391 | -11.693 | 8.405 | 1.00 | 1.01 | SEG1 |
| ATOM | 300 | C | SER | 21 | 8.820 | -13.220 | 7.030 | 1.00 | 0.56 | SEG1 |
| ATOM | 301 | O | SER | 21 | 9.613 | -14.118 | 6.826 | 1.00 | 1.22 | SEG1 |
| ATOM | 302 | N | SER | 22 | 7.817 | -13.378 | 7.863 | 1.00 | 0.86 | SEG1 |
| ATOM | 303 | HN | SER | 22 | 7.193 | -12.643 | 8.016 | 1.00 | 1.44 | SEG1 |
| ATOM | 304 | CA | SER | 22 | 7.615 | -14.675 | 8.592 | 1.00 | 0.95 | SEG1 |
| ATOM | 305 | HA | SER | 22 | 6.749 | -14.607 | 9.232 | 1.00 | 1.07 | SEG1 |
| ATOM | 306 | CB | SER | 22 | 7.374 | -15.735 | 7.512 | 1.00 | 1.04 | SEG1 |
| ATOM | 307 | HB1 | SER | 22 | 8.297 | -16.265 | 7.318 | 1.00 | 1.13 | SEG1 |
| ATOM | 308 | HB2 | SER | 22 | 7.039 | -15.260 | 6.605 | 1.00 | 1.30 | SEG1 |
| ATOM | 309 | OG | SER | 22 | 6.376 | -16.643 | 7.960 | 1.00 | 1.42 | SEG1 |
| ATOM | 310 | HG | SER | 22 | 6.500 | -17.474 | 7.495 | 1.00 | 1.68 | SEG1 |
| ATOM | 311 | C | SER | 22 | 8.855 | -15.024 | 9.424 | 1.00 | 0.91 | SEG1 |
| ATOM | 312 | O | SER | 22 | 9.120 | -16.180 | 9.698 | 1.00 | 0.94 | SEG1 |
| ATOM | 313 | N | LEU | 23 | 9.604 | -14.033 | 9.841 | 1.00 | 0.96 | SEG1 |
| ATOM | 314 | HN | LEU | 23 | 9.362 | -13.111 | 9.617 | 1.00 | 1.04 | SEG1 |
| ATOM | 315 | CA | LEU | 23 | 10.819 | -14.303 | 10.673 | 1.00 | 1.03 | SEG1 |
| ATOM | 316 | HA | LEU | 23 | 10.973 | -15.365 | 10.782 | 1.00 | 1.20 | SEG1 |
| ATOM | 317 | CB | LEU | 23 | 11.986 | -13.678 | 9.904 | 1.00 | 0.94 | SEG1 |
| ATOM | 318 | HB1 | LEU | 23 | 12.861 | -13.658 | 10.537 | 1.00 | 1.14 | SEG1 |
| ATOM | 319 | HB2 | LEU | 23 | 11.729 | -12.670 | 9.616 | 1.00 | 1.11 | SEG1 |
| ATOM | 320 | CG | LEU | 23 | 12.286 | -14.508 | 8.654 | 1.00 | 1.17 | SEG1 |
| ATOM | 321 | HG | LEU | 23 | 11.371 | -14.691 | 8.112 | 1.00 | 1.54 | SEG1 |
| ATOM | 322 | CD1 | LEU | 23 | 13.270 | -13.748 | 7.762 | 1.00 | 1.51 | SEG1 |
| ATOM | 323 | HD11 | LEU | 23 | 12.805 | -12.843 | 7.401 | 1.00 | 1.96 | SEG1 |
| ATOM | 324 | HD12 | LEU | 23 | 13.547 | -14.368 | 6.921 | 1.00 | 2.02 | SEG1 |
| ATOM | 325 | HD13 | LEU | 23 | 14.153 | -13.497 | 8.331 | 1.00 | 1.83 | SEG1 |
| ATOM | 326 | CD2 | LEU | 23 | 12.914 | -15.839 | 9.073 | 1.00 | 1.52 | SEG1 |
| ATOM | 327 | HD21 | LEU | 23 | 13.458 | -16.258 | 8.240 | 1.00 | 1.93 | SEG1 |
| ATOM | 328 | HD22 | LEU | 23 | 12.138 | -16.524 | 9.378 | 1.00 | 2.01 | SEG1 |
| ATOM | 329 | HD23 | LEU | 23 | 13.592 | -15.672 | 9.898 | 1.00 | 1.88 | SEG1 |
| ATOM | 330 | C | LEU | 23 | 10.668 | -13.638 | 12.043 | 1.00 | 1.14 | SEG1 |
| ATOM | 331 | O | LEU | 23 | 10.726 | -12.430 | 12.165 | 1.00 | 1.44 | SEG1 |
| ATOM | 332 | N | ASP | 24 | 10.479 | -14.422 | 13.073 | 1.00 | 1.17 | SEG1 |
| ATOM | 333 | HN | ASP | 24 | 10.438 | -15.393 | 12.943 | 1.00 | 1.26 | SEG1 |
| ATOM | 334 | CA | ASP | 24 | 10.324 | -13.844 | 14.444 | 1.00 | 1.33 | SEG1 |
| ATOM | 335 | HA | ASP | 24 | 9.561 | -13.082 | 14.444 | 1.00 | 1.51 | SEG1 |
| ATOM | 336 | CB | ASP | 24 | 9.887 | -15.016 | 15.327 | 1.00 | 1.68 | SEG1 |
| ATOM | 337 | HB1 | ASP | 24 | 9.925 | -14.718 | 16.365 | 1.00 | 1.96 | SEG1 |
| ATOM | 338 | HB2 | ASP | 24 | 10.552 | -15.851 | 15.169 | 1.00 | 1.96 | SEG1 |
| ATOM | 339 | CG | ASP | 24 | 8.455 | -15.430 | 14.972 | 1.00 | 1.87 | SEG1 |
| ATOM | 340 | OD1 | ASP | 24 | 8.137 | -16.594 | 15.151 | 1.00 | 2.18 | SEG1 |
| ATOM | 341 | OD2 | ASP | 24 | 7.700 | -14.577 | 14.532 | 1.00 | 2.42 | SEG1 |
| ATOM | 342 | C | ASP | 24 | 11.654 | -13.263 | 14.943 | 1.00 | 1.21 | SEG1 |
| ATOM | 343 | O | ASP | 24 | 11.680 | -12.453 | 15.850 | 1.00 | 1.73 | SEG1 |
| ATOM | 344 | N | LYS | 25 | 12.757 | -13.677 | 14.367 | 1.00 | 1.40 | SEG1 |
| ATOM | 345 | HN | LYS | 25 | 12.714 | -14.337 | 13.644 | 1.00 | 1.84 | SEG1 |
| ATOM | 346 | CA | LYS | 25 | 14.086 | -13.157 | 14.816 | 1.00 | 1.71 | SEG1 |
| ATOM | 347 | HA | LYS | 25 | 14.109 | -13.063 | 15.889 | 1.00 | 1.98 | SEG1 |
| ATOM | 348 | CB | LYS | 25 | 15.096 | -14.216 | 14.368 | 1.00 | 2.08 | SEG1 |
| ATOM | 349 | HB1 | LYS | 25 | 16.098 | -13.842 | 14.519 | 1.00 | 2.36 | SEG1 |
| ATOM | 350 | HB2 | LYS | 25 | 14.947 | -14.430 | 13.320 | 1.00 | 1.98 | SEG1 |
| ATOM | 351 | CG | LYS | 25 | 14.905 | -15.498 | 15.181 | 1.00 | 2.37 | SEG1 |
| ATOM | 352 | HG1 | LYS | 25 | 13.906 | -15.877 | 15.028 | 1.00 | 2.26 | SEG1 |
| ATOM | 353 | HG2 | LYS | 25 | 15.054 | -15.286 | 16.230 | 1.00 | 2.63 | SEG1 |
| ATOM | 354 | CD | LYS | 25 | 15.922 | -16.545 | 14.720 | 1.00 | 2.85 | SEG1 |
| ATOM | 355 | HD1 | LYS | 25 | 16.921 | -16.166 | 14.874 | 1.00 | 3.30 | SEG1 |
| ATOM | 356 | HD2 | LYS | 25 | 15.774 | -16.753 | 13.670 | 1.00 | 2.96 | SEG1 |
| ATOM | 357 | CE | LYS | 25 | 15.738 | -17.833 | 15.527 | 1.00 | 3.10 | SEG1 |
| ATOM | 358 | HE1 | LYS | 25 | 14.780 | -18.279 | 15.310 | 1.00 | 3.12 | SEG1 |
| ATOM | 359 | HE2 | LYS | 25 | 15.831 | -17.629 | 16.584 | 1.00 | 3.39 | SEG1 |
| ATOM | 360 | NZ | LYS | 25 | 16.834 | -18.732 | 15.069 | 1.00 | 3.59 | SEG1 |
| ATOM | 361 | HZ1 | LYS | 25 | 17.748 | -18.362 | 15.398 | 1.00 | 3.96 | SEG1 |
| ATOM | 362 | HZ2 | LYS | 25 | 16.833 | -18.778 | 14.029 | 1.00 | 3.70 | SEG1 |
| ATOM | 363 | HZ3 | LYS | 25 | 16.688 | -19.684 | 15.458 | 1.00 | 3.91 | SEG1 |
| ATOM | 364 | C | LYS | 25 | 14.414 | -11.811 | 14.152 | 1.00 | 1.50 | SEG1 |
| ATOM | 365 | O | LYS | 25 | 15.402 | -11.183 | 14.489 | 1.00 | 1.60 | SEG1 |
| ATOM | 366 | N | VAL | 26 | 13.614 | -11.362 | 13.211 | 1.00 | 1.35 | SEG1 |
| ATOM | 367 | HN | VAL | 26 | 12.826 | -11.876 | 12.943 | 1.00 | 1.43 | SEG1 |
| ATOM | 368 | CA | VAL | 26 | 13.912 | -10.062 | 12.538 | 1.00 | 1.21 | SEG1 |
| ATOM | 369 | HA | VAL | 26 | 14.886 | -9.702 | 12.832 | 1.00 | 1.29 | SEG1 |
| ATOM | 370 | CB | VAL | 26 | 13.903 | -10.380 | 11.037 | 1.00 | 1.42 | SEG1 |
| ATOM | 371 | HB | VAL | 26 | 12.932 | -10.761 | 10.756 | 1.00 | 1.62 | SEG1 |
| ATOM | 372 | CG1 | VAL | 26 | 14.200 | -9.108 | 10.237 | 1.00 | 1.89 | SEG1 |

FIG. 2

| | | | | | | | | | |
|---|---|---|---|---|---|---|---|---|---|
| ATOM | 373 | HG11 | VAL | 26 | 13.971 | -9.273 | 9.195 | 1.00 | 2.27 | SEG1 |
| ATOM | 374 | HG12 | VAL | 26 | 15.244 | -8.354 | 10.340 | 1.00 | 2.38 | SEG1 |
| ATOM | 375 | HG13 | VAL | 26 | 13.594 | -8.297 | 10.611 | 1.00 | 2.31 | SEG1 |
| ATOM | 376 | CG2 | VAL | 26 | 14.973 | -11.431 | 10.729 | 1.00 | 2.08 | SEG1 |
| ATOM | 377 | HG21 | VAL | 26 | 15.828 | -11.275 | 11.370 | 1.00 | 2.45 | SEG1 |
| ATOM | 378 | HG22 | VAL | 26 | 15.278 | -11.342 | 9.596 | 1.00 | 2.51 | SEG1 |
| ATOM | 379 | HG23 | VAL | 26 | 14.569 | -12.418 | 10.900 | 1.00 | 2.57 | SEG1 |
| ATOM | 380 | C | VAL | 26 | 12.836 | -9.026 | 12.877 | 1.00 | 1.02 | SEG1 |
| ATOM | 381 | O | VAL | 26 | 11.670 | -9.210 | 12.577 | 1.00 | 1.13 | SEG1 |
| ATOM | 382 | N | VAL | 27 | 13.225 | -7.935 | 13.484 | 1.00 | 0.99 | SEG1 |
| ATOM | 383 | HN | VAL | 27 | 14.171 | -7.811 | 13.703 | 1.00 | 1.14 | SEG1 |
| ATOM | 384 | CA | VAL | 27 | 12.232 | -6.973 | 13.827 | 1.00 | 1.00 | SEG1 |
| ATOM | 385 | HA | VAL | 27 | 11.271 | -7.317 | 14.042 | 1.00 | 1.11 | SEG1 |
| ATOM | 386 | CB | VAL | 27 | 12.783 | -6.182 | 15.085 | 1.00 | 1.28 | SEG1 |
| ATOM | 387 | HB | VAL | 27 | 12.091 | -5.413 | 15.399 | 1.00 | 1.71 | SEG1 |
| ATOM | 388 | CG1 | VAL | 27 | 12.928 | -7.213 | 16.209 | 1.00 | 1.74 | SEG1 |
| ATOM | 389 | HG11 | VAL | 27 | 11.949 | -7.521 | 16.544 | 1.00 | 2.16 | SEG1 |
| ATOM | 390 | HG12 | VAL | 27 | 13.470 | -6.773 | 17.033 | 1.00 | 2.26 | SEG1 |
| ATOM | 391 | HG13 | VAL | 27 | 13.469 | -8.072 | 15.841 | 1.00 | 2.14 | SEG1 |
| ATOM | 392 | CG2 | VAL | 27 | 14.154 | -5.547 | 14.792 | 1.00 | 1.90 | SEG1 |
| ATOM | 393 | HG21 | VAL | 27 | 14.856 | -5.818 | 15.568 | 1.00 | 2.40 | SEG1 |
| ATOM | 394 | HG22 | VAL | 27 | 14.051 | -4.473 | 14.763 | 1.00 | 2.42 | SEG1 |
| ATOM | 395 | HG23 | VAL | 27 | 14.521 | -5.896 | 13.838 | 1.00 | 2.26 | SEG1 |
| ATOM | 396 | C | VAL | 27 | 12.112 | -5.891 | 12.655 | 1.00 | 0.83 | SEG1 |
| ATOM | 397 | O | VAL | 27 | 12.578 | -4.769 | 12.717 | 1.00 | 0.80 | SEG1 |
| ATOM | 398 | N | LEU | 28 | 11.497 | -6.319 | 11.581 | 1.00 | 0.77 | SEG1 |
| ATOM | 399 | HN | LEU | 28 | 11.142 | -7.236 | 11.559 | 1.00 | 0.85 | SEG1 |
| ATOM | 400 | CA | LEU | 28 | 11.353 | -5.429 | 10.385 | 1.00 | 0.65 | SEG1 |
| ATOM | 401 | HA | LEU | 28 | 12.323 | -5.176 | 9.987 | 1.00 | 0.73 | SEG1 |
| ATOM | 402 | CB | LEU | 28 | 10.571 | -6.248 | 9.359 | 1.00 | 0.66 | SEG1 |
| ATOM | 403 | HB1 | LEU | 28 | 10.277 | -5.610 | 8.539 | 1.00 | 0.81 | SEG1 |
| ATOM | 404 | HB2 | LEU | 28 | 9.689 | -6.660 | 9.829 | 1.00 | 0.72 | SEG1 |
| ATOM | 405 | CG | LEU | 28 | 11.445 | -7.384 | 8.832 | 1.00 | 1.04 | SEG1 |
| ATOM | 406 | HG | LEU | 28 | 11.877 | -7.921 | 9.664 | 1.00 | 1.45 | SEG1 |
| ATOM | 407 | CD1 | LEU | 28 | 10.588 | -8.336 | 8.001 | 1.00 | 1.13 | SEG1 |
| ATOM | 408 | HD11 | LEU | 28 | 9.882 | -7.766 | 7.415 | 1.00 | 1.40 | SEG1 |
| ATOM | 409 | HD12 | LEU | 28 | 10.052 | -9.005 | 8.658 | 1.00 | 1.73 | SEG1 |
| ATOM | 410 | HD13 | LEU | 28 | 11.222 | -8.910 | 7.342 | 1.00 | 1.54 | SEG1 |
| ATOM | 411 | CD2 | LEU | 28 | 12.560 | -6.805 | 7.959 | 1.00 | 1.38 | SEG1 |
| ATOM | 412 | HD21 | LEU | 28 | 12.188 | -5.943 | 7.425 | 1.00 | 1.93 | SEG1 |
| ATOM | 413 | HD22 | LEU | 28 | 12.889 | -7.553 | 7.253 | 1.00 | 1.66 | SEG1 |
| ATOM | 414 | HD23 | LEU | 28 | 13.391 | -6.510 | 8.584 | 1.00 | 1.78 | SEG1 |
| ATOM | 415 | C | LEU | 28 | 10.576 | -4.160 | 10.737 | 1.00 | 0.52 | SEG1 |
| ATOM | 416 | O | LEU | 28 | 10.902 | -3.082 | 10.279 | 1.00 | 0.49 | SEG1 |
| ATOM | 417 | N | SER | 29 | 9.547 | -4.279 | 11.537 | 1.00 | 0.53 | SEG1 |
| ATOM | 418 | HN | SER | 29 | 9.302 | -5.163 | 11.885 | 1.00 | 0.61 | SEG1 |
| ATOM | 419 | CA | SER | 29 | 8.735 | -3.075 | 11.909 | 1.00 | 0.50 | SEG1 |
| ATOM | 420 | HA | SER | 29 | 8.245 | -2.669 | 11.037 | 1.00 | 0.45 | SEG1 |
| ATOM | 421 | CB | SER | 29 | 7.690 | -3.587 | 12.903 | 1.00 | 0.64 | SEG1 |
| ATOM | 422 | HB1 | SER | 29 | 7.195 | -4.456 | 12.489 | 1.00 | 0.68 | SEG1 |
| ATOM | 423 | HB2 | SER | 29 | 6.961 | -2.817 | 13.090 | 1.00 | 0.69 | SEG1 |
| ATOM | 424 | OG | SER | 29 | 8.332 | -3.930 | 14.125 | 1.00 | 0.74 | SEG1 |
| ATOM | 425 | HG | SER | 29 | 7.660 | -4.234 | 14.739 | 1.00 | 1.18 | SEG1 |
| ATOM | 426 | C | SER | 29 | 9.622 | -2.014 | 12.569 | 1.00 | 0.51 | SEG1 |
| ATOM | 427 | O | SER | 29 | 9.388 | -0.827 | 12.436 | 1.00 | 0.47 | SEG1 |
| ATOM | 428 | N | ASP | 30 | 10.640 | -2.436 | 13.274 | 1.00 | 0.61 | SEG1 |
| ATOM | 429 | HN | ASP | 30 | 10.805 | -3.399 | 13.361 | 1.00 | 0.66 | SEG1 |
| ATOM | 430 | CA | ASP | 30 | 11.555 | -1.459 | 13.946 | 1.00 | 0.70 | SEG1 |
| ATOM | 431 | HA | ASP | 30 | 11.012 | -0.874 | 14.672 | 1.00 | 0.74 | SEG1 |
| ATOM | 432 | CB | ASP | 30 | 12.614 | -2.315 | 14.651 | 1.00 | 0.86 | SEG1 |
| ATOM | 433 | HB1 | ASP | 30 | 13.205 | -2.833 | 13.911 | 1.00 | 1.25 | SEG1 |
| ATOM | 434 | HB2 | ASP | 30 | 12.123 | -3.037 | 15.288 | 1.00 | 0.89 | SEG1 |
| ATOM | 435 | CG | ASP | 30 | 13.531 | -1.426 | 15.500 | 1.00 | 1.76 | SEG1 |
| ATOM | 436 | OD1 | ASP | 30 | 13.699 | -0.267 | 15.156 | 1.00 | 2.44 | SEG1 |
| ATOM | 437 | OD2 | ASP | 30 | 14.049 | -1.922 | 16.488 | 1.00 | 2.38 | SEG1 |
| ATOM | 438 | C | ASP | 30 | 12.203 | -0.543 | 12.901 | 1.00 | 0.66 | SEG1 |
| ATOM | 439 | O | ASP | 30 | 12.366 | 0.643 | 13.120 | 1.00 | 0.69 | SEG1 |
| ATOM | 440 | N | ALA | 31 | 12.580 | -1.089 | 11.774 | 1.00 | 0.65 | SEG1 |
| ATOM | 441 | HN | ALA | 31 | 12.442 | -2.049 | 11.629 | 1.00 | 0.64 | SEG1 |
| ATOM | 442 | CA | ALA | 31 | 13.229 | -0.259 | 10.710 | 1.00 | 0.69 | SEG1 |
| ATOM | 443 | HA | ALA | 31 | 14.158 | 0.154 | 11.072 | 1.00 | 0.81 | SEG1 |
| ATOM | 444 | CB | ALA | 31 | 13.506 | -1.226 | 9.556 | 1.00 | 0.73 | SEG1 |
| ATOM | 445 | HB1 | ALA | 31 | 13.622 | -2.227 | 9.945 | 1.00 | 1.33 | SEG1 |
| ATOM | 446 | HB2 | ALA | 31 | 14.413 | -0.930 | 9.048 | 1.00 | 1.15 | SEG1 |
| ATOM | 447 | HB3 | ALA | 31 | 12.681 | -1.203 | 8.860 | 1.00 | 1.27 | SEG1 |
| ATOM | 448 | C | ALA | 31 | 12.290 | 0.862 | 10.254 | 1.00 | 0.59 | SEG1 |
| ATOM | 449 | O | ALA | 31 | 12.716 | 1.974 | 10.014 | 1.00 | 0.66 | SEG1 |

| ATOM | 450 | N    | TYR  | 32 | 11.018 | 0.584  | 10.133 | 1.00 | 0.37 | SEG1 |
| ---- | --- | ---- | ---- | -- | ------ | ------ | ------ | ---- | ---- | ---- |
| ATOM | 451 | HN   | TYR  | 32 | 10.692 | -0.329 | 10.330 | 1.00 | 0.45 | SEG1 |
| ATOM | 452 | CA   | TYR  | 32 | 10.059 | 1.643  | 9.690  | 1.00 | 0.41 | SEG1 |
| ATOM | 453 | HA   | TYR  | 32 | 10.466 | 2.199  | 8.954  | 1.00 | 0.46 | SEG1 |
| ATOM | 454 | CB   | TYR  | 32 | 8.803  | 0.884  | 9.250  | 1.00 | 0.38 | SEG1 |
| ATOM | 455 | HB1  | TYR  | 32 | 8.056  | 1.556  | 8.915  | 1.00 | 0.40 | SEG1 |
| ATOM | 456 | HB2  | TYR  | 32 | 8.416  | 0.316  | 10.084 | 1.00 | 0.39 | SEG1 |
| ATOM | 457 | CG   | TYR  | 32 | 9.152  | -0.058 | 8.119  | 1.00 | 0.40 | SEG1 |
| ATOM | 458 | CD1  | TYR  | 32 | 9.232  | 0.419  | 6.805  | 1.00 | 1.24 | SEG1 |
| ATOM | 459 | HD1  | TYR  | 32 | 9.041  | 1.462  | 6.597  | 1.00 | 2.11 | SEG1 |
| ATOM | 460 | CD2  | TYR  | 32 | 9.399  | -1.410 | 8.388  | 1.00 | 1.23 | SEG1 |
| ATOM | 461 | HD2  | TYR  | 32 | 9.334  | -1.778 | 9.400  | 1.00 | 2.09 | SEG1 |
| ATOM | 462 | CE1  | TYR  | 32 | 9.560  | -0.456 | 5.762  | 1.00 | 1.25 | SEG1 |
| ATOM | 463 | HE1  | TYR  | 32 | 9.622  | -0.089 | 4.749  | 1.00 | 2.11 | SEG1 |
| ATOM | 464 | CE2  | TYR  | 32 | 9.727  | -2.283 | 7.345  | 1.00 | 1.26 | SEG1 |
| ATOM | 465 | HE2  | TYR  | 32 | 9.918  | -3.326 | 7.553  | 1.00 | 2.13 | SEG1 |
| ATOM | 466 | CZ   | TYR  | 32 | 9.808  | -1.806 | 6.031  | 1.00 | 0.49 | SEG1 |
| ATOM | 467 | OH   | TYR  | 32 | 10.132 | -2.668 | 5.002  | 1.00 | 0.55 | SEG1 |
| ATOM | 468 | HH   | TYR  | 32 | 9.706  | -3.511 | 5.174  | 1.00 | 1.03 | SEG1 |
| ATOM | 469 | C    | TYR  | 32 | 9.734  | 2.605  | 10.847 | 1.00 | 0.40 | SEG1 |
| ATOM | 470 | O    | TYR  | 32 | 9.132  | 3.642  | 10.644 | 1.00 | 0.42 | SEG1 |
| ATOM | 471 | N    | ALA  | 33 | 10.123 | 2.271  | 12.057 | 1.00 | 0.43 | SEG1 |
| ATOM | 472 | HN   | ALA  | 33 | 10.604 | 1.430  | 12.202 | 1.00 | 0.47 | SEG1 |
| ATOM | 473 | CA   | ALA  | 33 | 9.832  | 3.167  | 13.224 | 1.00 | 0.46 | SEG1 |
| ATOM | 474 | HA   | ALA  | 33 | 8.769  | 3.274  | 13.357 | 1.00 | 0.50 | SEG1 |
| ATOM | 475 | CB   | ALA  | 33 | 10.438 | 2.455  | 14.435 | 1.00 | 0.54 | SEG1 |
| ATOM | 476 | HB1  | ALA  | 33 | 11.504 | 2.351  | 14.294 | 1.00 | 1.26 | SEG1 |
| ATOM | 477 | HB2  | ALA  | 33 | 9.993  | 1.476  | 14.538 | 1.00 | 1.17 | SEG1 |
| ATOM | 478 | HB3  | ALA  | 33 | 10.247 | 3.033  | 15.327 | 1.00 | 0.97 | SEG1 |
| ATOM | 479 | C    | ALA  | 33 | 10.485 | 4.541  | 13.037 | 1.00 | 0.41 | SEG1 |
| ATOM | 480 | O    | ALA  | 33 | 9.906  | 5.560  | 13.364 | 1.00 | 0.44 | SEG1 |
| ATOM | 481 | N    | HIS  | 34 | 11.687 | 4.572  | 12.526 | 1.00 | 0.39 | SEG1 |
| ATOM | 482 | HN   | HIS  | 34 | 12.130 | 3.733  | 12.280 | 1.00 | 0.41 | SEG1 |
| ATOM | 483 | CA   | HIS  | 34 | 12.392 | 5.880  | 12.327 | 1.00 | 0.39 | SEG1 |
| ATOM | 484 | HA   | HIS  | 34 | 12.419 | 6.436  | 13.251 | 1.00 | 0.44 | SEG1 |
| ATOM | 485 | CB   | HIS  | 34 | 13.814 | 5.502  | 11.904 | 1.00 | 0.43 | SEG1 |
| ATOM | 486 | HB1  | HIS  | 34 | 13.885 | 5.515  | 10.827 | 1.00 | 0.43 | SEG1 |
| ATOM | 487 | HB2  | HIS  | 34 | 14.043 | 4.512  | 12.269 | 1.00 | 0.46 | SEG1 |
| ATOM | 488 | CG   | HIS  | 34 | 14.795 | 6.485  | 12.483 | 1.00 | 0.52 | SEG1 |
| ATOM | 489 | ND1  | HIS  | 34 | 15.735 | 7.139  | 11.702 | 1.00 | 0.57 | SEG1 |
| ATOM | 490 | HD1  | HIS  | 34 | 15.854 | 7.041  | 10.735 | 1.00 | 0.64 | SEG1 |
| ATOM | 491 | CD2  | HIS  | 34 | 14.998 | 6.930  | 13.766 | 1.00 | 0.70 | SEG1 |
| ATOM | 492 | HD2  | HIS  | 34 | 14.430 | 6.617  | 14.630 | 1.00 | 0.86 | SEG1 |
| ATOM | 493 | CE1  | HIS  | 34 | 16.454 | 7.935  | 12.515 | 1.00 | 0.66 | SEG1 |
| ATOM | 494 | HE1  | HIS  | 34 | 17.263 | 8.568  | 12.183 | 1.00 | 0.73 | SEG1 |
| ATOM | 495 | NE2  | HIS  | 34 | 16.045 | 7.846  | 13.784 | 1.00 | 0.75 | SEG1 |
| ATOM | 496 | C    | HIS  | 34 | 11.697 | 6.701  | 11.227 | 1.00 | 0.37 | SEG1 |
| ATOM | 497 | O    | HIS  | 34 | 11.149 | 6.139  | 10.300 | 1.00 | 0.35 | SEG1 |
| ATOM | 498 | N    | PRO  | 35 | 11.734 | 8.013  | 11.362 | 1.00 | 0.42 | SEG1 |
| ATOM | 499 | CA   | PRO  | 35 | 11.085 | 8.890  | 10.355 | 1.00 | 0.44 | SEG1 |
| ATOM | 500 | HA   | PRO  | 35 | 10.074 | 8.566  | 10.165 | 1.00 | 0.44 | SEG1 |
| ATOM | 501 | CB   | PRO  | 35 | 11.075 | 10.263 | 11.021 | 1.00 | 0.55 | SEG1 |
| ATOM | 502 | HB1  | PRO  | 35 | 10.140 | 10.425 | 11.535 | 1.00 | 0.59 | SEG1 |
| ATOM | 503 | HB2  | PRO  | 35 | 11.240 | 11.038 | 10.285 | 1.00 | 0.59 | SEG1 |
| ATOM | 504 | CG   | PRO  | 35 | 12.199 | 10.228 | 12.005 | 1.00 | 0.58 | SEG1 |
| ATOM | 505 | HG1  | PRO  | 35 | 11.959 | 10.841 | 12.861 | 1.00 | 0.65 | SEG1 |
| ATOM | 506 | HG2  | PRO  | 35 | 13.107 | 10.583 | 11.538 | 1.00 | 0.61 | SEG1 |
| ATOM | 507 | CD   | PRO  | 35 | 12.366 | 8.795  | 12.440 | 1.00 | 0.49 | SEG1 |
| ATOM | 508 | HD2  | PRO  | 35 | 13.415 | 8.550  | 12.526 | 1.00 | 0.51 | SEG1 |
| ATOM | 509 | HD1  | PRO  | 35 | 11.857 | 8.620  | 13.374 | 1.00 | 0.51 | SEG1 |
| ATOM | 510 | C    | PRO  | 35 | 11.895 | 8.917  | 9.054  | 1.00 | 0.43 | SEG1 |
| ATOM | 511 | O    | PRO  | 35 | 11.339 | 8.898  | 7.972  | 1.00 | 0.42 | SEG1 |
| ATOM | 512 | N    | GLN  | 36 | 13.204 | 8.958  | 9.149  | 1.00 | 0.46 | SEG1 |
| ATOM | 513 | HN   | GLN  | 36 | 13.628 | 8.971  | 10.032 | 1.00 | 0.48 | SEG1 |
| ATOM | 514 | CA   | GLN  | 36 | 14.048 | 8.983  | 7.910  | 1.00 | 0.49 | SEG1 |
| ATOM | 515 | HA   | GLN  | 36 | 13.841 | 9.867  | 7.329  | 1.00 | 0.52 | SEG1 |
| ATOM | 516 | CB   | GLN  | 36 | 15.497 | 9.005  | 8.402  | 1.00 | 0.56 | SEG1 |
| ATOM | 517 | HB1  | GLN  | 36 | 16.163 | 8.849  | 7.565  | 1.00 | 0.92 | SEG1 |
| ATOM | 518 | HB2  | GLN  | 36 | 15.644 | 8.220  | 9.129  | 1.00 | 0.96 | SEG1 |
| ATOM | 519 | CG   | GLN  | 36 | 15.801 | 10.360 | 9.044  | 1.00 | 1.47 | SEG1 |
| ATOM | 520 | HG1  | GLN  | 36 | 15.086 | 10.555 | 9.828  | 1.00 | 2.04 | SEG1 |
| ATOM | 521 | HG2  | GLN  | 36 | 15.737 | 11.136 | 8.294  | 1.00 | 2.03 | SEG1 |
| ATOM | 522 | CD   | GLN  | 36 | 17.211 | 10.337 | 9.636  | 1.00 | 1.79 | SEG1 |
| ATOM | 523 | OE1  | GLN  | 36 | 17.670 | 9.313  | 10.102 | 1.00 | 1.72 | SEG1 |
| ATOM | 524 | NE2  | GLN  | 36 | 17.922 | 11.430 | 9.638  | 1.00 | 2.68 | SEG1 |
| ATOM | 525 | HE21 | GLN  | 36 | 17.553 | 12.256 | 9.261  | 1.00 | 3.14 | SEG1 |
| ATOM | 526 | HE22 | GLN  | 36 | 18.827 | 11.426 | 10.015 | 1.00 | 3.03 | SEG1 |

| ATOM | 527 | C | GLN | 36 | 13.794 | 7.724 | 7.081 | 1.00 | 0.44 | SEG1 |
| ATOM | 528 | O | GLN | 36 | 13.599 | 7.773 | 5.868 | 1.00 | 0.45 | SEG1 |
| ATOM | 529 | N | GLN | 37 | 13.641 | 6.502 | 7.734 | 1.00 | 0.41 | SEG1 |
| ATOM | 530 | HN | GLN | 37 | 13.704 | 6.599 | 8.714 | 1.00 | 0.41 | SEG1 |
| ATOM | 531 | CA | GLN | 37 | 13.363 | 5.331 | 7.003 | 1.00 | 0.40 | SEG1 |
| ATOM | 532 | HA | GLN | 37 | 14.080 | 5.199 | 6.213 | 1.00 | 0.45 | SEG1 |
| ATOM | 533 | CB | GLN | 37 | 13.518 | 4.228 | 9.052 | 1.00 | 0.41 | SEG1 |
| ATOM | 534 | HB1 | GLN | 37 | 13.168 | 3.290 | 7.649 | 1.00 | 0.42 | SEG1 |
| ATOM | 535 | HB2 | GLN | 37 | 12.944 | 4.483 | 8.932 | 1.00 | 0.38 | SEG1 |
| ATOM | 536 | CG | GLN | 37 | 14.999 | 4.103 | 8.424 | 1.00 | 0.48 | SEG1 |
| ATOM | 537 | HG1 | GLN | 37 | 15.356 | 5.048 | 8.803 | 1.00 | 0.60 | SEG1 |
| ATOM | 538 | HG2 | GLN | 37 | 15.566 | 3.830 | 7.546 | 1.00 | 0.64 | SEG1 |
| ATOM | 539 | CD | GLN | 37 | 15.178 | 3.027 | 9.497 | 1.00 | 0.50 | SEG1 |
| ATOM | 540 | OE1 | GLN | 37 | 14.775 | 3.208 | 10.626 | 1.00 | 1.10 | SEG1 |
| ATOM | 541 | NE2 | GLN | 37 | 15.773 | 1.907 | 9.193 | 1.00 | 0.90 | SEG1 |
| ATOM | 542 | HE21 | GLN | 37 | 16.103 | 1.758 | 8.282 | 1.00 | 1.44 | SEG1 |
| ATOM | 543 | HE22 | GLN | 37 | 15.889 | 1.213 | 9.876 | 1.00 | 0.99 | SEG1 |
| ATOM | 544 | C | GLN | 37 | 11.950 | 5.366 | 6.422 | 1.00 | 0.36 | SEG1 |
| ATOM | 545 | O | GLN | 37 | 11.706 | 4.870 | 5.340 | 1.00 | 0.37 | SEG1 |
| ATOM | 546 | N | LYS | 38 | 11.022 | 5.968 | 7.125 | 1.00 | 0.33 | SEG1 |
| ATOM | 547 | HN | LYS | 38 | 11.253 | 6.372 | 7.987 | 1.00 | 0.33 | SEG1 |
| ATOM | 548 | CA | LYS | 38 | 9.620 | 6.055 | 6.604 | 1.00 | 0.31 | SEG1 |
| ATOM | 549 | HA | LYS | 38 | 9.196 | 5.071 | 6.484 | 1.00 | 0.32 | SEG1 |
| ATOM | 550 | CB | LYS | 38 | 8.849 | 6.839 | 7.672 | 1.00 | 0.33 | SEG1 |
| ATOM | 551 | HB1 | LYS | 38 | 9.294 | 7.815 | 7.792 | 1.00 | 0.35 | SEG1 |
| ATOM | 552 | HB2 | LYS | 38 | 8.894 | 6.306 | 8.610 | 1.00 | 0.34 | SEG1 |
| ATOM | 553 | CG | LYS | 38 | 7.388 | 6.999 | 7.251 | 1.00 | 0.36 | SEG1 |
| ATOM | 554 | HG1 | LYS | 38 | 6.937 | 6.024 | 7.138 | 1.00 | 0.37 | SEG1 |
| ATOM | 555 | HG2 | LYS | 38 | 7.338 | 7.532 | 6.312 | 1.00 | 0.36 | SEG1 |
| ATOM | 556 | CD | LYS | 38 | 6.635 | 7.784 | 8.328 | 1.00 | 0.46 | SEG1 |
| ATOM | 557 | HD1 | LYS | 38 | 7.088 | 8.756 | 8.450 | 1.00 | 1.19 | SEG1 |
| ATOM | 558 | HD2 | LYS | 38 | 6.682 | 7.244 | 9.264 | 1.00 | 1.04 | SEG1 |
| ATOM | 559 | CE | LYS | 38 | 5.175 | 7.953 | 7.910 | 1.00 | 1.07 | SEG1 |
| ATOM | 560 | HE1 | LYS | 38 | 4.696 | 6.991 | 7.826 | 1.00 | 1.63 | SEG1 |
| ATOM | 561 | HE2 | LYS | 38 | 5.113 | 8.490 | 6.973 | 1.00 | 1.71 | SEG1 |
| ATOM | 562 | NZ | LYS | 38 | 4.547 | 8.742 | 9.007 | 1.00 | 1.03 | SEG1 |
| ATOM | 563 | HZ1 | LYS | 38 | 5.129 | 9.580 | 9.207 | 1.00 | 1.31 | SEG1 |
| ATOM | 564 | HZ2 | LYS | 38 | 4.478 | 8.152 | 9.862 | 1.00 | 1.61 | SEG1 |
| ATOM | 565 | HZ3 | LYS | 38 | 3.596 | 9.044 | 8.716 | 1.00 | 1.33 | SEG1 |
| ATOM | 566 | C | LYS | 38 | 9.619 | 6.811 | 5.269 | 1.00 | 0.32 | SEG1 |
| ATOM | 567 | O | LYS | 38 | 8.966 | 6.417 | 4.321 | 1.00 | 0.34 | SEG1 |
| ATOM | 568 | N | VAL | 39 | 10.366 | 7.883 | 5.191 | 1.00 | 0.33 | SEG1 |
| ATOM | 569 | HN | VAL | 39 | 10.888 | 8.164 | 5.969 | 1.00 | 0.34 | SEG1 |
| ATOM | 570 | CA | VAL | 39 | 10.439 | 8.664 | 3.917 | 1.00 | 0.35 | SEG1 |
| ATOM | 571 | HA | VAL | 39 | 9.447 | 8.907 | 3.564 | 1.00 | 0.36 | SEG1 |
| ATOM | 572 | CB | VAL | 39 | 11.208 | 9.947 | 4.274 | 1.00 | 0.38 | SEG1 |
| ATOM | 573 | HB | VAL | 39 | 12.149 | 9.682 | 4.733 | 1.00 | 0.39 | SEG1 |
| ATOM | 574 | CG1 | VAL | 39 | 11.479 | 10.772 | 3.009 | 1.00 | 0.42 | SEG1 |
| ATOM | 575 | HG11 | VAL | 39 | 11.881 | 11.735 | 3.286 | 1.00 | 1.12 | SEG1 |
| ATOM | 576 | HG12 | VAL | 39 | 10.557 | 10.910 | 2.465 | 1.00 | 1.09 | SEG1 |
| ATOM | 577 | HG13 | VAL | 39 | 12.190 | 10.251 | 2.385 | 1.00 | 1.05 | SEG1 |
| ATOM | 578 | CG2 | VAL | 39 | 10.381 | 10.782 | 5.253 | 1.00 | 0.38 | SEG1 |
| ATOM | 579 | HG21 | VAL | 39 | 10.683 | 11.816 | 5.188 | 1.00 | 1.08 | SEG1 |
| ATOM | 580 | HG22 | VAL | 39 | 10.545 | 10.422 | 6.258 | 1.00 | 1.12 | SEG1 |
| ATOM | 581 | HG23 | VAL | 39 | 9.334 | 10.695 | 5.005 | 1.00 | 1.03 | SEG1 |
| ATOM | 582 | C | VAL | 39 | 11.203 | 7.842 | 2.870 | 1.00 | 0.37 | SEG1 |
| ATOM | 583 | O | VAL | 39 | 10.831 | 7.796 | 1.713 | 1.00 | 0.40 | SEG1 |
| ATOM | 584 | N | ALA | 40 | 12.260 | 7.178 | 3.277 | 1.00 | 0.39 | SEG1 |
| ATOM | 585 | HN | ALA | 40 | 12.533 | 7.222 | 4.218 | 1.00 | 0.38 | SEG1 |
| ATOM | 586 | CA | ALA | 40 | 13.035 | 6.340 | 2.310 | 1.00 | 0.42 | SEG1 |
| ATOM | 587 | HA | ALA | 40 | 13.366 | 6.933 | 1.471 | 1.00 | 0.46 | SEG1 |
| ATOM | 588 | CB | ALA | 40 | 14.234 | 5.810 | 3.098 | 1.00 | 0.45 | SEG1 |
| ATOM | 589 | HB1 | ALA | 40 | 14.571 | 6.566 | 3.793 | 1.00 | 1.04 | SEG1 |
| ATOM | 590 | HB2 | ALA | 40 | 15.035 | 5.566 | 2.416 | 1.00 | 1.12 | SEG1 |
| ATOM | 591 | HB3 | ALA | 40 | 13.943 | 4.924 | 3.644 | 1.00 | 1.11 | SEG1 |
| ATOM | 592 | C | ALA | 40 | 12.142 | 5.193 | 1.842 | 1.00 | 0.40 | SEG1 |
| ATOM | 593 | O | ALA | 40 | 12.097 | 4.854 | 0.675 | 1.00 | 0.42 | SEG1 |
| ATOM | 594 | N | VAL | 41 | 11.401 | 4.625 | 2.756 | 1.00 | 0.38 | SEG1 |
| ATOM | 595 | HN | VAL | 41 | 11.447 | 4.948 | 3.681 | 1.00 | 0.37 | SEG1 |
| ATOM | 596 | CA | VAL | 41 | 10.457 | 3.522 | 2.402 | 1.00 | 0.38 | SEG1 |
| ATOM | 597 | HA | VAL | 41 | 10.991 | 2.697 | 1.958 | 1.00 | 0.41 | SEG1 |
| ATOM | 598 | CB | VAL | 41 | 9.836 | 3.092 | 3.741 | 1.00 | 0.37 | SEG1 |
| ATOM | 599 | HB | VAL | 41 | 9.493 | 3.965 | 4.276 | 1.00 | 0.35 | SEG1 |
| ATOM | 600 | CG1 | VAL | 41 | 8.663 | 2.133 | 3.508 | 1.00 | 0.38 | SEG1 |
| ATOM | 601 | HG11 | VAL | 41 | 7.767 | 2.703 | 3.315 | 1.00 | 0.97 | SEG1 |
| ATOM | 602 | HG12 | VAL | 41 | 8.518 | 1.522 | 4.387 | 1.00 | 1.10 | SEG1 |
| ATOM | 603 | HG13 | VAL | 41 | 8.878 | 1.500 | 2.660 | 1.00 | 1.07 | SEG1 |

FIG. 2

| | | | | | | | | | |
|---|---|---|---|---|---|---|---|---|---|
| ATOM | 604 | CG2 | VAL | 41 | 10.901 | 2.375 | 4.573 | 1.00 | 0.39 | SEG1 |
| ATOM | 605 | HG21 | VAL | 41 | 11.363 | 2.833 | 4.395 | 1.00 | 1.06 | SEG1 |
| ATOM | 606 | HG22 | VAL | 41 | 10.940 | 1.335 | 4.290 | 1.00 | 1.05 | SEG1 |
| ATOM | 607 | HG23 | VAL | 41 | 10.654 | 2.456 | 5.622 | 1.00 | 1.11 | SEG1 |
| ATOM | 608 | C | VAL | 41 | 9.411 | 4.070 | 1.424 | 1.00 | 0.37 | SEG1 |
| ATOM | 609 | O | VAL | 41 | 9.028 | 3.416 | 0.473 | 1.00 | 0.39 | SEG1 |
| ATOM | 610 | N | TYR | 42 | 8.958 | 5.273 | 1.655 | 1.00 | 0.37 | SEG1 |
| ATOM | 611 | HN | TYR | 42 | 9.295 | 5.778 | 2.427 | 1.00 | 0.37 | SEG1 |
| ATOM | 612 | CA | TYR | 42 | 7.941 | 5.909 | 0.746 | 1.00 | 0.40 | SEG1 |
| ATOM | 613 | HA | TYR | 42 | 6.973 | 5.454 | 0.886 | 1.00 | 0.40 | SEG1 |
| ATOM | 614 | CB | TYR | 42 | 7.896 | 7.390 | 1.168 | 1.00 | 0.43 | SEG1 |
| ATOM | 615 | HB1 | TYR | 42 | 8.104 | 8.016 | 0.312 | 1.00 | 0.53 | SEG1 |
| ATOM | 616 | HB2 | TYR | 42 | 8.641 | 7.570 | 1.926 | 1.00 | 0.47 | SEG1 |
| ATOM | 617 | CG | TYR | 42 | 6.539 | 7.749 | 1.724 | 1.00 | 0.41 | SEG1 |
| ATOM | 618 | CD1 | TYR | 42 | 5.881 | 8.890 | 1.251 | 1.00 | 1.26 | SEG1 |
| ATOM | 619 | HD1 | TYR | 42 | 6.341 | 9.499 | 0.488 | 1.00 | 2.09 | SEG1 |
| ATOM | 620 | CD2 | TYR | 42 | 5.944 | 6.960 | 2.715 | 1.00 | 1.17 | SEG1 |
| ATOM | 621 | HD2 | TYR | 42 | 6.450 | 6.081 | 3.082 | 1.00 | 2.02 | SEG1 |
| ATOM | 622 | CE1 | TYR | 42 | 4.631 | 9.242 | 1.764 | 1.00 | 1.31 | SEG1 |
| ATOM | 623 | HE1 | TYR | 42 | 4.129 | 10.125 | 1.397 | 1.00 | 2.16 | SEG1 |
| ATOM | 624 | CE2 | TYR | 42 | 4.691 | 7.311 | 3.228 | 1.00 | 1.19 | SEG1 |
| ATOM | 625 | HE2 | TYR | 42 | 4.233 | 6.703 | 3.991 | 1.00 | 2.02 | SEG1 |
| ATOM | 626 | CZ | TYR | 42 | 4.034 | 8.453 | 2.754 | 1.00 | 0.60 | SEG1 |
| ATOM | 627 | OH | TYR | 42 | 2.799 | 8.799 | 3.261 | 1.00 | 0.75 | SEG1 |
| ATOM | 628 | HH | TYR | 42 | 2.917 | 9.056 | 4.179 | 1.00 | 1.20 | SEG1 |
| ATOM | 629 | C | TYR | 42 | 8.385 | 5.801 | -0.722 | 1.00 | 0.43 | SEG1 |
| ATOM | 630 | O | TYR | 42 | 7.621 | 5.411 | -1.584 | 1.00 | 0.42 | SEG1 |
| ATOM | 631 | N | ARG | 43 | 9.615 | 6.155 | -1.004 | 1.00 | 0.49 | SEG1 |
| ATOM | 632 | HN | ARG | 43 | 10.206 | 6.471 | -0.288 | 1.00 | 0.51 | SEG1 |
| ATOM | 633 | CA | ARG | 43 | 10.116 | 6.086 | -2.411 | 1.00 | 0.54 | SEG1 |
| ATOM | 634 | HA | ARG | 43 | 9.465 | 6.640 | -3.069 | 1.00 | 0.56 | SEG1 |
| ATOM | 635 | CB | ARG | 43 | 11.501 | 6.736 | -2.380 | 1.00 | 0.66 | SEG1 |
| ATOM | 636 | HB1 | ARG | 43 | 11.994 | 6.578 | -3.327 | 1.00 | 1.44 | SEG1 |
| ATOM | 637 | HB2 | ARG | 43 | 12.089 | 6.292 | -1.589 | 1.00 | 1.20 | SEG1 |
| ATOM | 638 | CG | ARG | 43 | 11.358 | 8.238 | -2.128 | 1.00 | 0.88 | SEG1 |
| ATOM | 639 | HG1 | ARG | 43 | 10.875 | 8.398 | -1.175 | 1.00 | 1.42 | SEG1 |
| ATOM | 640 | HG2 | ARG | 43 | 10.762 | 8.680 | -2.914 | 1.00 | 1.62 | SEG1 |
| ATOM | 641 | CD | ARG | 43 | 12.746 | 8.887 | -2.107 | 1.00 | 0.77 | SEG1 |
| ATOM | 642 | HD1 | ARG | 43 | 13.387 | 8.381 | -1.402 | 1.00 | 1.04 | SEG1 |
| ATOM | 643 | HD2 | ARG | 43 | 12.665 | 9.937 | -1.859 | 1.00 | 1.12 | SEG1 |
| ATOM | 644 | NE | ARG | 43 | 13.278 | 8.717 | -3.497 | 1.00 | 1.91 | SEG1 |
| ATOM | 645 | HE | ARG | 43 | 12.718 | 8.291 | -4.180 | 1.00 | 2.62 | SEG1 |
| ATOM | 646 | CZ | ARG | 43 | 14.490 | 9.118 | -3.823 | 1.00 | 2.29 | SEG1 |
| ATOM | 647 | NH1 | ARG | 43 | 14.915 | 8.932 | -5.042 | 1.00 | 3.44 | SEG1 |
| ATOM | 648 | HH11 | ARG | 43 | 14.323 | 8.491 | -5.716 | 1.00 | 4.07 | SEG1 |
| ATOM | 649 | HH12 | ARG | 43 | 15.832 | 9.231 | -5.303 | 1.00 | 3.79 | SEG1 |
| ATOM | 650 | NH2 | ARG | 43 | 15.279 | 9.704 | -2.952 | 1.00 | 1.85 | SEG1 |
| ATOM | 651 | HH21 | ARG | 43 | 14.973 | 9.860 | -2.014 | 1.00 | 1.42 | SEG1 |
| ATOM | 652 | HH22 | ARG | 43 | 16.195 | 9.997 | -3.230 | 1.00 | 2.34 | SEG1 |
| ATOM | 653 | C | ARG | 43 | 10.227 | 4.630 | -2.874 | 1.00 | 0.50 | SEG1 |
| ATOM | 654 | O | ARG | 43 | 9.908 | 4.304 | -4.002 | 1.00 | 0.50 | SEG1 |
| ATOM | 655 | N | ALA | 44 | 10.680 | 3.754 | -2.011 | 1.00 | 0.51 | SEG1 |
| ATOM | 656 | HN | ALA | 44 | 10.931 | 4.044 | -1.108 | 1.00 | 0.52 | SEG1 |
| ATOM | 657 | CA | ALA | 44 | 10.816 | 2.315 | -2.400 | 1.00 | 0.52 | SEG1 |
| ATOM | 658 | HA | ALA | 44 | 11.458 | 2.217 | -3.261 | 1.00 | 0.57 | SEG1 |
| ATOM | 659 | CB | ALA | 44 | 11.454 | 1.627 | -1.191 | 1.00 | 0.54 | SEG1 |
| ATOM | 660 | HB1 | ALA | 44 | 10.679 | 1.303 | -0.511 | 1.00 | 1.08 | SEG1 |
| ATOM | 661 | HB2 | ALA | 44 | 12.108 | 2.321 | -0.686 | 1.00 | 1.23 | SEG1 |
| ATOM | 662 | HB3 | ALA | 44 | 12.023 | 0.771 | -1.522 | 1.00 | 1.10 | SEG1 |
| ATOM | 663 | C | ALA | 44 | 9.439 | 1.714 | -2.690 | 1.00 | 0.45 | SEG1 |
| ATOM | 664 | O | ALA | 44 | 9.255 | 0.999 | -3.657 | 1.00 | 0.47 | SEG1 |
| ATOM | 665 | N | LEU | 45 | 8.474 | 2.001 | -1.855 | 1.00 | 0.41 | SEG1 |
| ATOM | 666 | HN | LEU | 45 | 8.655 | 2.581 | -1.084 | 1.00 | 0.42 | SEG1 |
| ATOM | 667 | CA | LEU | 45 | 7.101 | 1.454 | -2.069 | 1.00 | 0.38 | SEG1 |
| ATOM | 668 | HA | LEU | 45 | 7.139 | 0.384 | -2.197 | 1.00 | 0.41 | SEG1 |
| ATOM | 669 | CB | LEU | 45 | 6.323 | 1.802 | -0.801 | 1.00 | 0.37 | SEG1 |
| ATOM | 670 | HB1 | LEU | 45 | 5.278 | 1.582 | -0.951 | 1.00 | 0.37 | SEG1 |
| ATOM | 671 | HB2 | LEU | 45 | 6.442 | 2.854 | -0.581 | 1.00 | 0.37 | SEG1 |
| ATOM | 672 | CG | LEU | 45 | 6.852 | 0.971 | 0.368 | 1.00 | 0.40 | SEG1 |
| ATOM | 673 | HG | LEU | 45 | 7.928 | 1.054 | 0.410 | 1.00 | 0.41 | SEG1 |
| ATOM | 674 | CD1 | LEU | 45 | 6.251 | 1.494 | 1.673 | 1.00 | 0.42 | SEG1 |
| ATOM | 675 | HD11 | LEU | 45 | 5.183 | 1.332 | 1.658 | 1.00 | 0.91 | SEG1 |
| ATOM | 676 | HD12 | LEU | 45 | 6.455 | 2.550 | 1.764 | 1.00 | 1.16 | SEG1 |
| ATOM | 677 | HD13 | LEU | 45 | 6.692 | 0.968 | 2.507 | 1.00 | 1.10 | SEG1 |
| ATOM | 678 | CD2 | LEU | 45 | 6.457 | -0.495 | 0.176 | 1.00 | 0.45 | SEG1 |
| ATOM | 679 | HD21 | LEU | 45 | 7.249 | -1.016 | -0.341 | 1.00 | 1.17 | SEG1 |
| ATOM | 680 | HD22 | LEU | 45 | 5.550 | -0.551 | -0.408 | 1.00 | 1.07 | SEG1 |

FIG. 2

| | | | | | | | | | | |
|---|---|---|---|---|---|---|---|---|---|---|
| ATOM | 681 | HD23 | LEU | 45 | 6.294 | -0.954 | 1.140 | 1.00 | 1.06 | SEG1 |
| ATOM | 682 | C | LEU | 45 | 6.457 | 2.115 | -3.290 | 1.00 | 0.37 | SEG1 |
| ATOM | 683 | O | LEU | 45 | 5.698 | 1.500 | -4.014 | 1.00 | 0.37 | SEG1 |
| ATOM | 684 | N | GLN | 46 | 6.755 | 3.369 | -3.513 | 1.00 | 0.37 | SEG1 |
| ATOM | 685 | HN | GLN | 46 | 7.368 | 3.836 | -2.906 | 1.00 | 0.39 | SEG1 |
| ATOM | 686 | CA | GLN | 46 | 6.162 | 4.094 | -4.680 | 1.00 | 0.38 | SEG1 |
| ATOM | 687 | HA | GLN | 46 | 5.089 | 4.141 | -4.588 | 1.00 | 0.39 | SEG1 |
| ATOM | 688 | CB | GLN | 46 | 6.756 | 5.506 | -4.611 | 1.00 | 0.42 | SEG1 |
| ATOM | 689 | HB1 | GLN | 46 | 7.831 | 5.447 | -4.681 | 1.00 | 0.42 | SEG1 |
| ATOM | 690 | HB2 | GLN | 46 | 6.482 | 5.963 | -3.671 | 1.00 | 0.43 | SEG1 |
| ATOM | 691 | CG | GLN | 46 | 6.220 | 6.358 | -5.767 | 1.00 | 0.46 | SEG1 |
| ATOM | 692 | HG1 | GLN | 46 | 5.144 | 6.415 | -5.702 | 1.00 | 0.54 | SEG1 |
| ATOM | 693 | HG2 | GLN | 46 | 6.500 | 5.905 | -6.706 | 1.00 | 0.65 | SEG1 |
| ATOM | 694 | CD | GLN | 46 | 6.808 | 7.772 | -5.687 | 1.00 | 0.92 | SEG1 |
| ATOM | 695 | OE1 | GLN | 46 | 7.395 | 8.149 | -4.690 | 1.00 | 1.16 | SEG1 |
| ATOM | 696 | NE2 | GLN | 46 | 6.687 | 8.573 | -6.710 | 1.00 | 1.46 | SEG1 |
| ATOM | 697 | HE21 | GLN | 46 | 6.225 | 8.269 | -7.519 | 1.00 | 1.64 | SEG1 |
| ATOM | 698 | HE22 | GLN | 46 | 7.057 | 9.480 | -6.669 | 1.00 | 1.83 | SEG1 |
| ATOM | 699 | C | GLN | 46 | 6.555 | 3.402 | -5.989 | 1.00 | 0.37 | SEG1 |
| ATOM | 700 | O | GLN | 46 | 5.752 | 3.272 | -6.895 | 1.00 | 0.37 | SEG1 |
| ATOM | 701 | N | ALA | 47 | 7.781 | 2.957 | -6.092 | 1.00 | 0.39 | SEG1 |
| ATOM | 702 | HN | ALA | 47 | 8.405 | 3.072 | -5.345 | 1.00 | 0.41 | SEG1 |
| ATOM | 703 | CA | ALA | 47 | 8.226 | 2.267 | -7.341 | 1.00 | 0.41 | SEG1 |
| ATOM | 704 | HA | ALA | 47 | 8.001 | 2.873 | -8.204 | 1.00 | 0.41 | SEG1 |
| ATOM | 705 | CB | ALA | 47 | 9.740 | 2.105 | -7.195 | 1.00 | 0.46 | SEG1 |
| ATOM | 706 | HB1 | ALA | 47 | 9.958 | 1.155 | -6.730 | 1.00 | 1.14 | SEG1 |
| ATOM | 707 | HB2 | ALA | 47 | 10.131 | 2.904 | -6.582 | 1.00 | 1.11 | SEG1 |
| ATOM | 708 | HB3 | ALA | 47 | 10.202 | 2.143 | -8.171 | 1.00 | 1.09 | SEG1 |
| ATOM | 709 | C | ALA | 47 | 7.550 | 0.898 | -7.462 | 1.00 | 0.39 | SEG1 |
| ATOM | 710 | O | ALA | 47 | 7.154 | 0.487 | -8.536 | 1.00 | 0.39 | SEG1 |
| ATOM | 711 | N | ALA | 48 | 7.422 | 0.191 | -6.368 | 1.00 | 0.40 | SEG1 |
| ATOM | 712 | HN | ALA | 48 | 7.755 | 0.547 | -5.516 | 1.00 | 0.41 | SEG1 |
| ATOM | 713 | CA | ALA | 48 | 6.777 | -1.159 | -6.414 | 1.00 | 0.42 | SEG1 |
| ATOM | 714 | HA | ALA | 48 | 7.346 | -1.823 | -7.045 | 1.00 | 0.45 | SEG1 |
| ATOM | 715 | CB | ALA | 48 | 6.800 | -1.669 | -4.972 | 1.00 | 0.46 | SEG1 |
| ATOM | 716 | HB1 | ALA | 48 | 6.464 | -0.887 | -4.307 | 1.00 | 1.10 | SEG1 |
| ATOM | 717 | HB2 | ALA | 48 | 7.807 | -1.958 | -4.708 | 1.00 | 1.01 | SEG1 |
| ATOM | 718 | HB3 | ALA | 48 | 6.146 | -2.524 | -4.882 | 1.00 | 0.97 | SEG1 |
| ATOM | 719 | C | ALA | 48 | 5.336 | -1.051 | -6.921 | 1.00 | 0.39 | SEG1 |
| ATOM | 720 | O | ALA | 48 | 4.896 | -1.843 | -7.734 | 1.00 | 0.40 | SEG1 |
| ATOM | 721 | N | LEU | 49 | 4.598 | -0.079 | -6.446 | 1.00 | 0.36 | SEG1 |
| ATOM | 722 | HN | LEU | 49 | 4.977 | 0.544 | -5.790 | 1.00 | 0.36 | SEG1 |
| ATOM | 723 | CA | LEU | 49 | 3.181 | 0.083 | -6.896 | 1.00 | 0.35 | SEG1 |
| ATOM | 724 | HA | LEU | 49 | 2.603 | -0.787 | -6.632 | 1.00 | 0.38 | SEG1 |
| ATOM | 725 | CB | LEU | 49 | 2.647 | 1.305 | -6.154 | 1.00 | 0.33 | SEG1 |
| ATOM | 726 | HB1 | LEU | 49 | 1.643 | 1.509 | -6.490 | 1.00 | 0.35 | SEG1 |
| ATOM | 727 | HB2 | LEU | 49 | 3.275 | 2.156 | -6.362 | 1.00 | 0.33 | SEG1 |
| ATOM | 728 | CG | LEU | 49 | 2.634 | 1.032 | -4.650 | 1.00 | 0.35 | SEG1 |
| ATOM | 729 | HG | LEU | 49 | 3.604 | 0.669 | -4.341 | 1.00 | 0.37 | SEG1 |
| ATOM | 730 | CD1 | LEU | 49 | 2.312 | 2.326 | -3.902 | 1.00 | 0.37 | SEG1 |
| ATOM | 731 | HD11 | LEU | 49 | 2.785 | 2.309 | -2.932 | 1.00 | 1.08 | SEG1 |
| ATOM | 732 | HD12 | LEU | 49 | 1.242 | 2.414 | -3.781 | 1.00 | 1.06 | SEG1 |
| ATOM | 733 | HD13 | LEU | 49 | 2.680 | 3.169 | -4.467 | 1.00 | 1.10 | SEG1 |
| ATOM | 734 | CD2 | LEU | 49 | 1.568 | -0.017 | -4.329 | 1.00 | 0.39 | SEG1 |
| ATOM | 735 | HD21 | LEU | 49 | 1.954 | -1.002 | -4.549 | 1.00 | 1.04 | SEG1 |
| ATOM | 736 | HD22 | LEU | 49 | 0.689 | 0.168 | -4.928 | 1.00 | 1.15 | SEG1 |
| ATOM | 737 | HD23 | LEU | 49 | 1.309 | 0.043 | -3.282 | 1.00 | 1.02 | SEG1 |
| ATOM | 738 | C | LEU | 49 | 3.124 | 0.321 | -8.406 | 1.00 | 0.36 | SEG1 |
| ATOM | 739 | O | LEU | 49 | 2.256 | -0.188 | -9.089 | 1.00 | 0.38 | SEG1 |
| ATOM | 740 | N | ALA | 50 | 4.041 | 1.101 | -8.932 | 1.00 | 0.36 | SEG1 |
| ATOM | 741 | HN | ALA | 50 | 4.726 | 1.504 | -8.355 | 1.00 | 0.35 | SEG1 |
| ATOM | 742 | CA | ALA | 50 | 4.040 | 1.388 | -10.404 | 1.00 | 0.39 | SEG1 |
| ATOM | 743 | HA | ALA | 50 | 3.192 | 1.998 | -10.667 | 1.00 | 0.40 | SEG1 |
| ATOM | 744 | CB | ALA | 50 | 5.338 | 2.158 | -10.664 | 1.00 | 0.42 | SEG1 |
| ATOM | 745 | HB1 | ALA | 50 | 5.640 | 2.669 | -9.761 | 1.00 | 1.08 | SEG1 |
| ATOM | 746 | HB2 | ALA | 50 | 5.177 | 2.880 | -11.449 | 1.00 | 1.10 | SEG1 |
| ATOM | 747 | HB3 | ALA | 50 | 6.112 | 1.468 | -10.963 | 1.00 | 1.13 | SEG1 |
| ATOM | 748 | C | ALA | 50 | 4.025 | 0.082 | -11.202 | 1.00 | 0.41 | SEG1 |
| ATOM | 749 | O | ALA | 50 | 3.347 | -0.037 | -12.205 | 1.00 | 0.44 | SEG1 |
| ATOM | 750 | N | GLU | 51 | 4.759 | -0.897 | -10.749 | 1.00 | 0.42 | SEG1 |
| ATOM | 751 | HN | GLU | 51 | 5.285 | -0.771 | -9.932 | 1.00 | 0.40 | SEG1 |
| ATOM | 752 | CA | GLU | 51 | 4.788 | -2.209 | -11.460 | 1.00 | 0.46 | SEG1 |
| ATOM | 753 | HA | GLU | 51 | 5.054 | -2.070 | -12.495 | 1.00 | 0.50 | SEG1 |
| ATOM | 754 | CB | GLU | 51 | 5.864 | -3.033 | -10.750 | 1.00 | 0.49 | SEG1 |
| ATOM | 755 | HB1 | GLU | 51 | 5.823 | -4.055 | -11.096 | 1.00 | 0.53 | SEG1 |
| ATOM | 756 | HB2 | GLU | 51 | 5.693 | -3.006 | -9.684 | 1.00 | 0.47 | SEG1 |
| ATOM | 757 | CG | GLU | 51 | 7.245 | -2.446 | -11.064 | 1.00 | 0.52 | SEG1 |

FIG. 2

| ATOM | 758 | HG1 | GLU | 51 | 7.284 | -1.423 | -10.720 | 1.00 | 0.83 | SEG1 |
|------|-----|-----|-----|----|-------|--------|---------|------|------|------|
| ATOM | 759 | HG2 | GLU | 51 | 7.409 | -2.470 | -12.131 | 1.00 | 0.71 | SEG1 |
| ATOM | 760 | CD | GLU | 51 | 8.343 | -3.257 | -10.361 | 1.00 | 0.92 | SEG1 |
| ATOM | 761 | OE1 | GLU | 51 | 8.013 | -4.095 | -9.533 | 1.00 | 1.57 | SEG1 |
| ATOM | 762 | OE2 | GLU | 51 | 9.502 | -3.025 | -10.664 | 1.00 | 1.58 | SEG1 |
| ATOM | 763 | C | GLU | 51 | 3.422 | -2.895 | -11.347 | 1.00 | 0.46 | SEG1 |
| ATOM | 764 | O | GLU | 51 | 2.956 | -3.522 | -12.279 | 1.00 | 0.50 | SEG1 |
| ATOM | 765 | N | SER | 52 | 2.784 | -2.789 | -10.205 | 1.00 | 0.42 | SEG1 |
| ATOM | 766 | HN | SER | 52 | 3.185 | -2.283 | -9.466 | 1.00 | 0.39 | SEG1 |
| ATOM | 767 | CA | SER | 52 | 1.451 | -3.445 | -10.022 | 1.00 | 0.43 | SEG1 |
| ATOM | 768 | HA | SER | 52 | 1.453 | -4.420 | -10.480 | 1.00 | 0.47 | SEG1 |
| ATOM | 769 | CB | SER | 52 | 1.287 | -3.588 | -8.510 | 1.00 | 0.42 | SEG1 |
| ATOM | 770 | HB1 | SER | 52 | 0.312 | -4.003 | -8.293 | 1.00 | 1.06 | SEG1 |
| ATOM | 771 | HB2 | SER | 52 | 1.375 | -2.622 | -8.043 | 1.00 | 0.95 | SEG1 |
| ATOM | 772 | OG | SER | 52 | 2.304 | -4.445 | -8.007 | 1.00 | 1.34 | SEG1 |
| ATOM | 773 | HG | SER | 52 | 2.885 | -3.922 | -7.451 | 1.00 | 1.64 | SEG1 |
| ATOM | 774 | C | SER | 52 | 0.316 | -2.587 | -10.604 | 1.00 | 0.42 | SEG1 |
| ATOM | 775 | O | SER | 52 | -0.808 | -3.043 | -10.713 | 1.00 | 0.46 | SEG1 |
| ATOM | 776 | N | GLY | 53 | 0.591 | -1.361 | -10.984 | 1.00 | 0.41 | SEG1 |
| ATOM | 777 | HN | GLY | 53 | 1.500 | -1.009 | -10.891 | 1.00 | 0.40 | SEG1 |
| ATOM | 778 | CA | GLY | 53 | -0.483 | -0.497 | -11.563 | 1.00 | 0.42 | SEG1 |
| ATOM | 779 | HA1 | GLY | 53 | -1.350 | -1.102 | -11.778 | 1.00 | 0.45 | SEG1 |
| ATOM | 780 | HA2 | GLY | 53 | -0.125 | -0.048 | -12.477 | 1.00 | 0.45 | SEG1 |
| ATOM | 781 | C | GLY | 53 | -0.876 | 0.610 | -10.576 | 1.00 | 0.39 | SEG1 |
| ATOM | 782 | O | GLY | 53 | -1.904 | 1.244 | -10.731 | 1.00 | 0.41 | SEG1 |
| ATOM | 783 | N | GLY | 54 | -0.068 | 0.858 | -9.574 | 1.00 | 0.37 | SEG1 |
| ATOM | 784 | HN | GLY | 54 | 0.758 | 0.348 | -9.472 | 1.00 | 0.38 | SEG1 |
| ATOM | 785 | CA | GLY | 54 | -0.395 | 1.933 | -8.594 | 1.00 | 0.35 | SEG1 |
| ATOM | 786 | HA1 | GLY | 54 | -0.294 | 1.551 | -7.589 | 1.00 | 0.35 | SEG1 |
| ATOM | 787 | HA2 | GLY | 54 | -1.408 | 2.274 | -8.754 | 1.00 | 0.35 | SEG1 |
| ATOM | 788 | C | GLY | 54 | 0.578 | 3.091 | -8.797 | 1.00 | 0.38 | SEG1 |
| ATOM | 789 | O | GLY | 54 | 1.469 | 3.314 | -7.999 | 1.00 | 0.40 | SEG1 |
| ATOM | 790 | N | SER | 55 | 0.417 | 3.823 | -9.869 | 1.00 | 0.41 | SEG1 |
| ATOM | 791 | HN | SER | 55 | -0.305 | 3.610 | -10.497 | 1.00 | 0.41 | SEG1 |
| ATOM | 792 | CA | SER | 55 | 1.338 | 4.969 | -10.146 | 1.00 | 0.46 | SEG1 |
| ATOM | 793 | HA | SER | 55 | 2.352 | 4.618 | -10.258 | 1.00 | 0.50 | SEG1 |
| ATOM | 794 | CB | SER | 55 | 0.846 | 5.576 | -11.463 | 1.00 | 0.50 | SEG1 |
| ATOM | 795 | HB1 | SER | 55 | 0.676 | 4.784 | -12.181 | 1.00 | 0.50 | SEG1 |
| ATOM | 796 | HB2 | SER | 55 | 1.587 | 6.254 | -11.850 | 1.00 | 0.59 | SEG1 |
| ATOM | 797 | OG | SER | 55 | -0.363 | 6.286 | -11.233 | 1.00 | 0.49 | SEG1 |
| ATOM | 798 | HG | SER | 55 | -0.161 | 7.225 | -11.238 | 1.00 | 0.74 | SEG1 |
| ATOM | 799 | C | SER | 55 | 1.248 | 6.001 | -9.012 | 1.00 | 0.46 | SEG1 |
| ATOM | 800 | O | SER | 55 | 0.277 | 6.023 | -8.283 | 1.00 | 0.42 | SEG1 |
| ATOM | 801 | N | PRO | 56 | 2.265 | 6.826 | -8.889 | 1.00 | 0.54 | SEG1 |
| ATOM | 802 | CA | PRO | 56 | 2.267 | 7.855 | -7.818 | 1.00 | 0.56 | SEG1 |
| ATOM | 803 | HA | PRO | 56 | 2.081 | 7.403 | -6.858 | 1.00 | 0.55 | SEG1 |
| ATOM | 804 | CB | PRO | 56 | 3.685 | 8.417 | -7.861 | 1.00 | 0.66 | SEG1 |
| ATOM | 805 | HB1 | PRO | 56 | 4.314 | 7.904 | -7.151 | 1.00 | 0.69 | SEG1 |
| ATOM | 806 | HB2 | PRO | 56 | 3.673 | 9.480 | -7.659 | 1.00 | 0.68 | SEG1 |
| ATOM | 807 | CG | PRO | 56 | 4.163 | 8.154 | -9.252 | 1.00 | 0.70 | SEG1 |
| ATOM | 808 | HG1 | PRO | 56 | 5.233 | 8.017 | -9.258 | 1.00 | 0.77 | SEG1 |
| ATOM | 809 | HG2 | PRO | 56 | 3.890 | 8.978 | -9.898 | 1.00 | 0.72 | SEG1 |
| ATOM | 810 | CD | PRO | 56 | 3.487 | 6.889 | -9.711 | 1.00 | 0.64 | SEG1 |
| ATOM | 811 | HD2 | PRO | 56 | 3.240 | 6.952 | -10.763 | 1.00 | 0.65 | SEG1 |
| ATOM | 812 | HD1 | PRO | 56 | 4.111 | 6.032 | -9.515 | 1.00 | 0.67 | SEG1 |
| ATOM | 813 | C | PRO | 56 | 1.241 | 8.958 | -8.105 | 1.00 | 0.55 | SEG1 |
| ATOM | 814 | O | PRO | 56 | 0.942 | 9.765 | -7.244 | 1.00 | 0.57 | SEG1 |
| ATOM | 815 | N | ASP | 57 | 0.695 | 9.001 | -9.298 | 1.00 | 0.56 | SEG1 |
| ATOM | 816 | HN | ASP | 57 | 0.940 | 8.342 | -9.978 | 1.00 | 0.56 | SEG1 |
| ATOM | 817 | CA | ASP | 57 | -0.310 | 10.053 | -9.621 | 1.00 | 0.60 | SEG1 |
| ATOM | 818 | HA | ASP | 57 | -0.082 | 10.966 | -9.095 | 1.00 | 0.65 | SEG1 |
| ATOM | 819 | CB | ASP | 57 | -0.185 | 10.273 | -11.129 | 1.00 | 0.68 | SEG1 |
| ATOM | 820 | HB1 | ASP | 57 | -0.999 | 10.894 | -11.470 | 1.00 | 1.04 | SEG1 |
| ATOM | 821 | HB2 | ASP | 57 | -0.223 | 9.320 | -11.636 | 1.00 | 1.22 | SEG1 |
| ATOM | 822 | CG | ASP | 57 | 1.146 | 10.965 | -11.444 | 1.00 | 1.17 | SEG1 |
| ATOM | 823 | OD1 | ASP | 57 | 1.650 | 10.762 | -12.536 | 1.00 | 1.87 | SEG1 |
| ATOM | 824 | OD2 | ASP | 57 | 1.636 | 11.689 | -10.591 | 1.00 | 1.84 | SEG1 |
| ATOM | 825 | C | ASP | 57 | -1.713 | 9.565 | -9.264 | 1.00 | 0.57 | SEG1 |
| ATOM | 826 | O | ASP | 57 | -2.603 | 10.355 | -9.006 | 1.00 | 0.66 | SEG1 |
| ATOM | 827 | N | VAL | 58 | -1.921 | 8.271 | -9.259 | 1.00 | 0.49 | SEG1 |
| ATOM | 828 | HN | VAL | 58 | -1.192 | 7.654 | -9.479 | 1.00 | 0.47 | SEG1 |
| ATOM | 829 | CA | VAL | 58 | -3.271 | 7.737 | -8.930 | 1.00 | 0.50 | SEG1 |
| ATOM | 830 | HA | VAL | 58 | -3.985 | 8.545 | -8.933 | 1.00 | 0.54 | SEG1 |
| ATOM | 831 | CB | VAL | 58 | -3.603 | 6.764 | -10.083 | 1.00 | 0.51 | SEG1 |
| ATOM | 832 | HB | VAL | 58 | -3.274 | 7.198 | -11.015 | 1.00 | 0.55 | SEG1 |
| ATOM | 833 | CG1 | VAL | 58 | -2.905 | 5.406 | -9.905 | 1.00 | 0.46 | SEG1 |
| ATOM | 834 | HG11 | VAL | 58 | -3.317 | 4.899 | -9.045 | 1.00 | 1.04 | SEG1 |

| | | | | | | | | | |
|---|---|---|---|---|---|---|---|---|---|
| ATOM | 835 | HG12 | VAL | 58 | -1.849 | 5.558 | -9.760 | 1.00 | 1.10 | SEG1 |
| ATOM | 836 | HG13 | VAL | 58 | -3.063 | 4.803 | -10.786 | 1.00 | 1.17 | SEG1 |
| ATOM | 837 | CG2 | VAL | 58 | -5.116 | 6.560 | -10.141 | 1.00 | 0.64 | SEG1 |
| ATOM | 838 | HG21 | VAL | 58 | -5.442 | 6.592 | -11.169 | 1.00 | 1.17 | SEG1 |
| ATOM | 839 | HG22 | VAL | 58 | -5.610 | 7.344 | -9.585 | 1.00 | 1.24 | SEG1 |
| ATOM | 840 | HG23 | VAL | 58 | -5.369 | 5.602 | -9.712 | 1.00 | 1.13 | SEG1 |
| ATOM | 841 | C | VAL | 58 | -3.277 | 7.052 | -7.549 | 1.00 | 0.45 | SEG1 |
| ATOM | 842 | O | VAL | 58 | -4.179 | 7.252 | -6.757 | 1.00 | 0.49 | SEG1 |
| ATOM | 843 | N | LEU | 59 | -2.280 | 6.252 | -7.261 | 1.00 | 0.40 | SEG1 |
| ATOM | 844 | HN | LEU | 59 | -1.564 | 6.110 | -7.912 | 1.00 | 0.40 | SEG1 |
| ATOM | 845 | CA | LEU | 59 | -2.224 | 5.559 | -5.937 | 1.00 | 0.36 | SEG1 |
| ATOM | 846 | HA | LEU | 59 | -3.151 | 5.698 | -5.405 | 1.00 | 0.38 | SEG1 |
| ATOM | 847 | CB | LEU | 59 | -2.030 | 4.076 | -6.269 | 1.00 | 0.34 | SEG1 |
| ATOM | 848 | HB1 | LEU | 59 | -1.319 | 3.643 | -5.581 | 1.00 | 0.32 | SEG1 |
| ATOM | 849 | HB2 | LEU | 59 | -1.659 | 3.980 | -7.279 | 1.00 | 0.35 | SEG1 |
| ATOM | 850 | CG | LEU | 59 | -3.366 | 3.339 | -6.147 | 1.00 | 0.35 | SEG1 |
| ATOM | 851 | HG | LEU | 59 | -4.177 | 4.025 | -6.348 | 1.00 | 0.37 | SEG1 |
| ATOM | 852 | CD1 | LEU | 59 | -3.408 | 2.186 | -7.150 | 1.00 | 0.36 | SEG1 |
| ATOM | 853 | HD11 | LEU | 59 | -2.581 | 1.517 | -6.964 | 1.00 | 1.01 | SEG1 |
| ATOM | 854 | HD12 | LEU | 59 | -3.337 | 2.579 | -8.153 | 1.00 | 1.15 | SEG1 |
| ATOM | 855 | HD13 | LEU | 59 | -4.338 | 1.648 | -7.040 | 1.00 | 1.03 | SEG1 |
| ATOM | 856 | CD2 | LEU | 59 | -3.506 | 2.778 | -4.730 | 1.00 | 0.34 | SEG1 |
| ATOM | 857 | HD21 | LEU | 59 | -3.064 | 1.793 | -4.688 | 1.00 | 0.99 | SEG1 |
| ATOM | 858 | HD22 | LEU | 59 | -4.552 | 2.714 | -4.469 | 1.00 | 0.92 | SEG1 |
| ATOM | 859 | HD23 | LEU | 59 | -3.000 | 3.430 | -4.033 | 1.00 | 1.10 | SEG1 |
| ATOM | 860 | C | LEU | 59 | -1.053 | 6.088 | -5.106 | 1.00 | 0.34 | SEG1 |
| ATOM | 861 | O | LEU | 59 | 0.087 | 6.060 | -5.532 | 1.00 | 0.36 | SEG1 |
| ATOM | 862 | N | GLN | 60 | -1.331 | 6.565 | -3.921 | 1.00 | 0.34 | SEG1 |
| ATOM | 863 | HN | GLN | 60 | -2.259 | 6.572 | -3.605 | 1.00 | 0.36 | SEG1 |
| ATOM | 864 | CA | GLN | 60 | -0.248 | 7.099 | -3.044 | 1.00 | 0.34 | SEG1 |
| ATOM | 865 | HA | GLN | 60 | 0.721 | 6.849 | -3.443 | 1.00 | 0.35 | SEG1 |
| ATOM | 866 | CB | GLN | 60 | -0.447 | 8.615 | -3.053 | 1.00 | 0.39 | SEG1 |
| ATOM | 867 | HB1 | GLN | 60 | 0.187 | 9.067 | -2.304 | 1.00 | 0.61 | SEG1 |
| ATOM | 868 | HB2 | GLN | 60 | -1.480 | 8.843 | -2.835 | 1.00 | 0.60 | SEG1 |
| ATOM | 869 | CG | GLN | 60 | -0.081 | 9.170 | -4.430 | 1.00 | 0.80 | SEG1 |
| ATOM | 870 | HG1 | GLN | 60 | -0.599 | 8.610 | -5.194 | 1.00 | 1.24 | SEG1 |
| ATOM | 871 | HG2 | GLN | 60 | 0.986 | 9.084 | -4.581 | 1.00 | 1.15 | SEG1 |
| ATOM | 872 | CD | GLN | 60 | -0.492 | 10.641 | -4.513 | 1.00 | 1.13 | SEG1 |
| ATOM | 873 | OE1 | GLN | 60 | -1.398 | 11.070 | -3.827 | 1.00 | 1.43 | SEG1 |
| ATOM | 874 | NE2 | GLN | 60 | 0.141 | 11.438 | -5.330 | 1.00 | 1.63 | SEG1 |
| ATOM | 875 | HE21 | GLN | 60 | 0.873 | 11.093 | -5.882 | 1.00 | 1.87 | SEG1 |
| ATOM | 876 | HE22 | GLN | 60 | -0.115 | 12.382 | -5.390 | 1.00 | 1.98 | SEG1 |
| ATOM | 877 | C | GLN | 60 | -0.406 | 6.545 | -1.626 | 1.00 | 0.30 | SEG1 |
| ATOM | 878 | O | GLN | 60 | -1.482 | 6.135 | -1.231 | 1.00 | 0.30 | SEG1 |
| ATOM | 879 | N | MET | 61 | 0.654 | 6.535 | -0.857 | 1.00 | 0.30 | SEG1 |
| ATOM | 880 | HN | MET | 61 | 1.508 | 6.874 | -1.196 | 1.00 | 0.33 | SEG1 |
| ATOM | 881 | CA | MET | 61 | 0.560 | 6.012 | 0.539 | 1.00 | 0.28 | SEG1 |
| ATOM | 882 | HA | MET | 61 | -0.211 | 5.264 | 0.609 | 1.00 | 0.27 | SEG1 |
| ATOM | 883 | CB | MET | 61 | 1.926 | 5.387 | 0.820 | 1.00 | 0.31 | SEG1 |
| ATOM | 884 | HB1 | MET | 61 | 1.999 | 5.139 | 1.868 | 1.00 | 0.35 | SEG1 |
| ATOM | 885 | HB2 | MET | 61 | 2.704 | 6.090 | 0.560 | 1.00 | 0.35 | SEG1 |
| ATOM | 886 | CG | MET | 61 | 2.084 | 4.116 | -0.014 | 1.00 | 0.32 | SEG1 |
| ATOM | 887 | HG1 | MET | 61 | 1.880 | 4.339 | -1.051 | 1.00 | 0.64 | SEG1 |
| ATOM | 888 | HG2 | MET | 61 | 1.389 | 3.368 | 0.337 | 1.00 | 0.57 | SEG1 |
| ATOM | 889 | SD | MET | 61 | 3.773 | 3.494 | 0.150 | 1.00 | 0.71 | SEG1 |
| ATOM | 890 | CE | MET | 61 | 4.507 | 4.495 | -1.167 | 1.00 | 0.46 | SEG1 |
| ATOM | 891 | HE1 | MET | 61 | 5.558 | 4.643 | -0.963 | 1.00 | 1.11 | SEG1 |
| ATOM | 892 | HE2 | MET | 61 | 4.013 | 5.453 | -1.210 | 1.00 | 1.09 | SEG1 |
| ATOM | 893 | HE3 | MET | 61 | 4.385 | 3.987 | -2.114 | 1.00 | 1.09 | SEG1 |
| ATOM | 894 | C | MET | 61 | 0.284 | 7.164 | 1.505 | 1.00 | 0.30 | SEG1 |
| ATOM | 895 | O | MET | 61 | 1.066 | 8.090 | 1.617 | 1.00 | 0.40 | SEG1 |
| ATOM | 896 | N | LEU | 62 | -0.829 | 7.119 | 2.191 | 1.00 | 0.29 | SEG1 |
| ATOM | 897 | HN | LEU | 62 | -1.445 | 6.365 | 2.073 | 1.00 | 0.35 | SEG1 |
| ATOM | 898 | CA | LEU | 62 | -1.168 | 8.220 | 3.144 | 1.00 | 0.32 | SEG1 |
| ATOM | 899 | HA | LEU | 62 | -1.099 | 9.175 | 2.645 | 1.00 | 0.36 | SEG1 |
| ATOM | 900 | CB | LEU | 62 | -2.618 | 7.961 | 3.556 | 1.00 | 0.33 | SEG1 |
| ATOM | 901 | HB1 | LEU | 62 | -2.884 | 8.613 | 4.373 | 1.00 | 0.84 | SEG1 |
| ATOM | 902 | HB2 | LEU | 62 | -2.727 | 6.930 | 3.865 | 1.00 | 0.78 | SEG1 |
| ATOM | 903 | CG | LEU | 62 | -3.536 | 8.239 | 2.364 | 1.00 | 1.02 | SEG1 |
| ATOM | 904 | HG | LEU | 62 | -3.166 | 7.713 | 1.496 | 1.00 | 1.76 | SEG1 |
| ATOM | 905 | CD1 | LEU | 62 | -4.952 | 7.760 | 2.683 | 1.00 | 1.40 | SEG1 |
| ATOM | 906 | HD11 | LEU | 62 | -4.962 | 6.682 | 2.744 | 1.00 | 1.72 | SEG1 |
| ATOM | 907 | HD12 | LEU | 62 | -5.625 | 8.082 | 1.902 | 1.00 | 2.05 | SEG1 |
| ATOM | 908 | HD13 | LEU | 62 | -5.270 | 8.178 | 3.626 | 1.00 | 1.83 | SEG1 |
| ATOM | 909 | CD2 | LEU | 62 | -3.557 | 9.742 | 2.080 | 1.00 | 1.50 | SEG1 |
| ATOM | 910 | HD21 | LEU | 62 | -4.406 | 9.980 | 1.456 | 1.00 | 2.18 | SEG1 |
| ATOM | 911 | HD22 | LEU | 62 | -2.647 | 10.025 | 1.572 | 1.00 | 1.77 | SEG1 |

FIG. 2

| ATOM | 912 | HD23 | LEU | 62 | -3.632 | 10.294 | 3.011 | 1.00 | 1.93 | SEG1 |
|---|---|---|---|---|---|---|---|---|---|---|
| ATOM | 913 | C | LEU | 62 | -0.242 | 8.195 | 4.363 | 1.00 | 0.31 | SEG1 |
| ATOM | 914 | O | LEU | 62 | 0.188 | 9.230 | 4.837 | 1.00 | 0.34 | SEG1 |
| ATOM | 915 | N | LYS | 63 | 0.076 | 7.026 | 4.974 | 1.00 | 0.31 | SEG1 |
| ATOM | 916 | HN | LYS | 63 | -0.278 | 6.202 | 4.477 | 1.00 | 0.34 | SEG1 |
| ATOM | 917 | CA | LYS | 63 | 0.984 | 6.956 | 6.062 | 1.00 | 0.33 | SEG1 |
| ATOM | 918 | HA | LYS | 63 | 1.947 | 7.582 | 5.998 | 1.00 | 0.37 | SEG1 |
| ATOM | 919 | CB | LYS | 63 | 0.154 | 7.496 | 7.235 | 1.00 | 0.37 | SEG1 |
| ATOM | 920 | HB1 | LYS | 63 | -0.723 | 6.860 | 7.368 | 1.00 | 0.67 | SEG1 |
| ATOM | 921 | HB2 | LYS | 63 | -0.150 | 8.511 | 7.023 | 1.00 | 0.76 | SEG1 |
| ATOM | 922 | CG | LYS | 63 | 0.990 | 7.471 | 8.522 | 1.00 | 0.78 | SEG1 |
| ATOM | 923 | HG1 | LYS | 63 | 1.867 | 8.087 | 8.393 | 1.00 | 1.25 | SEG1 |
| ATOM | 924 | HG2 | LYS | 63 | 1.291 | 6.456 | 8.735 | 1.00 | 1.17 | SEG1 |
| ATOM | 925 | CD | LYS | 63 | 0.157 | 8.011 | 9.666 | 1.00 | 0.83 | SEG1 |
| ATOM | 926 | HD1 | LYS | 63 | -0.722 | 7.399 | 9.815 | 1.00 | 1.08 | SEG1 |
| ATOM | 927 | HD2 | LYS | 63 | -0.139 | 9.026 | 9.471 | 1.00 | 1.00 | SEG1 |
| ATOM | 928 | CE | LYS | 63 | 0.990 | 7.984 | 10.970 | 1.00 | 1.32 | SEG1 |
| ATOM | 929 | HE1 | LYS | 63 | 1.895 | 8.558 | 10.846 | 1.00 | 1.73 | SEG1 |
| ATOM | 930 | HE2 | LYS | 63 | 1.223 | 6.965 | 11.244 | 1.00 | 1.74 | SEG1 |
| ATOM | 931 | NZ | LYS | 63 | 0.123 | 8.617 | 12.004 | 1.00 | 1.53 | SEG1 |
| ATOM | 932 | HZ1 | LYS | 63 | -0.025 | 9.618 | 11.768 | 1.00 | 1.85 | SEG1 |
| ATOM | 933 | HZ2 | LYS | 63 | 0.583 | 8.544 | 12.934 | 1.00 | 1.93 | SEG1 |
| ATOM | 934 | HZ3 | LYS | 63 | -0.796 | 8.130 | 12.032 | 1.00 | 1.91 | SEG1 |
| ATOM | 935 | C | LYS | 63 | 1.419 | 5.514 | 6.336 | 1.00 | 0.29 | SEG1 |
| ATOM | 936 | O | LYS | 63 | 0.778 | 4.566 | 5.924 | 1.00 | 0.28 | SEG1 |
| ATOM | 937 | N | ILE | 64 | 2.499 | 5.357 | 7.056 | 1.00 | 0.28 | SEG1 |
| ATOM | 938 | HN | ILE | 64 | 2.978 | 6.141 | 7.385 | 1.00 | 0.31 | SEG1 |
| ATOM | 939 | CA | ILE | 64 | 2.990 | 3.993 | 7.402 | 1.00 | 0.27 | SEG1 |
| ATOM | 940 | HA | ILE | 64 | 2.589 | 3.257 | 6.724 | 1.00 | 0.26 | SEG1 |
| ATOM | 941 | CB | ILE | 64 | 4.521 | 4.064 | 7.279 | 1.00 | 0.29 | SEG1 |
| ATOM | 942 | HB | ILE | 64 | 4.905 | 4.737 | 8.033 | 1.00 | 0.30 | SEG1 |
| ATOM | 943 | CG1 | ILE | 64 | 4.931 | 4.574 | 5.883 | 1.00 | 0.31 | SEG1 |
| ATOM | 944 | HG11 | ILE | 64 | 6.011 | 4.594 | 5.813 | 1.00 | 0.33 | SEG1 |
| ATOM | 945 | HG12 | ILE | 64 | 4.547 | 5.574 | 5.742 | 1.00 | 0.32 | SEG1 |
| ATOM | 946 | CG2 | ILE | 64 | 5.114 | 2.671 | 7.507 | 1.00 | 0.30 | SEG1 |
| ATOM | 947 | HG21 | ILE | 64 | 6.108 | 2.629 | 7.085 | 1.00 | 1.02 | SEG1 |
| ATOM | 948 | HG22 | ILE | 64 | 4.489 | 1.931 | 7.030 | 1.00 | 1.02 | SEG1 |
| ATOM | 949 | HG23 | ILE | 64 | 5.165 | 2.471 | 8.567 | 1.00 | 1.04 | SEG1 |
| ATOM | 950 | CD1 | ILE | 64 | 4.368 | 3.654 | 4.791 | 1.00 | 0.30 | SEG1 |
| ATOM | 951 | HD11 | ILE | 64 | 4.830 | 3.894 | 3.844 | 1.00 | 1.02 | SEG1 |
| ATOM | 952 | HD12 | ILE | 64 | 3.300 | 3.796 | 4.714 | 1.00 | 1.05 | SEG1 |
| ATOM | 953 | HD13 | ILE | 64 | 4.577 | 2.625 | 5.042 | 1.00 | 1.09 | SEG1 |
| ATOM | 954 | C | ILE | 64 | 2.583 | 3.686 | 8.847 | 1.00 | 0.26 | SEG1 |
| ATOM | 955 | O | ILE | 64 | 3.032 | 4.337 | 9.773 | 1.00 | 0.29 | SEG1 |
| ATOM | 956 | N | HIS | 65 | 1.728 | 2.716 | 9.047 | 1.00 | 0.27 | SEG1 |
| ATOM | 957 | HN | HIS | 65 | 1.371 | 2.214 | 8.284 | 1.00 | 0.28 | SEG1 |
| ATOM | 958 | CA | HIS | 65 | 1.280 | 2.384 | 10.435 | 1.00 | 0.27 | SEG1 |
| ATOM | 959 | HA | HIS | 65 | 1.387 | 3.243 | 11.077 | 1.00 | 0.30 | SEG1 |
| ATOM | 960 | CB | HIS | 65 | -0.200 | 2.025 | 10.296 | 1.00 | 0.28 | SEG1 |
| ATOM | 961 | HB1 | HIS | 65 | -0.543 | 1.551 | 11.203 | 1.00 | 0.31 | SEG1 |
| ATOM | 962 | HB2 | HIS | 65 | -0.329 | 1.350 | 9.464 | 1.00 | 0.29 | SEG1 |
| ATOM | 963 | CG | HIS | 65 | -0.999 | 3.275 | 10.051 | 1.00 | 0.30 | SEG1 |
| ATOM | 964 | ND1 | HIS | 65 | -1.426 | 4.092 | 11.086 | 1.00 | 1.11 | SEG1 |
| ATOM | 965 | HD1 | HIS | 65 | -1.262 | 3.949 | 12.041 | 1.00 | 1.90 | SEG1 |
| ATOM | 966 | CD2 | HIS | 65 | -1.456 | 3.862 | 8.897 | 1.00 | 0.97 | SEG1 |
| ATOM | 967 | HD2 | HIS | 65 | -1.297 | 3.479 | 7.900 | 1.00 | 1.89 | SEG1 |
| ATOM | 968 | CE1 | HIS | 65 | -2.107 | 5.115 | 10.540 | 1.00 | 0.85 | SEG1 |
| ATOM | 969 | HE1 | HIS | 65 | -2.560 | 5.914 | 11.109 | 1.00 | 1.46 | SEG1 |
| ATOM | 970 | NE2 | HIS | 65 | -2.156 | 5.024 | 9.208 | 1.00 | 0.58 | SEG1 |
| ATOM | 971 | C | HIS | 65 | 2.072 | 1.201 | 10.995 | 1.00 | 0.28 | SEG1 |
| ATOM | 972 | O | HIS | 65 | 2.183 | 0.163 | 10.372 | 1.00 | 0.27 | SEG1 |
| ATOM | 973 | N | ARG | 66 | 2.628 | 1.359 | 12.170 | 1.00 | 0.35 | SEG1 |
| ATOM | 974 | HN | ARG | 66 | 2.527 | 2.208 | 12.647 | 1.00 | 0.41 | SEG1 |
| ATOM | 975 | CA | ARG | 66 | 3.420 | 0.258 | 12.786 | 1.00 | 0.39 | SEG1 |
| ATOM | 976 | HA | ARG | 66 | 3.636 | -0.510 | 12.058 | 1.00 | 0.36 | SEG1 |
| ATOM | 977 | CB | ARG | 66 | 4.712 | 0.930 | 13.235 | 1.00 | 0.49 | SEG1 |
| ATOM | 978 | HB1 | ARG | 66 | 5.293 | 0.239 | 13.821 | 1.00 | 0.54 | SEG1 |
| ATOM | 979 | HB2 | ARG | 66 | 4.477 | 1.800 | 13.831 | 1.00 | 0.51 | SEG1 |
| ATOM | 980 | CG | ARG | 66 | 5.516 | 1.354 | 12.005 | 1.00 | 0.54 | SEG1 |
| ATOM | 981 | HG1 | ARG | 66 | 4.935 | 2.048 | 11.417 | 1.00 | 0.61 | SEG1 |
| ATOM | 982 | HG2 | ARG | 66 | 5.748 | 0.483 | 11.410 | 1.00 | 0.71 | SEG1 |
| ATOM | 983 | CD | ARG | 66 | 6.815 | 2.029 | 12.448 | 1.00 | 0.64 | SEG1 |
| ATOM | 984 | HD1 | ARG | 66 | 7.385 | 2.345 | 11.592 | 1.00 | 1.19 | SEG1 |
| ATOM | 985 | HD2 | ARG | 66 | 7.396 | 1.353 | 13.060 | 1.00 | 0.78 | SEG1 |
| ATOM | 986 | NE | ARG | 66 | 6.385 | 3.219 | 13.248 | 1.00 | 1.37 | SEG1 |
| ATOM | 987 | HE | ARG | 66 | 6.366 | 3.156 | 14.225 | 1.00 | 1.94 | SEG1 |
| ATOM | 988 | CZ | ARG | 66 | 6.041 | 4.354 | 12.669 | 1.00 | 2.05 | SEG1 |

FIG. 2

```
ATOM    989  NH1  ARG  66    5.696   5.367  13.415  1.00  2.83      SEG1
ATOM    990  HH11 ARG  66    5.693   5.277  14.411  1.00  3.08      SEG1
ATOM    991  HH12 ARG  66    5.435   6.234  12.991  1.00  3.45      SEG1
ATOM    992  NH2  ARG  66    6.027   4.487  11.362  1.00  2.58      SEG1
ATOM    993  HH21 ARG  66    6.277   3.723  10.771  1.00  2.48      SEG1
ATOM    994  HH22 ARG  66    5.764   5.362  10.956  1.00  3.40      SEG1
ATOM    995  C    ARG  66    2.674  -0.330  13.999  1.00  0.43      SEG1
ATOM    996  O    ARG  66    2.379   0.364  14.945  1.00  0.49      SEG1
ATOM    997  N    SER  67    2.379  -1.604  13.954  1.00  0.42      SEG1
ATOM    998  HN   SER  67    2.635  -2.141  13.175  1.00  0.39      SEG1
ATOM    999  CA   SER  67    1.662  -2.250  15.097  1.00  0.49      SEG1
ATOM   1000  HA   SER  67    1.880  -1.735  16.019  1.00  0.54      SEG1
ATOM   1001  CB   SER  67    0.177  -2.121  14.760  1.00  0.52      SEG1
ATOM   1002  HB1  SER  67   -0.042  -2.702  13.874  1.00  0.53      SEG1
ATOM   1003  HB2  SER  67   -0.064  -1.087  14.576  1.00  0.53      SEG1
ATOM   1004  OG   SER  67   -0.596  -2.593  15.856  1.00  0.57      SEG1
ATOM   1005  HG   SER  67   -0.742  -3.534  15.732  1.00  1.01      SEG1
ATOM   1006  C    SER  67    2.070  -3.721  15.193  1.00  0.49      SEG1
ATOM   1007  O    SER  67    2.287  -4.364  14.187  1.00  0.47      SEG1
ATOM   1008  N    ASP  68    2.182  -4.252  16.398  1.00  0.54      SEG1
ATOM   1009  HN   ASP  68    2.003  -3.695  17.185  1.00  0.56      SEG1
ATOM   1010  CA   ASP  68    2.584  -5.694  16.591  1.00  0.57      SEG1
ATOM   1011  HA   ASP  68    2.852  -5.851  17.625  1.00  0.61      SEG1
ATOM   1012  CB   ASP  68    1.298  -6.497  16.270  1.00  0.60      SEG1
ATOM   1013  HB1  ASP  68    0.449  -5.962  16.671  1.00  0.62      SEG1
ATOM   1014  HB2  ASP  68    1.349  -7.461  16.746  1.00  0.64      SEG1
ATOM   1015  CG   ASP  68    1.092  -6.685  14.758  1.00  0.56      SEG1
ATOM   1016  OD1  ASP  68    1.946  -7.284  14.125  1.00  1.22      SEG1
ATOM   1017  OD2  ASP  68    0.080  -6.221  14.260  1.00  1.18      SEG1
ATOM   1018  C    ASP  68    3.799  -6.044  15.691  1.00  0.53      SEG1
ATOM   1019  O    ASP  68    4.412  -5.146  15.145  1.00  0.49      SEG1
ATOM   1020  N    PRO  69    4.131  -7.314  15.552  1.00  0.55      SEG1
ATOM   1021  CA   PRO  69    5.288  -7.686  14.697  1.00  0.54      SEG1
ATOM   1022  HA   PRO  69    6.116  -7.018  14.871  1.00  0.53      SEG1
ATOM   1023  CB   PRO  69    5.649  -9.089  15.170  1.00  0.60      SEG1
ATOM   1024  HB1  PRO  69    6.420  -9.043  15.922  1.00  0.63      SEG1
ATOM   1025  HB2  PRO  69    5.974  -9.691  14.333  1.00  0.60      SEG1
ATOM   1026  CG   PRO  69    4.393  -9.652  15.760  1.00  0.64      SEG1
ATOM   1027  HG1  PRO  69    4.631 -10.242  16.631  1.00  0.69      SEG1
ATOM   1028  HG2  PRO  69    3.889 -10.267  15.027  1.00  0.64      SEG1
ATOM   1029  CD   PRO  69    3.503  -8.498  16.160  1.00  0.62      SEG1
ATOM   1030  HD2  PRO  69    2.509  -8.648  15.769  1.00  0.62      SEG1
ATOM   1031  HD1  PRO  69    3.477  -8.395  17.234  1.00  0.67      SEG1
ATOM   1032  C    PRO  69    4.905  -7.692  13.206  1.00  0.51      SEG1
ATOM   1033  O    PRO  69    5.179  -8.639  12.494  1.00  0.71      SEG1
ATOM   1034  N    GLN  70    4.290  -6.636  12.729  1.00  0.39      SEG1
ATOM   1035  HN   GLN  70    4.095  -5.881  13.315  1.00  0.48      SEG1
ATOM   1036  CA   GLN  70    3.901  -6.556  11.289  1.00  0.34      SEG1
ATOM   1037  HA   GLN  70    4.557  -7.162  10.678  1.00  0.34      SEG1
ATOM   1038  CB   GLN  70    2.465  -7.086  11.214  1.00  0.37      SEG1
ATOM   1039  HB1  GLN  70    2.064  -6.894  10.230  1.00  0.35      SEG1
ATOM   1040  HB2  GLN  70    1.859  -6.583  11.953  1.00  0.40      SEG1
ATOM   1041  CG   GLN  70    2.446  -8.593  11.481  1.00  0.42      SEG1
ATOM   1042  HG1  GLN  70    2.834  -8.790  12.467  1.00  0.45      SEG1
ATOM   1043  HG2  GLN  70    3.054  -9.098  10.747  1.00  0.41      SEG1
ATOM   1044  CD   GLN  70    1.008  -9.109  11.399  1.00  0.47      SEG1
ATOM   1045  OE1  GLN  70    0.070  -8.372  11.633  1.00  0.63      SEG1
ATOM   1046  NE2  GLN  70    0.794 -10.353  11.070  1.00  0.47      SEG1
ATOM   1047  HE21 GLN  70    1.552 -10.946  10.880  1.00  0.53      SEG1
ATOM   1048  HE22 GLN  70   -0.122 -10.695  11.011  1.00  0.51      SEG1
ATOM   1049  C    GLN  70    3.944  -5.090  10.849  1.00  0.31      SEG1
ATOM   1050  O    GLN  70    3.883  -4.195  11.671  1.00  0.36      SEG1
ATOM   1051  N    LEU  71    4.042  -4.831   9.570  1.00  0.28      SEG1
ATOM   1052  HN   LEU  71    4.087  -5.567   8.921  1.00  0.31      SEG1
ATOM   1053  CA   LEU  71    4.081  -3.413   9.097  1.00  0.26      SEG1
ATOM   1054  HA   LEU  71    4.186  -2.741   9.933  1.00  0.25      SEG1
ATOM   1055  CB   LEU  71    5.316  -3.329   8.200  1.00  0.27      SEG1
ATOM   1056  HB1  LEU  71    5.213  -4.021   7.378  1.00  0.29      SEG1
ATOM   1057  HB2  LEU  71    6.196  -3.582   8.776  1.00  0.28      SEG1
ATOM   1058  CG   LEU  71    5.462  -1.908   7.650  1.00  0.27      SEG1
ATOM   1059  HG   LEU  71    4.550  -1.621   7.146  1.00  0.28      SEG1
ATOM   1060  CD1  LEU  71    5.737  -0.936   8.801  1.00  0.28      SEG1
ATOM   1061  HD11 LEU  71    4.801  -0.569   9.194  1.00  1.03      SEG1
ATOM   1062  HD12 LEU  71    6.325  -0.106   8.437  1.00  1.04      SEG1
ATOM   1063  HD13 LEU  71    6.280  -1.447   9.581  1.00  1.09      SEG1
ATOM   1064  CD2  LEU  71    6.628  -1.868   6.663  1.00  0.31      SEG1
ATOM   1065  HD21 LEU  71    6.253  -1.997   5.659  1.00  1.05      SEG1
```

FIG. 2

| | | | | | | | | | |
|---|---|---|---|---|---|---|---|---|---|
| ATOM | 1066 | HD22 | LEU | 71 | 7.320 | -2.662 | 6.394 | 1.00 | 1.05 | SEG1 |
| ATOM | 1067 | HD23 | LEU | 71 | 7.132 | -0.917 | 6.740 | 1.00 | 1.09 | SEG1 |
| ATOM | 1068 | C | LEU | 71 | 2.806 | -3.091 | 8.310 | 1.00 | 0.25 | SEG1 |
| ATOM | 1069 | O | LEU | 71 | 2.418 | -3.825 | 7.421 | 1.00 | 0.27 | SEG1 |
| ATOM | 1070 | N | ILE | 72 | 2.149 | -2.005 | 8.639 | 1.00 | 0.23 | SEG1 |
| ATOM | 1071 | HN | ILE | 72 | 2.478 | -1.433 | 9.362 | 1.00 | 0.23 | SEG1 |
| ATOM | 1072 | CA | ILE | 72 | 0.892 | -1.642 | 7.917 | 1.00 | 0.23 | SEG1 |
| ATOM | 1073 | HA | ILE | 72 | 0.559 | -2.464 | 7.305 | 1.00 | 0.25 | SEG1 |
| ATOM | 1074 | CB | ILE | 72 | -0.139 | -1.356 | 9.017 | 1.00 | 0.24 | SEG1 |
| ATOM | 1075 | HB | ILE | 72 | 0.210 | -0.540 | 9.631 | 1.00 | 0.24 | SEG1 |
| ATOM | 1076 | CG1 | ILE | 72 | -0.335 | -2.600 | 9.886 | 1.00 | 0.27 | SEG1 |
| ATOM | 1077 | HG11 | ILE | 72 | 0.624 | -2.961 | 10.222 | 1.00 | 0.27 | SEG1 |
| ATOM | 1078 | HG12 | ILE | 72 | -0.829 | -3.364 | 9.312 | 1.00 | 0.30 | SEG1 |
| ATOM | 1079 | CG2 | ILE | 72 | -1.481 | -0.977 | 8.384 | 1.00 | 0.26 | SEG1 |
| ATOM | 1080 | HG21 | ILE | 72 | -1.631 | -1.553 | 7.483 | 1.00 | 1.07 | SEG1 |
| ATOM | 1081 | HG22 | ILE | 72 | -1.481 | 0.076 | 8.143 | 1.00 | 1.08 | SEG1 |
| ATOM | 1082 | HG23 | ILE | 72 | -2.279 | -1.186 | 9.081 | 1.00 | 0.93 | SEG1 |
| ATOM | 1083 | CD1 | ILE | 72 | -1.194 | -2.239 | 11.097 | 1.00 | 0.30 | SEG1 |
| ATOM | 1084 | HD11 | ILE | 72 | -0.584 | -1.745 | 11.838 | 1.00 | 1.01 | SEG1 |
| ATOM | 1085 | HD12 | ILE | 72 | -1.617 | -3.139 | 11.519 | 1.00 | 1.05 | SEG1 |
| ATOM | 1086 | HD13 | ILE | 72 | -1.991 | -1.578 | 10.786 | 1.00 | 1.01 | SEG1 |
| ATOM | 1087 | C | ILE | 72 | 1.114 | -0.390 | 7.061 | 1.00 | 0.22 | SEG1 |
| ATOM | 1088 | O | ILE | 72 | 1.602 | 0.618 | 7.535 | 1.00 | 0.22 | SEG1 |
| ATOM | 1089 | N | VAL | 73 | 0.737 | -0.446 | 5.811 | 1.00 | 0.23 | SEG1 |
| ATOM | 1090 | HN | VAL | 73 | 0.333 | -1.269 | 5.462 | 1.00 | 0.24 | SEG1 |
| ATOM | 1091 | CA | VAL | 73 | 0.895 | 0.741 | 4.916 | 1.00 | 0.23 | SEG1 |
| ATOM | 1092 | HA | VAL | 73 | 1.357 | 1.557 | 5.450 | 1.00 | 0.24 | SEG1 |
| ATOM | 1093 | CB | VAL | 73 | 1.799 | 0.273 | 3.771 | 1.00 | 0.26 | SEG1 |
| ATOM | 1094 | HB | VAL | 73 | 1.328 | -0.551 | 3.255 | 1.00 | 1.09 | SEG1 |
| ATOM | 1095 | CG1 | VAL | 73 | 2.023 | 1.427 | 2.790 | 1.00 | 1.38 | SEG1 |
| ATOM | 1096 | HG11 | VAL | 73 | 2.971 | 1.295 | 2.290 | 1.00 | 1.97 | SEG1 |
| ATOM | 1097 | HG12 | VAL | 73 | 2.027 | 2.363 | 3.329 | 1.00 | 2.06 | SEG1 |
| ATOM | 1098 | HG13 | VAL | 73 | 1.229 | 1.436 | 2.059 | 1.00 | 1.87 | SEG1 |
| ATOM | 1099 | CG2 | VAL | 73 | 3.150 | -0.178 | 4.334 | 1.00 | 1.35 | SEG1 |
| ATOM | 1100 | HG21 | VAL | 73 | 3.022 | -1.098 | 4.885 | 1.00 | 1.90 | SEG1 |
| ATOM | 1101 | HG22 | VAL | 73 | 3.540 | 0.585 | 4.991 | 1.00 | 1.99 | SEG1 |
| ATOM | 1102 | HG23 | VAL | 73 | 3.842 | -0.340 | 3.521 | 1.00 | 1.95 | SEG1 |
| ATOM | 1103 | C | VAL | 73 | -0.483 | 1.152 | 4.386 | 1.00 | 0.22 | SEG1 |
| ATOM | 1104 | O | VAL | 73 | -1.230 | 0.325 | 3.896 | 1.00 | 0.23 | SEG1 |
| ATOM | 1105 | N | GLN | 74 | -0.833 | 2.412 | 4.485 | 1.00 | 0.22 | SEG1 |
| ATOM | 1106 | HN | GLN | 74 | -0.219 | 3.066 | 4.891 | 1.00 | 0.24 | SEG1 |
| ATOM | 1107 | CA | GLN | 74 | -2.175 | 2.849 | 3.989 | 1.00 | 0.22 | SEG1 |
| ATOM | 1108 | HA | GLN | 74 | -2.902 | 2.065 | 4.130 | 1.00 | 0.22 | SEG1 |
| ATOM | 1109 | CB | GLN | 74 | -2.544 | 4.062 | 4.843 | 1.00 | 0.25 | SEG1 |
| ATOM | 1110 | HB1 | GLN | 74 | -1.839 | 4.859 | 4.658 | 1.00 | 0.26 | SEG1 |
| ATOM | 1111 | HB2 | GLN | 74 | -2.516 | 3.793 | 5.888 | 1.00 | 0.26 | SEG1 |
| ATOM | 1112 | CG | GLN | 74 | -3.952 | 4.536 | 4.468 | 1.00 | 0.28 | SEG1 |
| ATOM | 1113 | HG1 | GLN | 74 | -4.634 | 3.699 | 4.510 | 1.00 | 0.28 | SEG1 |
| ATOM | 1114 | HG2 | GLN | 74 | -3.940 | 4.938 | 3.466 | 1.00 | 0.28 | SEG1 |
| ATOM | 1115 | CD | GLN | 74 | -4.419 | 5.618 | 5.447 | 1.00 | 0.35 | SEG1 |
| ATOM | 1116 | OE1 | GLN | 74 | -3.790 | 5.858 | 6.459 | 1.00 | 0.45 | SEG1 |
| ATOM | 1117 | NE2 | GLN | 74 | -5.513 | 6.281 | 5.189 | 1.00 | 0.49 | SEG1 |
| ATOM | 1118 | HE21 | GLN | 74 | -6.026 | 6.083 | 4.377 | 1.00 | 0.62 | SEG1 |
| ATOM | 1119 | HE22 | GLN | 74 | -5.823 | 6.976 | 5.806 | 1.00 | 0.55 | SEG1 |
| ATOM | 1120 | C | GLN | 74 | -2.091 | 3.243 | 2.513 | 1.00 | 0.23 | SEG1 |
| ATOM | 1121 | O | GLN | 74 | -1.270 | 4.053 | 2.130 | 1.00 | 0.26 | SEG1 |
| ATOM | 1122 | N | LEU | 75 | -2.936 | 2.678 | 1.683 | 1.00 | 0.22 | SEG1 |
| ATOM | 1123 | HN | LEU | 75 | -3.589 | 2.029 | 2.018 | 1.00 | 0.22 | SEG1 |
| ATOM | 1124 | CA | LEU | 75 | -2.905 | 3.023 | 0.229 | 1.00 | 0.24 | SEG1 |
| ATOM | 1125 | HA | LEU | 75 | -2.012 | 3.580 | -0.002 | 1.00 | 0.27 | SEG1 |
| ATOM | 1126 | CB | LEU | 75 | -2.884 | 1.681 | -0.516 | 1.00 | 0.24 | SEG1 |
| ATOM | 1127 | HB1 | LEU | 75 | -2.825 | 1.861 | -1.580 | 1.00 | 0.30 | SEG1 |
| ATOM | 1128 | HB2 | LEU | 75 | -3.792 | 1.138 | -0.296 | 1.00 | 0.28 | SEG1 |
| ATOM | 1129 | CG | LEU | 75 | -1.673 | 0.841 | -0.080 | 1.00 | 0.27 | SEG1 |
| ATOM | 1130 | HG | LEU | 75 | -1.797 | 0.552 | 0.954 | 1.00 | 0.62 | SEG1 |
| ATOM | 1131 | CD1 | LEU | 75 | -1.597 | -0.414 | -0.948 | 1.00 | 0.68 | SEG1 |
| ATOM | 1132 | HD11 | LEU | 75 | -1.949 | -0.184 | -1.943 | 1.00 | 1.14 | SEG1 |
| ATOM | 1133 | HD12 | LEU | 75 | -2.214 | -1.187 | -0.517 | 1.00 | 1.42 | SEG1 |
| ATOM | 1134 | HD13 | LEU | 75 | -0.574 | -0.755 | -0.998 | 1.00 | 1.28 | SEG1 |
| ATOM | 1135 | CD2 | LEU | 75 | -0.372 | 1.642 | -0.241 | 1.00 | 0.52 | SEG1 |
| ATOM | 1136 | HD21 | LEU | 75 | -0.490 | 2.365 | -1.035 | 1.00 | 1.19 | SEG1 |
| ATOM | 1137 | HD22 | LEU | 75 | 0.437 | 0.970 | -0.484 | 1.00 | 1.30 | SEG1 |
| ATOM | 1138 | HD23 | LEU | 75 | -0.147 | 2.154 | 0.684 | 1.00 | 1.09 | SEG1 |
| ATOM | 1139 | C | LEU | 75 | -4.152 | 3.830 | -0.150 | 1.00 | 0.25 | SEG1 |
| ATOM | 1140 | O | LEU | 75 | -5.206 | 3.672 | 0.436 | 1.00 | 0.26 | SEG1 |
| ATOM | 1141 | N | ARG | 76 | -4.034 | 4.693 | -1.127 | 1.00 | 0.29 | SEG1 |
| ATOM | 1142 | HN | ARG | 76 | -3.171 | 4.798 | -1.580 | 1.00 | 0.32 | SEG1 |

FIG. 2

| ATOM | 1143 | CA   | ARG | 76 | -5.203  | 5.520  | -1.557  | 1.00 | 0.32 | SEG1 |
|------|------|------|-----|----|---------|--------|---------|------|------|------|
| ATOM | 1144 | HA   | ARG | 76 | -6.060  | 5.318  | -0.935  | 1.00 | 0.32 | SEG1 |
| ATOM | 1145 | CB   | ARG | 76 | -4.748  | 6.970  | -1.372  | 1.00 | 0.37 | SEG1 |
| ATOM | 1146 | HB1  | ARG | 76 | -3.882  | 7.157  | -1.989  | 1.00 | 0.64 | SEG1 |
| ATOM | 1147 | HB2  | ARG | 76 | -4.494  | 7.138  | -0.335  | 1.00 | 0.71 | SEG1 |
| ATOM | 1148 | CG   | ARG | 76 | -5.876  | 7.920  | -1.781  | 1.00 | 0.83 | SEG1 |
| ATOM | 1149 | HG1  | ARG | 76 | -6.743  | 7.735  | -1.164  | 1.00 | 1.20 | SEG1 |
| ATOM | 1150 | HG2  | ARG | 76 | -6.130  | 7.750  | -2.917  | 1.00 | 1.15 | SEG1 |
| ATOM | 1151 | CD   | ARG | 76 | -5.423  | 9.370  | -1.597  | 1.00 | 0.84 | SEG1 |
| ATOM | 1152 | HD1  | ARG | 76 | -4.576  | 9.583  | -2.230  | 1.00 | 1.07 | SEG1 |
| ATOM | 1153 | HD2  | ARG | 76 | -5.177  | 9.558  | -0.560  | 1.00 | 1.13 | SEG1 |
| ATOM | 1154 | NE   | ARG | 76 | -6.597  | 10.197 | -2.018  | 1.00 | 1.21 | SEG1 |
| ATOM | 1155 | HE   | ARG | 76 | -7.484  | 9.782  | -2.069  | 1.00 | 1.76 | SEG1 |
| ATOM | 1156 | CZ   | ARG | 76 | -6.467  | 11.473 | -2.321  | 1.00 | 1.51 | SEG1 |
| ATOM | 1157 | NH1  | ARG | 76 | -7.523  | 12.150 | -2.683  | 1.00 | 2.15 | SEG1 |
| ATOM | 1158 | HH11 | ARG | 76 | -8.415  | 11.700 | -2.726  | 1.00 | 2.53 | SEG1 |
| ATOM | 1159 | HH12 | ARG | 76 | -7.440  | 13.119 | -2.917  | 1.00 | 2.50 | SEG1 |
| ATOM | 1160 | NH2  | ARG | 76 | -5.302  | 12.078 | -2.268  | 1.00 | 1.85 | SEG1 |
| ATOM | 1161 | HH21 | ARG | 76 | -4.483  | 11.576 | -1.994  | 1.00 | 1.91 | SEG1 |
| ATOM | 1162 | HH22 | ARG | 76 | -5.235  | 13.048 | -2.505  | 1.00 | 2.40 | SEG1 |
| ATOM | 1163 | C    | ARG | 76 | -5.526  | 5.241  | -3.029  | 1.00 | 0.32 | SEG1 |
| ATOM | 1164 | O    | ARG | 76 | -4.637  | 5.099  | -3.845  | 1.00 | 0.37 | SEG1 |
| ATOM | 1165 | N    | PHE | 77 | -6.790  | 5.165  | -3.376  | 1.00 | 0.32 | SEG1 |
| ATOM | 1166 | HN   | PHE | 77 | -7.492  | 5.289  | -2.701  | 1.00 | 0.34 | SEG1 |
| ATOM | 1167 | CA   | PHE | 77 | -7.160  | 4.895  | -4.800  | 1.00 | 0.34 | SEG1 |
| ATOM | 1168 | HA   | PHE | 77 | -6.278  | 4.660  | -5.377  | 1.00 | 0.34 | SEG1 |
| ATOM | 1169 | CB   | PHE | 77 | -8.093  | 3.683  | -4.759  | 1.00 | 0.35 | SEG1 |
| ATOM | 1170 | HB1  | PHE | 77 | -8.486  | 3.502  | -5.746  | 1.00 | 0.38 | SEG1 |
| ATOM | 1171 | HB2  | PHE | 77 | -8.908  | 3.872  | -4.076  | 1.00 | 0.38 | SEG1 |
| ATOM | 1172 | CG   | PHE | 77 | -7.324  | 2.467  | -4.306  | 1.00 | 0.34 | SEG1 |
| ATOM | 1173 | CD1  | PHE | 77 | -6.691  | 1.653  | -5.253  | 1.00 | 1.33 | SEG1 |
| ATOM | 1174 | HD1  | PHE | 77 | -6.750  | 1.900  | -6.303  | 1.00 | 2.22 | SEG1 |
| ATOM | 1175 | CD2  | PHE | 77 | -7.248  | 2.149  | -2.946  | 1.00 | 1.14 | SEG1 |
| ATOM | 1176 | HD2  | PHE | 77 | -7.737  | 2.778  | -2.216  | 1.00 | 2.04 | SEG1 |
| ATOM | 1177 | CE1  | PHE | 77 | -5.981  | 0.521  | -4.839  | 1.00 | 1.37 | SEG1 |
| ATOM | 1178 | HE1  | PHE | 77 | -5.493  | -0.107 | -5.570  | 1.00 | 2.28 | SEG1 |
| ATOM | 1179 | CE2  | PHE | 77 | -6.537  | 1.017  | -2.531  | 1.00 | 1.13 | SEG1 |
| ATOM | 1180 | HE2  | PHE | 77 | -6.478  | 0.772  | -1.480  | 1.00 | 2.01 | SEG1 |
| ATOM | 1181 | CZ   | PHE | 77 | -5.904  | 0.203  | -3.477  | 1.00 | 0.45 | SEG1 |
| ATOM | 1182 | HZ   | PHE | 77 | -5.356  | -0.671 | -3.157  | 1.00 | 0.53 | SEG1 |
| ATOM | 1183 | C    | PHE | 77 | -7.881  | 6.105  | -5.399  | 1.00 | 0.41 | SEG1 |
| ATOM | 1184 | O    | PHE | 77 | -8.479  | 6.894  | -4.693  | 1.00 | 0.45 | SEG1 |
| ATOM | 1185 | N    | CYS | 78 | -7.815  | 6.257  | -6.696  | 1.00 | 0.48 | SEG1 |
| ATOM | 1186 | HN   | CYS | 78 | -7.319  | 5.608  | -7.233  | 1.00 | 0.52 | SEG1 |
| ATOM | 1187 | CA   | CYS | 78 | -8.484  | 7.423  | -7.356  | 1.00 | 0.55 | SEG1 |
| ATOM | 1188 | HA   | CYS | 78 | -9.355  | 7.722  | -6.795  | 1.00 | 0.58 | SEG1 |
| ATOM | 1189 | CB   | CYS | 78 | -7.438  | 8.538  | -7.320  | 1.00 | 0.65 | SEG1 |
| ATOM | 1190 | HB1  | CYS | 78 | -6.626  | 8.291  | -7.989  | 1.00 | 0.80 | SEG1 |
| ATOM | 1191 | HB2  | CYS | 78 | -7.056  | 8.641  | -6.315  | 1.00 | 0.92 | SEG1 |
| ATOM | 1192 | SG   | CYS | 78 | -8.194  | 10.098 | -7.840  | 1.00 | 1.03 | SEG1 |
| ATOM | 1193 | HG   | CYS | 78 | -9.034  | 9.895  | -8.259  | 1.00 | 1.50 | SEG1 |
| ATOM | 1194 | C    | CYS | 78 | -8.869  | 7.094  | -8.807  | 1.00 | 0.53 | SEG1 |
| ATOM | 1195 | O    | CYS | 78 | -9.898  | 7.525  | -9.293  | 1.00 | 0.60 | SEG1 |
| ATOM | 1196 | N    | GLY | 79 | -8.051  | 6.342  | -9.499  | 1.00 | 0.50 | SEG1 |
| ATOM | 1197 | HN   | GLY | 79 | -7.232  | 6.011  | -9.087  | 1.00 | 0.52 | SEG1 |
| ATOM | 1198 | CA   | GLY | 79 | -8.359  | 5.990  | -10.917 | 1.00 | 0.52 | SEG1 |
| ATOM | 1199 | HA1  | GLY | 79 | -7.461  | 6.072  | -11.510 | 1.00 | 0.57 | SEG1 |
| ATOM | 1200 | HA2  | GLY | 79 | -9.106  | 6.671  | -11.300 | 1.00 | 0.57 | SEG1 |
| ATOM | 1201 | C    | GLY | 79 | -8.887  | 4.557  | -10.998 | 1.00 | 0.44 | SEG1 |
| ATOM | 1202 | O    | GLY | 79 | -8.355  | 3.654  | -10.379 | 1.00 | 0.39 | SEG1 |
| ATOM | 1203 | N    | ARG | 80 | -9.926  | 4.344  | -11.762 | 1.00 | 0.48 | SEG1 |
| ATOM | 1204 | HN   | ARG | 80 | -10.329 | 5.093  | -12.252 | 1.00 | 0.54 | SEG1 |
| ATOM | 1205 | CA   | ARG | 80 | -10.498 | 2.968  | -11.900 | 1.00 | 0.47 | SEG1 |
| ATOM | 1206 | HA   | ARG | 80 | -10.700 | 2.549  | -10.927 | 1.00 | 0.46 | SEG1 |
| ATOM | 1207 | CB   | ARG | 80 | -11.810 | 3.158  | -12.668 | 1.00 | 0.57 | SEG1 |
| ATOM | 1208 | HB1  | ARG | 80 | -11.602 | 3.592  | -13.634 | 1.00 | 1.05 | SEG1 |
| ATOM | 1209 | HB2  | ARG | 80 | -12.461 | 3.816  | -12.110 | 1.00 | 1.00 | SEG1 |
| ATOM | 1210 | CG   | ARG | 80 | -12.497 | 1.804  | -12.859 | 1.00 | 1.37 | SEG1 |
| ATOM | 1211 | HG1  | ARG | 80 | -12.708 | 1.367  | -11.894 | 1.00 | 1.87 | SEG1 |
| ATOM | 1212 | HG2  | ARG | 80 | -11.846 | 1.147  | -13.417 | 1.00 | 1.95 | SEG1 |
| ATOM | 1213 | CD   | ARG | 80 | -13.806 | 1.999  | -13.626 | 1.00 | 1.53 | SEG1 |
| ATOM | 1214 | HD1  | ARG | 80 | -13.604 | 2.294  | -14.644 | 1.00 | 1.92 | SEG1 |
| ATOM | 1215 | HD2  | ARG | 80 | -14.421 | 2.740  | -13.134 | 1.00 | 1.71 | SEG1 |
| ATOM | 1216 | NE   | ARG | 80 | -14.477 | 0.662  | -13.605 | 1.00 | 2.30 | SEG1 |
| ATOM | 1217 | HE   | ARG | 80 | -14.158 | -0.027 | -12.984 | 1.00 | 2.85 | SEG1 |
| ATOM | 1218 | CZ   | ARG | 80 | -15.495 | 0.392  | -14.397 | 1.00 | 2.84 | SEG1 |
| ATOM | 1219 | NH1  | ARG | 80 | -16.058 | -0.783 | -14.331 | 1.00 | 3.87 | SEG1 |

FIG. 2

| | | | | | | | | | |
|---|---|---|---|---|---|---|---|---|---|
| ATOM | 1220 | HH11 | ARG | 80 | -15.716 | -1.465 | -13.685 | 1.00 | 4.32 | SEG1 |
| ATOM | 1221 | HH12 | ARG | 80 | -16.832 | -1.001 | -14.926 | 1.00 | 4.40 | SEG1 |
| ATOM | 1222 | NH2 | ARG | 80 | -15.953 | 1.276 | -15.255 | 1.00 | 2.85 | SEG1 |
| ATOM | 1223 | HH21 | ARG | 80 | -15.533 | 2.181 | -15.325 | 1.00 | 2.56 | SEG1 |
| ATOM | 1224 | HH22 | ARG | 80 | -16.729 | 1.042 | -15.843 | 1.00 | 3.51 | SEG1 |
| ATOM | 1225 | C | ARG | 80 | -9.537 | 2.062 | -12.685 | 1.00 | 0.43 | SEG1 |
| ATOM | 1226 | O | ARG | 80 | -9.369 | 0.900 | -12.366 | 1.00 | 0.41 | SEG1 |
| ATOM | 1227 | N | GLN | 81 | -8.919 | 2.584 | -13.715 | 1.00 | 0.45 | SEG1 |
| ATOM | 1228 | HN | GLN | 81 | -9.082 | 3.521 | -13.954 | 1.00 | 0.50 | SEG1 |
| ATOM | 1229 | CA | GLN | 81 | -7.978 | 1.757 | -14.538 | 1.00 | 0.45 | SEG1 |
| ATOM | 1230 | HA | GLN | 81 | -8.518 | 0.952 | -15.012 | 1.00 | 0.47 | SEG1 |
| ATOM | 1231 | CB | GLN | 81 | -7.437 | 2.708 | -15.611 | 1.00 | 0.51 | SEG1 |
| ATOM | 1232 | HB1 | GLN | 81 | -6.520 | 2.310 | -16.019 | 1.00 | 0.53 | SEG1 |
| ATOM | 1233 | HB2 | GLN | 81 | -7.248 | 3.676 | -15.172 | 1.00 | 0.51 | SEG1 |
| ATOM | 1234 | CG | GLN | 81 | -8.474 | 2.949 | -16.729 | 1.00 | 0.57 | SEG1 |
| ATOM | 1235 | HG1 | GLN | 81 | -9.329 | 3.394 | -16.358 | 1.00 | 0.93 | SEG1 |
| ATOM | 1236 | HG2 | GLN | 81 | -8.787 | 1.867 | -17.054 | 1.00 | 1.00 | SEG1 |
| ATOM | 1237 | CD | GLN | 81 | -7.863 | 3.607 | -17.909 | 1.00 | 1.27 | SEG1 |
| ATOM | 1238 | OE1 | GLN | 81 | -6.983 | 4.425 | -17.732 | 1.00 | 1.91 | SEG1 |
| ATOM | 1239 | NE2 | GLN | 81 | -8.299 | 3.368 | -19.116 | 1.00 | 2.02 | SEG1 |
| ATOM | 1240 | HE21 | GLN | 81 | -9.010 | 2.708 | -19.259 | 1.00 | 2.34 | SEG1 |
| ATOM | 1241 | HE22 | GLN | 81 | -7.917 | 3.849 | -19.880 | 1.00 | 2.61 | SEG1 |
| ATOM | 1242 | C | GLN | 81 | -6.834 | 1.182 | -13.678 | 1.00 | 0.41 | SEG1 |
| ATOM | 1243 | O | GLN | 81 | -6.637 | -0.018 | -13.664 | 1.00 | 0.40 | SEG1 |
| ATOM | 1244 | N | PRO | 82 | -6.113 | 2.035 | -12.975 | 1.00 | 0.40 | SEG1 |
| ATOM | 1245 | CA | PRO | 82 | -5.002 | 1.541 | -12.119 | 1.00 | 0.39 | SEG1 |
| ATOM | 1246 | HA | PRO | 82 | -4.301 | 0.972 | -12.709 | 1.00 | 0.41 | SEG1 |
| ATOM | 1247 | CB | PRO | 82 | -4.332 | 2.818 | -11.614 | 1.00 | 0.42 | SEG1 |
| ATOM | 1248 | HB1 | PRO | 82 | -3.488 | 3.078 | -12.233 | 1.00 | 0.47 | SEG1 |
| ATOM | 1249 | HB2 | PRO | 82 | -4.023 | 2.698 | -10.584 | 1.00 | 0.42 | SEG1 |
| ATOM | 1250 | CG | PRO | 82 | -5.382 | 3.868 | -11.719 | 1.00 | 0.43 | SEG1 |
| ATOM | 1251 | HG1 | PRO | 82 | -4.921 | 4.825 | -11.895 | 1.00 | 0.47 | SEG1 |
| ATOM | 1252 | HG2 | PRO | 82 | -5.973 | 3.894 | -10.814 | 1.00 | 0.41 | SEG1 |
| ATOM | 1253 | CD | PRO | 82 | -6.244 | 3.499 | -12.896 | 1.00 | 0.44 | SEG1 |
| ATOM | 1254 | HD2 | PRO | 82 | -7.265 | 3.790 | -12.715 | 1.00 | 0.45 | SEG1 |
| ATOM | 1255 | HD1 | PRO | 82 | -5.868 | 3.956 | -13.798 | 1.00 | 0.48 | SEG1 |
| ATOM | 1256 | C | PRO | 82 | -5.539 | 0.688 | -10.964 | 1.00 | 0.35 | SEG1 |
| ATOM | 1257 | O | PRO | 82 | -4.823 | -0.122 | -10.404 | 1.00 | 0.38 | SEG1 |
| ATOM | 1258 | N | CYS | 83 | -6.793 | 0.847 | -10.614 | 1.00 | 0.31 | SEG1 |
| ATOM | 1259 | HN | CYS | 83 | -7.356 | 1.496 | -11.086 | 1.00 | 0.32 | SEG1 |
| ATOM | 1260 | CA | CYS | 83 | -7.370 | 0.024 | -9.507 | 1.00 | 0.30 | SEG1 |
| ATOM | 1261 | HA | CYS | 83 | -6.782 | 0.134 | -8.608 | 1.00 | 0.31 | SEG1 |
| ATOM | 1262 | CB | CYS | 83 | -8.783 | 0.568 | -9.282 | 1.00 | 0.34 | SEG1 |
| ATOM | 1263 | HB1 | CYS | 83 | -9.409 | 0.301 | -10.121 | 1.00 | 0.66 | SEG1 |
| ATOM | 1264 | HB2 | CYS | 83 | -8.745 | 1.643 | -9.188 | 1.00 | 0.77 | SEG1 |
| ATOM | 1265 | SG | CYS | 83 | -9.469 | -0.147 | -7.767 | 1.00 | 0.99 | SEG1 |
| ATOM | 1266 | HG | CYS | 83 | -10.419 | -0.228 | -7.881 | 1.00 | 1.67 | SEG1 |
| ATOM | 1267 | C | CYS | 83 | -7.422 | -1.444 | -9.938 | 1.00 | 0.29 | SEG1 |
| ATOM | 1268 | O | CYS | 83 | -7.020 | -2.331 | -9.209 | 1.00 | 0.28 | SEG1 |
| ATOM | 1269 | N | GLY | 84 | -7.908 | -1.700 | -11.129 | 1.00 | 0.30 | SEG1 |
| ATOM | 1270 | HN | GLY | 84 | -8.216 | -0.962 | -11.696 | 1.00 | 0.32 | SEG1 |
| ATOM | 1271 | CA | GLY | 84 | -7.984 | -3.104 | -11.635 | 1.00 | 0.31 | SEG1 |
| ATOM | 1272 | HA1 | GLY | 84 | -8.409 | -3.109 | -12.627 | 1.00 | 0.33 | SEG1 |
| ATOM | 1273 | HA2 | GLY | 84 | -8.606 | -3.691 | -10.973 | 1.00 | 0.31 | SEG1 |
| ATOM | 1274 | C | GLY | 84 | -6.579 | -3.706 | -11.684 | 1.00 | 0.30 | SEG1 |
| ATOM | 1275 | O | GLY | 84 | -6.374 | -4.861 | -11.358 | 1.00 | 0.30 | SEG1 |
| ATOM | 1276 | N | ARG | 85 | -5.609 | -2.928 | -12.090 | 1.00 | 0.31 | SEG1 |
| ATOM | 1277 | HN | ARG | 85 | -5.804 | -2.002 | -12.347 | 1.00 | 0.32 | SEG1 |
| ATOM | 1278 | CA | ARG | 85 | -4.209 | -3.444 | -12.158 | 1.00 | 0.32 | SEG1 |
| ATOM | 1279 | HA | ARG | 85 | -4.174 | -4.358 | -12.731 | 1.00 | 0.34 | SEG1 |
| ATOM | 1280 | CB | ARG | 85 | -3.404 | -2.351 | -12.866 | 1.00 | 0.35 | SEG1 |
| ATOM | 1281 | HB1 | ARG | 85 | -2.351 | -2.578 | -12.797 | 1.00 | 0.70 | SEG1 |
| ATOM | 1282 | HB2 | ARG | 85 | -3.600 | -1.398 | -12.396 | 1.00 | 0.87 | SEG1 |
| ATOM | 1283 | CG | ARG | 85 | -3.814 | -2.286 | -14.339 | 1.00 | 0.87 | SEG1 |
| ATOM | 1284 | HG1 | ARG | 85 | -4.866 | -2.058 | -14.411 | 1.00 | 1.41 | SEG1 |
| ATOM | 1285 | HG2 | ARG | 85 | -3.618 | -3.239 | -14.810 | 1.00 | 1.40 | SEG1 |
| ATOM | 1286 | CD | ARG | 85 | -3.009 | -1.193 | -15.048 | 1.00 | 1.12 | SEG1 |
| ATOM | 1287 | HD1 | ARG | 85 | -1.958 | -1.439 | -15.049 | 1.00 | 1.59 | SEG1 |
| ATOM | 1288 | HD2 | ARG | 85 | -3.174 | -0.237 | -14.569 | 1.00 | 1.64 | SEG1 |
| ATOM | 1289 | NE | ARG | 85 | -3.530 | -1.173 | -16.451 | 1.00 | 1.63 | SEG1 |
| ATOM | 1290 | HE | ARG | 85 | -4.064 | -1.928 | -16.777 | 1.00 | 2.16 | SEG1 |
| ATOM | 1291 | CZ | ARG | 85 | -3.292 | -0.158 | -17.259 | 1.00 | 2.06 | SEG1 |
| ATOM | 1292 | NH1 | ARG | 85 | -3.780 | -0.179 | -18.469 | 1.00 | 2.88 | SEG1 |
| ATOM | 1293 | HH11 | ARG | 85 | -4.327 | -0.959 | -18.773 | 1.00 | 3.33 | SEG1 |
| ATOM | 1294 | HH12 | ARG | 85 | -3.608 | 0.584 | -19.091 | 1.00 | 3.28 | SEG1 |
| ATOM | 1295 | NH2 | ARG | 85 | -2.572 | 0.973 | -16.877 | 1.00 | 2.26 | SEG1 |
| ATOM | 1296 | HH21 | ARG | 85 | -2.186 | 0.908 | -15.956 | 1.00 | 2.26 | SEG1 |

FIG. 2

| ATOM | 1297 | HH22 | ARG | 85 | -2.411 | .628 | -17.513 | 1.00 | 2.81 | SEG1 |
| --- | --- | --- | --- | --- | --- | --- | --- | --- | --- | --- |
| ATOM | 1298 | C | ARG | 85 | -3.672 | -1.680 | -10.741 | 1.00 | 0.29 | SEG1 |
| ATOM | 1299 | O | ARG | 85 | -2.915 | -1.600 | -10.501 | 1.00 | 0.29 | SEG1 |
| ATOM | 1300 | N | PHE | 86 | -4.055 | -1.643 | -9.308 | 1.00 | 0.27 | SEG1 |
| ATOM | 1301 | HN | PHE | 86 | -4.661 | -2.106 | -10.038 | 1.00 | 0.28 | SEG1 |
| ATOM | 1302 | CA | PHE | 86 | -3.563 | -2.999 | -8.400 | 1.00 | 0.26 | SEG1 |
| ATOM | 1303 | HA | PHE | 86 | -2.493 | -2.880 | -8.360 | 1.00 | 0.28 | SEG1 |
| ATOM | 1304 | CB | PHE | 86 | -4.245 | -1.859 | -7.626 | 1.00 | 0.27 | SEG1 |
| ATOM | 1305 | HB1 | PHE | 86 | -5.317 | -1.950 | -7.727 | 1.00 | 0.28 | SEG1 |
| ATOM | 1306 | HB2 | PHE | 86 | -3.927 | -0.911 | -8.034 | 1.00 | 0.28 | SEG1 |
| ATOM | 1307 | CG | PHE | 86 | -3.875 | -1.918 | -6.159 | 1.00 | 0.25 | SEG1 |
| ATOM | 1308 | CD1 | PHE | 86 | -4.611 | -2.735 | -5.292 | 1.00 | 1.23 | SEG1 |
| ATOM | 1309 | HD1 | PHE | 86 | -5.430 | -3.327 | -5.675 | 1.00 | 2.16 | SEG1 |
| ATOM | 1310 | CD2 | PHE | 86 | -2.813 | -1.149 | -5.663 | 1.00 | 1.24 | SEG1 |
| ATOM | 1311 | HD2 | PHE | 86 | -2.242 | -0.517 | -6.330 | 1.00 | 2.17 | SEG1 |
| ATOM | 1312 | CE1 | PHE | 86 | -4.286 | -2.788 | -3.932 | 1.00 | 1.23 | SEG1 |
| ATOM | 1313 | HE1 | PHE | 86 | -4.855 | -3.420 | -3.265 | 1.00 | 2.16 | SEG1 |
| ATOM | 1314 | CE2 | PHE | 86 | -2.488 | -1.203 | -4.300 | 1.00 | 1.24 | SEG1 |
| ATOM | 1315 | HE2 | PHE | 86 | -1.671 | -0.609 | -3.914 | 1.00 | 2.17 | SEG1 |
| ATOM | 1316 | CZ | PHE | 86 | -3.225 | -2.022 | -3.435 | 1.00 | 0.26 | SEG1 |
| ATOM | 1317 | HZ | PHE | 86 | -2.974 | -2.063 | -2.385 | 1.00 | 0.28 | SEG1 |
| ATOM | 1318 | C | PHE | 86 | -3.973 | -4.364 | -7.822 | 1.00 | 0.25 | SEG1 |
| ATOM | 1319 | O | PHE | 86 | -3.152 | -5.079 | -7.278 | 1.00 | 0.27 | SEG1 |
| ATOM | 1320 | N | LEU | 87 | -5.229 | -4.726 | -7.926 | 1.00 | 0.25 | SEG1 |
| ATOM | 1321 | HN | LEU | 87 | -5.875 | -4.131 | -8.358 | 1.00 | 0.25 | SEG1 |
| ATOM | 1322 | CA | LEU | 87 | -5.673 | -6.045 | -7.366 | 1.00 | 0.25 | SEG1 |
| ATOM | 1323 | HA | LEU | 87 | -5.279 | -6.160 | -6.369 | 1.00 | 0.26 | SEG1 |
| ATOM | 1324 | CB | LEU | 87 | -7.210 | -5.988 | -7.297 | 1.00 | 0.26 | SEG1 |
| ATOM | 1325 | HB1 | LEU | 87 | -7.506 | -5.182 | -6.641 | 1.00 | 0.27 | SEG1 |
| ATOM | 1326 | HB2 | LEU | 87 | -7.580 | -6.922 | -6.899 | 1.00 | 0.28 | SEG1 |
| ATOM | 1327 | CG | LEU | 87 | -7.818 | -5.758 | -8.685 | 1.00 | 0.28 | SEG1 |
| ATOM | 1328 | HG | LEU | 87 | -7.108 | -5.253 | -9.314 | 1.00 | 0.28 | SEG1 |
| ATOM | 1329 | CD1 | LEU | 87 | -8.194 | -7.100 | -9.314 | 1.00 | 0.32 | SEG1 |
| ATOM | 1330 | HD11 | LEU | 87 | -9.169 | -7.402 | -8.963 | 1.00 | 1.08 | SEG1 |
| ATOM | 1331 | HD12 | LEU | 87 | -7.465 | -7.846 | -9.036 | 1.00 | 1.03 | SEG1 |
| ATOM | 1332 | HD13 | LEU | 87 | -8.215 | -7.000 | -10.389 | 1.00 | 1.05 | SEG1 |
| ATOM | 1333 | CD2 | LEU | 87 | -9.078 | -4.897 | -8.551 | 1.00 | 0.30 | SEG1 |
| ATOM | 1334 | HD21 | LEU | 87 | -8.798 | -3.887 | -8.293 | 1.00 | 1.03 | SEG1 |
| ATOM | 1335 | HD22 | LEU | 87 | -9.711 | -5.304 | -7.778 | 1.00 | 1.02 | SEG1 |
| ATOM | 1336 | HD23 | LEU | 87 | -9.612 | -4.893 | -9.490 | 1.00 | 1.08 | SEG1 |
| ATOM | 1337 | C | LEU | 87 | -5.191 | -7.214 | -8.241 | 1.00 | 0.25 | SEG1 |
| ATOM | 1338 | O | LEU | 87 | -4.769 | -8.240 | -7.732 | 1.00 | 0.27 | SEG1 |
| ATOM | 1339 | N | ARG | 88 | -5.240 | -7.072 | -9.544 | 1.00 | 0.26 | SEG1 |
| ATOM | 1340 | HN | ARG | 88 | -5.573 | -6.239 | -9.934 | 1.00 | 0.26 | SEG1 |
| ATOM | 1341 | CA | ARG | 88 | -4.777 | -8.183 | -10.434 | 1.00 | 0.27 | SEG1 |
| ATOM | 1342 | HA | ARG | 88 | -5.320 | -9.088 | -10.219 | 1.00 | 0.28 | SEG1 |
| ATOM | 1343 | CB | ARG | 88 | -5.079 | -7.716 | -11.860 | 1.00 | 0.29 | SEG1 |
| ATOM | 1344 | HB1 | ARG | 88 | -4.464 | -6.862 | -12.099 | 1.00 | 0.79 | SEG1 |
| ATOM | 1345 | HB2 | ARG | 88 | -6.122 | -7.443 | -11.936 | 1.00 | 0.79 | SEG1 |
| ATOM | 1346 | CG | ARG | 88 | -4.774 | -8.850 | -12.841 | 1.00 | 1.08 | SEG1 |
| ATOM | 1347 | HG1 | ARG | 88 | -5.390 | -9.705 | -12.604 | 1.00 | 1.57 | SEG1 |
| ATOM | 1348 | HG2 | ARG | 88 | -3.732 | -9.123 | -12.761 | 1.00 | 1.56 | SEG1 |
| ATOM | 1349 | CD | ARG | 88 | -5.075 | -8.391 | -14.270 | 1.00 | 1.09 | SEG1 |
| ATOM | 1350 | HD1 | ARG | 88 | -4.345 | -7.665 | -14.593 | 1.00 | 1.19 | SEG1 |
| ATOM | 1351 | HD2 | ARG | 88 | -6.072 | -7.977 | -14.328 | 1.00 | 1.44 | SEG1 |
| ATOM | 1352 | NE | ARG | 88 | -4.972 | -9.628 | -15.109 | 1.00 | 2.05 | SEG1 |
| ATOM | 1353 | HE | ARG | 88 | -4.837 | -10.496 | -14.674 | 1.00 | 2.70 | SEG1 |
| ATOM | 1354 | CZ | ARG | 88 | -5.058 | -9.575 | -16.423 | 1.00 | 2.54 | SEG1 |
| ATOM | 1355 | NH1 | ARG | 88 | -4.962 | -10.680 | -17.111 | 1.00 | 3.60 | SEG1 |
| ATOM | 1356 | HH11 | ARG | 88 | -4.825 | -11.552 | -16.640 | 1.00 | 4.10 | SEG1 |
| ATOM | 1357 | HH12 | ARG | 88 | -5.026 | -10.655 | -18.108 | 1.00 | 4.07 | SEG1 |
| ATOM | 1358 | NH2 | ARG | 88 | -5.240 | -8.439 | -17.056 | 1.00 | 2.48 | SEG1 |
| ATOM | 1359 | HH21 | ARG | 88 | -5.318 | -7.583 | -16.548 | 1.00 | 2.17 | SEG1 |
| ATOM | 1360 | HH22 | ARG | 88 | -5.301 | -8.432 | -18.054 | 1.00 | 3.15 | SEG1 |
| ATOM | 1361 | C | ARG | 88 | -3.278 | -8.413 | -10.244 | 1.00 | 0.28 | SEG1 |
| ATOM | 1362 | O | ARG | 88 | -2.823 | -9.536 | -10.140 | 1.00 | 0.30 | SEG1 |
| ATOM | 1363 | N | ALA | 89 | -2.514 | -7.354 | -10.182 | 1.00 | 0.29 | SEG1 |
| ATOM | 1364 | HN | ALA | 89 | -2.912 | -6.461 | -10.258 | 1.00 | 0.29 | SEG1 |
| ATOM | 1365 | CA | ALA | 89 | -1.041 | -7.500 | -9.980 | 1.00 | 0.31 | SEG1 |
| ATOM | 1366 | HA | ALA | 89 | -0.633 | -8.202 | -10.690 | 1.00 | 0.33 | SEG1 |
| ATOM | 1367 | CB | ALA | 89 | -0.457 | -6.110 | -10.226 | 1.00 | 0.35 | SEG1 |
| ATOM | 1368 | HB1 | ALA | 89 | 0.588 | -6.201 | -10.481 | 1.00 | 1.03 | SEG1 |
| ATOM | 1369 | HB2 | ALA | 89 | -0.560 | -5.513 | -9.331 | 1.00 | 1.04 | SEG1 |
| ATOM | 1370 | HB3 | ALA | 89 | -0.986 | -5.635 | -11.039 | 1.00 | 1.09 | SEG1 |
| ATOM | 1371 | C | ALA | 89 | -0.750 | -7.957 | -8.549 | 1.00 | 0.30 | SEG1 |
| ATOM | 1372 | O | ALA | 89 | 0.284 | -8.537 | -8.273 | 1.00 | 0.31 | SEG1 |
| ATOM | 1373 | N | TYR | 90 | -1.651 | -7.689 | -7.634 | 1.00 | 0.30 | SEG1 |

FIG. 2 (19 of 35)

| ATOM | 1374 | HN | TYR | 90 | -2.471 | -7.213 | -7.781 | 1.00 | 0.30 | SEG1 |
|------|------|------|-----|----|--------|--------|--------|------|------|------|
| ATOM | 1375 | CA | TYR | 90 | -1.427 | -8.096 | -6.114 | 1.00 | 0.31 | SEG1 |
| ATOM | 1376 | HA | TYR | 90 | -0.554 | -7.599 | -5.819 | 1.00 | 0.34 | SEG1 |
| ATOM | 1377 | CB | TYR | 90 | -2.676 | -7.634 | -5.058 | 1.00 | 0.33 | SEG1 |
| ATOM | 1378 | HB1 | TYR | 90 | -3.544 | -8.133 | -5.859 | 1.00 | 0.41 | SEG1 |
| ATOM | 1379 | HB2 | TYR | 90 | -2.790 | -6.565 | -5.572 | 1.00 | 0.34 | SEG1 |
| ATOM | 1380 | CG | TYR | 90 | -2.535 | -7.972 | -3.994 | 1.00 | 0.44 | SEG1 |
| ATOM | 1381 | CD1 | TYR | 90 | -1.951 | -7.050 | -3.117 | 1.00 | 1.36 | SEG1 |
| ATOM | 1382 | HD1 | TYR | 90 | -1.603 | -6.097 | -3.488 | 1.00 | 2.21 | SEG1 |
| ATOM | 1383 | CD2 | TYR | 90 | -2.984 | -9.207 | -3.514 | 1.00 | 1.28 | SEG1 |
| ATOM | 1384 | HD2 | TYR | 90 | -3.436 | -9.918 | -4.191 | 1.00 | 2.18 | SEG1 |
| ATOM | 1385 | CE1 | TYR | 90 | -1.818 | -7.363 | -1.761 | 1.00 | 1.49 | SEG1 |
| ATOM | 1386 | HE1 | TYR | 90 | -1.367 | -6.653 | -1.084 | 1.00 | 2.40 | SEG1 |
| ATOM | 1387 | CE2 | TYR | 90 | -2.850 | -9.520 | -2.158 | 1.00 | 1.32 | SEG1 |
| ATOM | 1388 | HE2 | TYR | 90 | -3.192 | -10.475 | -1.788 | 1.00 | 2.17 | SEG1 |
| ATOM | 1389 | CZ | TYR | 90 | -2.266 | -8.597 | -1.282 | 1.00 | 0.83 | SEG1 |
| ATOM | 1390 | OH | TYR | 90 | -2.139 | -8.902 | 0.055 | 1.00 | 1.04 | SEG1 |
| ATOM | 1391 | HH | TYR | 90 | -1.881 | -9.824 | 0.126 | 1.00 | 1.37 | SEG1 |
| ATOM | 1392 | C | TYR | 90 | -1.263 | -9.617 | -6.114 | 1.00 | 0.31 | SEG1 |
| ATOM | 1393 | O | TYR | 90 | -0.349 | -10.104 | -5.475 | 1.00 | 0.33 | SEG1 |
| ATOM | 1394 | N | ARG | 91 | -2.138 | -10.373 | -6.741 | 1.00 | 0.31 | SEG1 |
| ATOM | 1395 | HN | ARG | 91 | -2.868 | -9.958 | -7.252 | 1.00 | 0.32 | SEG1 |
| ATOM | 1396 | CA | ARG | 91 | -2.015 | -11.866 | -6.674 | 1.00 | 0.34 | SEG1 |
| ATOM | 1397 | HA | ARG | 91 | -2.099 | -12.206 | -5.657 | 1.00 | 0.38 | SEG1 |
| ATOM | 1398 | CB | ARG | 91 | -3.175 | -12.418 | -7.509 | 1.00 | 0.39 | SEG1 |
| ATOM | 1399 | HB1 | ARG | 91 | -3.089 | -12.066 | -8.525 | 1.00 | 0.91 | SEG1 |
| ATOM | 1400 | HB2 | ARG | 91 | -4.111 | -12.081 | -7.087 | 1.00 | 0.81 | SEG1 |
| ATOM | 1401 | CG | ARG | 91 | -3.130 | -13.950 | -7.493 | 1.00 | 1.12 | SEG1 |
| ATOM | 1402 | HG1 | ARG | 91 | -3.219 | -14.301 | -6.475 | 1.00 | 1.64 | SEG1 |
| ATOM | 1403 | HG2 | ARG | 91 | -2.190 | -14.285 | -7.908 | 1.00 | 1.67 | SEG1 |
| ATOM | 1404 | CD | ARG | 91 | -4.287 | -14.512 | -8.325 | 1.00 | 1.16 | SEG1 |
| ATOM | 1405 | HD1 | ARG | 91 | -4.191 | -14.204 | -9.355 | 1.00 | 1.49 | SEG1 |
| ATOM | 1406 | HD2 | ARG | 91 | -5.235 | -14.185 | -7.920 | 1.00 | 1.29 | SEG1 |
| ATOM | 1407 | NE | ARG | 91 | -4.160 | -16.002 | -8.224 | 1.00 | 2.06 | SEG1 |
| ATOM | 1408 | HE | ARG | 91 | -3.413 | -16.391 | -7.720 | 1.00 | 2.61 | SEG1 |
| ATOM | 1409 | CZ | ARG | 91 | -5.036 | -16.806 | -8.796 | 1.00 | 2.58 | SEG1 |
| ATOM | 1410 | NH1 | ARG | 91 | -4.891 | -18.097 | -8.674 | 1.00 | 3.56 | SEG1 |
| ATOM | 1411 | HH11 | ARG | 91 | -4.124 | -18.466 | -8.151 | 1.00 | 4.00 | SEG1 |
| ATOM | 1412 | HH12 | ARG | 91 | -5.549 | -18.716 | -9.103 | 1.00 | 4.01 | SEG1 |
| ATOM | 1413 | NH2 | ARG | 91 | -6.050 | -16.338 | -9.487 | 1.00 | 2.55 | SEG1 |
| ATOM | 1414 | HH21 | ARG | 91 | -6.180 | -15.354 | -9.595 | 1.00 | 2.26 | SEG1 |
| ATOM | 1415 | HH22 | ARG | 91 | -6.698 | -16.973 | -9.908 | 1.00 | 3.16 | SEG1 |
| ATOM | 1416 | C | ARG | 91 | -0.668 | -12.297 | -7.258 | 1.00 | 0.32 | SEG1 |
| ATOM | 1417 | O | ARG | 91 | -0.004 | -13.170 | -6.730 | 1.00 | 0.33 | SEG1 |
| ATOM | 1418 | N | GLU | 92 | -0.251 | -11.671 | -8.328 | 1.00 | 0.30 | SEG1 |
| ATOM | 1419 | HN | GLU | 92 | -0.802 | -10.957 | -8.721 | 1.00 | 0.31 | SEG1 |
| ATOM | 1420 | CA | GLU | 92 | 1.070 | -12.021 | -8.933 | 1.00 | 0.32 | SEG1 |
| ATOM | 1421 | HA | GLU | 92 | 1.090 | -13.061 | -9.213 | 1.00 | 0.34 | SEG1 |
| ATOM | 1422 | CB | GLU | 92 | 1.201 | -11.139 | -10.177 | 1.00 | 0.38 | SEG1 |
| ATOM | 1423 | HB1 | GLU | 92 | 2.205 | -11.212 | -10.567 | 1.00 | 0.42 | SEG1 |
| ATOM | 1424 | HB2 | GLU | 92 | 0.989 | -10.112 | -9.914 | 1.00 | 0.38 | SEG1 |
| ATOM | 1425 | CG | GLU | 92 | 0.206 | -11.612 | -11.243 | 1.00 | 0.42 | SEG1 |
| ATOM | 1426 | HG1 | GLU | 92 | -0.798 | -11.545 | -10.851 | 1.00 | 0.56 | SEG1 |
| ATOM | 1427 | HG2 | GLU | 92 | 0.421 | -12.638 | -11.500 | 1.00 | 0.63 | SEG1 |
| ATOM | 1428 | CD | GLU | 92 | 0.317 | -10.739 | -12.503 | 1.00 | 0.87 | SEG1 |
| ATOM | 1429 | OE1 | GLU | 92 | -0.277 | -11.108 | -13.503 | 1.00 | 1.48 | SEG1 |
| ATOM | 1430 | OE2 | GLU | 92 | 0.983 | -9.715 | -12.449 | 1.00 | 1.58 | SEG1 |
| ATOM | 1431 | C | GLU | 92 | 2.187 | -11.716 | -7.931 | 1.00 | 0.33 | SEG1 |
| ATOM | 1432 | O | GLU | 92 | 3.138 | -12.462 | -7.796 | 1.00 | 0.35 | SEG1 |
| ATOM | 1433 | N | GLY | 93 | 2.068 | -10.618 | -7.229 | 1.00 | 0.35 | SEG1 |
| ATOM | 1434 | HN | GLY | 93 | 1.289 | -10.040 | -7.363 | 1.00 | 0.35 | SEG1 |
| ATOM | 1435 | CA | GLY | 93 | 3.107 | -10.238 | -6.226 | 1.00 | 0.40 | SEG1 |
| ATOM | 1436 | HA1 | GLY | 93 | 2.839 | -9.297 | -5.770 | 1.00 | 0.45 | SEG1 |
| ATOM | 1437 | HA2 | GLY | 93 | 4.062 | -10.137 | -6.722 | 1.00 | 0.43 | SEG1 |
| ATOM | 1438 | C | GLY | 93 | 3.208 | -11.314 | -5.141 | 1.00 | 0.37 | SEG1 |
| ATOM | 1439 | O | GLY | 93 | 4.291 | -11.691 | -4.733 | 1.00 | 0.39 | SEG1 |
| ATOM | 1440 | N | ALA | 94 | 2.089 | -11.816 | -4.671 | 1.00 | 0.37 | SEG1 |
| ATOM | 1441 | HN | ALA | 94 | 1.229 | -11.498 | -5.017 | 1.00 | 0.37 | SEG1 |
| ATOM | 1442 | CA | ALA | 94 | 2.125 | -12.877 | -3.611 | 1.00 | 0.41 | SEG1 |
| ATOM | 1443 | HA | ALA | 94 | 2.591 | -12.499 | -2.714 | 1.00 | 0.46 | SEG1 |
| ATOM | 1444 | CB | ALA | 94 | 0.661 | -13.227 | -3.336 | 1.00 | 0.47 | SEG1 |
| ATOM | 1445 | HB1 | ALA | 94 | 0.613 | -14.032 | -2.617 | 1.00 | 1.13 | SEG1 |
| ATOM | 1446 | HB2 | ALA | 94 | 0.186 | -13.536 | -4.255 | 1.00 | 1.16 | SEG1 |
| ATOM | 1447 | HB3 | ALA | 94 | 0.152 | -12.361 | -2.941 | 1.00 | 1.08 | SEG1 |
| ATOM | 1448 | C | ALA | 94 | 2.882 | -14.100 | -4.134 | 1.00 | 0.36 | SEG1 |
| ATOM | 1449 | O | ALA | 94 | 3.673 | -14.708 | -3.435 | 1.00 | 0.39 | SEG1 |
| ATOM | 1450 | N | LEU | 95 | 2.654 | -14.446 | -5.373 | 1.00 | 0.32 | SEG1 |

FIG. 2

| | | | | | | | | | |
|---|---|---|---|---|---|---|---|---|---|
| ATOM | 1451 | HN | LEU | 95 | 2.023 | -13.923 | -5.914 | 1.00 | 0.31 | SEG1 |
| ATOM | 1452 | CA | LEU | 95 | 3.364 | -15.612 | -5.978 | 1.00 | 0.34 | SEG1 |
| ATOM | 1453 | HA | LEU | 95 | 3.152 | -16.510 | -5.423 | 1.00 | 0.39 | SEG1 |
| ATOM | 1454 | CB | LEU | 95 | 2.804 | -15.722 | -7.395 | 1.00 | 0.35 | SEG1 |
| ATOM | 1455 | HB1 | LEU | 95 | 3.329 | -16.496 | -7.933 | 1.00 | 0.40 | SEG1 |
| ATOM | 1456 | HB2 | LEU | 95 | 2.926 | -14.777 | -7.907 | 1.00 | 0.33 | SEG1 |
| ATOM | 1457 | CG | LEU | 95 | 1.318 | -16.077 | -7.312 | 1.00 | 0.39 | SEG1 |
| ATOM | 1458 | HG | LEU | 95 | 0.885 | -15.596 | -6.446 | 1.00 | 0.39 | SEG1 |
| ATOM | 1459 | CD1 | LEU | 95 | 0.591 | -15.596 | -8.574 | 1.00 | 0.39 | SEG1 |
| ATOM | 1460 | HD11 | LEU | 95 | -0.039 | -16.386 | -8.955 | 1.00 | 1.13 | SEG1 |
| ATOM | 1461 | HD12 | LEU | 95 | 1.314 | -15.318 | -9.326 | 1.00 | 1.12 | SEG1 |
| ATOM | 1462 | HD13 | LEU | 95 | -0.020 | -14.738 | -8.328 | 1.00 | 1.04 | SEG1 |
| ATOM | 1463 | CD2 | LEU | 95 | 1.170 | -17.596 | -7.176 | 1.00 | 0.55 | SEG1 |
| ATOM | 1464 | HD21 | LEU | 95 | 1.790 | -18.086 | -7.912 | 1.00 | 1.27 | SEG1 |
| ATOM | 1465 | HD22 | LEU | 95 | 0.137 | -17.873 | -7.332 | 1.00 | 1.12 | SEG1 |
| ATOM | 1466 | HD23 | LEU | 95 | 1.478 | -17.901 | -6.196 | 1.00 | 1.12 | SEG1 |
| ATOM | 1467 | C | LEU | 95 | 4.867 | -15.330 | -5.990 | 1.00 | 0.33 | SEG1 |
| ATOM | 1468 | O | LEU | 95 | 5.677 | -16.193 | -5.713 | 1.00 | 0.38 | SEG1 |
| ATOM | 1469 | N | ARG | 96 | 5.235 | -14.111 | -6.293 | 1.00 | 0.32 | SEG1 |
| ATOM | 1470 | HN | ARG | 96 | 4.553 | -13.438 | -6.497 | 1.00 | 0.31 | SEG1 |
| ATOM | 1471 | CA | ARG | 96 | 6.681 | -13.734 | -6.311 | 1.00 | 0.39 | SEG1 |
| ATOM | 1472 | HA | ARG | 96 | 7.212 | -14.310 | -7.051 | 1.00 | 0.43 | SEG1 |
| ATOM | 1473 | CB | ARG | 96 | 6.715 | -12.247 | -6.679 | 1.00 | 0.46 | SEG1 |
| ATOM | 1474 | HB1 | ARG | 96 | 6.207 | -11.676 | -5.917 | 1.00 | 1.01 | SEG1 |
| ATOM | 1475 | HB2 | ARG | 96 | 6.223 | -12.099 | -7.629 | 1.00 | 0.84 | SEG1 |
| ATOM | 1476 | CG | ARG | 96 | 8.170 | -11.783 | -6.775 | 1.00 | 1.29 | SEG1 |
| ATOM | 1477 | HG1 | ARG | 96 | 8.680 | -12.356 | -7.535 | 1.00 | 1.76 | SEG1 |
| ATOM | 1478 | HG2 | ARG | 96 | 8.657 | -11.934 | -5.824 | 1.00 | 2.06 | SEG1 |
| ATOM | 1479 | CD | ARG | 96 | 8.216 | -10.299 | -7.143 | 1.00 | 1.52 | SEG1 |
| ATOM | 1480 | HD1 | ARG | 96 | 9.233 | -9.938 | -7.124 | 1.00 | 1.96 | SEG1 |
| ATOM | 1481 | HD2 | ARG | 96 | 7.599 | -9.726 | -6.465 | 1.00 | 1.67 | SEG1 |
| ATOM | 1482 | NE | ARG | 96 | 7.673 | -10.230 | -8.534 | 1.00 | 2.44 | SEG1 |
| ATOM | 1483 | HE | ARG | 96 | 6.756 | -9.913 | -8.674 | 1.00 | 2.95 | SEG1 |
| ATOM | 1484 | CZ | ARG | 96 | 8.400 | -10.582 | -9.576 | 1.00 | 3.12 | SEG1 |
| ATOM | 1485 | NH1 | ARG | 96 | 7.881 | -10.497 | -10.771 | 1.00 | 4.14 | SEG1 |
| ATOM | 1486 | HH11 | ARG | 96 | 6.944 | -10.169 | -10.887 | 1.00 | 4.47 | SEG1 |
| ATOM | 1487 | HH12 | ARG | 96 | 8.421 | -10.762 | -11.571 | 1.00 | 4.77 | SEG1 |
| ATOM | 1488 | NH2 | ARG | 96 | 9.632 | -11.019 | -9.440 | 1.00 | 3.27 | SEG1 |
| ATOM | 1489 | HH21 | ARG | 96 | 10.046 | -11.094 | -8.534 | 1.00 | 2.90 | SEG1 |
| ATOM | 1490 | HH22 | ARG | 96 | 10.159 | -11.279 | -10.249 | 1.00 | 4.07 | SEG1 |
| ATOM | 1491 | C | ARG | 96 | 7.289 | -13.955 | -4.922 | 1.00 | 0.40 | SEG1 |
| ATOM | 1492 | O | ARG | 96 | 8.434 | -14.341 | -4.790 | 1.00 | 0.46 | SEG1 |
| ATOM | 1493 | N | ALA | 97 | 6.523 | -13.714 | -3.884 | 1.00 | 0.40 | SEG1 |
| ATOM | 1494 | HN | ALA | 97 | 5.603 | -13.403 | -4.021 | 1.00 | 0.38 | SEG1 |
| ATOM | 1495 | CA | ALA | 97 | 7.048 | -13.910 | -2.495 | 1.00 | 0.46 | SEG1 |
| ATOM | 1496 | HA | ALA | 97 | 7.867 | -13.237 | -2.302 | 1.00 | 0.51 | SEG1 |
| ATOM | 1497 | CB | ALA | 97 | 5.874 | -13.592 | -1.568 | 1.00 | 0.52 | SEG1 |
| ATOM | 1498 | HB1 | ALA | 97 | 6.194 | -13.678 | -0.541 | 1.00 | 1.09 | SEG1 |
| ATOM | 1499 | HB2 | ALA | 97 | 5.071 | -14.289 | -1.752 | 1.00 | 1.19 | SEG1 |
| ATOM | 1500 | HB3 | ALA | 97 | 5.530 | -12.586 | -1.755 | 1.00 | 1.12 | SEG1 |
| ATOM | 1501 | C | ALA | 97 | 7.491 | -15.361 | -2.312 | 1.00 | 0.46 | SEG1 |
| ATOM | 1502 | O | ALA | 97 | 8.513 | -15.635 | -1.711 | 1.00 | 0.50 | SEG1 |
| ATOM | 1503 | N | ALA | 98 | 6.739 | -16.288 | -2.845 | 1.00 | 0.46 | SEG1 |
| ATOM | 1504 | HN | ALA | 98 | 5.928 | -16.034 | -3.337 | 1.00 | 0.43 | SEG1 |
| ATOM | 1505 | CA | ALA | 98 | 7.128 | -17.728 | -2.728 | 1.00 | 0.51 | SEG1 |
| ATOM | 1506 | HA | ALA | 98 | 7.177 | -18.023 | -1.692 | 1.00 | 0.56 | SEG1 |
| ATOM | 1507 | CB | ALA | 98 | 6.029 | -18.510 | -3.452 | 1.00 | 0.55 | SEG1 |
| ATOM | 1508 | HB1 | ALA | 98 | 6.167 | -18.422 | -4.520 | 1.00 | 1.20 | SEG1 |
| ATOM | 1509 | HB2 | ALA | 98 | 5.064 | -18.110 | -3.180 | 1.00 | 1.10 | SEG1 |
| ATOM | 1510 | HB3 | ALA | 98 | 6.081 | -19.551 | -3.167 | 1.00 | 1.06 | SEG1 |
| ATOM | 1511 | C | ALA | 98 | 8.484 | -17.938 | -3.411 | 1.00 | 0.52 | SEG1 |
| ATOM | 1512 | O | ALA | 98 | 9.337 | -18.652 | -2.922 | 1.00 | 0.57 | SEG1 |
| ATOM | 1513 | N | LEU | 99 | 8.684 | -17.296 | -4.536 | 1.00 | 0.50 | SEG1 |
| ATOM | 1514 | HN | LEU | 99 | 7.978 | -16.717 | -4.895 | 1.00 | 0.47 | SEG1 |
| ATOM | 1515 | CA | LEU | 99 | 9.983 | -17.421 | -5.265 | 1.00 | 0.55 | SEG1 |
| ATOM | 1516 | HA | LEU | 99 | 10.159 | -18.448 | -5.546 | 1.00 | 0.60 | SEG1 |
| ATOM | 1517 | CB | LEU | 99 | 9.840 | -16.549 | -6.517 | 1.00 | 0.57 | SEG1 |
| ATOM | 1518 | HB1 | LEU | 99 | 9.677 | -15.524 | -6.223 | 1.00 | 0.54 | SEG1 |
| ATOM | 1519 | HB2 | LEU | 99 | 9.001 | -16.895 | -7.101 | 1.00 | 0.58 | SEG1 |
| ATOM | 1520 | CG | LEU | 99 | 11.118 | -16.638 | -7.356 | 1.00 | 0.66 | SEG1 |
| ATOM | 1521 | HG | LEU | 99 | 11.953 | -16.885 | -6.717 | 1.00 | 0.67 | SEG1 |
| ATOM | 1522 | CD1 | LEU | 99 | 10.956 | -17.726 | -8.419 | 1.00 | 0.73 | SEG1 |
| ATOM | 1523 | HD11 | LEU | 99 | 11.553 | -17.476 | -9.284 | 1.00 | 1.16 | SEG1 |
| ATOM | 1524 | HD12 | LEU | 99 | 9.917 | -17.796 | -8.708 | 1.00 | 1.14 | SEG1 |
| ATOM | 1525 | HD13 | LEU | 99 | 11.282 | -18.673 | -8.017 | 1.00 | 1.42 | SEG1 |
| ATOM | 1526 | CD2 | LEU | 99 | 11.376 | -15.291 | -8.036 | 1.00 | 0.70 | SEG1 |
| ATOM | 1527 | HD21 | LEU | 99 | 12.164 | -15.401 | -8.767 | 1.00 | 1.16 | SEG1 |

FIG. 2

| | | | | | | | | | |
|---|---|---|---|---|---|---|---|---|---|
| ATOM | 1528 | HD22 | LEU | 99 | 11.673 | -14.565 | -7.293 | 1.00 | 1.32 | SEG1 |
| ATOM | 1529 | HD23 | LEU | 99 | 10.474 | -14.956 | -8.527 | 1.00 | 1.12 | SEG1 |
| ATOM | 1530 | C | LEU | 99 | 11.121 | -16.906 | -4.379 | 1.00 | 0.54 | SEG1 |
| ATOM | 1531 | O | LEU | 99 | 12.204 | -17.457 | -4.362 | 1.00 | 0.59 | SEG1 |
| ATOM | 1532 | N | GLN | 100 | 10.881 | -15.843 | -3.648 | 1.00 | 0.50 | SEG1 |
| ATOM | 1533 | HN | GLN | 100 | 9.999 | -15.415 | -3.686 | 1.00 | 0.47 | SEG1 |
| ATOM | 1534 | CA | GLN | 100 | 11.949 | -15.274 | -2.767 | 1.00 | 0.52 | SEG1 |
| ATOM | 1535 | HA | GLN | 100 | 12.788 | -14.937 | -3.355 | 1.00 | 0.57 | SEG1 |
| ATOM | 1536 | CB | GLN | 100 | 11.300 | -14.084 | -2.049 | 1.00 | 0.51 | SEG1 |
| ATOM | 1537 | HB1 | GLN | 100 | 11.958 | -13.734 | -1.269 | 1.00 | 0.55 | SEG1 |
| ATOM | 1538 | HB2 | GLN | 100 | 10.363 | -14.397 | -1.614 | 1.00 | 0.47 | SEG1 |
| ATOM | 1539 | CG | GLN | 100 | 11.043 | -12.947 | -3.042 | 1.00 | 0.54 | SEG1 |
| ATOM | 1540 | HG1 | GLN | 100 | 10.565 | -12.126 | -2.529 | 1.00 | 1.00 | SEG1 |
| ATOM | 1541 | HG2 | GLN | 100 | 10.400 | -13.301 | -3.835 | 1.00 | 1.14 | SEG1 |
| ATOM | 1542 | CD | GLN | 100 | 12.369 | -12.468 | -3.637 | 1.00 | 1.30 | SEG1 |
| ATOM | 1543 | OE1 | GLN | 100 | 13.079 | -11.692 | -3.030 | 1.00 | 1.83 | SEG1 |
| ATOM | 1544 | NE2 | GLN | 100 | 12.739 | -12.919 | -4.803 | 1.00 | 2.26 | SEG1 |
| ATOM | 1545 | HE21 | GLN | 100 | 12.169 | -13.557 | -5.282 | 1.00 | 2.51 | SEG1 |
| ATOM | 1546 | HE22 | GLN | 100 | 13.583 | -12.620 | -5.199 | 1.00 | 2.99 | SEG1 |
| ATOM | 1547 | C | GLN | 100 | 12.393 | -16.320 | -1.747 | 1.00 | 0.53 | SEG1 |
| ATOM | 1548 | O | GLN | 100 | 13.567 | -16.453 | -1.455 | 1.00 | 0.57 | SEG1 |
| ATOM | 1549 | N | ARG | 101 | 11.464 | -17.068 | -1.213 | 1.00 | 0.51 | SEG1 |
| ATOM | 1550 | HN | ARG | 101 | 10.526 | -16.941 | -1.475 | 1.00 | 0.50 | SEG1 |
| ATOM | 1551 | CA | ARG | 101 | 11.832 | -18.118 | -0.213 | 1.00 | 0.55 | SEG1 |
| ATOM | 1552 | HA | ARG | 101 | 12.287 | -17.668 | 0.656 | 1.00 | 0.54 | SEG1 |
| ATOM | 1553 | CB | ARG | 101 | 10.511 | -18.789 | 0.173 | 1.00 | 0.58 | SEG1 |
| ATOM | 1554 | HB1 | ARG | 101 | 10.061 | -19.231 | -0.702 | 1.00 | 0.62 | SEG1 |
| ATOM | 1555 | HB2 | ARG | 101 | 9.841 | -18.048 | 0.587 | 1.00 | 0.56 | SEG1 |
| ATOM | 1556 | CG | ARG | 101 | 10.772 | -19.878 | 1.216 | 1.00 | 0.64 | SEG1 |
| ATOM | 1557 | HG1 | ARG | 101 | 11.219 | -19.436 | 2.094 | 1.00 | 0.62 | SEG1 |
| ATOM | 1558 | HG2 | ARG | 101 | 11.444 | -20.617 | 0.803 | 1.00 | 0.67 | SEG1 |
| ATOM | 1559 | CD | ARG | 101 | 9.450 | -20.545 | 1.601 | 1.00 | 0.70 | SEG1 |
| ATOM | 1560 | HD1 | ARG | 101 | 9.077 | -21.143 | 0.784 | 1.00 | 1.17 | SEG1 |
| ATOM | 1561 | HD2 | ARG | 101 | 8.724 | -19.797 | 1.885 | 1.00 | 1.21 | SEG1 |
| ATOM | 1562 | NE | ARG | 101 | 9.785 | -21.423 | 2.766 | 1.00 | 1.42 | SEG1 |
| ATOM | 1563 | HE | ARG | 101 | 10.714 | -21.706 | 2.902 | 1.00 | 1.98 | SEG1 |
| ATOM | 1564 | CZ | ARG | 101 | 8.861 | -21.815 | 3.621 | 1.00 | 1.81 | SEG1 |
| ATOM | 1565 | NH1 | ARG | 101 | 9.209 | -22.561 | 4.633 | 1.00 | 2.84 | SEG1 |
| ATOM | 1566 | HH11 | ARG | 101 | 10.165 | -22.827 | 4.753 | 1.00 | 3.38 | SEG1 |
| ATOM | 1567 | HH12 | ARG | 101 | 8.519 | -22.866 | 5.290 | 1.00 | 3.17 | SEG1 |
| ATOM | 1568 | NH2 | ARG | 101 | 7.599 | -21.479 | 3.475 | 1.00 | 1.50 | SEG1 |
| ATOM | 1569 | HH21 | ARG | 101 | 7.310 | -20.915 | 2.704 | 1.00 | 1.32 | SEG1 |
| ATOM | 1570 | HH22 | ARG | 101 | 6.923 | -21.791 | 4.143 | 1.00 | 1.89 | SEG1 |
| ATOM | 1571 | C | ARG | 101 | 12.794 | -19.130 | -0.855 | 1.00 | 0.63 | SEG1 |
| ATOM | 1572 | O | ARG | 101 | 13.839 | -19.433 | -0.312 | 1.00 | 0.66 | SEG1 |
| ATOM | 1573 | N | SER | 102 | 12.450 | -19.639 | -2.014 | 1.00 | 0.67 | SEG1 |
| ATOM | 1574 | HN | SER | 102 | 11.606 | -19.368 | -2.433 | 1.00 | 0.65 | SEG1 |
| ATOM | 1575 | CA | SER | 102 | 13.350 | -20.619 | -2.703 | 1.00 | 0.76 | SEG1 |
| ATOM | 1576 | HA | SER | 102 | 13.558 | -21.458 | -2.058 | 1.00 | 0.81 | SEG1 |
| ATOM | 1577 | CB | SER | 102 | 12.571 | -21.083 | -3.935 | 1.00 | 0.80 | SEG1 |
| ATOM | 1578 | HB1 | SER | 102 | 13.223 | -21.667 | -4.571 | 1.00 | 1.16 | SEG1 |
| ATOM | 1579 | HB2 | SER | 102 | 12.213 | -20.227 | -4.482 | 1.00 | 1.31 | SEG1 |
| ATOM | 1580 | OG | SER | 102 | 11.462 | -21.870 | -3.520 | 1.00 | 1.48 | SEG1 |
| ATOM | 1581 | HG | SER | 102 | 10.933 | -21.343 | -2.918 | 1.00 | 1.81 | SEG1 |
| ATOM | 1582 | C | SER | 102 | 14.652 | -19.929 | -3.125 | 1.00 | 0.78 | SEG1 |
| ATOM | 1583 | O | SER | 102 | 15.727 | -20.489 | -3.014 | 1.00 | 0.85 | SEG1 |
| ATOM | 1584 | N | LEU | 103 | 14.556 | -18.713 | -3.599 | 1.00 | 0.74 | SEG1 |
| ATOM | 1585 | HN | LEU | 103 | 13.676 | -18.287 | -3.667 | 1.00 | 0.69 | SEG1 |
| ATOM | 1586 | CA | LEU | 103 | 15.779 | -17.963 | -4.027 | 1.00 | 0.79 | SEG1 |
| ATOM | 1587 | HA | LEU | 103 | 16.362 | -18.562 | -4.710 | 1.00 | 0.86 | SEG1 |
| ATOM | 1588 | CB | LEU | 103 | 15.262 | -16.712 | -4.742 | 1.00 | 0.77 | SEG1 |
| ATOM | 1589 | HB1 | LEU | 103 | 15.875 | -15.865 | -4.473 | 1.00 | 0.80 | SEG1 |
| ATOM | 1590 | HB2 | LEU | 103 | 14.240 | -16.525 | -4.448 | 1.00 | 0.71 | SEG1 |
| ATOM | 1591 | CG | LEU | 103 | 15.328 | -16.923 | -6.257 | 1.00 | 0.83 | SEG1 |
| ATOM | 1592 | HG | LEU | 103 | 16.340 | -17.176 | -6.532 | 1.00 | 0.90 | SEG1 |
| ATOM | 1593 | CD1 | LEU | 103 | 14.391 | -18.063 | -6.668 | 1.00 | 0.82 | SEG1 |
| ATOM | 1594 | HD11 | LEU | 103 | 13.618 | -18.179 | -5.926 | 1.00 | 1.34 | SEG1 |
| ATOM | 1595 | HD12 | LEU | 103 | 14.955 | -18.980 | -6.746 | 1.00 | 1.29 | SEG1 |
| ATOM | 1596 | HD13 | LEU | 103 | 13.943 | -17.836 | -7.623 | 1.00 | 1.23 | SEG1 |
| ATOM | 1597 | CD2 | LEU | 103 | 14.909 | -15.636 | -6.970 | 1.00 | 0.84 | SEG1 |
| ATOM | 1598 | HD21 | LEU | 103 | 14.934 | -15.792 | -8.038 | 1.00 | 1.29 | SEG1 |
| ATOM | 1599 | HD22 | LEU | 103 | 15.591 | -14.841 | -6.706 | 1.00 | 1.31 | SEG1 |
| ATOM | 1600 | HD23 | LEU | 103 | 13.907 | -15.366 | -6.668 | 1.00 | 1.28 | SEG1 |
| ATOM | 1601 | C | LEU | 103 | 16.623 | -17.580 | -2.813 | 1.00 | 0.79 | SEG1 |
| ATOM | 1602 | O | LEU | 103 | 17.820 | -17.386 | -2.917 | 1.00 | 0.87 | SEG1 |
| ATOM | 1603 | N | ALA | 104 | 16.009 | -17.465 | -1.662 | 1.00 | 0.72 | SEG1 |
| ATOM | 1604 | HN | ALA | 104 | 15.044 | -17.623 | -1.611 | 1.00 | 0.67 | SEG1 |

FIG. 2

| | | | | | | | | | | |
|---|---|---|---|---|---|---|---|---|---|---|
| ATOM | 1605 | CA | ALA | 104 | 16.772 | -17.039 | -0.428 | 1.00 | 0.74 | SEG1 |
| ATOM | 1606 | HA | ALA | 104 | 17.126 | -16.074 | -0.497 | 1.00 | 0.76 | SEG1 |
| ATOM | 1607 | CB | ALA | 104 | 15.765 | -17.216 | 0.717 | 1.00 | 0.68 | SEG1 |
| ATOM | 1608 | HB1 | ALA | 104 | 15.952 | -16.444 | 1.449 | 1.00 | 1.17 | SEG1 |
| ATOM | 1609 | HB2 | ALA | 104 | 15.869 | -18.195 | 1.192 | 1.00 | 1.16 | SEG1 |
| ATOM | 1610 | HB3 | ALA | 104 | 14.763 | -17.109 | 0.328 | 1.00 | 1.31 | SEG1 |
| ATOM | 1611 | C | ALA | 104 | 17.944 | -18.055 | -0.218 | 1.00 | 0.83 | SEG1 |
| ATOM | 1612 | O | ALA | 104 | 19.073 | -17.641 | -0.042 | 1.00 | 0.90 | SEG1 |
| ATOM | 1613 | N | ALA | 105 | 17.681 | -19.335 | -0.254 | 1.00 | 0.85 | SEG1 |
| ATOM | 1614 | HN | ALA | 105 | 16.762 | -19.639 | -0.411 | 1.00 | 0.81 | SEG1 |
| ATOM | 1615 | CA | ALA | 105 | 18.779 | -20.333 | -0.073 | 1.00 | 0.95 | SEG1 |
| ATOM | 1616 | HA | ALA | 105 | 19.323 | -20.137 | 0.838 | 1.00 | 0.95 | SEG1 |
| ATOM | 1617 | CB | ALA | 105 | 18.082 | -21.692 | 0.012 | 1.00 | 0.98 | SEG1 |
| ATOM | 1618 | HB1 | ALA | 105 | 17.663 | -21.821 | 0.999 | 1.00 | 1.41 | SEG1 |
| ATOM | 1619 | HB2 | ALA | 105 | 18.797 | -22.477 | -0.181 | 1.00 | 1.44 | SEG1 |
| ATOM | 1620 | HB3 | ALA | 105 | 17.291 | -21.738 | -0.723 | 1.00 | 1.39 | SEG1 |
| ATOM | 1621 | C | ALA | 105 | 19.719 | -20.287 | -1.280 | 1.00 | 1.03 | SEG1 |
| ATOM | 1622 | O | ALA | 105 | 20.914 | -20.482 | -1.160 | 1.00 | 1.11 | SEG1 |
| ATOM | 1623 | N | ALA | 106 | 19.177 | -20.032 | -2.443 | 1.00 | 1.04 | SEG1 |
| ATOM | 1624 | HN | ALA | 106 | 18.210 | -19.882 | -2.503 | 1.00 | 0.98 | SEG1 |
| ATOM | 1625 | CA | ALA | 106 | 20.019 | -19.972 | -3.678 | 1.00 | 1.14 | SEG1 |
| ATOM | 1626 | HA | ALA | 106 | 20.573 | -20.889 | -3.798 | 1.00 | 1.22 | SEG1 |
| ATOM | 1627 | CB | ALA | 106 | 19.027 | -19.812 | -4.833 | 1.00 | 1.13 | SEG1 |
| ATOM | 1628 | HB1 | ALA | 106 | 19.566 | -19.771 | -5.767 | 1.00 | 1.31 | SEG1 |
| ATOM | 1629 | HB2 | ALA | 106 | 18.466 | -18.898 | -4.701 | 1.00 | 1.58 | SEG1 |
| ATOM | 1630 | HB3 | ALA | 106 | 18.349 | -20.652 | -4.844 | 1.00 | 1.56 | SEG1 |
| ATOM | 1631 | C | ALA | 106 | 20.974 | -18.775 | -3.628 | 1.00 | 1.18 | SEG1 |
| ATOM | 1632 | O | ALA | 106 | 22.086 | -18.844 | -4.117 | 1.00 | 1.29 | SEG1 |
| ATOM | 1633 | N | LEU | 107 | 20.546 | -17.677 | -3.054 | 1.00 | 1.11 | SEG1 |
| ATOM | 1634 | HN | LEU | 107 | 19.644 | -17.642 | -2.674 | 1.00 | 1.02 | SEG1 |
| ATOM | 1635 | CA | LEU | 107 | 21.426 | -16.473 | -2.990 | 1.00 | 1.18 | SEG1 |
| ATOM | 1636 | HA | LEU | 107 | 22.066 | -16.433 | -3.857 | 1.00 | 1.27 | SEG1 |
| ATOM | 1637 | CB | LEU | 107 | 20.463 | -15.285 | -3.003 | 1.00 | 1.12 | SEG1 |
| ATOM | 1638 | HB1 | LEU | 107 | 21.007 | -14.376 | -2.794 | 1.00 | 1.19 | SEG1 |
| ATOM | 1639 | HB2 | LEU | 107 | 19.701 | -15.431 | -2.251 | 1.00 | 1.05 | SEG1 |
| ATOM | 1640 | CG | LEU | 107 | 19.808 | -15.180 | -4.382 | 1.00 | 1.12 | SEG1 |
| ATOM | 1641 | HG | LEU | 107 | 19.415 | -16.145 | -4.666 | 1.00 | 1.14 | SEG1 |
| ATOM | 1642 | CD1 | LEU | 107 | 18.669 | -14.161 | -4.334 | 1.00 | 1.21 | SEG1 |
| ATOM | 1643 | HD11 | LEU | 107 | 18.997 | -13.278 | -3.806 | 1.00 | 1.78 | SEG1 |
| ATOM | 1644 | HD12 | LEU | 107 | 17.821 | -14.592 | -3.822 | 1.00 | 1.60 | SEG1 |
| ATOM | 1645 | HD13 | LEU | 107 | 18.383 | -13.893 | -5.341 | 1.00 | 1.41 | SEG1 |
| ATOM | 1646 | CD2 | LEU | 107 | 20.851 | -14.730 | -5.407 | 1.00 | 1.24 | SEG1 |
| ATOM | 1647 | HD21 | LEU | 107 | 21.517 | -14.011 | -4.953 | 1.00 | 1.62 | SEG1 |
| ATOM | 1648 | HD22 | LEU | 107 | 20.353 | -14.277 | -6.252 | 1.00 | 1.68 | SEG1 |
| ATOM | 1649 | HD23 | LEU | 107 | 21.419 | -15.585 | -5.742 | 1.00 | 1.59 | SEG1 |
| ATOM | 1650 | C | LEU | 107 | 22.270 | -16.490 | -1.708 | 1.00 | 1.21 | SEG1 |
| ATOM | 1651 | O | LEU | 107 | 23.433 | -16.849 | -1.734 | 1.00 | 1.31 | SEG1 |
| ATOM | 1652 | N | ALA | 108 | 21.701 | -16.107 | -0.589 | 1.00 | 1.13 | SEG1 |
| ATOM | 1653 | HN | ALA | 108 | 20.762 | -15.822 | -0.590 | 1.00 | 1.05 | SEG1 |
| ATOM | 1654 | CA | ALA | 108 | 22.483 | -16.105 | 0.688 | 1.00 | 1.17 | SEG1 |
| ATOM | 1655 | HA | ALA | 108 | 23.036 | -17.024 | 0.790 | 1.00 | 1.21 | SEG1 |
| ATOM | 1656 | CB | ALA | 108 | 23.449 | -14.927 | 0.561 | 1.00 | 1.29 | SEG1 |
| ATOM | 1657 | HB1 | ALA | 108 | 24.163 | -14.958 | 1.371 | 1.00 | 1.64 | SEG1 |
| ATOM | 1658 | HB2 | ALA | 108 | 22.896 | -14.001 | 0.603 | 1.00 | 1.68 | SEG1 |
| ATOM | 1659 | HB3 | ALA | 108 | 23.972 | -14.991 | -0.382 | 1.00 | 1.65 | SEG1 |
| ATOM | 1660 | C | ALA | 108 | 21.556 | -15.907 | 1.891 | 1.00 | 1.08 | SEG1 |
| ATOM | 1661 | O | ALA | 108 | 21.911 | -15.258 | 2.857 | 1.00 | 1.13 | SEG1 |
| ATOM | 1662 | N | GLN | 109 | 20.372 | -16.458 | 1.836 | 1.00 | 0.97 | SEG1 |
| ATOM | 1663 | HN | GLN | 109 | 20.112 | -16.973 | 1.044 | 1.00 | 0.95 | SEG1 |
| ATOM | 1664 | CA | GLN | 109 | 19.413 | -16.303 | 2.971 | 1.00 | 0.90 | SEG1 |
| ATOM | 1665 | HA | GLN | 109 | 19.905 | -15.884 | 3.833 | 1.00 | 0.96 | SEG1 |
| ATOM | 1666 | CB | GLN | 109 | 18.352 | -15.334 | 2.447 | 1.00 | 0.85 | SEG1 |
| ATOM | 1667 | HB1 | GLN | 109 | 17.531 | -15.286 | 3.146 | 1.00 | 0.80 | SEG1 |
| ATOM | 1668 | HB2 | GLN | 109 | 17.990 | -15.680 | 1.489 | 1.00 | 0.82 | SEG1 |
| ATOM | 1669 | CG | GLN | 109 | 18.965 | -13.942 | 2.289 | 1.00 | 0.98 | SEG1 |
| ATOM | 1670 | HG1 | GLN | 109 | 19.887 | -14.017 | 1.734 | 1.00 | 1.16 | SEG1 |
| ATOM | 1671 | HG2 | GLN | 109 | 19.165 | -13.527 | 3.265 | 1.00 | 1.25 | SEG1 |
| ATOM | 1672 | CD | GLN | 109 | 17.994 | -13.028 | 1.537 | 1.00 | 1.42 | SEG1 |
| ATOM | 1673 | OE1 | GLN | 109 | 17.061 | -13.490 | 0.910 | 1.00 | 1.91 | SEG1 |
| ATOM | 1674 | NE2 | GLN | 109 | 18.183 | -11.738 | 1.565 | 1.00 | 1.74 | SEG1 |
| ATOM | 1675 | HE21 | GLN | 109 | 18.940 | -11.366 | 2.064 | 1.00 | 1.72 | SEG1 |
| ATOM | 1676 | HE22 | GLN | 109 | 17.569 | -11.142 | 1.087 | 1.00 | 2.24 | SEG1 |
| ATOM | 1677 | C | GLN | 109 | 18.775 | -17.652 | 3.311 | 1.00 | 0.85 | SEG1 |
| ATOM | 1678 | O | GLN | 109 | 18.443 | -18.423 | 2.432 | 1.00 | 0.83 | SEG1 |
| ATOM | 1679 | N | HIS | 110 | 18.587 | -17.941 | 4.576 | 1.00 | 0.87 | SEG1 |
| ATOM | 1680 | HN | HIS | 110 | 18.852 | -17.302 | 5.270 | 1.00 | 0.92 | SEG1 |
| ATOM | 1681 | CA | HIS | 110 | 17.951 | -19.240 | 4.950 | 1.00 | 0.89 | SEG1 |

FIG. 2

| | | | | | | | | | |
|---|---|---|---|---|---|---|---|---|---|
| ATOM | 1682 | HA | HIS | 110 | 18.501 | -20.367 | 4.529 | 1.00 | 0.94 | SEG1 |
| ATOM | 1683 | CB | HIS | 110 | 17.997 | -19.298 | 6.479 | 1.00 | 0.95 | SEG1 |
| ATOM | 1684 | HB1 | HIS | 110 | 17.393 | -20.124 | 6.825 | 1.00 | 1.35 | SEG1 |
| ATOM | 1685 | HB2 | HIS | 110 | 17.611 | -18.375 | 6.685 | 1.00 | 1.16 | SEG1 |
| ATOM | 1686 | CG | HIS | 110 | 19.416 | -19.492 | 6.934 | 1.00 | 1.24 | SEG1 |
| ATOM | 1687 | ND1 | HIS | 110 | 20.255 | -18.426 | 7.216 | 1.00 | 2.20 | SEG1 |
| ATOM | 1688 | HD1 | HIS | 110 | 20.025 | -17.476 | 7.152 | 1.00 | 2.77 | SEG1 |
| ATOM | 1689 | CD2 | HIS | 110 | 20.157 | -20.624 | 7.162 | 1.00 | 1.69 | SEG1 |
| ATOM | 1690 | HD2 | HIS | 110 | 19.802 | -21.636 | 7.334 | 1.00 | 2.16 | SEG1 |
| ATOM | 1691 | CE1 | HIS | 110 | 21.442 | -18.934 | 7.595 | 1.00 | 2.66 | SEG1 |
| ATOM | 1692 | HE1 | HIS | 110 | 22.295 | -18.335 | 7.877 | 1.00 | 3.53 | SEG1 |
| ATOM | 1693 | NE2 | HIS | 110 | 21.436 | -20.270 | 7.580 | 1.00 | 2.33 | SEG1 |
| ATOM | 1694 | C | HIS | 110 | 16.503 | -19.253 | 4.460 | 1.00 | 0.83 | SEG1 |
| ATOM | 1695 | O | HIS | 110 | 16.013 | -20.249 | 3.962 | 1.00 | 1.08 | SEG1 |
| ATOM | 1696 | N | SER | 111 | 15.820 | -18.141 | 4.587 | 1.00 | 0.58 | SEG1 |
| ATOM | 1697 | HN | SER | 111 | 16.249 | -17.353 | 4.984 | 1.00 | 0.77 | SEG1 |
| ATOM | 1698 | CA | SER | 111 | 14.400 | -18.053 | 4.121 | 1.00 | 0.61 | SEG1 |
| ATOM | 1699 | HA | SER | 111 | 14.329 | -18.326 | 3.080 | 1.00 | 0.63 | SEG1 |
| ATOM | 1700 | CB | SER | 111 | 13.618 | -19.051 | 4.982 | 1.00 | 0.66 | SEG1 |
| ATOM | 1701 | HB1 | SER | 111 | 13.856 | -18.888 | 6.025 | 1.00 | 1.14 | SEG1 |
| ATOM | 1702 | HB2 | SER | 111 | 13.889 | -20.056 | 4.708 | 1.00 | 1.08 | SEG1 |
| ATOM | 1703 | OG | SER | 111 | 12.225 | -18.866 | 4.767 | 1.00 | 1.38 | SEG1 |
| ATOM | 1704 | HG | SER | 111 | 11.755 | -19.295 | 5.485 | 1.00 | 1.53 | SEG1 |
| ATOM | 1705 | C | SER | 111 | 13.862 | -16.637 | 4.341 | 1.00 | 0.51 | SEG1 |
| ATOM | 1706 | O | SER | 111 | 13.860 | -16.132 | 5.449 | 1.00 | 0.54 | SEG1 |
| ATOM | 1707 | N | VAL | 112 | 13.392 | -16.000 | 3.299 | 1.00 | 0.47 | SEG1 |
| ATOM | 1708 | HN | VAL | 112 | 13.395 | -16.433 | 2.420 | 1.00 | 0.51 | SEG1 |
| ATOM | 1709 | CA | VAL | 112 | 12.834 | -14.620 | 3.448 | 1.00 | 0.42 | SEG1 |
| ATOM | 1710 | HA | VAL | 112 | 12.698 | -14.386 | 4.492 | 1.00 | 0.41 | SEG1 |
| ATOM | 1711 | CB | VAL | 112 | 13.882 | -13.674 | 2.833 | 1.00 | 0.54 | SEG1 |
| ATOM | 1712 | HB | VAL | 112 | 14.788 | -13.721 | 3.420 | 1.00 | 0.61 | SEG1 |
| ATOM | 1713 | CG1 | VAL | 112 | 14.195 | -14.094 | 1.390 | 1.00 | 0.61 | SEG1 |
| ATOM | 1714 | HG11 | VAL | 112 | 13.434 | -14.775 | 1.038 | 1.00 | 1.32 | SEG1 |
| ATOM | 1715 | HG12 | VAL | 112 | 15.158 | -14.584 | 1.361 | 1.00 | 1.02 | SEG1 |
| ATOM | 1716 | HG13 | VAL | 112 | 14.219 | -13.221 | 0.754 | 1.00 | 1.21 | SEG1 |
| ATOM | 1717 | CG2 | VAL | 112 | 13.344 | -12.234 | 2.844 | 1.00 | 0.58 | SEG1 |
| ATOM | 1718 | HG21 | VAL | 112 | 12.561 | -12.147 | 3.587 | 1.00 | 1.18 | SEG1 |
| ATOM | 1719 | HG22 | VAL | 112 | 12.943 | -11.993 | 1.870 | 1.00 | 1.21 | SEG1 |
| ATOM | 1720 | HG23 | VAL | 112 | 14.145 | -11.552 | 3.082 | 1.00 | 1.13 | SEG1 |
| ATOM | 1721 | C | VAL | 112 | 11.491 | -14.519 | 2.704 | 1.00 | 0.40 | SEG1 |
| ATOM | 1722 | O | VAL | 112 | 11.400 | -13.850 | 1.693 | 1.00 | 0.46 | SEG1 |
| ATOM | 1723 | N | PRO | 113 | 10.483 | -15.181 | 3.228 | 1.00 | 0.41 | SEG1 |
| ATOM | 1724 | CA | PRO | 113 | 9.151 | -15.136 | 2.587 | 1.00 | 0.50 | SEG1 |
| ATOM | 1725 | HA | PRO | 113 | 9.232 | -15.296 | 1.525 | 1.00 | 0.57 | SEG1 |
| ATOM | 1726 | CB | PRO | 113 | 8.398 | -16.294 | 3.234 | 1.00 | 0.64 | SEG1 |
| ATOM | 1727 | HB1 | PRO | 113 | 8.486 | -17.184 | 2.631 | 1.00 | 0.72 | SEG1 |
| ATOM | 1728 | HB2 | PRO | 113 | 7.357 | -16.032 | 3.370 | 1.00 | 0.71 | SEG1 |
| ATOM | 1729 | CG | PRO | 113 | 9.061 | -16.507 | 4.558 | 1.00 | 0.62 | SEG1 |
| ATOM | 1730 | HG1 | PRO | 113 | 9.056 | -17.557 | 4.807 | 1.00 | 0.75 | SEG1 |
| ATOM | 1731 | HG2 | PRO | 113 | 8.542 | -15.944 | 5.321 | 1.00 | 0.66 | SEG1 |
| ATOM | 1732 | CD | PRO | 113 | 10.483 | -16.022 | 4.438 | 1.00 | 0.47 | SEG1 |
| ATOM | 1733 | HD2 | PRO | 113 | 10.757 | -15.440 | 5.308 | 1.00 | 0.47 | SEG1 |
| ATOM | 1734 | HD1 | PRO | 113 | 11.158 | -16.854 | 4.311 | 1.00 | 0.50 | SEG1 |
| ATOM | 1735 | C | PRO | 113 | 8.458 | -13.803 | 2.886 | 1.00 | 0.47 | SEG1 |
| ATOM | 1736 | O | PRO | 113 | 7.929 | -13.597 | 3.962 | 1.00 | 0.53 | SEG1 |
| ATOM | 1737 | N | LEU | 114 | 8.447 | -12.905 | 1.934 | 1.00 | 0.51 | SEG1 |
| ATOM | 1738 | HN | LEU | 114 | 8.872 | -13.102 | 1.073 | 1.00 | 0.59 | SEG1 |
| ATOM | 1739 | CA | LEU | 114 | 7.778 | -11.586 | 2.147 | 1.00 | 0.54 | SEG1 |
| ATOM | 1740 | HA | LEU | 114 | 7.662 | -11.378 | 3.199 | 1.00 | 0.50 | SEG1 |
| ATOM | 1741 | CB | LEU | 114 | 8.709 | -10.559 | 1.501 | 1.00 | 0.62 | SEG1 |
| ATOM | 1742 | HB1 | LEU | 114 | 8.194 | -9.615 | 1.409 | 1.00 | 1.24 | SEG1 |
| ATOM | 1743 | HB2 | LEU | 114 | 9.001 | -10.907 | 0.521 | 1.00 | 1.15 | SEG1 |
| ATOM | 1744 | CG | LEU | 114 | 9.953 | -10.375 | 2.368 | 1.00 | 1.00 | SEG1 |
| ATOM | 1745 | HG | LEU | 114 | 10.362 | -11.341 | 2.624 | 1.00 | 1.82 | SEG1 |
| ATOM | 1746 | CD1 | LEU | 114 | 10.995 | -9.566 | 1.594 | 1.00 | 1.41 | SEG1 |
| ATOM | 1747 | HD11 | LEU | 114 | 10.713 | -8.523 | 1.593 | 1.00 | 1.88 | SEG1 |
| ATOM | 1748 | HD12 | LEU | 114 | 11.047 | -9.926 | 0.578 | 1.00 | 1.82 | SEG1 |
| ATOM | 1749 | HD13 | LEU | 114 | 11.960 | -9.677 | 2.066 | 1.00 | 2.03 | SEG1 |
| ATOM | 1750 | CD2 | LEU | 114 | 9.572 | -9.617 | 3.643 | 1.00 | 1.66 | SEG1 |
| ATOM | 1751 | HD21 | LEU | 114 | 8.980 | -10.256 | 4.279 | 1.00 | 2.15 | SEG1 |
| ATOM | 1752 | HD22 | LEU | 114 | 8.998 | -8.740 | 3.382 | 1.00 | 2.23 | SEG1 |
| ATOM | 1753 | HD23 | LEU | 114 | 10.469 | -9.319 | 4.166 | 1.00 | 2.01 | SEG1 |
| ATOM | 1754 | C | LEU | 114 | 6.427 | -11.590 | 1.442 | 1.00 | 0.65 | SEG1 |
| ATOM | 1755 | O | LEU | 114 | 6.353 | -11.590 | 0.228 | 1.00 | 0.86 | SEG1 |
| ATOM | 1756 | N | GLN | 115 | 5.359 | -11.604 | 2.194 | 1.00 | 0.58 | SEG1 |
| ATOM | 1757 | HN | GLN | 115 | 5.447 | -11.613 | 3.170 | 1.00 | 0.51 | SEG1 |
| ATOM | 1758 | CA | GLN | 115 | 4.008 | -11.628 | 1.570 | 1.00 | 0.71 | SEG1 |

FIG. 2

| | | | | | | | | | | |
|---|---|---|---|---|---|---|---|---|---|---|
| ATOM | 1759 | HA | GLN | 115 | 4.095 | -11.643 | 0.495 | 1.00 | 0.84 | SEG1 |
| ATOM | 1760 | CB | GLN | 115 | 3.368 | -12.929 | 2.052 | 1.00 | 0.86 | SEG1 |
| ATOM | 1761 | HB1 | GLN | 115 | 3.309 | -12.918 | 3.139 | 1.00 | 0.94 | SEG1 |
| ATOM | 1762 | HB2 | GLN | 115 | 3.972 | -13.768 | 1.742 | 1.00 | 1.29 | SEG1 |
| ATOM | 1763 | CG | GLN | 115 | 1.959 | -13.065 | 1.477 | 1.00 | 1.26 | SEG1 |
| ATOM | 1764 | HG1 | GLN | 115 | 2.018 | -13.077 | 0.398 | 1.00 | 1.92 | SEG1 |
| ATOM | 1765 | HG2 | GLN | 115 | 1.358 | -12.225 | 1.793 | 1.00 | 1.92 | SEG1 |
| ATOM | 1766 | CD | GLN | 115 | 1.312 | -14.366 | 1.963 | 1.00 | 0.81 | SEG1 |
| ATOM | 1767 | OE1 | GLN | 115 | 1.964 | -15.205 | 2.553 | 1.00 | 1.12 | SEG1 |
| ATOM | 1768 | NE2 | GLN | 115 | 0.045 | -14.571 | 1.730 | 1.00 | 0.81 | SEG1 |
| ATOM | 1769 | HE21 | GLN | 115 | -0.481 | -13.897 | 1.248 | 1.00 | 0.83 | SEG1 |
| ATOM | 1770 | HE22 | GLN | 115 | -0.382 | -15.399 | 2.035 | 1.00 | 1.18 | SEG1 |
| ATOM | 1771 | C | GLN | 115 | 3.189 | -10.414 | 2.011 | 1.00 | 0.56 | SEG1 |
| ATOM | 1772 | O | GLN | 115 | 3.430 | -9.822 | 3.053 | 1.00 | 0.46 | SEG1 |
| ATOM | 1773 | N | LEU | 116 | 2.224 | -10.047 | 1.210 | 1.00 | 0.59 | SEG1 |
| ATOM | 1774 | HN | LEU | 116 | 2.068 | -10.548 | 0.382 | 1.00 | 0.70 | SEG1 |
| ATOM | 1775 | CA | LEU | 116 | 1.362 | -8.878 | 1.533 | 1.00 | 0.48 | SEG1 |
| ATOM | 1776 | HA | LEU | 116 | 1.742 | -8.340 | 2.382 | 1.00 | 0.42 | SEG1 |
| ATOM | 1777 | CB | LEU | 116 | 1.414 | -7.993 | 0.284 | 1.00 | 0.53 | SEG1 |
| ATOM | 1778 | HB1 | LEU | 116 | 0.809 | -7.113 | 0.443 | 1.00 | 0.52 | SEG1 |
| ATOM | 1779 | HB2 | LEU | 116 | 1.027 | -8.545 | -0.560 | 1.00 | 0.62 | SEG1 |
| ATOM | 1780 | CG | LEU | 116 | 2.859 | -7.567 | -0.008 | 1.00 | 0.55 | SEG1 |
| ATOM | 1781 | HG | LEU | 116 | 3.464 | -8.446 | -0.174 | 1.00 | 0.59 | SEG1 |
| ATOM | 1782 | CD1 | LEU | 116 | 2.880 | -6.691 | -1.261 | 1.00 | 0.69 | SEG1 |
| ATOM | 1783 | HD11 | LEU | 116 | 2.685 | -5.665 | -0.986 | 1.00 | 1.24 | SEG1 |
| ATOM | 1784 | HD12 | LEU | 116 | 2.119 | -7.030 | -1.950 | 1.00 | 1.29 | SEG1 |
| ATOM | 1785 | HD13 | LEU | 116 | 3.849 | -6.760 | -1.732 | 1.00 | 1.07 | SEG1 |
| ATOM | 1786 | CD2 | LEU | 116 | 3.422 | -6.771 | 1.175 | 1.00 | 0.48 | SEG1 |
| ATOM | 1787 | HD21 | LEU | 116 | 2.704 | -6.026 | 1.484 | 1.00 | 1.17 | SEG1 |
| ATOM | 1788 | HD22 | LEU | 116 | 4.339 | -6.284 | 0.876 | 1.00 | 1.11 | SEG1 |
| ATOM | 1789 | HD23 | LEU | 116 | 3.623 | -7.442 | 1.998 | 1.00 | 1.09 | SEG1 |
| ATOM | 1790 | C | LEU | 116 | -0.071 | -9.349 | 1.783 | 1.00 | 0.48 | SEG1 |
| ATOM | 1791 | O | LEU | 116 | -0.511 | -10.339 | 1.229 | 1.00 | 0.53 | SEG1 |
| ATOM | 1792 | N | GLU | 117 | -0.801 | -8.643 | 2.604 | 1.00 | 0.43 | SEG1 |
| ATOM | 1793 | HN | GLU | 117 | -0.421 | -7.846 | 3.030 | 1.00 | 0.40 | SEG1 |
| ATOM | 1794 | CA | GLU | 117 | -2.217 | -9.030 | 2.884 | 1.00 | 0.44 | SEG1 |
| ATOM | 1795 | HA | GLU | 117 | -2.535 | -9.813 | 2.214 | 1.00 | 0.49 | SEG1 |
| ATOM | 1796 | CB | GLU | 117 | -2.220 | -9.533 | 4.327 | 1.00 | 0.47 | SEG1 |
| ATOM | 1797 | HB1 | GLU | 117 | -3.228 | -9.790 | 4.617 | 1.00 | 0.74 | SEG1 |
| ATOM | 1798 | HB2 | GLU | 117 | -1.844 | -8.760 | 4.979 | 1.00 | 0.64 | SEG1 |
| ATOM | 1799 | CG | GLU | 117 | -1.329 | -10.776 | 4.433 | 1.00 | 0.95 | SEG1 |
| ATOM | 1800 | HG1 | GLU | 117 | -0.322 | -10.520 | 4.137 | 1.00 | 1.24 | SEG1 |
| ATOM | 1801 | HG2 | GLU | 117 | -1.709 | -11.544 | 3.775 | 1.00 | 1.29 | SEG1 |
| ATOM | 1802 | CD | GLU | 117 | -1.314 | -11.304 | 5.875 | 1.00 | 0.99 | SEG1 |
| ATOM | 1803 | OE1 | GLU | 117 | -1.813 | -10.617 | 6.754 | 1.00 | 1.61 | SEG1 |
| ATOM | 1804 | OE2 | GLU | 117 | -0.799 | -12.392 | 6.075 | 1.00 | 1.23 | SEG1 |
| ATOM | 1805 | C | GLU | 117 | -3.104 | -7.796 | 2.731 | 1.00 | 0.37 | SEG1 |
| ATOM | 1806 | O | GLU | 117 | -2.623 | -6.682 | 2.781 | 1.00 | 0.39 | SEG1 |
| ATOM | 1807 | N | LEU | 118 | -4.386 | -7.975 | 2.527 | 1.00 | 0.34 | SEG1 |
| ATOM | 1808 | HN | LEU | 118 | -4.755 | -8.881 | 2.477 | 1.00 | 0.37 | SEG1 |
| ATOM | 1809 | CA | LEU | 118 | -5.277 | -6.788 | 2.355 | 1.00 | 0.29 | SEG1 |
| ATOM | 1810 | HA | LEU | 118 | -4.699 | -5.878 | 2.367 | 1.00 | 0.27 | SEG1 |
| ATOM | 1811 | CB | LEU | 118 | -5.931 | -6.962 | 0.987 | 1.00 | 0.30 | SEG1 |
| ATOM | 1812 | HB1 | LEU | 118 | -6.637 | -6.161 | 0.826 | 1.00 | 0.28 | SEG1 |
| ATOM | 1813 | HB2 | LEU | 118 | -6.451 | -7.907 | 0.956 | 1.00 | 0.32 | SEG1 |
| ATOM | 1814 | CG | LEU | 118 | -4.865 | -6.918 | -0.104 | 1.00 | 0.31 | SEG1 |
| ATOM | 1815 | HG | LEU | 118 | -4.058 | -7.590 | 0.150 | 1.00 | 0.34 | SEG1 |
| ATOM | 1816 | CD1 | LEU | 118 | -5.483 | -7.338 | -1.438 | 1.00 | 0.36 | SEG1 |
| ATOM | 1817 | HD11 | LEU | 118 | -4.712 | -7.729 | -2.085 | 1.00 | 1.00 | SEG1 |
| ATOM | 1818 | HD12 | LEU | 118 | -5.946 | -6.481 | -1.906 | 1.00 | 1.02 | SEG1 |
| ATOM | 1819 | HD13 | LEU | 118 | -6.229 | -8.099 | -1.265 | 1.00 | 1.09 | SEG1 |
| ATOM | 1820 | CD2 | LEU | 118 | -4.329 | -5.491 | -0.218 | 1.00 | 0.29 | SEG1 |
| ATOM | 1821 | HD21 | LEU | 118 | -3.997 | -5.309 | -1.229 | 1.00 | 1.02 | SEG1 |
| ATOM | 1822 | HD22 | LEU | 118 | -3.502 | -5.366 | 0.461 | 1.00 | 1.06 | SEG1 |
| ATOM | 1823 | HD23 | LEU | 118 | -5.113 | -4.790 | 0.036 | 1.00 | 1.07 | SEG1 |
| ATOM | 1824 | C | LEU | 118 | -6.364 | -6.741 | 3.418 | 1.00 | 0.32 | SEG1 |
| ATOM | 1825 | O | LEU | 118 | -7.051 | -7.715 | 3.665 | 1.00 | 0.38 | SEG1 |
| ATOM | 1826 | N | ARG | 119 | -6.556 | -5.595 | 4.009 | 1.00 | 0.29 | SEG1 |
| ATOM | 1827 | HN | ARG | 119 | -6.006 | -4.816 | 3.761 | 1.00 | 0.28 | SEG1 |
| ATOM | 1828 | CA | ARG | 119 | -7.638 | -5.447 | 5.019 | 1.00 | 0.34 | SEG1 |
| ATOM | 1829 | HA | ARG | 119 | -8.268 | -5.324 | 5.027 | 1.00 | 0.38 | SEG1 |
| ATOM | 1830 | CB | ARG | 119 | -6.939 | -5.284 | 6.366 | 1.00 | 0.38 | SEG1 |
| ATOM | 1831 | HB1 | ARG | 119 | -6.351 | -4.379 | 6.361 | 1.00 | 0.61 | SEG1 |
| ATOM | 1832 | HB2 | ARG | 119 | -6.294 | -6.134 | 6.543 | 1.00 | 0.77 | SEG1 |
| ATOM | 1833 | CG | ARG | 119 | -7.993 | -5.200 | 7.473 | 1.00 | 0.70 | SEG1 |
| ATOM | 1834 | HG1 | ARG | 119 | -8.644 | -6.058 | 7.417 | 1.00 | 1.23 | SEG1 |
| ATOM | 1835 | HG2 | ARG | 119 | -8.574 | -4.297 | 7.348 | 1.00 | 1.36 | SEG1 |

FIG. 2

| | | | | | | | | | |
|---|---|---|---|---|---|---|---|---|---|
| ATOM | 1836 | CD | ARG | 119 | -7.300 | -5.177 | 8.835 | 1.00 0.84 | SEG1 |
| ATOM | 1837 | HD1 | ARG | 119 | -6.660 | -4.314 | 8.916 | 1.00 1.40 | SEG1 |
| ATOM | 1838 | HD2 | ARG | 119 | -6.730 | -6.086 | 8.975 | 1.00 1.09 | SEG1 |
| ATOM | 1839 | NE | ARG | 119 | -8.402 | -5.094 | 9.946 | 1.00 1.43 | SEG1 |
| ATOM | 1840 | HE | ARG | 119 | -9.323 | -4.949 | 9.545 | 1.00 1.78 | SEG1 |
| ATOM | 1841 | CZ | ARG | 119 | -8.156 | -5.211 | 11.137 | 1.00 2.13 | SEG1 |
| ATOM | 1842 | NH1 | ARG | 119 | -9.146 | -5.133 | 11.984 | 1.00 2.72 | SEG1 |
| ATOM | 1843 | HH11 | ARG | 119 | -10.078 | -4.937 | 11.652 | 1.00 2.79 | SEG1 |
| ATOM | 1844 | HH12 | ARG | 119 | -8.973 | -5.220 | 12.964 | 1.00 3.33 | SEG1 |
| ATOM | 1845 | NH2 | ARG | 119 | -6.938 | -5.401 | 11.591 | 1.00 2.69 | SEG1 |
| ATOM | 1846 | HH21 | ARG | 119 | -6.165 | -5.461 | 10.961 | 1.00 2.58 | SEG1 |
| ATOM | 1847 | HH22 | ARG | 119 | -6.783 | -5.485 | 12.576 | 1.00 3.46 | SEG1 |
| ATOM | 1848 | C | ARG | 119 | -8.453 | -4.207 | 4.667 | 1.00 0.31 | SEG1 |
| ATOM | 1849 | O | ARG | 119 | -8.041 | -3.090 | 4.921 | 1.00 0.30 | SEG1 |
| ATOM | 1850 | N | ALA | 120 | -9.593 | -4.399 | 4.059 | 1.00 0.33 | SEG1 |
| ATOM | 1851 | HN | ALA | 120 | -9.885 | -5.314 | 3.846 | 1.00 0.34 | SEG1 |
| ATOM | 1852 | CA | ALA | 120 | -10.432 | -3.231 | 3.658 | 1.00 0.33 | SEG1 |
| ATOM | 1853 | HA | ALA | 120 | -9.842 | -2.327 | 3.679 | 1.00 0.33 | SEG1 |
| ATOM | 1854 | CB | ALA | 120 | -10.859 | -3.532 | 2.221 | 1.00 0.35 | SEG1 |
| ATOM | 1855 | HB1 | ALA | 120 | -11.394 | -4.469 | 2.194 | 1.00 1.06 | SEG1 |
| ATOM | 1856 | HB2 | ALA | 120 | -9.984 | -3.598 | 1.592 | 1.00 1.10 | SEG1 |
| ATOM | 1857 | HB3 | ALA | 120 | -11.501 | -2.740 | 1.863 | 1.00 1.05 | SEG1 |
| ATOM | 1858 | C | ALA | 120 | -11.665 | -3.096 | 4.562 | 1.00 0.38 | SEG1 |
| ATOM | 1859 | O | ALA | 120 | -12.261 | -2.038 | 4.649 | 1.00 0.42 | SEG1 |
| ATOM | 1860 | N | GLY | 121 | -12.054 | -4.154 | 5.230 | 1.00 0.40 | SEG1 |
| ATOM | 1861 | HN | GLY | 121 | -11.562 | -4.996 | 5.142 | 1.00 0.40 | SEG1 |
| ATOM | 1862 | CA | GLY | 121 | -13.250 | -4.083 | 6.122 | 1.00 0.46 | SEG1 |
| ATOM | 1863 | HA1 | GLY | 121 | -14.119 | -3.816 | 5.540 | 1.00 0.49 | SEG1 |
| ATOM | 1864 | HA2 | GLY | 121 | -13.085 | -3.338 | 6.887 | 1.00 0.48 | SEG1 |
| ATOM | 1865 | C | GLY | 121 | -13.481 | -5.446 | 6.776 | 1.00 0.49 | SEG1 |
| ATOM | 1866 | O | GLY | 121 | -12.594 | -6.003 | 7.396 | 1.00 0.50 | SEG1 |
| ATOM | 1867 | N | ALA | 122 | -14.666 | -5.986 | 6.640 | 1.00 0.53 | SEG1 |
| ATOM | 1868 | HN | ALA | 122 | -15.361 | -5.515 | 6.134 | 1.00 0.54 | SEG1 |
| ATOM | 1869 | CA | ALA | 122 | -14.962 | -7.317 | 7.252 | 1.00 0.58 | SEG1 |
| ATOM | 1870 | HA | ALA | 122 | -14.535 | -7.376 | 8.241 | 1.00 0.60 | SEG1 |
| ATOM | 1871 | CB | ALA | 122 | -16.487 | -7.382 | 7.341 | 1.00 0.64 | SEG1 |
| ATOM | 1872 | HB1 | ALA | 122 | -16.917 | -7.030 | 6.416 | 1.00 1.23 | SEG1 |
| ATOM | 1873 | HB2 | ALA | 122 | -16.826 | -6.759 | 8.156 | 1.00 1.17 | SEG1 |
| ATOM | 1874 | HB3 | ALA | 122 | -16.794 | -8.402 | 7.516 | 1.00 1.23 | SEG1 |
| ATOM | 1875 | C | ALA | 122 | -14.425 | -8.458 | 6.372 | 1.00 0.56 | SEG1 |
| ATOM | 1876 | O | ALA | 122 | -14.455 | -9.610 | 6.763 | 1.00 0.60 | SEG1 |
| ATOM | 1877 | N | GLU | 123 | -13.932 | -8.151 | 5.193 | 1.00 0.52 | SEG1 |
| ATOM | 1878 | HN | GLU | 123 | -13.912 | -7.220 | 4.894 | 1.00 0.51 | SEG1 |
| ATOM | 1879 | CA | GLU | 123 | -13.392 | -9.220 | 4.301 | 1.00 0.51 | SEG1 |
| ATOM | 1880 | HA | GLU | 123 | -13.761 | -10.187 | 4.606 | 1.00 0.56 | SEG1 |
| ATOM | 1881 | CB | GLU | 123 | -13.919 | -8.875 | 2.908 | 1.00 0.52 | SEG1 |
| ATOM | 1882 | HB1 | GLU | 123 | -13.430 | -9.494 | 2.173 | 1.00 0.60 | SEG1 |
| ATOM | 1883 | HB2 | GLU | 123 | -13.716 | -7.835 | 2.696 | 1.00 0.62 | SEG1 |
| ATOM | 1884 | CG | GLU | 123 | -15.432 | -9.122 | 2.860 | 1.00 0.81 | SEG1 |
| ATOM | 1885 | HG1 | GLU | 123 | -15.919 | -8.503 | 3.598 | 1.00 1.14 | SEG1 |
| ATOM | 1886 | HG2 | GLU | 123 | -15.630 | -10.161 | 3.078 | 1.00 1.08 | SEG1 |
| ATOM | 1887 | CD | GLU | 123 | -15.985 | -8.781 | 1.468 | 1.00 1.04 | SEG1 |
| ATOM | 1888 | OE1 | GLU | 123 | -15.256 | -8.207 | 0.673 | 1.00 1.61 | SEG1 |
| ATOM | 1889 | OE2 | GLU | 123 | -17.134 | -9.109 | 1.219 | 1.00 1.62 | SEG1 |
| ATOM | 1890 | C | GLU | 123 | -11.861 | -9.201 | 4.324 | 1.00 0.46 | SEG1 |
| ATOM | 1891 | O | GLU | 123 | -11.242 | -8.169 | 4.146 | 1.00 0.45 | SEG1 |
| ATOM | 1892 | N | ARG | 124 | -11.251 | -10.338 | 4.545 | 1.00 0.49 | SEG1 |
| ATOM | 1893 | HN | ARG | 124 | -11.777 | -11.152 | 4.688 | 1.00 0.54 | SEG1 |
| ATOM | 1894 | CA | ARG | 124 | -9.759 | -10.401 | 4.587 | 1.00 0.49 | SEG1 |
| ATOM | 1895 | HA | ARG | 124 | -9.364 | -9.483 | 4.993 | 1.00 0.48 | SEG1 |
| ATOM | 1896 | CB | ARG | 124 | -9.435 | -11.562 | 5.529 | 1.00 0.56 | SEG1 |
| ATOM | 1897 | HB1 | ARG | 124 | -8.385 | -11.798 | 5.467 | 1.00 0.58 | SEG1 |
| ATOM | 1898 | HB2 | ARG | 124 | -10.018 | -12.427 | 5.248 | 1.00 0.57 | SEG1 |
| ATOM | 1899 | CG | ARG | 124 | -9.781 | -11.156 | 6.954 | 1.00 0.61 | SEG1 |
| ATOM | 1900 | HG1 | ARG | 124 | -10.832 | -10.919 | 7.028 | 1.00 0.61 | SEG1 |
| ATOM | 1901 | HG2 | ARG | 124 | -9.199 | -10.288 | 7.240 | 1.00 0.60 | SEG1 |
| ATOM | 1902 | CD | ARG | 124 | -9.461 | -12.312 | 7.918 | 1.00 0.70 | SEG1 |
| ATOM | 1903 | HD1 | ARG | 124 | -8.407 | -12.546 | 7.886 | 1.00 1.17 | SEG1 |
| ATOM | 1904 | HD2 | ARG | 124 | -10.048 | -13.182 | 7.661 | 1.00 1.17 | SEG1 |
| ATOM | 1905 | NE | ARG | 124 | -9.832 | -11.814 | 9.281 | 1.00 1.59 | SEG1 |
| ATOM | 1906 | HE | ARG | 124 | -10.282 | -10.947 | 9.372 | 1.00 2.17 | SEG1 |
| ATOM | 1907 | CZ | ARG | 124 | -9.567 | -12.517 | 10.365 | 1.00 2.20 | SEG1 |
| ATOM | 1908 | NH1 | ARG | 124 | -9.908 | -12.042 | 11.532 | 1.00 3.24 | SEG1 |
| ATOM | 1909 | HH11 | ARG | 124 | -10.364 | -11.155 | 11.596 | 1.00 3.68 | SEG1 |
| ATOM | 1910 | HH12 | ARG | 124 | -9.713 | -12.565 | 12.361 | 1.00 3.76 | SEG1 |
| ATOM | 1911 | NH2 | ARG | 124 | -8.967 | -13.683 | 10.300 | 1.00 2.24 | SEG1 |
| ATOM | 1912 | HH21 | ARG | 124 | -8.696 | -14.065 | 9.418 | 1.00 2.00 | SEG1 |

FIG. 2

```
ATOM   1913 HH22 ARG  124   -8.780 -14.194  11.139  1.00  2.90      SEG1
ATOM   1914  C   ARG  124   -9.185 -10.648   3.183  1.00  0.46      SEG1
ATOM   1915  O   ARG  124   -9.872 -10.511   2.193  1.00  0.44      SEG1
ATOM   1916  N   LEU  125   -7.923 -10.993   3.109  1.00  0.49      SEG1
ATOM   1917  HN  LEU  125   -7.393 -11.079   3.928  1.00  0.53      SEG1
ATOM   1918  CA  LEU  125   -7.283 -11.230   1.777  1.00  0.49      SEG1
ATOM   1919  HA  LEU  125   -7.297 -10.326   1.191  1.00  0.50      SEG1
ATOM   1920  CB  LEU  125   -5.835 -11.627   2.096  1.00  0.58      SEG1
ATOM   1921  HB1 LEU  125   -5.834 -12.518   2.704  1.00  0.60      SEG1
ATOM   1922  HB2 LEU  125   -5.353 -10.823   2.635  1.00  0.62      SEG1
ATOM   1923  CG  LEU  125   -5.069 -11.899   0.798  1.00  0.62      SEG1
ATOM   1924  HG  LEU  125   -5.615 -12.621   0.206  1.00  0.79      SEG1
ATOM   1925  CD1 LEU  125   -4.915 -10.500  -0.003  1.00  1.11      SEG1
ATOM   1926 HD11 LEU  125   -3.896 -10.254   0.051  1.00  1.61      SEG1
ATOM   1927 HD12 LEU  125   -5.573  -9.844   0.397  1.00  1.75      SEG1
ATOM   1928 HD13 LEU  125   -5.167 -10.784  -1.037  1.00  1.55      SEG1
ATOM   1929  CD2 LEU  125   -3.686 -12.463   1.139  1.00  1.28      SEG1
ATOM   1930 HD21 LEU  125   -3.790 -13.260   1.959  1.00  1.80      SEG1
ATOM   1931 HD22 LEU  125   -3.071 -11.679   1.556  1.00  1.84      SEG1
ATOM   1932 HD23 LEU  125   -3.222 -12.847   0.242  1.00  1.73      SEG1
ATOM   1933  C   LEU  125   -7.994 -12.362   1.028  1.00  0.46      SEG1
ATOM   1934  O   LEU  125   -8.299 -12.236  -0.144  1.00  0.45      SEG1
ATOM   1935  N   ASP  126   -8.261 -13.458   1.688  1.00  0.49      SEG1
ATOM   1936  HN  ASP  126   -8.007 -13.537   2.632  1.00  0.53      SEG1
ATOM   1937  CA  ASP  126   -8.956 -14.590   1.001  1.00  0.50      SEG1
ATOM   1938  HA  ASP  126   -8.381 -14.913   0.145  1.00  0.49      SEG1
ATOM   1939  CB  ASP  126   -9.025 -15.723   2.038  1.00  0.57      SEG1
ATOM   1940  HB1 ASP  126   -8.025 -15.964   2.369  1.00  0.58      SEG1
ATOM   1941  HB2 ASP  126   -9.469 -16.596   1.583  1.00  0.59      SEG1
ATOM   1942  CG  ASP  126   -9.868 -15.299   3.251  1.00  0.62      SEG1
ATOM   1943  OD1 ASP  126  -10.047 -14.108   3.446  1.00  1.28      SEG1
ATOM   1944  OD2 ASP  126  -10.322 -16.179   3.964  1.00  1.21      SEG1
ATOM   1945  C   ASP  126  -10.360 -14.158   0.559  1.00  0.51      SEG1
ATOM   1946  O   ASP  126  -10.948 -14.746  -0.329  1.00  0.53      SEG1
ATOM   1947  N   ALA  127  -10.899 -13.135   1.177  1.00  0.52      SEG1
ATOM   1948  HN  ALA  127  -10.406 -12.680   1.890  1.00  0.52      SEG1
ATOM   1949  CA  ALA  127  -12.263 -12.658   0.803  1.00  0.57      SEG1
ATOM   1950  HA  ALA  127  -12.905 -13.496   0.584  1.00  0.60      SEG1
ATOM   1951  CB  ALA  127  -12.773 -11.927   2.046  1.00  0.64      SEG1
ATOM   1952  HB1 ALA  127  -12.036 -11.203   2.368  1.00  1.19      SEG1
ATOM   1953  HB2 ALA  127  -12.944 -12.642   2.838  1.00  1.26      SEG1
ATOM   1954  HB3 ALA  127  -13.697 -11.422   1.811  1.00  1.17      SEG1
ATOM   1955  C   ALA  127  -12.209 -11.698  -0.398  1.00  0.55      SEG1
ATOM   1956  O   ALA  127  -13.236 -11.313  -0.925  1.00  0.62      SEG1
ATOM   1957  N   LEU  128  -11.031 -11.301  -0.832  1.00  0.50      SEG1
ATOM   1958  HN  LEU  128  -10.212 -11.614  -0.396  1.00  0.47      SEG1
ATOM   1959  CA  LEU  128  -10.943 -10.360  -1.994  1.00  0.52      SEG1
ATOM   1960  HA  LEU  128  -11.895  -9.885  -2.163  1.00  0.57      SEG1
ATOM   1961  CB  LEU  128   -9.903  -9.313  -1.585  1.00  0.53      SEG1
ATOM   1962  HB1 LEU  128   -9.780  -8.598  -2.385  1.00  0.87      SEG1
ATOM   1963  HB2 LEU  128   -8.958  -9.801  -1.393  1.00  0.70      SEG1
ATOM   1964  CG  LEU  128  -10.366  -8.583  -0.321  1.00  1.03      SEG1
ATOM   1965  HG  LEU  128  -10.624  -9.310   0.437  1.00  1.71      SEG1
ATOM   1966  CD1 LEU  128   -9.231  -7.694   0.196  1.00  1.29      SEG1
ATOM   1967 HD11 LEU  128   -8.688  -7.281  -0.641  1.00  1.79      SEG1
ATOM   1968 HD12 LEU  128   -8.562  -8.283   0.805  1.00  1.73      SEG1
ATOM   1969 HD13 LEU  128   -9.644  -6.891   0.789  1.00  1.77      SEG1
ATOM   1970  CD2 LEU  128  -11.594  -7.715  -0.640  1.00  1.58      SEG1
ATOM   1971 HD21 LEU  128  -11.309  -6.673  -0.659  1.00  2.06      SEG1
ATOM   1972 HD22 LEU  128  -12.346  -7.866   0.120  1.00  1.98      SEG1
ATOM   1973 HD23 LEU  128  -11.997  -7.994  -1.602  1.00  2.07      SEG1
ATOM   1974  C   LEU  128  -10.481 -11.091  -3.259  1.00  0.50      SEG1
ATOM   1975  O   LEU  128  -10.738 -10.647  -4.362  1.00  0.55      SEG1
ATOM   1976  N   LEU  129   -9.800 -12.201  -3.113  1.00  0.47      SEG1
ATOM   1977  HN  LEU  129   -9.601 -12.539  -2.214  1.00  0.46      SEG1
ATOM   1978  CA  LEU  129   -9.322 -12.948  -4.318  1.00  0.49      SEG1
ATOM   1979  HA  LEU  129   -8.785 -12.283  -4.976  1.00  0.53      SEG1
ATOM   1980  CB  LEU  129   -8.372 -14.026  -3.796  1.00  0.49      SEG1
ATOM   1981  HB1 LEU  129   -8.025 -14.635  -4.607  1.00  0.53      SEG1
ATOM   1982  HB2 LEU  129   -8.898 -14.647  -3.075  1.00  0.48      SEG1
ATOM   1983  CG  LEU  129   -7.167 -13.372  -3.095  1.00  0.50      SEG1
ATOM   1984  HG  LEU  129   -7.513 -12.769  -2.268  1.00  0.48      SEG1
ATOM   1985  CD1 LEU  129   -6.229 -14.460  -2.570  1.00  0.54      SEG1
ATOM   1986 HD11 LEU  129   -6.789 -15.368  -2.400  1.00  1.15      SEG1
ATOM   1987 HD12 LEU  129   -5.782 -14.134  -1.643  1.00  1.15      SEG1
ATOM   1988 HD13 LEU  129   -5.452 -14.648  -3.297  1.00  1.18      SEG1
ATOM   1989  CD2 LEU  129   -6.406 -12.490  -4.094  1.00  0.59      SEG1
```

FIG. 2

| | | | | | | | | | |
|---|---|---|---|---|---|---|---|---|---|
| ATOM | 1990 | HD21 | LEU | 129 | -6.990 -11.598 -4.296 | 1.00 | 1.13 | SEG1 |
| ATOM | 1991 | HD22 | LEU | 129 | -6.253 -13.036 -5.013 | 1.00 | 1.11 | SEG1 |
| ATOM | 1992 | HD23 | LEU | 129 | -5.450 -12.215 -3.675 | 1.00 | 1.28 | SEG1 |
| ATOM | 1993 | C | LEU | 129 | -10.501 -13.585 -5.061 | 1.00 | 0.54 | SEG1 |
| ATOM | 1994 | O | LEU | 129 | -10.542 -13.597 -6.278 | 1.00 | 0.60 | SEG1 |
| ATOM | 1995 | N | ALA | 130 | -11.454 -14.118 -4.340 | 1.00 | 0.56 | SEG1 |
| ATOM | 1996 | HN | ALA | 130 | -11.393 -14.098 -3.361 | 1.00 | 0.54 | SEG1 |
| ATOM | 1997 | CA | ALA | 130 | -12.631 -14.765 -5.003 | 1.00 | 0.64 | SEG1 |
| ATOM | 1998 | HA | ALA | 130 | -12.299 -15.512 -5.706 | 1.00 | 0.73 | SEG1 |
| ATOM | 1999 | CB | ALA | 130 | -13.418 -15.429 -3.871 | 1.00 | 0.72 | SEG1 |
| ATOM | 2000 | HB1 | ALA | 130 | -14.057 -16.197 -4.281 | 1.00 | 1.23 | SEG1 |
| ATOM | 2001 | HB2 | ALA | 130 | -14.022 -14.688 -3.369 | 1.00 | 1.22 | SEG1 |
| ATOM | 2002 | HB3 | ALA | 130 | -12.730 -15.871 -3.166 | 1.00 | 1.30 | SEG1 |
| ATOM | 2003 | C | ALA | 130 | -13.497 -13.718 -5.711 | 1.00 | 0.59 | SEG1 |
| ATOM | 2004 | O | ALA | 130 | -13.759 -13.818 -6.895 | 1.00 | 0.64 | SEG1 |
| ATOM | 2005 | N | ASP | 131 | -13.948 -12.720 -4.992 | 1.00 | 0.55 | SEG1 |
| ATOM | 2006 | HN | ASP | 131 | -13.727 -12.567 -4.039 | 1.00 | 0.57 | SEG1 |
| ATOM | 2007 | CA | ASP | 131 | -14.807 -11.669 -5.616 | 1.00 | 0.53 | SEG1 |
| ATOM | 2008 | HA | ASP | 131 | -15.173 -12.001 -6.574 | 1.00 | 0.58 | SEG1 |
| ATOM | 2009 | CB | ASP | 131 | -15.975 -11.489 -4.646 | 1.00 | 0.61 | SEG1 |
| ATOM | 2010 | HB1 | ASP | 131 | -16.552 -10.623 -4.934 | 1.00 | 0.74 | SEG1 |
| ATOM | 2011 | HB2 | ASP | 131 | -15.592 -11.350 -3.645 | 1.00 | 0.91 | SEG1 |
| ATOM | 2012 | CG | ASP | 131 | -16.867 -12.730 -4.685 | 1.00 | 0.99 | SEG1 |
| ATOM | 2013 | OD1 | ASP | 131 | -17.317 -13.145 -3.630 | 1.00 | 1.79 | SEG1 |
| ATOM | 2014 | OD2 | ASP | 131 | -17.089 -13.242 -5.770 | 1.00 | 1.43 | SEG1 |
| ATOM | 2015 | C | ASP | 131 | -14.029 -10.359 -5.764 | 1.00 | 0.45 | SEG1 |
| ATOM | 2016 | O | ASP | 131 | -13.505 -9.828 -4.803 | 1.00 | 0.42 | SEG1 |
| ATOM | 2017 | N | GLU | 132 | -13.956 -9.838 -6.962 | 1.00 | 0.46 | SEG1 |
| ATOM | 2018 | HN | GLU | 132 | -14.390 -10.287 -7.717 | 1.00 | 0.51 | SEG1 |
| ATOM | 2019 | CA | GLU | 132 | -13.217 -8.561 -7.183 | 1.00 | 0.45 | SEG1 |
| ATOM | 2020 | HA | GLU | 132 | -12.367 -8.499 -6.522 | 1.00 | 0.44 | SEG1 |
| ATOM | 2021 | CB | GLU | 132 | -12.744 -8.621 -8.637 | 1.00 | 0.54 | SEG1 |
| ATOM | 2022 | HB1 | GLU | 132 | -12.350 -7.659 -8.928 | 1.00 | 1.06 | SEG1 |
| ATOM | 2023 | HB2 | GLU | 132 | -13.576 -8.878 -9.276 | 1.00 | 0.88 | SEG1 |
| ATOM | 2024 | CG | GLU | 132 | -11.645 -9.683 -8.771 | 1.00 | 1.23 | SEG1 |
| ATOM | 2025 | HG1 | GLU | 132 | -12.041 -10.644 -8.476 | 1.00 | 1.67 | SEG1 |
| ATOM | 2026 | HG2 | GLU | 132 | -10.818 -9.425 -8.126 | 1.00 | 1.77 | SEG1 |
| ATOM | 2027 | CD | GLU | 132 | -11.152 -9.764 -10.224 | 1.00 | 1.29 | SEG1 |
| ATOM | 2028 | OE1 | GLU | 132 | -10.154 -10.430 -10.447 | 1.00 | 1.79 | SEG1 |
| ATOM | 2029 | OE2 | GLU | 132 | -11.777 -9.167 -11.088 | 1.00 | 1.59 | SEG1 |
| ATOM | 2030 | C | GLU | 132 | -14.150 -7.366 -6.964 | 1.00 | 0.43 | SEG1 |
| ATOM | 2031 | O | GLU | 132 | -13.732 -6.321 -6.510 | 1.00 | 0.42 | SEG1 |
| ATOM | 2032 | N | GLU | 133 | -15.410 -7.511 -7.280 | 1.00 | 0.46 | SEG1 |
| ATOM | 2033 | HN | GLU | 133 | -15.727 -8.365 -7.645 | 1.00 | 0.49 | SEG1 |
| ATOM | 2034 | CA | GLU | 133 | -16.367 -6.377 -7.082 | 1.00 | 0.47 | SEG1 |
| ATOM | 2035 | HA | GLU | 133 | -16.061 -5.520 -7.660 | 1.00 | 0.50 | SEG1 |
| ATOM | 2036 | CB | GLU | 133 | -17.717 -6.894 -7.586 | 1.00 | 0.53 | SEG1 |
| ATOM | 2037 | HB1 | GLU | 133 | -18.493 -6.195 -7.315 | 1.00 | 0.71 | SEG1 |
| ATOM | 2038 | HB2 | GLU | 133 | -17.924 -7.855 -7.136 | 1.00 | 0.75 | SEG1 |
| ATOM | 2039 | CG | GLU | 133 | -17.676 -7.041 -9.111 | 1.00 | 0.96 | SEG1 |
| ATOM | 2040 | HG1 | GLU | 133 | -16.898 -7.739 -9.381 | 1.00 | 1.39 | SEG1 |
| ATOM | 2041 | HG2 | GLU | 133 | -17.465 -6.081 -9.558 | 1.00 | 1.25 | SEG1 |
| ATOM | 2042 | CD | GLU | 133 | -19.025 -7.560 -9.633 | 1.00 | 1.18 | SEG1 |
| ATOM | 2043 | OE1 | GLU | 133 | -19.853 -7.956 -8.824 | 1.00 | 1.50 | SEG1 |
| ATOM | 2044 | OE2 | GLU | 133 | -19.207 -7.554 -10.840 | 1.00 | 1.83 | SEG1 |
| ATOM | 2045 | C | GLU | 133 | -16.460 -6.017 -5.594 | 1.00 | 0.41 | SEG1 |
| ATOM | 2046 | O | GLU | 133 | -16.538 -4.858 -5.228 | 1.00 | 0.41 | SEG1 |
| ATOM | 2047 | N | ARG | 134 | -16.469 -7.008 -4.738 | 1.00 | 0.40 | SEG1 |
| ATOM | 2048 | HN | ARG | 134 | -16.419 -7.931 -5.065 | 1.00 | 0.42 | SEG1 |
| ATOM | 2049 | CA | ARG | 134 | -16.581 -6.744 -3.268 | 1.00 | 0.39 | SEG1 |
| ATOM | 2050 | HA | ARG | 134 | -17.502 -6.226 -3.058 | 1.00 | 0.42 | SEG1 |
| ATOM | 2051 | CB | ARG | 134 | -16.619 -8.118 -2.603 | 1.00 | 0.44 | SEG1 |
| ATOM | 2052 | HB1 | ARG | 134 | -16.526 -8.002 -1.534 | 1.00 | 0.68 | SEG1 |
| ATOM | 2053 | HB2 | ARG | 134 | -15.802 -8.720 -2.974 | 1.00 | 0.63 | SEG1 |
| ATOM | 2054 | CG | ARG | 134 | -17.947 -8.802 -2.925 | 1.00 | 0.71 | SEG1 |
| ATOM | 2055 | HG1 | ARG | 134 | -18.030 -8.947 -3.991 | 1.00 | 1.28 | SEG1 |
| ATOM | 2056 | HG2 | ARG | 134 | -18.764 -8.186 -2.578 | 1.00 | 1.12 | SEG1 |
| ATOM | 2057 | CD | ARG | 134 | -17.992 -10.158 -2.222 | 1.00 | 1.16 | SEG1 |
| ATOM | 2058 | HD1 | ARG | 134 | -17.945 -10.023 -1.153 | 1.00 | 1.47 | SEG1 |
| ATOM | 2059 | HD2 | ARG | 134 | -17.175 -10.779 -2.559 | 1.00 | 1.71 | SEG1 |
| ATOM | 2060 | NE | ARG | 134 | -19.306 -10.767 -2.603 | 1.00 | 1.51 | SEG1 |
| ATOM | 2061 | HE | ARG | 134 | -19.918 -10.269 -3.156 | 1.00 | 1.74 | SEG1 |
| ATOM | 2062 | CZ | ARG | 134 | -19.655 -11.965 -2.177 | 1.00 | 2.12 | SEG1 |
| ATOM | 2063 | NH1 | ARG | 134 | -20.802 -12.464 -2.549 | 1.00 | 2.52 | SEG1 |
| ATOM | 2064 | HH11 | ARG | 134 | -21.405 -11.938 -3.149 | 1.00 | 2.52 | SEG1 |
| ATOM | 2065 | HH12 | ARG | 134 | -21.078 -13.372 -2.234 | 1.00 | 3.06 | SEG1 |
| ATOM | 2066 | NH2 | ARG | 134 | -18.878 -12.667 -1.383 | 1.00 | 2.76 | SEG1 |

FIG. 2

| ATOM | 2067 | HH21 | ARG | 134 | -17.998 | -12.302 | -1.083 | 1.00 | 2.75 | SEG1 |
| --- | --- | --- | --- | --- | --- | --- | --- | --- | --- | --- |
| ATOM | 2068 | HH22 | ARG | 134 | -19.169 | -13.573 | -1.077 | 1.00 | 3.44 | SEG1 |
| ATOM | 2069 | C | ARG | 134 | -15.395 | -5.931 | -2.734 | 1.00 | 0.34 | SEG1 |
| ATOM | 2070 | O | ARG | 134 | -15.571 | -5.067 | -1.895 | 1.00 | 0.36 | SEG1 |
| ATOM | 2071 | N | CYS | 135 | -14.188 | -6.202 | -3.184 | 1.00 | 0.33 | SEG1 |
| ATOM | 2072 | HN | CYS | 135 | -14.056 | -6.911 | -3.848 | 1.00 | 0.34 | SEG1 |
| ATOM | 2073 | CA | CYS | 135 | -13.012 | -5.435 | -2.655 | 1.00 | 0.31 | SEG1 |
| ATOM | 2074 | HA | CYS | 135 | -12.925 | -5.615 | -1.594 | 1.00 | 0.32 | SEG1 |
| ATOM | 2075 | CB | CYS | 135 | -11.763 | -6.017 | -3.370 | 1.00 | 0.35 | SEG1 |
| ATOM | 2076 | HB1 | CYS | 135 | -11.888 | -7.086 | -3.473 | 1.00 | 0.38 | SEG1 |
| ATOM | 2077 | HB2 | CYS | 135 | -10.893 | -5.826 | -2.763 | 1.00 | 0.37 | SEG1 |
| ATOM | 2078 | SG | CYS | 135 | -11.491 | -5.291 | -5.018 | 1.00 | 0.41 | SEG1 |
| ATOM | 2079 | HG | CYS | 135 | -10.551 | -5.117 | -5.113 | 1.00 | 0.98 | SEG1 |
| ATOM | 2080 | C | CYS | 135 | -13.203 | -3.927 | -2.892 | 1.00 | 0.31 | SEG1 |
| ATOM | 2081 | O | CYS | 135 | -12.861 | -3.112 | -2.056 | 1.00 | 0.32 | SEG1 |
| ATOM | 2082 | N | LEU | 136 | -13.754 | -3.560 | -4.022 | 1.00 | 0.34 | SEG1 |
| ATOM | 2083 | HN | LEU | 136 | -14.026 | -4.240 | -4.675 | 1.00 | 0.36 | SEG1 |
| ATOM | 2084 | CA | LEU | 136 | -13.977 | -2.111 | -4.312 | 1.00 | 0.39 | SEG1 |
| ATOM | 2085 | HA | LEU | 136 | -13.043 | -1.573 | -4.293 | 1.00 | 0.41 | SEG1 |
| ATOM | 2086 | CB | LEU | 136 | -14.578 | -2.074 | -5.720 | 1.00 | 0.44 | SEG1 |
| ATOM | 2087 | HB1 | LEU | 136 | -14.869 | -1.063 | -5.962 | 1.00 | 0.48 | SEG1 |
| ATOM | 2088 | HB2 | LEU | 136 | -15.445 | -2.718 | -5.757 | 1.00 | 0.44 | SEG1 |
| ATOM | 2089 | CG | LEU | 136 | -13.538 | -2.559 | -6.730 | 1.00 | 0.46 | SEG1 |
| ATOM | 2090 | HG | LEU | 136 | -13.158 | -3.522 | -6.420 | 1.00 | 0.48 | SEG1 |
| ATOM | 2091 | CD1 | LEU | 136 | -14.188 | -2.690 | -8.109 | 1.00 | 0.54 | SEG1 |
| ATOM | 2092 | HD11 | LEU | 136 | -14.407 | -1.707 | -8.498 | 1.00 | 1.21 | SEG1 |
| ATOM | 2093 | HD12 | LEU | 136 | -15.104 | -3.256 | -8.022 | 1.00 | 1.19 | SEG1 |
| ATOM | 2094 | HD13 | LEU | 136 | -13.511 | -3.201 | -8.778 | 1.00 | 1.03 | SEG1 |
| ATOM | 2095 | CD2 | LEU | 136 | -12.388 | -1.553 | -6.802 | 1.00 | 0.49 | SEG1 |
| ATOM | 2096 | HD21 | LEU | 136 | -11.833 | -1.575 | -5.875 | 1.00 | 1.08 | SEG1 |
| ATOM | 2097 | HD22 | LEU | 136 | -12.785 | -0.562 | -6.960 | 1.00 | 1.12 | SEG1 |
| ATOM | 2098 | HD23 | LEU | 136 | -11.732 | -1.813 | -7.620 | 1.00 | 1.19 | SEG1 |
| ATOM | 2099 | C | LEU | 136 | -14.959 | -1.519 | -3.296 | 1.00 | 0.39 | SEG1 |
| ATOM | 2100 | O | LEU | 136 | -14.768 | -0.426 | -2.797 | 1.00 | 0.43 | SEG1 |
| ATOM | 2101 | N | SER | 137 | -16.009 | -2.240 | -2.989 | 1.00 | 0.38 | SEG1 |
| ATOM | 2102 | HN | SER | 137 | -16.134 | -3.118 | -3.410 | 1.00 | 0.37 | SEG1 |
| ATOM | 2103 | CA | SER | 137 | -17.017 | -1.733 | -2.003 | 1.00 | 0.43 | SEG1 |
| ATOM | 2104 | HA | SER | 137 | -17.464 | -0.822 | -2.363 | 1.00 | 0.48 | SEG1 |
| ATOM | 2105 | CB | SER | 137 | -18.078 | -2.830 | -1.911 | 1.00 | 0.48 | SEG1 |
| ATOM | 2106 | HB1 | SER | 137 | -18.773 | -2.591 | -1.117 | 1.00 | 1.02 | SEG1 |
| ATOM | 2107 | HB2 | SER | 137 | -17.605 | -3.775 | -1.698 | 1.00 | 1.21 | SEG1 |
| ATOM | 2108 | OG | SER | 137 | -18.768 | -2.922 | -3.150 | 1.00 | 1.35 | SEG1 |
| ATOM | 2109 | HG | SER | 137 | -18.239 | -3.459 | -3.745 | 1.00 | 1.57 | SEG1 |
| ATOM | 2110 | C | SER | 137 | -16.371 | -1.502 | -0.633 | 1.00 | 0.41 | SEG1 |
| ATOM | 2111 | O | SER | 137 | -16.674 | -0.542 | 0.050 | 1.00 | 0.46 | SEG1 |
| ATOM | 2112 | N | CYS | 138 | -15.499 | -2.386 | -0.225 | 1.00 | 0.36 | SEG1 |
| ATOM | 2113 | HN | CYS | 138 | -15.285 | -3.154 | -0.795 | 1.00 | 0.35 | SEG1 |
| ATOM | 2114 | CA | CYS | 138 | -14.839 | -2.239 | 1.111 | 1.00 | 0.37 | SEG1 |
| ATOM | 2115 | HA | CYS | 138 | -15.576 | -2.070 | 1.877 | 1.00 | 0.42 | SEG1 |
| ATOM | 2116 | CB | CYS | 138 | -14.131 | -3.571 | 1.358 | 1.00 | 0.39 | SEG1 |
| ATOM | 2117 | HB1 | CYS | 138 | -13.360 | -3.435 | 2.101 | 1.00 | 0.40 | SEG1 |
| ATOM | 2118 | HB2 | CYS | 138 | -13.685 | -3.917 | 0.436 | 1.00 | 0.38 | SEG1 |
| ATOM | 2119 | SG | CYS | 138 | -15.330 | -4.793 | 1.944 | 1.00 | 0.46 | SEG1 |
| ATOM | 2120 | HG | CYS | 138 | -15.160 | -4.953 | 2.875 | 1.00 | 0.97 | SEG1 |
| ATOM | 2121 | C | CYS | 138 | -13.819 | -1.102 | 1.096 | 1.00 | 0.35 | SEG1 |
| ATOM | 2122 | O | CYS | 138 | -13.814 | -0.249 | 1.964 | 1.00 | 0.40 | SEG1 |
| ATOM | 2123 | N | ILE | 139 | -12.950 | -1.094 | 0.123 | 1.00 | 0.33 | SEG1 |
| ATOM | 2124 | HN | ILE | 139 | -12.979 | -1.798 | -0.557 | 1.00 | 0.33 | SEG1 |
| ATOM | 2125 | CA | ILE | 139 | -11.913 | -0.019 | 0.049 | 1.00 | 0.35 | SEG1 |
| ATOM | 2126 | HA | ILE | 139 | -11.300 | -0.030 | 0.938 | 1.00 | 0.37 | SEG1 |
| ATOM | 2127 | CB | ILE | 139 | -11.060 | -0.363 | -1.178 | 1.00 | 0.37 | SEG1 |
| ATOM | 2128 | HB | ILE | 139 | -11.686 | -0.387 | -2.059 | 1.00 | 0.39 | SEG1 |
| ATOM | 2129 | CG1 | ILE | 139 | -10.397 | -1.729 | -0.980 | 1.00 | 0.37 | SEG1 |
| ATOM | 2130 | HG11 | ILE | 139 | -11.136 | -2.454 | -0.677 | 1.00 | 0.35 | SEG1 |
| ATOM | 2131 | HG12 | ILE | 139 | -9.635 | -1.651 | -0.218 | 1.00 | 0.40 | SEG1 |
| ATOM | 2132 | CG2 | ILE | 139 | -9.968 | 0.694 | -1.355 | 1.00 | 0.43 | SEG1 |
| ATOM | 2133 | HG21 | ILE | 139 | -10.413 | 1.677 | -1.347 | 1.00 | 1.04 | SEG1 |
| ATOM | 2134 | HG22 | ILE | 139 | -9.462 | 0.535 | -2.296 | 1.00 | 1.13 | SEG1 |
| ATOM | 2135 | HG23 | ILE | 139 | -9.257 | 0.613 | -0.546 | 1.00 | 1.14 | SEG1 |
| ATOM | 2136 | CD1 | ILE | 139 | -9.757 | -2.175 | -2.295 | 1.00 | 0.44 | SEG1 |
| ATOM | 2137 | HD11 | ILE | 139 | -8.882 | -2.772 | -2.088 | 1.00 | 1.04 | SEG1 |
| ATOM | 2138 | HD12 | ILE | 139 | -9.473 | -1.305 | -2.969 | 1.00 | 1.04 | SEG1 |
| ATOM | 2139 | HD13 | ILE | 139 | -10.468 | -2.761 | -2.859 | 1.00 | 1.12 | SEG1 |
| ATOM | 2140 | C | ILE | 139 | -12.584 | 1.351 | -0.113 | 1.00 | 0.42 | SEG1 |
| ATOM | 2141 | O | ILE | 139 | -12.169 | 2.323 | 0.490 | 1.00 | 0.49 | SEG1 |
| ATOM | 2142 | N | LEU | 140 | -13.614 | 1.435 | -0.918 | 1.00 | 0.44 | SEG1 |
| ATOM | 2143 | HN | LEU | 140 | -13.932 | 0.638 | -1.393 | 1.00 | 0.41 | SEG1 |

FIG. 2

| | | | | | | | | | |
|---|---|---|---|---|---|---|---|---|---|
| ATOM | 2144 | CA | LEU | 140 | -14.306 | 2.745 | -1.114 | 1.00 | 0.55 | SEG1 |
| ATOM | 2145 | HA | LEU | 140 | -13.576 | 3.535 | -1.113 | 1.00 | 0.57 | SEG1 |
| ATOM | 2146 | CB | LEU | 140 | -14.942 | 2.645 | -2.525 | 1.00 | 0.64 | SEG1 |
| ATOM | 2147 | HB1 | LEU | 140 | -14.431 | 1.871 | -3.076 | 1.00 | 0.65 | SEG1 |
| ATOM | 2148 | HB2 | LEU | 140 | -14.805 | 3.585 | -3.041 | 1.00 | 0.87 | SEG1 |
| ATOM | 2149 | CG | LEU | 140 | -16.445 | 2.313 | -2.473 | 1.00 | 0.63 | SEG1 |
| ATOM | 2150 | HG | LEU | 140 | -16.635 | 1.638 | -1.651 | 1.00 | 0.60 | SEG1 |
| ATOM | 2151 | CD1 | LEU | 140 | -17.251 | 3.602 | -2.271 | 1.00 | 0.95 | SEG1 |
| ATOM | 2152 | HD11 | LEU | 140 | -16.602 | 4.380 | -1.896 | 1.00 | 1.34 | SEG1 |
| ATOM | 2153 | HD12 | LEU | 140 | -18.043 | 3.422 | -1.558 | 1.00 | 1.52 | SEG1 |
| ATOM | 2154 | HD13 | LEU | 140 | -17.679 | 3.915 | -3.212 | 1.00 | 1.37 | SEG1 |
| ATOM | 2155 | CD2 | LEU | 140 | -16.862 | 1.649 | -3.798 | 1.00 | 0.62 | SEG1 |
| ATOM | 2156 | HD21 | LEU | 140 | -17.839 | 1.204 | -3.673 | 1.00 | 1.13 | SEG1 |
| ATOM | 2157 | HD22 | LEU | 140 | -16.146 | 0.884 | -4.048 | 1.00 | 1.26 | SEG1 |
| ATOM | 2158 | HD23 | LEU | 140 | -16.895 | 2.391 | -4.572 | 1.00 | 1.20 | SEG1 |
| ATOM | 2159 | C | LEU | 140 | -15.323 | 3.001 | 0.020 | 1.00 | 0.59 | SEG1 |
| ATOM | 2160 | O | LEU | 140 | -15.806 | 4.106 | 0.184 | 1.00 | 0.71 | SEG1 |
| ATOM | 2161 | N | ALA | 141 | -15.638 | 1.997 | 0.905 | 1.00 | 0.54 | SEG1 |
| ATOM | 2162 | HN | ALA | 141 | -15.231 | 1.117 | 0.664 | 1.00 | 0.47 | SEG1 |
| ATOM | 2163 | CA | ALA | 141 | -16.605 | 2.196 | 1.928 | 1.00 | 0.63 | SEG1 |
| ATOM | 2164 | HA | ALA | 141 | -17.502 | 2.676 | 1.571 | 1.00 | 0.73 | SEG1 |
| ATOM | 2165 | CB | ALA | 141 | -16.931 | 0.790 | 2.436 | 1.00 | 0.67 | SEG1 |
| ATOM | 2166 | HB1 | ALA | 141 | -16.138 | 0.112 | 2.153 | 1.00 | 1.22 | SEG1 |
| ATOM | 2167 | HB2 | ALA | 141 | -17.862 | 0.457 | 2.001 | 1.00 | 1.22 | SEG1 |
| ATOM | 2168 | HB3 | ALA | 141 | -17.022 | 0.807 | 3.511 | 1.00 | 1.18 | SEG1 |
| ATOM | 2169 | C | ALA | 141 | -15.958 | 3.032 | 3.040 | 1.00 | 0.61 | SEG1 |
| ATOM | 2170 | O | ALA | 141 | -16.639 | 3.641 | 3.844 | 1.00 | 0.65 | SEG1 |
| ATOM | 2171 | N | GLN | 142 | -14.646 | 3.066 | 3.090 | 1.00 | 0.61 | SEG1 |
| ATOM | 2172 | HN | GLN | 142 | -14.118 | 2.569 | 2.433 | 1.00 | 0.64 | SEG1 |
| ATOM | 2173 | CA | GLN | 142 | -13.951 | 3.862 | 4.144 | 1.00 | 0.64 | SEG1 |
| ATOM | 2174 | HA | GLN | 142 | -14.603 | 4.024 | 4.987 | 1.00 | 0.70 | SEG1 |
| ATOM | 2175 | CB | GLN | 142 | -12.756 | 3.000 | 4.564 | 1.00 | 0.65 | SEG1 |
| ATOM | 2176 | HB1 | GLN | 142 | -12.100 | 3.577 | 5.197 | 1.00 | 1.05 | SEG1 |
| ATOM | 2177 | HB2 | GLN | 142 | -12.217 | 2.678 | 3.682 | 1.00 | 1.01 | SEG1 |
| ATOM | 2178 | CG | GLN | 142 | -13.256 | 1.772 | 5.332 | 1.00 | 1.11 | SEG1 |
| ATOM | 2179 | HG1 | GLN | 142 | -14.028 | 1.279 | 4.761 | 1.00 | 1.54 | SEG1 |
| ATOM | 2180 | HG2 | GLN | 142 | -13.658 | 2.085 | 6.285 | 1.00 | 1.56 | SEG1 |
| ATOM | 2181 | CD | GLN | 142 | -12.096 | 0.798 | 5.563 | 1.00 | 1.13 | SEG1 |
| ATOM | 2182 | OE1 | GLN | 142 | -11.089 | 0.860 | 4.887 | 1.00 | 0.88 | SEG1 |
| ATOM | 2183 | NE2 | GLN | 142 | -12.200 | -0.110 | 6.496 | 1.00 | 1.49 | SEG1 |
| ATOM | 2184 | HE21 | GLN | 142 | -13.014 | -0.163 | 7.039 | 1.00 | 1.77 | SEG1 |
| ATOM | 2185 | HE22 | GLN | 142 | -11.464 | -0.737 | 6.653 | 1.00 | 1.52 | SEG1 |
| ATOM | 2186 | C | GLN | 142 | -13.480 | 5.202 | 3.566 | 1.00 | 0.65 | SEG1 |
| ATOM | 2187 | O | GLN | 142 | -12.790 | 5.247 | 2.566 | 1.00 | 0.65 | SEG1 |
| ATOM | 2188 | N | GLN | 143 | -13.855 | 6.292 | 4.190 | 1.00 | 0.74 | SEG1 |
| ATOM | 2189 | HN | GLN | 143 | -14.414 | 6.225 | 4.992 | 1.00 | 0.80 | SEG1 |
| ATOM | 2190 | CA | GLN | 143 | -13.439 | 7.636 | 3.682 | 1.00 | 0.83 | SEG1 |
| ATOM | 2191 | HA | GLN | 143 | -13.555 | 7.684 | 2.611 | 1.00 | 0.85 | SEG1 |
| ATOM | 2192 | CB | GLN | 143 | -14.388 | 8.631 | 4.353 | 1.00 | 0.97 | SEG1 |
| ATOM | 2193 | HB1 | GLN | 143 | -14.037 | 9.637 | 4.178 | 1.00 | 1.46 | SEG1 |
| ATOM | 2194 | HB2 | GLN | 143 | -14.416 | 8.439 | 5.416 | 1.00 | 1.09 | SEG1 |
| ATOM | 2195 | CG | GLN | 143 | -15.793 | 8.476 | 3.769 | 1.00 | 1.27 | SEG1 |
| ATOM | 2196 | HG1 | GLN | 143 | -16.159 | 7.480 | 3.968 | 1.00 | 1.58 | SEG1 |
| ATOM | 2197 | HG2 | GLN | 143 | -15.760 | 8.642 | 2.701 | 1.00 | 1.81 | SEG1 |
| ATOM | 2198 | CD | GLN | 143 | -16.727 | 9.499 | 4.417 | 1.00 | 1.60 | SEG1 |
| ATOM | 2199 | OE1 | GLN | 143 | -16.864 | 9.534 | 5.624 | 1.00 | 1.78 | SEG1 |
| ATOM | 2200 | NE2 | GLN | 143 | -17.377 | 10.343 | 3.663 | 1.00 | 2.32 | SEG1 |
| ATOM | 2201 | HE21 | GLN | 143 | -17.265 | 10.317 | 2.689 | 1.00 | 2.64 | SEG1 |
| ATOM | 2202 | HE22 | GLN | 143 | -17.978 | 11.002 | 4.070 | 1.00 | 2.75 | SEG1 |
| ATOM | 2203 | C | GLN | 143 | -11.984 | 7.936 | 4.075 | 1.00 | 0.85 | SEG1 |
| ATOM | 2204 | O | GLN | 143 | -11.506 | 7.443 | 5.078 | 1.00 | 0.92 | SEG1 |
| ATOM | 2205 | N | PRO | 144 | -11.317 | 8.740 | 3.272 | 1.00 | 0.88 | SEG1 |
| ATOM | 2206 | CA | PRO | 144 | -9.905 | 9.093 | 3.561 | 1.00 | 0.95 | SEG1 |
| ATOM | 2207 | HA | PRO | 144 | -9.322 | 8.206 | 3.736 | 1.00 | 1.00 | SEG1 |
| ATOM | 2208 | CB | PRO | 144 | -9.435 | 9.784 | 2.283 | 1.00 | 1.01 | SEG1 |
| ATOM | 2209 | HB1 | PRO | 144 | -8.960 | 9.074 | 1.624 | 1.00 | 1.08 | SEG1 |
| ATOM | 2210 | HB2 | PRO | 144 | -8.757 | 10.592 | 2.522 | 1.00 | 1.06 | SEG1 |
| ATOM | 2211 | CG | PRO | 144 | -10.680 | 10.315 | 1.651 | 1.00 | 1.03 | SEG1 |
| ATOM | 2212 | HG1 | PRO | 144 | -10.574 | 10.327 | 0.577 | 1.00 | 1.13 | SEG1 |
| ATOM | 2213 | HG2 | PRO | 144 | -10.882 | 11.313 | 2.015 | 1.00 | 1.06 | SEG1 |
| ATOM | 2214 | CD | PRO | 144 | -11.798 | 9.385 | 2.039 | 1.00 | 0.96 | SEG1 |
| ATOM | 2215 | HD2 | PRO | 144 | -12.705 | 9.943 | 2.228 | 1.00 | 1.00 | SEG1 |
| ATOM | 2216 | HD1 | PRO | 144 | -11.958 | 8.644 | 1.273 | 1.00 | 1.01 | SEG1 |
| ATOM | 2217 | C | PRO | 144 | -9.821 | 10.047 | 4.759 | 1.00 | 0.99 | SEG1 |
| ATOM | 2218 | O | PRO | 144 | -10.815 | 10.594 | 5.199 | 1.00 | 1.45 | SEG1 |
| ATOM | 2219 | N | ASP | 145 | -8.638 | 10.250 | 5.283 | 1.00 | 0.92 | SEG1 |
| ATOM | 2220 | HN | ASP | 145 | -7.856 | 9.800 | 4.904 | 1.00 | 1.14 | SEG1 |

FIG. 2

| | | | | | | | | | |
|---|---|---|---|---|---|---|---|---|---|
| ATOM | 2221 | CA | ASP | 145 | -8.471 | 11.168 | 6.448 | 1.00 | 1.02 | SEG1 |
| ATOM | 2222 | HA | ASP | 145 | -9.243 | 11.921 | 6.450 | 1.00 | 1.13 | SEG1 |
| ATOM | 2223 | CB | ASP | 145 | -8.505 | 10.277 | 7.683 | 1.00 | 1.23 | SEG1 |
| ATOM | 2224 | HB1 | ASP | 145 | -7.754 | 9.617 | 7.744 | 1.00 | 1.40 | SEG1 |
| ATOM | 2225 | HB2 | ASP | 145 | -9.511 | 9.693 | 7.607 | 1.00 | 1.68 | SEG1 |
| ATOM | 2226 | CG | ASP | 145 | -8.663 | 11.150 | 8.938 | 1.00 | 1.86 | SEG1 |
| ATOM | 2227 | OD1 | ASP | 145 | -9.712 | 11.193 | 9.559 | 1.00 | 2.54 | SEG1 |
| ATOM | 2228 | OD2 | ASP | 145 | -7.656 | 11.761 | 9.257 | 1.00 | 2.40 | SEG1 |
| ATOM | 2229 | C | ASP | 145 | -7.086 | 11.818 | 6.405 | 1.00 | 0.94 | SEG1 |
| ATOM | 2230 | O | ASP | 145 | -6.127 | 11.296 | 6.943 | 1.00 | 0.94 | SEG1 |
| ATOM | 2231 | N | ARG | 146 | -6.980 | 12.951 | 5.763 | 1.00 | 1.05 | SEG1 |
| ATOM | 2232 | HN | ARG | 146 | -7.770 | 13.341 | 5.337 | 1.00 | 1.19 | SEG1 |
| ATOM | 2233 | CA | ARG | 146 | -5.662 | 13.650 | 5.669 | 1.00 | 1.10 | SEG1 |
| ATOM | 2234 | HA | ARG | 146 | -4.856 | 12.934 | 5.648 | 1.00 | 1.16 | SEG1 |
| ATOM | 2235 | CB | ARG | 146 | -5.720 | 14.400 | 4.339 | 1.00 | 1.42 | SEG1 |
| ATOM | 2236 | HB1 | ARG | 146 | -4.879 | 15.074 | 4.269 | 1.00 | 1.92 | SEG1 |
| ATOM | 2237 | HB2 | ARG | 146 | -6.639 | 14.965 | 4.287 | 1.00 | 1.98 | SEG1 |
| ATOM | 2238 | CG | ARG | 146 | -5.668 | 13.403 | 3.181 | 1.00 | 1.52 | SEG1 |
| ATOM | 2239 | HG1 | ARG | 146 | -6.469 | 12.687 | 3.283 | 1.00 | 1.96 | SEG1 |
| ATOM | 2240 | HG2 | ARG | 146 | -4.719 | 12.896 | 3.193 | 1.00 | 1.91 | SEG1 |
| ATOM | 2241 | CD | ARG | 146 | -5.826 | 14.157 | 1.858 | 1.00 | 1.77 | SEG1 |
| ATOM | 2242 | HD1 | ARG | 146 | -6.739 | 14.730 | 1.864 | 1.00 | 2.23 | SEG1 |
| ATOM | 2243 | HD2 | ARG | 146 | -5.818 | 13.463 | 1.028 | 1.00 | 1.99 | SEG1 |
| ATOM | 2244 | NE | ARG | 146 | -4.645 | 15.074 | 1.789 | 1.00 | 2.23 | SEG1 |
| ATOM | 2245 | HE | ARG | 146 | -3.845 | 14.864 | 2.315 | 1.00 | 2.67 | SEG1 |
| ATOM | 2246 | CZ | ARG | 146 | -4.656 | 16.158 | 1.037 | 1.00 | 2.70 | SEG1 |
| ATOM | 2247 | NH1 | ARG | 146 | -3.598 | 16.921 | 1.010 | 1.00 | 3.55 | SEG1 |
| ATOM | 2248 | HH11 | ARG | 146 | -2.794 | 16.682 | 1.556 | 1.00 | 3.97 | SEG1 |
| ATOM | 2249 | HH12 | ARG | 146 | -3.590 | 17.746 | 0.443 | 1.00 | 3.99 | SEG1 |
| ATOM | 2250 | NH2 | ARG | 146 | -5.703 | 16.487 | 0.313 | 1.00 | 2.82 | SEG1 |
| ATOM | 2251 | HH21 | ARG | 146 | -6.522 | 15.917 | 0.317 | 1.00 | 2.74 | SEG1 |
| ATOM | 2252 | HH22 | ARG | 146 | -5.679 | 17.317 | -0.245 | 1.00 | 3.37 | SEG1 |
| ATOM | 2253 | C | ARG | 146 | -5.469 | 14.641 | 6.829 | 1.00 | 0.99 | SEG1 |
| ATOM | 2254 | O | ARG | 146 | -4.407 | 15.215 | 6.981 | 1.00 | 0.96 | SEG1 |
| ATOM | 2255 | N | LEU | 147 | -6.480 | 14.856 | 7.640 | 1.00 | 1.03 | SEG1 |
| ATOM | 2256 | HN | LEU | 147 | -7.330 | 14.391 | 7.500 | 1.00 | 1.10 | SEG1 |
| ATOM | 2257 | CA | LEU | 147 | -6.336 | 15.821 | 8.777 | 1.00 | 1.07 | SEG1 |
| ATOM | 2258 | HA | LEU | 147 | -6.140 | 16.813 | 8.406 | 1.00 | 1.17 | SEG1 |
| ATOM | 2259 | CB | LEU | 147 | -7.683 | 15.794 | 9.504 | 1.00 | 1.28 | SEG1 |
| ATOM | 2260 | HB1 | LEU | 147 | -7.603 | 16.343 | 10.431 | 1.00 | 1.65 | SEG1 |
| ATOM | 2261 | HB2 | LEU | 147 | -7.958 | 14.770 | 9.716 | 1.00 | 1.48 | SEG1 |
| ATOM | 2262 | CG | LEU | 147 | -8.755 | 16.439 | 8.625 | 1.00 | 1.81 | SEG1 |
| ATOM | 2263 | HG | LEU | 147 | -8.746 | 15.975 | 7.649 | 1.00 | 2.37 | SEG1 |
| ATOM | 2264 | CD1 | LEU | 147 | -10.128 | 16.239 | 9.268 | 1.00 | 2.27 | SEG1 |
| ATOM | 2265 | HD11 | LEU | 147 | -10.862 | 16.833 | 8.743 | 1.00 | 2.67 | SEG1 |
| ATOM | 2266 | HD12 | LEU | 147 | -10.089 | 16.548 | 10.302 | 1.00 | 2.60 | SEG1 |
| ATOM | 2267 | HD13 | LEU | 147 | -10.403 | 15.197 | 9.214 | 1.00 | 2.67 | SEG1 |
| ATOM | 2268 | CD2 | LEU | 147 | -8.471 | 17.936 | 8.485 | 1.00 | 2.31 | SEG1 |
| ATOM | 2269 | HD21 | LEU | 147 | -9.400 | 18.467 | 8.341 | 1.00 | 2.50 | SEG1 |
| ATOM | 2270 | HD22 | LEU | 147 | -7.827 | 18.103 | 7.634 | 1.00 | 2.84 | SEG1 |
| ATOM | 2271 | HD23 | LEU | 147 | -7.985 | 18.296 | 9.380 | 1.00 | 2.68 | SEG1 |
| ATOM | 2272 | C | LEU | 147 | -5.217 | 15.372 | 9.720 | 1.00 | 0.95 | SEG1 |
| ATOM | 2273 | O | LEU | 147 | -4.415 | 16.168 | 10.171 | 1.00 | 1.02 | SEG1 |
| ATOM | 2274 | N | ARG | 148 | -5.166 | 14.103 | 10.020 | 1.00 | 0.90 | SEG1 |
| ATOM | 2275 | HN | ARG | 148 | -5.829 | 13.489 | 9.643 | 1.00 | 0.90 | SEG1 |
| ATOM | 2276 | CA | ARG | 148 | -4.108 | 13.582 | 10.939 | 1.00 | 1.02 | SEG1 |
| ATOM | 2277 | HA | ARG | 148 | -3.994 | 14.241 | 11.785 | 1.00 | 1.19 | SEG1 |
| ATOM | 2278 | CB | ARG | 148 | -4.616 | 12.221 | 11.414 | 1.00 | 1.08 | SEG1 |
| ATOM | 2279 | HB1 | ARG | 148 | -3.828 | 11.707 | 11.943 | 1.00 | 1.58 | SEG1 |
| ATOM | 2280 | HB2 | ARG | 148 | -4.920 | 11.632 | 10.560 | 1.00 | 1.16 | SEG1 |
| ATOM | 2281 | CG | ARG | 148 | -5.809 | 12.416 | 12.349 | 1.00 | 1.69 | SEG1 |
| ATOM | 2282 | HG1 | ARG | 148 | -6.602 | 12.921 | 11.818 | 1.00 | 2.05 | SEG1 |
| ATOM | 2283 | HG2 | ARG | 148 | -5.507 | 13.011 | 13.198 | 1.00 | 2.34 | SEG1 |
| ATOM | 2284 | CD | ARG | 148 | -6.309 | 11.052 | 12.827 | 1.00 | 1.94 | SEG1 |
| ATOM | 2285 | HD1 | ARG | 148 | -5.530 | 10.532 | 13.364 | 1.00 | 2.37 | SEG1 |
| ATOM | 2286 | HD2 | ARG | 148 | -6.650 | 10.461 | 11.987 | 1.00 | 2.25 | SEG1 |
| ATOM | 2287 | NE | ARG | 148 | -7.443 | 11.363 | 13.746 | 1.00 | 2.31 | SEG1 |
| ATOM | 2288 | HE | ARG | 148 | -8.363 | 11.204 | 13.446 | 1.00 | 2.69 | SEG1 |
| ATOM | 2289 | CZ | ARG | 148 | -7.232 | 11.843 | 14.957 | 1.00 | 2.75 | SEG1 |
| ATOM | 2290 | NH1 | ARG | 148 | -8.253 | 12.092 | 15.731 | 1.00 | 3.51 | SEG1 |
| ATOM | 2291 | HH11 | ARG | 148 | -9.181 | 11.918 | 15.404 | 1.00 | 3.86 | SEG1 |
| ATOM | 2292 | HH12 | ARG | 148 | -8.106 | 12.458 | 16.650 | 1.00 | 3.96 | SEG1 |
| ATOM | 2293 | NH2 | ARG | 148 | -6.018 | 12.081 | 15.402 | 1.00 | 2.95 | SEG1 |
| ATOM | 2294 | HH21 | ARG | 148 | -5.222 | 11.899 | 14.825 | 1.00 | 2.88 | SEG1 |
| ATOM | 2295 | HH22 | ARG | 148 | -5.890 | 12.446 | 16.324 | 1.00 | 3.50 | SEG1 |
| ATOM | 2296 | C | ARG | 148 | -2.769 | 13.418 | 10.215 | 1.00 | 1.06 | SEG1 |
| ATOM | 2297 | O | ARG | 148 | -1.730 | 13.342 | 10.844 | 1.00 | 1.28 | SEG1 |

FIG. 2

| | | | | | | | | | | |
|---|---|---|---|---|---|---|---|---|---|---|
| ATOM | 2298 | N | ASP | 149 | -2.782 | 13.330 | 8.904 | 1.00 | 1.01 | SEG1 |
| ATOM | 2299 | HN | ASP | 149 | -3.631 | 13.370 | 9.423 | 1.00 | 0.94 | SEG1 |
| ATOM | 2300 | CA | ASP | 149 | -1.501 | 13.135 | 8.164 | 1.00 | 1.21 | SEG1 |
| ATOM | 2301 | HA | ASP | 149 | -0.688 | 12.999 | 8.853 | 1.00 | 1.42 | SEG1 |
| ATOM | 2302 | CB | ASP | 149 | -1.708 | 11.849 | 7.361 | 1.00 | 1.48 | SEG1 |
| ATOM | 2303 | HB1 | ASP | 149 | -0.862 | 11.692 | 6.711 | 1.00 | 1.86 | SEG1 |
| ATOM | 2304 | HB2 | ASP | 149 | -2.606 | 11.938 | 6.767 | 1.00 | 1.80 | SEG1 |
| ATOM | 2305 | CG | ASP | 149 | -1.843 | 10.655 | 8.316 | 1.00 | 1.62 | SEG1 |
| ATOM | 2306 | OD1 | ASP | 149 | -2.324 | 9.624 | 7.874 | 1.00 | 2.12 | SEG1 |
| ATOM | 2307 | OD2 | ASP | 149 | -1.471 | 10.790 | 9.473 | 1.00 | 2.10 | SEG1 |
| ATOM | 2308 | C | ASP | 149 | -1.205 | 14.314 | 7.233 | 1.00 | 1.03 | SEG1 |
| ATOM | 2309 | O | ASP | 149 | -0.684 | 14.133 | 6.147 | 1.00 | 0.90 | SEG1 |
| ATOM | 2310 | N | GLU | 150 | -1.521 | 15.516 | 7.646 | 1.00 | 1.07 | SEG1 |
| ATOM | 2311 | HN | GLU | 150 | -1.934 | 15.638 | 8.527 | 1.00 | 1.23 | SEG1 |
| ATOM | 2312 | CA | GLU | 150 | -1.242 | 16.703 | 6.776 | 1.00 | 0.95 | SEG1 |
| ATOM | 2313 | HA | GLU | 150 | -1.797 | 16.629 | 5.855 | 1.00 | 0.95 | SEG1 |
| ATOM | 2314 | CB | GLU | 150 | -1.718 | 17.917 | 7.574 | 1.00 | 1.11 | SEG1 |
| ATOM | 2315 | HB1 | GLU | 150 | -1.378 | 18.821 | 7.092 | 1.00 | 1.44 | SEG1 |
| ATOM | 2316 | HB2 | GLU | 150 | -1.315 | 17.869 | 8.576 | 1.00 | 1.75 | SEG1 |
| ATOM | 2317 | CG | GLU | 150 | -3.246 | 17.919 | 7.638 | 1.00 | 1.35 | SEG1 |
| ATOM | 2318 | HG1 | GLU | 150 | -3.589 | 17.017 | 8.120 | 1.00 | 1.98 | SEG1 |
| ATOM | 2319 | HG2 | GLU | 150 | -3.646 | 17.968 | 6.635 | 1.00 | 1.71 | SEG1 |
| ATOM | 2320 | CD | GLU | 150 | -3.720 | 19.135 | 8.436 | 1.00 | 1.41 | SEG1 |
| ATOM | 2321 | OE1 | GLU | 150 | -3.787 | 19.033 | 9.650 | 1.00 | 1.66 | SEG1 |
| ATOM | 2322 | OE2 | GLU | 150 | -4.008 | 20.148 | 7.819 | 1.00 | 1.91 | SEG1 |
| ATOM | 2323 | C | GLU | 150 | 0.260 | 16.808 | 6.485 | 1.00 | 0.77 | SEG1 |
| ATOM | 2324 | O | GLU | 150 | 0.661 | 17.120 | 5.380 | 1.00 | 0.66 | SEG1 |
| ATOM | 2325 | N | GLU | 151 | 1.092 | 16.546 | 7.466 | 1.00 | 0.79 | SEG1 |
| ATOM | 2326 | HN | GLU | 151 | 0.744 | 16.293 | 8.347 | 1.00 | 0.90 | SEG1 |
| ATOM | 2327 | CA | GLU | 151 | 2.571 | 16.627 | 7.239 | 1.00 | 0.70 | SEG1 |
| ATOM | 2328 | HA | GLU | 151 | 2.853 | 17.630 | 6.967 | 1.00 | 0.73 | SEG1 |
| ATOM | 2329 | CB | GLU | 151 | 3.216 | 16.244 | 8.573 | 1.00 | 0.82 | SEG1 |
| ATOM | 2330 | HB1 | GLU | 151 | 4.279 | 16.114 | 8.434 | 1.00 | 1.27 | SEG1 |
| ATOM | 2331 | HB2 | GLU | 151 | 2.783 | 15.321 | 8.931 | 1.00 | 1.15 | SEG1 |
| ATOM | 2332 | CG | GLU | 151 | 2.971 | 17.356 | 9.600 | 1.00 | 1.41 | SEG1 |
| ATOM | 2333 | HG1 | GLU | 151 | 1.909 | 17.490 | 9.736 | 1.00 | 1.98 | SEG1 |
| ATOM | 2334 | HG2 | GLU | 151 | 3.404 | 18.277 | 9.239 | 1.00 | 1.90 | SEG1 |
| ATOM | 2335 | CD | GLU | 151 | 3.613 | 16.988 | 10.948 | 1.00 | 1.66 | SEG1 |
| ATOM | 2336 | OE1 | GLU | 151 | 3.401 | 17.725 | 11.898 | 1.00 | 2.04 | SEG1 |
| ATOM | 2337 | OE2 | GLU | 151 | 4.305 | 15.982 | 11.012 | 1.00 | 2.22 | SEG1 |
| ATOM | 2338 | C | GLU | 151 | 2.990 | 15.643 | 6.144 | 1.00 | 0.54 | SEG1 |
| ATOM | 2339 | O | GLU | 151 | 3.816 | 15.950 | 5.305 | 1.00 | 0.48 | SEG1 |
| ATOM | 2340 | N | LEU | 152 | 2.415 | 14.468 | 6.142 | 1.00 | 0.54 | SEG1 |
| ATOM | 2341 | HN | LEU | 152 | 1.747 | 14.252 | 6.825 | 1.00 | 0.63 | SEG1 |
| ATOM | 2342 | CA | LEU | 152 | 2.764 | 13.460 | 5.097 | 1.00 | 0.46 | SEG1 |
| ATOM | 2343 | HA | LEU | 152 | 3.830 | 13.295 | 5.078 | 1.00 | 0.44 | SEG1 |
| ATOM | 2344 | CB | LEU | 152 | 2.046 | 12.171 | 5.499 | 1.00 | 0.55 | SEG1 |
| ATOM | 2345 | HB1 | LEU | 152 | 2.098 | 11.463 | 4.686 | 1.00 | 0.56 | SEG1 |
| ATOM | 2346 | HB2 | LEU | 152 | 1.011 | 12.390 | 5.717 | 1.00 | 0.63 | SEG1 |
| ATOM | 2347 | CG | LEU | 152 | 2.710 | 11.569 | 6.736 | 1.00 | 0.59 | SEG1 |
| ATOM | 2348 | HG | LEU | 152 | 2.753 | 12.310 | 7.522 | 1.00 | 0.62 | SEG1 |
| ATOM | 2349 | CD1 | LEU | 152 | 1.897 | 10.365 | 7.209 | 1.00 | 0.70 | SEG1 |
| ATOM | 2350 | HD11 | LEU | 152 | 0.850 | 10.538 | 7.013 | 1.00 | 1.18 | SEG1 |
| ATOM | 2351 | HD12 | LEU | 152 | 2.046 | 10.223 | 8.269 | 1.00 | 1.17 | SEG1 |
| ATOM | 2352 | HD13 | LEU | 152 | 2.222 | 9.481 | 6.677 | 1.00 | 1.38 | SEG1 |
| ATOM | 2353 | CD2 | LEU | 152 | 4.126 | 11.112 | 6.379 | 1.00 | 0.56 | SEG1 |
| ATOM | 2354 | HD21 | LEU | 152 | 4.492 | 10.443 | 7.144 | 1.00 | 1.07 | SEG1 |
| ATOM | 2355 | HD22 | LEU | 152 | 4.777 | 11.971 | 6.311 | 1.00 | 1.17 | SEG1 |
| ATOM | 2356 | HD23 | LEU | 152 | 4.108 | 10.596 | 5.430 | 1.00 | 1.20 | SEG1 |
| ATOM | 2357 | C | LEU | 152 | 2.278 | 13.931 | 3.728 | 1.00 | 0.46 | SEG1 |
| ATOM | 2358 | O | LEU | 152 | 2.925 | 13.708 | 2.725 | 1.00 | 0.46 | SEG1 |
| ATOM | 2359 | N | ALA | 153 | 1.138 | 14.577 | 3.682 | 1.00 | 0.54 | SEG1 |
| ATOM | 2360 | HN | ALA | 153 | 0.636 | 14.739 | 4.509 | 1.00 | 0.57 | SEG1 |
| ATOM | 2361 | CA | ALA | 153 | 0.599 | 15.060 | 2.371 | 1.00 | 0.61 | SEG1 |
| ATOM | 2362 | HA | ALA | 153 | 0.408 | 14.225 | 1.715 | 1.00 | 0.65 | SEG1 |
| ATOM | 2363 | CB | ALA | 153 | -0.713 | 15.771 | 2.711 | 1.00 | 0.71 | SEG1 |
| ATOM | 2364 | HB1 | ALA | 153 | -1.536 | 15.081 | 2.600 | 1.00 | 1.20 | SEG1 |
| ATOM | 2365 | HB2 | ALA | 153 | -0.851 | 16.609 | 2.043 | 1.00 | 1.25 | SEG1 |
| ATOM | 2366 | HB3 | ALA | 153 | -0.676 | 16.126 | 3.730 | 1.00 | 1.26 | SEG1 |
| ATOM | 2367 | C | ALA | 153 | 1.587 | 16.033 | 1.723 | 1.00 | 0.58 | SEG1 |
| ATOM | 2368 | O | ALA | 153 | 1.810 | 15.997 | 0.527 | 1.00 | 0.63 | SEG1 |
| ATOM | 2369 | N | GLU | 154 | 2.191 | 16.893 | 2.502 | 1.00 | 0.53 | SEG1 |
| ATOM | 2370 | HN | GLU | 154 | 2.005 | 16.899 | 3.464 | 1.00 | 0.52 | SEG1 |
| ATOM | 2371 | CA | GLU | 154 | 3.183 | 17.844 | 1.924 | 1.00 | 0.55 | SEG1 |
| ATOM | 2372 | HA | GLU | 154 | 2.764 | 18.359 | 1.073 | 1.00 | 0.62 | SEG1 |
| ATOM | 2373 | CB | GLU | 154 | 3.501 | 18.837 | 3.044 | 1.00 | 0.56 | SEG1 |
| ATOM | 2374 | HB1 | GLU | 154 | 4.339 | 19.451 | 2.752 | 1.00 | 1.06 | SEG1 |

FIG. 2

| | | | | | | | | | |
|---|---|---|---|---|---|---|---|---|---|
| ATOM | 2375 | HE2 | GLU | 154 | 3.748 | 18.294 | 3.945 | 1.00 | 0.99 | SEG1 |
| ATOM | 2376 | CG | GLU | 154 | 2.283 | 19.729 | 3.300 | 1.00 | 1.00 | SEG1 |
| ATOM | 2377 | HG1 | GLU | 154 | 1.446 | 19.112 | 3.592 | 1.00 | 1.52 | SEG1 |
| ATOM | 2378 | HG2 | GLU | 154 | 2.034 | 20.265 | 2.396 | 1.00 | 1.58 | SEG1 |
| ATOM | 2379 | CD | GLU | 154 | 2.583 | 20.733 | 4.423 | 1.00 | 1.17 | SEG1 |
| ATOM | 2380 | OE1 | GLU | 154 | 1.777 | 21.631 | 4.612 | 1.00 | 1.60 | SEG1 |
| ATOM | 2381 | OE2 | GLU | 154 | 3.606 | 20.591 | 5.077 | 1.00 | 1.77 | SEG1 |
| ATOM | 2382 | C | GLU | 154 | 4.440 | 17.073 | 1.519 | 1.00 | 0.51 | SEG1 |
| ATOM | 2383 | O | GLU | 154 | 5.039 | 17.330 | 0.491 | 1.00 | 0.55 | SEG1 |
| ATOM | 2384 | N | LEU | 155 | 4.839 | 16.127 | 2.332 | 1.00 | 0.45 | SEG1 |
| ATOM | 2385 | HN | LEU | 155 | 4.332 | 15.950 | 3.153 | 1.00 | 0.44 | SEG1 |
| ATOM | 2386 | CA | LEU | 155 | 6.059 | 15.323 | 2.021 | 1.00 | 0.43 | SEG1 |
| ATOM | 2387 | HA | LEU | 155 | 6.921 | 15.964 | 1.958 | 1.00 | 0.47 | SEG1 |
| ATOM | 2388 | CB | LEU | 155 | 6.213 | 14.356 | 3.202 | 1.00 | 0.40 | SEG1 |
| ATOM | 2389 | HB1 | LEU | 155 | 5.335 | 13.731 | 3.270 | 1.00 | 0.40 | SEG1 |
| ATOM | 2390 | HB2 | LEU | 155 | 6.324 | 14.921 | 4.116 | 1.00 | 0.43 | SEG1 |
| ATOM | 2391 | CG | LEU | 155 | 7.447 | 13.473 | 2.994 | 1.00 | 0.42 | SEG1 |
| ATOM | 2392 | HG | LEU | 155 | 8.195 | 14.025 | 2.445 | 1.00 | 0.51 | SEG1 |
| ATOM | 2393 | CD1 | LEU | 155 | 8.016 | 13.060 | 4.353 | 1.00 | 0.42 | SEG1 |
| ATOM | 2394 | HD11 | LEU | 155 | 7.475 | 12.202 | 4.724 | 1.00 | 1.09 | SEG1 |
| ATOM | 2395 | HD12 | LEU | 155 | 7.914 | 13.875 | 5.050 | 1.00 | 1.01 | SEG1 |
| ATOM | 2396 | HD13 | LEU | 155 | 9.060 | 12.808 | 4.244 | 1.00 | 1.13 | SEG1 |
| ATOM | 2397 | CD2 | LEU | 155 | 7.054 | 12.221 | 2.208 | 1.00 | 0.51 | SEG1 |
| ATOM | 2398 | HD21 | LEU | 155 | 6.036 | 11.950 | 2.447 | 1.00 | 1.03 | SEG1 |
| ATOM | 2399 | HD22 | LEU | 155 | 7.714 | 11.408 | 2.472 | 1.00 | 1.18 | SEG1 |
| ATOM | 2400 | HD23 | LEU | 155 | 7.134 | 12.420 | 1.150 | 1.00 | 1.19 | SEG1 |
| ATOM | 2401 | C | LEU | 155 | 5.875 | 14.554 | 0.709 | 1.00 | 0.46 | SEG1 |
| ATOM | 2402 | O | LEU | 155 | 6.720 | 14.597 | -0.165 | 1.00 | 0.51 | SEG1 |
| ATOM | 2403 | N | GLU | 156 | 4.777 | 13.851 | 0.568 | 1.00 | 0.48 | SEG1 |
| ATOM | 2404 | HN | GLU | 156 | 4.115 | 13.832 | 1.289 | 1.00 | 0.47 | SEG1 |
| ATOM | 2405 | CA | GLU | 156 | 4.543 | 13.076 | -0.689 | 1.00 | 0.55 | SEG1 |
| ATOM | 2406 | HA | GLU | 156 | 5.339 | 12.362 | -0.829 | 1.00 | 0.54 | SEG1 |
| ATOM | 2407 | CB | GLU | 156 | 3.215 | 12.329 | -0.491 | 1.00 | 0.60 | SEG1 |
| ATOM | 2408 | HB1 | GLU | 156 | 3.292 | 11.687 | 0.374 | 1.00 | 0.58 | SEG1 |
| ATOM | 2409 | HB2 | GLU | 156 | 3.011 | 11.728 | -1.365 | 1.00 | 0.68 | SEG1 |
| ATOM | 2410 | CG | GLU | 156 | 2.070 | 13.318 | -0.281 | 1.00 | 0.64 | SEG1 |
| ATOM | 2411 | HG1 | GLU | 156 | 2.015 | 13.994 | -1.120 | 1.00 | 0.72 | SEG1 |
| ATOM | 2412 | HG2 | GLU | 156 | 2.245 | 13.874 | 0.623 | 1.00 | 0.57 | SEG1 |
| ATOM | 2413 | CD | GLU | 156 | 0.751 | 12.553 | -0.159 | 1.00 | 0.74 | SEG1 |
| ATOM | 2414 | OE1 | GLU | 156 | 0.015 | 12.523 | -1.132 | 1.00 | 1.30 | SEG1 |
| ATOM | 2415 | OE2 | GLU | 156 | 0.500 | 12.011 | 0.904 | 1.00 | 1.37 | SEG1 |
| ATOM | 2416 | C | GLU | 156 | 4.478 | 14.025 | -1.889 | 1.00 | 0.63 | SEG1 |
| ATOM | 2417 | O | GLU | 156 | 4.938 | 13.700 | -2.968 | 1.00 | 0.67 | SEG1 |
| ATOM | 2418 | N | ASP | 157 | 3.922 | 15.199 | -1.707 | 1.00 | 0.66 | SEG1 |
| ATOM | 2419 | HN | ASP | 157 | 3.566 | 15.441 | -0.826 | 1.00 | 0.63 | SEG1 |
| ATOM | 2420 | CA | ASP | 157 | 3.842 | 16.169 | -2.842 | 1.00 | 0.76 | SEG1 |
| ATOM | 2421 | HA | ASP | 157 | 3.408 | 15.697 | -3.708 | 1.00 | 0.81 | SEG1 |
| ATOM | 2422 | CB | ASP | 157 | 2.940 | 17.304 | -2.351 | 1.00 | 0.81 | SEG1 |
| ATOM | 2423 | HB1 | ASP | 157 | 2.980 | 18.123 | -3.053 | 1.00 | 0.88 | SEG1 |
| ATOM | 2424 | HB2 | ASP | 157 | 3.283 | 17.644 | -1.384 | 1.00 | 0.76 | SEG1 |
| ATOM | 2425 | CG | ASP | 157 | 1.496 | 16.805 | -2.235 | 1.00 | 0.84 | SEG1 |
| ATOM | 2426 | OD1 | ASP | 157 | 1.133 | 15.914 | -2.985 | 1.00 | 1.26 | SEG1 |
| ATOM | 2427 | OD2 | ASP | 157 | 0.778 | 17.324 | -1.397 | 1.00 | 1.49 | SEG1 |
| ATOM | 2428 | C | ASP | 157 | 5.237 | 16.691 | -3.171 | 1.00 | 0.76 | SEG1 |
| ATOM | 2429 | O | ASP | 157 | 5.597 | 16.841 | -4.323 | 1.00 | 0.82 | SEG1 |
| ATOM | 2430 | N | ALA | 158 | 6.029 | 16.950 | -2.165 | 1.00 | 0.70 | SEG1 |
| ATOM | 2431 | HN | ALA | 158 | 5.714 | 16.806 | -1.247 | 1.00 | 0.66 | SEG1 |
| ATOM | 2432 | CA | ALA | 158 | 7.414 | 17.444 | -2.412 | 1.00 | 0.74 | SEG1 |
| ATOM | 2433 | HA | ALA | 158 | 7.396 | 18.312 | -3.051 | 1.00 | 0.82 | SEG1 |
| ATOM | 2434 | CB | ALA | 158 | 7.969 | 17.814 | -1.034 | 1.00 | 0.72 | SEG1 |
| ATOM | 2435 | HB1 | ALA | 158 | 7.160 | 18.133 | -0.394 | 1.00 | 1.34 | SEG1 |
| ATOM | 2436 | HB2 | ALA | 158 | 8.684 | 18.617 | -1.138 | 1.00 | 1.21 | SEG1 |
| ATOM | 2437 | HB3 | ALA | 158 | 8.455 | 16.954 | -0.599 | 1.00 | 1.17 | SEG1 |
| ATOM | 2438 | C | ALA | 158 | 8.240 | 16.325 | -3.050 | 1.00 | 0.70 | SEG1 |
| ATOM | 2439 | O | ALA | 158 | 9.052 | 16.559 | -3.926 | 1.00 | 0.77 | SEG1 |
| ATOM | 2440 | N | LEU | 159 | 8.031 | 15.109 | -2.612 | 1.00 | 0.62 | SEG1 |
| ATOM | 2441 | HN | LEU | 159 | 7.369 | 14.957 | -1.905 | 1.00 | 0.58 | SEG1 |
| ATOM | 2442 | CA | LEU | 159 | 8.797 | 13.956 | -3.181 | 1.00 | 0.60 | SEG1 |
| ATOM | 2443 | HA | LEU | 159 | 9.850 | 14.072 | -2.989 | 1.00 | 0.63 | SEG1 |
| ATOM | 2444 | CB | LEU | 159 | 8.265 | 12.717 | -2.448 | 1.00 | 0.53 | SEG1 |
| ATOM | 2445 | HB1 | LEU | 159 | 7.206 | 12.617 | -2.633 | 1.00 | 0.53 | SEG1 |
| ATOM | 2446 | HB2 | LEU | 159 | 8.437 | 12.825 | -1.388 | 1.00 | 0.51 | SEG1 |
| ATOM | 2447 | CG | LEU | 159 | 8.988 | 11.465 | -2.956 | 1.00 | 0.54 | SEG1 |
| ATOM | 2448 | HG | LEU | 159 | 8.963 | 11.453 | -4.037 | 1.00 | 0.65 | SEG1 |
| ATOM | 2449 | CD1 | LEU | 159 | 10.446 | 11.479 | -2.482 | 1.00 | 0.76 | SEG1 |
| ATOM | 2450 | HD11 | LEU | 159 | 10.731 | 12.485 | -2.214 | 1.00 | 1.37 | SEG1 |
| ATOM | 2451 | HD12 | LEU | 159 | 11.086 | 11.124 | -3.276 | 1.00 | 1.37 | SEG1 |

```
ATOM   2452 HD13 LEU   159    10.552  10.835  -1.621  1.00  1.16      SEG1
ATOM   2453  CD2 LEU   159     8.283  10.221  -2.416  1.00  0.58      SEG1
ATOM   2454 HD21 LEU   159     8.485  10.124  -1.360  1.00  1.22      SEG1
ATOM   2455 HD22 LEU   159     8.647   9.347  -2.935  1.00  1.13      SEG1
ATOM   2456 HD23 LEU   159     7.218  10.315  -2.572  1.00  1.21      SEG1
ATOM   2457   C  LEU   159     8.534  13.836  -4.686  1.00  0.67      SEG1
ATOM   2458   O  LEU   159     9.438  13.579  -5.460  1.00  0.71      SEG1
ATOM   2459   N  ARG   160     7.303  14.019  -5.111  1.00  0.70      SEG1
ATOM   2460  HN  ARG   160     6.589  14.224  -4.467  1.00  0.68      SEG1
ATOM   2461  CA  ARG   160     6.988  13.912  -6.572  1.00  0.80      SEG1
ATOM   2462  HA  ARG   160     7.205  12.921  -6.932  1.00  0.80      SEG1
ATOM   2463  CB  ARG   160     5.486  14.197  -6.687  1.00  0.86      SEG1
ATOM   2464  HB1 ARG   160     5.277  15.186  -6.310  1.00  1.08      SEG1
ATOM   2465  HB2 ARG   160     4.938  13.467  -6.108  1.00  1.05      SEG1
ATOM   2466  CG  ARG   160     5.054  14.112  -8.156  1.00  1.22      SEG1
ATOM   2467  HG1 ARG   160     5.258  13.121  -8.533  1.00  1.67      SEG1
ATOM   2468  HG2 ARG   160     5.604  14.839  -8.736  1.00  1.51      SEG1
ATOM   2469  CD  ARG   160     3.552  14.396  -8.264  1.00  1.41      SEG1
ATOM   2470  HD1 ARG   160     3.334  15.392  -7.911  1.00  1.63      SEG1
ATOM   2471  HD2 ARG   160     2.992  13.665  -7.699  1.00  1.87      SEG1
ATOM   2472  NE  ARG   160     3.230  14.290  -9.723  1.00  1.88      SEG1
ATOM   2473  HE  ARG   160     3.876  13.972 -10.330  1.00  2.40      SEG1
ATOM   2474  CZ  ARG   160     2.091  14.750 -10.208  1.00  2.25      SEG1
ATOM   2475  NH1 ARG   160     1.851  14.638 -11.487  1.00  3.04      SEG1
ATOM   2476 HH11 ARG   160     2.525  14.208 -12.087  1.00  3.44      SEG1
ATOM   2477 HH12 ARG   160     0.992  14.983 -11.865  1.00  3.46      SEG1
ATOM   2478  NH2 ARG   160     1.193  15.318  -9.436  1.00  2.40      SEG1
ATOM   2479 HH21 ARG   160     1.357  15.414  -8.455  1.00  2.30      SEG1
ATOM   2480 HH22 ARG   160     0.340  15.656  -9.833  1.00  2.98      SEG1
ATOM   2481   C  ARG   160     7.800  14.953  -7.354  1.00  0.90      SEG1
ATOM   2482   O  ARG   160     8.332  14.673  -8.412  1.00  0.97      SEG1
ATOM   2483   N  ASN   161     7.904  16.145  -6.827  1.00  0.92      SEG1
ATOM   2484  HN  ASN   161     7.470  16.332  -5.969  1.00  0.87      SEG1
ATOM   2485  CA  ASN   161     8.690  17.214  -7.516  1.00  1.04      SEG1
ATOM   2486  HA  ASN   161     8.312  17.378  -8.511  1.00  1.11      SEG1
ATOM   2487  CB  ASN   161     8.495  18.472  -6.666  1.00  1.08      SEG1
ATOM   2488  HB1 ASN   161     9.172  19.244  -7.002  1.00  1.35      SEG1
ATOM   2489  HB2 ASN   161     8.697  18.241  -5.631  1.00  1.08      SEG1
ATOM   2490  CG  ASN   161     7.053  18.966  -6.806  1.00  1.59      SEG1
ATOM   2491  OD1 ASN   161     6.414  18.733  -7.812  1.00  2.33      SEG1
ATOM   2492  ND2 ASN   161     6.510  19.642  -5.831  1.00  1.73      SEG1
ATOM   2493 HD21 ASN   161     7.024  19.827  -5.017  1.00  1.70      SEG1
ATOM   2494 HD22 ASN   161     5.588  19.967  -5.913  1.00  2.23      SEG1
ATOM   2495   C  ASN   161    10.169  16.820  -7.563  1.00  1.05      SEG1
ATOM   2496   O  ASN   161    10.850  17.034  -8.548  1.00  1.13      SEG1
ATOM   2497   N  LEU   162    10.663  16.249  -6.497  1.00  0.97      SEG1
ATOM   2498  HN  LEU   162    10.083  16.096  -5.722  1.00  0.90      SEG1
ATOM   2499  CA  LEU   162    12.099  15.831  -6.451  1.00  1.01      SEG1
ATOM   2500  HA  LEU   162    12.742  16.692  -6.547  1.00  1.10      SEG1
ATOM   2501  CB  LEU   162    12.285  15.190  -5.070  1.00  0.95      SEG1
ATOM   2502  HB1 LEU   162    11.617  14.348  -4.973  1.00  1.27      SEG1
ATOM   2503  HB2 LEU   162    12.059  15.918  -4.305  1.00  1.20      SEG1
ATOM   2504  CG  LEU   162    13.732  14.713  -4.908  1.00  1.50      SEG1
ATOM   2505  HG  LEU   162    13.999  14.089  -5.749  1.00  2.22      SEG1
ATOM   2506  CD1 LEU   162    14.672  15.917  -4.852  1.00  1.92      SEG1
ATOM   2507 HD11 LEU   162    15.695  15.573  -4.813  1.00  2.34      SEG1
ATOM   2508 HD12 LEU   162    14.454  16.503  -3.971  1.00  2.30      SEG1
ATOM   2509 HD13 LEU   162    14.531  16.525  -5.732  1.00  2.35      SEG1
ATOM   2510  CD2 LEU   162    13.861  13.906  -3.613  1.00  1.89      SEG1
ATOM   2511 HD21 LEU   162    13.042  13.207  -3.541  1.00  2.44      SEG1
ATOM   2512 HD22 LEU   162    13.837  14.577  -2.766  1.00  2.30      SEG1
ATOM   2513 HD23 LEU   162    14.796  13.366  -3.618  1.00  2.12      SEG1
ATOM   2514   C  LEU   162    12.398  14.813  -7.555  1.00  1.00      SEG1
ATOM   2515   O  LEU   162    13.418  14.886  -8.215  1.00  1.08      SEG1
ATOM   2516   N  LYS   163    11.522  13.861  -7.751  1.00  0.94      SEG1
ATOM   2517  HN  LYS   163    10.711  13.821  -7.201  1.00  0.89      SEG1
ATOM   2518  CA  LYS   163    11.759  12.833  -8.808  1.00  0.96      SEG1
ATOM   2519  HA  LYS   163    12.800  12.550  -8.828  1.00  0.98      SEG1
ATOM   2520  CB  LYS   163    10.900  11.630  -8.406  1.00  0.95      SEG1
ATOM   2521  HB1 LYS   163     9.858  11.914  -8.413  1.00  1.38      SEG1
ATOM   2522  HB2 LYS   163    11.177  11.301  -7.414  1.00  1.07      SEG1
ATOM   2523  CG  LYS   163    11.120  10.491  -9.408  1.00  1.47      SEG1
ATOM   2524  HG1 LYS   163    12.163  10.211  -9.416  1.00  1.90      SEG1
ATOM   2525  HG2 LYS   163    10.830  10.822 -10.395  1.00  2.04      SEG1
ATOM   2526  CD  LYS   163    10.271   9.282  -9.007  1.00  1.66      SEG1
ATOM   2527  HD1 LYS   163     9.224   9.543  -9.061  1.00  1.94      SEG1
ATOM   2528  HD2 LYS   163    10.519   8.991  -7.997  1.00  1.60      SEG1
```

FIG. 2

| ATOM | 2529 | CE | LYS | 163 | 10.552 | 8.113 | -9.956 | 1.00 | 2.53 | SEG1 |
| --- | --- | --- | --- | --- | --- | --- | --- | --- | --- | --- |
| ATOM | 2530 | HE1 | LYS | 163 | 11.609 | 8.036 | -10.153 | 1.00 | 2.77 | SEG1 |
| ATOM | 2531 | HE2 | LYS | 163 | 9.998 | 8.236 | -10.878 | 1.00 | 3.08 | SEG1 |
| ATOM | 2532 | NZ | LYS | 163 | 10.082 | 6.907 | -9.219 | 1.00 | 3.06 | SEG1 |
| ATOM | 2533 | HZ1 | LYS | 163 | 9.068 | 7.001 | -9.011 | 1.00 | 3.11 | SEG1 |
| ATOM | 2534 | HZ2 | LYS | 163 | 10.613 | 6.819 | -8.328 | 1.00 | 3.52 | SEG1 |
| ATOM | 2535 | HZ3 | LYS | 163 | 10.237 | 6.061 | -9.802 | 1.00 | 3.54 | SEG1 |
| ATOM | 2536 | C | LYS | 163 | 11.325 | 13.370 | -10.172 | 1.00 | 1.08 | SEG1 |
| ATOM | 2537 | O | LYS | 163 | 10.223 | 13.858 | -10.332 | 1.00 | 1.51 | SEG1 |
| ATOM | 2538 | N | CYS | 164 | 12.185 | 13.278 | -11.154 | 1.00 | 1.37 | SEG1 |
| ATOM | 2539 | HN | CYS | 164 | 13.065 | 12.878 | -10.996 | 1.00 | 1.81 | SEG1 |
| ATOM | 2540 | CA | CYS | 164 | 11.828 | 13.776 | -12.516 | 1.00 | 1.52 | SEG1 |
| ATOM | 2541 | HA | CYS | 164 | 11.144 | 14.606 | -12.448 | 1.00 | 1.31 | SEG1 |
| ATOM | 2542 | CB | CYS | 164 | 13.149 | 14.234 | -13.135 | 1.00 | 2.17 | SEG1 |
| ATOM | 2543 | HB1 | CYS | 164 | 13.791 | 13.377 | -13.285 | 1.00 | 2.58 | SEG1 |
| ATOM | 2544 | HB2 | CYS | 164 | 13.634 | 14.936 | -12.472 | 1.00 | 2.61 | SEG1 |
| ATOM | 2545 | SG | CYS | 164 | 12.827 | 15.032 | -14.727 | 1.00 | 2.71 | SEG1 |
| ATOM | 2546 | HG | CYS | 164 | 12.479 | 15.910 | -14.555 | 1.00 | 3.08 | SEG1 |
| ATOM | 2547 | C | CYS | 164 | 11.217 | 12.641 | -13.340 | 1.00 | 2.18 | SEG1 |
| ATOM | 2548 | O | CYS | 164 | 11.906 | 11.728 | -13.755 | 1.00 | 2.81 | SEG1 |
| ATOM | 2549 | N | GLY | 165 | 9.930 | 12.688 | -13.573 | 1.00 | 2.69 | SEG1 |
| ATOM | 2550 | HN | GLY | 165 | 9.397 | 13.432 | -13.222 | 1.00 | 2.77 | SEG1 |
| ATOM | 2551 | CA | GLY | 165 | 9.269 | 11.608 | -14.364 | 1.00 | 3.67 | SEG1 |
| ATOM | 2552 | HA1 | GLY | 165 | 8.369 | 11.292 | -13.859 | 1.00 | 4.30 | SEG1 |
| ATOM | 2553 | HA2 | GLY | 165 | 9.944 | 10.768 | -14.450 | 1.00 | 4.00 | SEG1 |
| ATOM | 2554 | C | GLY | 165 | 8.915 | 12.119 | -15.765 | 1.00 | 3.89 | SEG1 |
| ATOM | 2555 | O | GLY | 165 | 7.759 | 12.181 | -16.140 | 1.00 | 3.93 | SEG1 |
| ATOM | 2556 | N | SER | 166 | 9.909 | 12.471 | -16.543 | 1.00 | 4.51 | SEG1 |
| ATOM | 2557 | HN | SER | 166 | 10.828 | 12.400 | -16.216 | 1.00 | 4.82 | SEG1 |
| ATOM | 2558 | CA | SER | 166 | 9.654 | 12.967 | -17.933 | 1.00 | 5.11 | SEG1 |
| ATOM | 2559 | HA | SER | 166 | 8.668 | 13.401 | -18.006 | 1.00 | 5.04 | SEG1 |
| ATOM | 2560 | CB | SER | 166 | 10.715 | 14.044 | -18.176 | 1.00 | 5.85 | SEG1 |
| ATOM | 2561 | HB1 | SER | 166 | 11.184 | 13.880 | -19.140 | 1.00 | 6.15 | SEG1 |
| ATOM | 2562 | HB2 | SER | 166 | 11.465 | 13.997 | -17.405 | 1.00 | 6.27 | SEG1 |
| ATOM | 2563 | OG | SER | 166 | 10.095 | 15.323 | -18.149 | 1.00 | 6.09 | SEG1 |
| ATOM | 2564 | HG | SER | 166 | 10.696 | 15.935 | -17.717 | 1.00 | 6.52 | SEG1 |
| ATOM | 2565 | C | SER | 166 | 9.818 | 11.829 | -18.953 | 1.00 | 5.69 | SEG1 |
| ATOM | 2566 | O | SER | 166 | 9.832 | 12.064 | -20.146 | 1.00 | 6.05 | SEG1 |
| ATOM | 2567 | N | GLY | 167 | 9.947 | 10.605 | -18.497 | 1.00 | 6.17 | SEG1 |
| ATOM | 2568 | HN | GLY | 167 | 9.933 | 10.434 | -17.533 | 1.00 | 6.15 | SEG1 |
| ATOM | 2569 | CA | GLY | 167 | 10.115 | 9.466 | -19.445 | 1.00 | 7.07 | SEG1 |
| ATOM | 2570 | HA1 | GLY | 167 | 9.356 | 9.521 | -20.209 | 1.00 | 7.56 | SEG1 |
| ATOM | 2571 | HA2 | GLY | 167 | 10.016 | 8.534 | -18.907 | 1.00 | 7.20 | SEG1 |
| ATOM | 2572 | C | GLY | 167 | 11.500 | 9.536 | -20.104 | 1.00 | 7.52 | SEG1 |
| ATOM | 2573 | O | GLY | 167 | 11.679 | 9.107 | -21.227 | 1.00 | 7.72 | SEG1 |
| ATOM | 2574 | N | ALA | 168 | 12.485 | 10.078 | -19.418 | 1.00 | 7.99 | SEG1 |
| ATOM | 2575 | HN | ALA | 168 | 12.317 | 10.421 | -18.514 | 1.00 | 8.05 | SEG1 |
| ATOM | 2576 | CA | ALA | 168 | 13.867 | 10.183 | -20.008 | 1.00 | 8.73 | SEG1 |
| ATOM | 2577 | HA | ALA | 168 | 14.530 | 10.691 | -19.325 | 1.00 | 8.71 | SEG1 |
| ATOM | 2578 | CB | ALA | 168 | 14.342 | 8.737 | -20.217 | 1.00 | 9.39 | SEG1 |
| ATOM | 2579 | HB1 | ALA | 168 | 13.732 | 8.068 | -19.631 | 1.00 | 9.67 | SEG1 |
| ATOM | 2580 | HB2 | ALA | 168 | 15.373 | 8.647 | -19.905 | 1.00 | 9.70 | SEG1 |
| ATOM | 2581 | HB3 | ALA | 168 | 14.258 | 8.477 | -21.263 | 1.00 | 9.50 | SEG1 |
| ATOM | 2582 | C | ALA | 168 | 13.814 | 10.921 | -21.351 | 1.00 | 9.19 | SEG1 |
| ATOM | 2583 | O | ALA | 168 | 12.802 | 11.496 | -21.707 | 1.00 | 9.45 | SEG1 |
| ATOM | 2584 | N | ARG | 169 | 14.889 | 10.898 | -22.102 | 1.00 | 9.54 | SEG1 |
| ATOM | 2585 | HN | ARG | 169 | 15.691 | 10.421 | -21.799 | 1.00 | 9.50 | SEG1 |
| ATOM | 2586 | CA | ARG | 169 | 14.885 | 11.589 | -23.430 | 1.00 | 10.22 | SEG1 |
| ATOM | 2587 | HA | ARG | 169 | 13.875 | 11.831 | -23.723 | 1.00 | 10.32 | SEG1 |
| ATOM | 2588 | CB | ARG | 169 | 15.717 | 12.879 | -23.280 | 1.00 | 10.36 | SEG1 |
| ATOM | 2589 | HB1 | ARG | 169 | 15.480 | 13.541 | -24.101 | 1.00 | 10.76 | SEG1 |
| ATOM | 2590 | HB2 | ARG | 169 | 16.766 | 12.635 | -23.319 | 1.00 | 10.21 | SEG1 |
| ATOM | 2591 | CG | ARG | 169 | 15.412 | 13.597 | -21.959 | 1.00 | 10.51 | SEG1 |
| ATOM | 2592 | HG1 | ARG | 169 | 15.902 | 13.079 | -21.148 | 1.00 | 10.29 | SEG1 |
| ATOM | 2593 | HG2 | ARG | 169 | 14.345 | 13.605 | -21.789 | 1.00 | 10.79 | SEG1 |
| ATOM | 2594 | CD | ARG | 169 | 15.931 | 15.037 | -22.030 | 1.00 | 10.93 | SEG1 |
| ATOM | 2595 | HD1 | ARG | 169 | 15.512 | 15.627 | -21.231 | 1.00 | 11.12 | SEG1 |
| ATOM | 2596 | HD2 | ARG | 169 | 15.682 | 15.474 | -22.988 | 1.00 | 11.10 | SEG1 |
| ATOM | 2597 | NE | ARG | 169 | 17.421 | 14.950 | -21.875 | 1.00 | 11.16 | SEG1 |
| ATOM | 2598 | HE | ARG | 169 | 17.987 | 14.946 | -22.675 | 1.00 | 11.22 | SEG1 |
| ATOM | 2599 | CZ | ARG | 169 | 17.988 | 14.956 | -20.684 | 1.00 | 11.49 | SEG1 |
| ATOM | 2600 | NH1 | ARG | 169 | 19.290 | 15.019 | -20.594 | 1.00 | 11.90 | SEG1 |
| ATOM | 2601 | HH11 | ARG | 169 | 19.848 | 15.062 | -21.421 | 1.00 | 11.96 | SEG1 |
| ATOM | 2602 | HH12 | ARG | 169 | 19.728 | 15.028 | -19.694 | 1.00 | 12.28 | SEG1 |
| ATOM | 2603 | NH2 | ARG | 169 | 17.276 | 14.870 | -19.586 | 1.00 | 11.63 | SEG1 |
| ATOM | 2604 | HH21 | ARG | 169 | 16.292 | 14.794 | -19.631 | 1.00 | 11.47 | SEG1 |
| ATOM | 2605 | HH22 | ARG | 169 | 17.732 | 14.883 | -18.697 | 1.00 | 12.03 | SEG1 |

```
ATOM   2606  C    ARG  169      15.534  10.580 -24.477  1.00 10.92      SEG1
ATOM   2607  OT1  ARG  169      15.667   9.498 -24.206  1.00 11.30      SEG1
ATOM   2608  OT2  ARG  169      15.898  11.193 -25.529  1.00 11.23      SEG1
END
```

FIG. 2

N-TRADD ACTIVE SITE AND USES THEREOF

This application is a divisional of, and claims priority under 35 U.S.C. §120, to U.S. patent application Ser. No. 09/821,819, filed Mar. 29, 2001 now abandoned, which, in turn, claims priority under 35 U.S.C. §119(e) to U.S. Provisional Application No. 60/195,370 filed Apr. 6, 2000.

FIELD OF THE INVENTION

The present invention relates to the three dimensional solution structure of the N-terminal domain of TNFR-1 associated death domain protein ("N-TRADD"), as well as the identification and characterization of a C-TRAF2 binding active site of N-TRADD. These structures are critical for the design and selection of potent and selective inhibitors of TNF signaling pathways.

BACKGROUND OF THE INVENTION

Tumor Necrosis Factor (TNF) is a pro-inflammatory cytokine that is involved in a variety of biological activities, through its binding to two distinct cell surface receptors, TNFR-1 and TNFR-2 (Tartaglia and Goeddel, *Immunol. Today* 13: 151-153, 1992; Rothe, et al., *Immunol. Rev.* 11: 81-90, 1992; Baker and Reddy, *Oncogene* 17: 3261-3270, 1998). Both TNF receptors are part of the larger TNF receptor superfamily (Smith, et al., *Cell* 76: 959-62, 1994; Grell, *J Inflamm.* 47: 8-17, 1995), which includes CD27, CD30, CD40 and Fas antigen, among others. These receptors share no obvious sequence similarities in the cytoplasmic domain, with the exception of TNFR-1 and Fas, which each have an ~80 amino acid 'death domain' (DD) at the C-terminal with ~28% sequence identity. These death domains can induce apoptosis by mediating self association of both TNFR-1 and Fas upon ligand binding to each receptor, a critical event to trigger downstream signaling pathways by recruiting and activating receptor-associated effector molecules (Boldin, et al., *J Biol Chem* 270: 7795-7798, 1995; Tartaglia, et al., *Immunol. Today* 13: 151-153, 1992). Recently, many of these downstream signaling proteins were identified and shown to contain a DD, which mediates the interaction with the receptor through a DD-DD interaction. For example, the DD of TRADD (TNFR-1 associated death domain protein) (Hsu, et al., *Cell* 81: 495-504, 1995), and MADD (Schievella, et al, *J Biol Chem* 272: 12069-75, 1997) have been shown to interact with TNFR1; FADD (Boldin, et al., *J Biol Chem* 270: 7795-7798, 1995; Chinnaiyan, et al., *Cell* 81: 505-512, 1995) and RIP (Stanger, et al., *Cell* 81: 513-523, 1995) have been shown to interact with FAS.

TRADD, one of the earlier TNFR-1 adapter proteins identified (Hsu, et al., *Cell* 81: 495-504, 1995), is a 34 kD protein that is recruited to the TNFR1 in a TNF dependent manner. TRADD contains two functionally separate domains, which allow the protein to couple to at least two distinct signaling pathways (Hsu, et al, *Cell* 84: 299-308, 1996). The C-terminal region of the protein (aa196-301) contains a death domain that mediates the interaction between TRADD and the death domains of TNFR1, FADD and RIP. The recruitment of FADD initiates the activation of the caspase cascade, which eventually leads to apoptosis. The N-terminal region of TRADD (N-TRADD) spanning from residues 1-169 appears to be a novel domain since a BLAST (Altschul, et al., *Nucl. Acids. Res.* 25: 3389-3402, 1997) search did not identify any sequence homology to known proteins. N-TRADD is responsible for the binding of TRAF2, a TNFR-associated factor (Hsu, et al, *Cell* 84: 299-308, 1996). This interaction is mediated through the TRAF domain located in the C-terminal region of TRAF2 (348-501), termed C-TRAF2. The interaction of N-TRADD with C-TRAF2 initiates TRAF2 mediated signaling processes central to the cellular inflammatory response, such as JNK and NF-kB activation (Reinhard, et al., *EMBO J.* 16: 1080-1092, 1997; Song, et al., *Proc. Natl. Acad. Sci.* 94: 9792-9796, 1997; Rothe, et al., *Immunol. Rev.* 11: 81-90, 1995; Cao, et al., *Nature* 383: 443-446, 1996). This crucial role of N-TRADD in TNF signaling is supported by the observation that the expression of N-TRADD (aa1-194) can inhibit TNF-mediated NF-κB and JNK activation in a dominant negative manner (Kieser, et al., *EMBO J.* 18: 2511-2521, 1999).

In addition to the TNFR-1 pathway, TRADD is also involved in LMP1 (Epstein-Barr virus latent membrane protein 1) mediated pathogenesis. LMP1 is a transforming viral oncogene product that recruits both TRADD and TRAF2 to exert its biological activities in the cell, which include activation of NF-κB, JNK and AP1 Juan, *Curr. Opin Cell Biol.* 9: 247-251, 1997; Farrell, *Trends Microbio.* 3: 105-109, 1998). Two domains in the C-terminus of LMP1 initiate the signaling processes. The CTAR1 domain binds to TRAF2, and the CTAR2 domain binds to TRADD. Although there are similarities between TNFR-1 and LMP1 in their adapter proteins, the signaling mechanisms differ. In LMP1 it is the N-TRADD region (Kieser, et al., *EMBO J.* 18: 2511-2521, 1999) that interacts with LMP1, instead of the DD region as it occurs with TNFR-1 (Hsu, *Cell* 81: 495-504, 1995). Also, whereas a dominant negative mutant of TRADD (1-194) can block both NF-κB and JNK signaling in the TNFR-1 pathway, only NF-κB activity is blocked by N-TRADD (1-194) in the LMP-1 signaling pathway (Kieser, et al., *EMBO J.* 18: 2511-2521, 1999).

Recently, structures of the DD of Fas (Huang, et al., *Nature* 384: 638-41, 1996), p75 (Liepinsh, et al., *EMBO J.* 16: 4999-5005, 1997) and FADD (Jeong, et al., *J Biol Chem* 274: 16337-42, 1999) have been solved, providing insight into the mechanisms by which they regulate apoptosis. In order to understand how N-TRADD may interact with the adapter protein TRAF2, the inventors have determined the three dimensional structure of N-TRADD (1-169) by NMR spectroscopy. The solution structure of N-TRADD consists of 5 alpha helices and four beta strands, arranged in a unique fashion. Using the structure, together with site-directed mutagenesis, a region of N-TRADD has been identified that interacts with C-TRAF2. This information, in addition to the recently published structures of C-TRAF2 (Park, et al., *Nature* 398: 533-538, 1999; PDB Accession Nos. 1CA4 and 1CA9; McWhirter, et al., *Proc. Natl. Acad. Sci. USA* 96: 8408-8413, 1999; PDB Accession No. 1QSC), provides insight into the interaction of N-TRADD and C-TRAF2, which is critical for the design and selection of potent and selective inhibitors of TNF signaling pathways.

SUMMARY OF THE INVENTION

The present invention relates to the three dimensional structure of the N-terminal domain of TNFR-1 associated death domain protein ("N-TRADD"), and more specifically, to the solution structure of N-TRADD, as determined using spectroscopy and various computer modeling techniques.

Particularly, the invention is further directed to the identification, characterization and three dimensional structure of an active site of N-TRADD that provides an attractive target for the rational design of potent and selective inhibitors of TNF signaling pathways.

Accordingly, the present invention discloses a solution comprising an N-terminal domain of TNFR-1 associated death domain protein ("N-TRADD"). The three dimensional solution structure of N-TRADD is provided by the relative atomic structural coordinates of FIG. 2, as obtained from spectroscopy data.

Also provided by the present invention is an active site of a C-TRAF2 binding protein or peptide, preferably of N-TRADD, wherein said active site is characterized by a three dimensional structure comprising the relative structural coordinates of amino acid residues Y16, F18, and H65 according to FIG. 2, +a root mean square deviation from the conserved backbone atoms of said amino acids of not more than 1.5 Å. Also provided for by the present invention is an N-TRADD binding active site of C-TRAF2, wherein said active site is characterized by a three dimensional structure comprising the relative structural coordinates of amino acid residues R393, Y395, D399, G400, F410, F447, R448, P449, D450, S453, S454, S455, I465, A466, S467, G468, and P470 according to the atomic coordinates specified in Accession Nos. 1CA4, 1CA9 and/or 1QSC of the Protein Data Bank, +a root mean square deviation from the conserved backbone atoms of said amino acids of not more than 1.5 Å.

The solution coordinates of N-TRADD, an N-TRADD complex or an N-TRADD analogue (or, in each case, portions thereof, such as a C-TRAF2 binding site of the N-TRADD molecule, complex or analogue) as provided by this invention may be stored in a machine-readable form on a machine-readable storage medium, e.g. a computer hard drive, diskette, DAT tape, etc., for display as a three-dimensional shape or for other uses involving computer-assisted manipulation of, or computation based on, the structural coordinates or the three-dimensional structures they define. By way of example, the data defining the three dimensional structure of N-TRADD, an N-TRADD complex or of an N-TRADD analogue, or a portion thereof, may be stored in a machine-readable storage medium, and may be displayed as a graphical three-dimensional representation of the relevant structural coordinates, typically using a computer capable of reading the data from said storage medium and programmed with instructions for creating the representation from such data.

Accordingly, the present invention provides a machine, such as a computer, programmed in memory with the coordinates of N-TRADD, an N-TRADD analogue or a molecule or molecular complex comprising N-TRADD or an N-TRADD analogue, or portions thereof, together with a program capable of converting the coordinates into a three dimensional graphical representation of the structural coordinates on a display connected to the machine. A machine having a memory containing such data aids in the rational design or selection of inhibitors of N-TRADD binding or activity, including the evaluation of the ability of a particular chemical entity to favorably associate with N-TRADD or with an N-TRADD complex as disclosed herein, as well as in the modeling of compounds, proteins, complexes, etc. related by structural or sequence homology to N-TRADD.

The present invention is additionally directed to a method of determining the three dimensional structure of a molecule or molecular complex whose structure is unknown, comprising the steps of first obtaining crystals or a solution of the molecule or molecular complex whose structure is unknown, and then generating X-ray diffraction data from the crystallized molecule or molecular complex and/or generating NMR data from the solution of the molecule or molecular complex. The generated diffraction or spectroscopy data from the molecule or molecular complex can then be compared with the known solution coordinates or three dimensional structure of N-TRADD as disclosed herein, and the three dimensional structure of the unknown molecule or molecular complex conformed to the known N-TRADD structure using standard techniques such as molecular replacement analysis, 2D, 3D and 4D isotope filtering, editing and triple resonance NMR techniques, and computer homology modeling. Alternatively, a three dimensional model of the unknown molecule may be generated by generating a sequence alignment between N-TRADD and the unknown molecule, based on any or all of amino acid sequence identity, secondary structure elements or tertiary folds, and then generating by computer modeling a three dimensional structure for the molecule using the three dimensional structure of, and sequence alignment with, N-TRADD.

The present invention further provides a method for identifying an agent that interacts with N-TRADD, comprising the steps of determining an active site of N-TRADD using the three dimensional N-TRADD structure, and then performing computer fitting analyses to identify an agent which interacts with the identified active site. Also provided is a method for identifying an agent which is a potential inhibitor of N-TRADD binding to C-TRAF2, comprising the steps of determining an N-TRADD binding active site of C-TRAF2 using a three dimensional structure of C-TRAF2 according to the atomic coordinates specified in Accession Nos. 1QSC, 1CA4 and/or 1CA9 of the Protein Data Bank, selecting or designing a candidate inhibitor of N-TRADD binding to C-TRAF2 by performing computer fitting analyses with the three dimensional structure of C-TRAF2, and obtaining or synthesizing the candidate inhibitor. The inhibitor may be selected by screening an appropriate database, may designed de novo by analyzing the steric configurations and charge potentials of an empty C-TRAF2 active site in conjunction with the appropriate software programs, or may be designed using characteristics of known inhibitors of N-TRADD binding to C-TRAF2 in order to create "hybrid" inhibitors.

Still further provided is a method for identifying a potential inhibitor of N-TRADD, comprising the steps of using a three dimensional structure of N-TRADD as defined by the relative structural coordinates of amino acids encoding N-TRADD to design or select a potential inhibitor, and obtaining or synthesizing said potential inhibitor. The inhibitor may be selected by screening an appropriate database, may designed de novo by analyzing the steric configurations and charge potentials of an empty N-TRADD active site in conjunction with the appropriate software programs, or may be designed using characteristics of known inhibitors of N-TRADD, an N-TRADD complex or of an N-TRADD analogue in order to create "hybrid" inhibitors. Also provided by the present invention are the inhibitors designed or selected using the methods disclosed herein.

BRIEF DESCRIPTION OF THE FIGURES

FIG. 1 depicts the 169 amino acid sequence (SEQ ID NO:1) encoding the N-terminal domain of human TNFR-1 associated death domain protein (wherein said N-terminal domain is referred to herein as "N-TRADD"), with the secondary structures noted below.

FIG. 2 lists the atomic structure coordinates for the restrained minimized mean structure of N-TRADD as derived by multidimensional NMR spectroscopy. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location (Å). All non-protein atoms are listed as HETATM instead of atoms using PDB conventions.

DETAILED DESCRIPTION OF THE INVENTION

Figure 3:
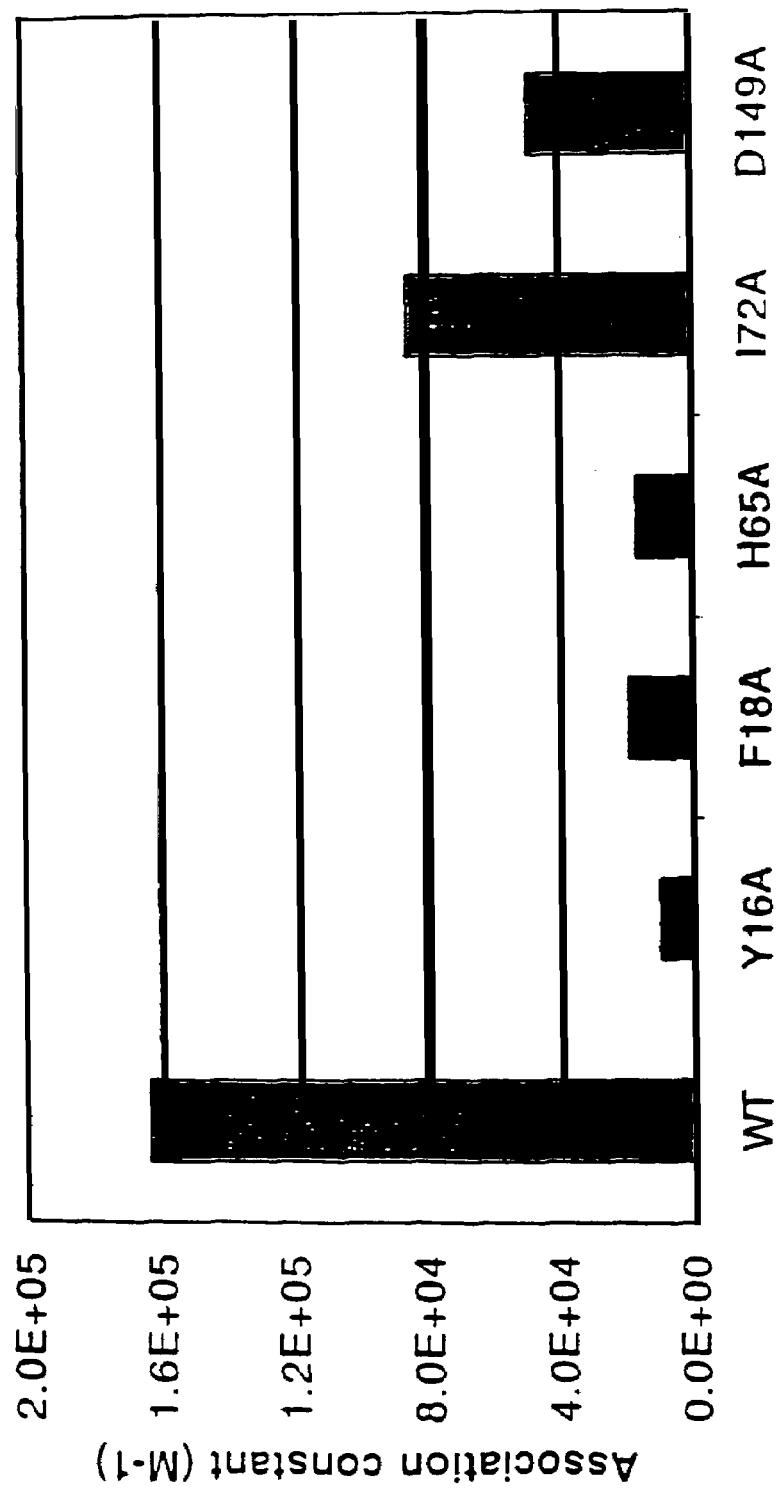
FIG. 3 depicts the relative binding affinities of wild type N-TRADD and five N-TRADD mutants to C-TRAF2. Each experiment was performed three times, and the standard deviation is shown as thin lines above the bars.

As used herein, the following terms and phrases shall have the meanings set forth below:

Unless otherwise noted, "N-TRADD" includes both the N-terminal domain of TRADD as encoded by the amino acid sequence of FIG. 1 (including conservative substitutions thereof), as well as "N-TRADD analogues", defined herein as proteins comprising a C-TRAF2 or C-TRAF2 like binding active site as defined by the present invention, including, but not limited to, an active site characterized by a three dimensional structure comprising the relative structural coordinates of amino acid residues Y16, F18, and H65 according to FIG. 2, or more preferably, further comprising the relative structural coordinates of amino acid residues L17, V58, L59, I72, and D149 according to FIG. 2, or even more preferably, still further comprising the relative structural coordinates of amino acid residues K63, I64, D68, Q70, V73, Q74, L75, C78, L118, G121, A122, R124, L125, E150, and L152 according to FIG. 2, in each case, +a root mean square deviation from the conserved backbone atoms (N, Cα, C, and O) of said amino acids of not more than 1.5 Å, or more preferably, not more than 1.0 Å, or most preferably, not more than 0.5 Å.

"N-TRADD function or activity" shall include LMP1 mediated pathogenesis and a variety of TNF signaling processes, such as TRAF2 mediated signaling processes central to the cellular inflammatory response, including, but not limited to, JNK and NF-κB activation.

Unless otherwise indicated, "protein" or "molecule" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original set provided in FIG. 2 by mathematical manipulation, such as by inversion or integer additions or subtractions. As such, it is recognized that the structural coordinates of the present invention are relative, and are in no way specifically limited by the actual x, y, z coordinates of FIG. 2.

An "agent" shall include a protein, polypeptide, peptide, nucleic acid, including DNA or RNA, molecule, compound, antibiotic or drug.

"Root mean square deviation" is the square root of the arithmetic mean of the squares of the deviations from the mean, and is a way of expressing deviation or variation from the structural coordinates described herein. The present invention includes all embodiments comprising conservative substitutions of the noted amino acid residues resulting in same structural coordinates within the stated root mean square deviation.

It will be obvious to the skilled practitioner that the numbering of the amino acid residues in the various isoforms of N-TRADD or in N-TRADD analogues covered by the present invention may be different than that set forth herein, or may contain certain conservative amino acid substitutions that yield the same three dimensional or solution structures as those defined by FIG. 2 herein. Corresponding amino acids and conservative substitutions in other isoforms or analogues are easily identified by visual inspection of the relevant amino acid sequences or by using commercially available homology software programs.

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic), and includes substitutions having an inconsequential effect on the three dimensional structure of N-TRADD with respect to the use of said structure for the identification and design of N-TRADD or N-TRADD complex inhibitors, for molecular replacement analyses and/or for homology modeling.

An "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound, antibiotic or drug) via various covalent and/or non-covalent binding forces. As such, an active site of the present invention may include both the actual site of C-TRAF2 binding with N-TRADD, as well as accessory binding sites adjacent to the actual site of C-TRAF2 binding that nonetheless may affect N-TRADD or N-TRADD complex activity upon interaction or association with a particular agent, either by direct interference with the actual site of C-TRAF2 binding or by indirectly affecting the steric conformation or charge potential of the N-TRADD molecule and thereby preventing or reducing C-TRAF2 binding to N-TRADD at the actual site of C-TRAF2 binding.

An "N-TRADD complex" refers to a co-complex of a molecule comprising the N-TRADD region in bound association with a protein, polypeptide, peptide, nucleic acid, including DNA or RNA, small molecule, compound, antibiotic or drug, either by covalent or non-covalent binding forces. A non-limiting example of an N-TRADD complex includes N-TRADD or an N-TRADD analogue bound to C-TRAF2.

The present invention relates to the three dimensional structure of N-TRADD or of an N-TRADD analogue, and more specifically, to the solution structure of N-TRADD as determined using multidimensional NMR spectroscopy and various computer modeling techniques. The solution coordinates of N-TRADD (disclosed herein at FIG. 2) are useful for a number of applications, including, but not limited to, the characterization of a three dimensional structure of N-TRADD, as well as the visualization, identification and characterization of N-TRADD active sites, including the site of C-TRAF2 binding to N-TRADD. The active site structures may then be used to predict the orientation and binding affinity of a designed or selected inhibitor of N-TRADD, an N-TRADD analogue or of an N-TRADD complex. Accordingly, the invention is particularly directed to the three dimensional structure of an N-TRADD active site, including but not limited to the C-TRAF2 binding site.

As used herein, N-TRADD comprises the N-terminal domain of TRADD, and more specifically comprises amino acid residues 1-169 of TRADD as shown in FIG. 1 ("N-TRADD"), or conservative substitutions thereof. The present invention provides a solution comprising an N-terminal domain of TNFR-1 associated death domain protein, wherein the N-terminal domain of TNFR-1 associated death domain protein preferably comprises amino acid residues 1-169 of FIG. 1, or conservative substitutions thereof. Preferably, the solution provided for herein comprises N-TRADD in a buffer comprising 20 mM imidazole, 200 mM NaCl, 20 mM DTT and 0.05% $NaN_3$, in either 90% $H_2O$/10% $D_{2O}$ or 100% $D_2O$. The concentration of protein in the solution should be high enough to yield a good signal-to-noise ratio in the NMR spectrum, but not so high as to result in precipitation or aggregation of the protein or protein complex. By way of example, the solutions of the present invention preferably comprise between 0.8-1.0 mM uncomplexed N-TRADD. However, it is understood that one of ordinary skill in the art may devise additional solutions using alternate molar concentrations that are still able to obtain a usable NMR spectrum. A preferred solution pH is around 6.6. Further, the N-TRADD of the solutions of the present invention may be either unlabeled, $^{15}N$ enriched or $^{15}N$, $^{13}C$ enriched, and is preferably biologically active.

The secondary structure of the N-TRADD used in the solutions of the present invention comprises four beta strands forming an antiparallel beta sheet, with five alpha helices packing around the beta sheet, wherein the beta strands and alpha helices are configured in the trace order β1, α1, α2, β2, β3, α3, β4, α4 and α5. The β1 strand comprises amino acid residues S14-E20 of N-TRADD, α1 comprises amino acid residues L28-Y32 of N-TRADD, α2 comprises amino acid residues P35-G53 of N-TRADD, β2 comprises amino acid residues Q60-R66 of N-TRADD, β3 comprises amino acid residues L71-R76 of N-TRADD, α3 comprises amino acid residues R80-L107 of N-TRADD, β4 comprises amino acid residues Q115-R119 of N-TRADD, α4 comprises amino acid residues E132-A141 of N-TRADD and α5 comprises amino acid residues E150-N161 of N-TRADD.

The protein used in the solutions of the present invention includes N-TRADD, as well as N-TRADD analogues, where said protein comprises an active site characterized by the three dimensional structure comprising the relative structural coordinates of amino acid residues Y16, F18, and H65 according to FIG. 2, ± a root mean square deviation from the conserved backbone atoms of said amino acids of not more than 1.5 Å, or preferably, not more than 1.0 Å, or more preferably not more than 0.5 Å. In a preferred embodiment, the protein used in the solutions of the present invention comprises an active site characterized by a three dimensional structure further comprising the relative structural coordinates of amino acid residues L17, V58, L59, I72, and D149 according to FIG. 2, +a root mean square deviation from the conserved backbone atoms of said amino acids of not more than 1.5 Å, or preferably, not more than 1.0 Å, or most preferably, not more than 0.5 Å. In still more preferred embodiment, the protein used in the solutions of the present invention comprises an active site characterized by the three dimensional structure still further comprising the relative structural coordinates of amino acid residues K63, I64, D68, Q70, V73, Q74, L75, C78, L118, G121, A122, R124, L125, E150, and L152 according to FIG. 2, ± a root mean square deviation from the conserved backbone atoms of said amino acids of not more than 1.5 Å, or preferably, not more than 1.0 Å, or most preferably not more than 0.5 Å. In the most preferred embodiment, the protein used in the solution of the present invention is characterized by a three dimensional structure comprising the complete structural coordinates of the amino acids according to FIG. 2, ± a root mean square deviation from the conserved backbone atoms of said amino acids of not more than 1.5 Å (or more preferably, not more than 1.0 Å, and most preferably, not more than 0.5 Å).

Molecular modeling methods known in the art may be used to identify an active site or binding pocket of N-TRADD, an N-TRADD molecular complex, or of an N-TRADD analogue. Specifically, the solution structural coordinates provided by the present invention may be used to characterize a three dimensional structure of the N-TRADD molecule, molecular complex or N-TRADD analogue. From such a structure, putative active sites may be computationally visualized, identified and characterized based on the surface structure of the molecule, surface charge, steric arrangement, the presence of reactive amino acids, regions of hydrophobicity or hydrophilicity, etc. Such putative active sites may be further refined using chemical shift perturbations of spectra generated from various and distinct N-TRADD complexes, competitive and non-competitive inhibition experiments, and/or by the generation and characterization of N-TRADD or ligand mutants to identify critical residues or characteristics of the active site.

The identification of putative active sites of a molecule or molecular complex is of great importance, as most often the biological activity of a molecule or molecular complex results from the interaction between an agent and one or more active sites of the molecule or molecular complex. Accordingly, the active sites of a molecule or molecular complex are the best targets to use in the design or selection of inhibitors that affect the activity of the molecule or molecular complex.

The present invention is directed to an active site of N-TRADD, an N-TRADD complex or of an N-TRADD analogue, that, as a result of its shape, reactivity, charge potential, etc., favorably interacts or associates with another agent (including, without limitation, a protein, polypeptide, peptide, nucleic acid, including DNA or RNA, molecule, compound, antibiotic or drug). Accordingly, the present invention is directed to an active site of the N-TRADD molecule characterized by the three dimensional structure comprising the relative structural coordinates of amino acid residues Y16, F18, and H65 according to FIG. 2, ± a root mean square deviation from the conserved backbone atoms of said amino acids of not more than 1.5 Å, or preferably, not more than 1.0 Å, or more preferably not more than 0.5 Å. Preferably, the active site of the N-TRADD molecule is characterized by the three dimensional structure further comprising the relative structural coordinates of amino acid residues L17, V58, L59, I72, and D149, ± a root mean square deviation from the conserved backbone atoms of said amino acids of not more than 1.5 Å, or preferably, not more than 1.0 Å, or more preferably not more than 0.5 Å. Most preferably, an active site of the N-TRADD molecule is characterized by the three dimensional structure still further comprising the relative structural coordinates of amino acid residues K63, I64, D68, Q70, V73, Q74, L75, C78, L118, G121, A122, R124, L125, E150, and L152 according to FIG. 2, ± a root mean square deviation from the conserved backbone atoms of said amino acids of not more than 1.5 Å, or preferably, not more than 1.0 Å, or more preferably not more than 0.5 Å.

In order to use the structural coordinates generated for a solution structure of the present invention as set forth in FIG. 2, it is often necessary to display the relevant coordinates as, or convert them to, a three dimensional shape or graphical representation, or to otherwise manipulate them. For example, a three dimensional representation of the structural coordinates is often used in rational drug design, molecular replacement analysis, homology modeling, and mutation analysis. This is typically accomplished using any of a wide variety of commercially available software programs capable of generating three dimensional graphical representations of molecules or portions thereof from a set of structural coordinates. Examples of said commercially available software programs include, without limitation, the following: GRID (Oxford University, Oxford, UK); MCSS (Molecular Simulations, San Diego, Calif.); AUTODOCK (Scripps Research Institute, La Jolla, Calif.); DOCK (University of California, San Francisco, Calif.); Flo99 (Thistlesoft, Morris Township, N.J.); Ludi (Molecular Simulations, San Diego, Calif.); QUANTA (Molecular Simulations, San Diego, Calif.); Insight (Molecular Simulations, San Diego, Calif.); SYBYL (TRIPOS, Inc., St. Louis. MO); and LEAPFROG (TRIPOS, Inc., St. Louis, Mo.).

For storage, transfer and use with such programs, a machine, such as a computer, is provided for that produces a three dimensional representation of the N-TRADD molecule, a portion thereof (such as an active site or a binding site), an N-TRADD molecular complex, or an N-TRADD analogue. The machine of the present invention comprises a machine-readable data storage medium comprising a data storage material encoded with machine-readable data. Machine-readable storage media comprising data storage material include conventional computer hard drives, floppy disks, DAT tape, CD-ROM, and other magnetic, magneto-optical, optical, floptical and other media which may be adapted for use with a computer. The machine of the present invention also comprises a working memory for storing instructions for processing the machine-readable data, as well as a central processing unit (CPU) coupled to the working memory and to the machine-readable data storage medium for the purpose of processing the machine-readable data into the desired three dimensional representation. Finally, the machine of the present invention further comprises a display connected to the CPU so that the three dimensional representation may be visualized by the user. Accordingly, when used with a machine programmed with instructions for using said data, e.g., a computer loaded with one or more programs of the sort identified above, the machine provided for herein is capable of displaying a graphical three-dimensional representation of any of the molecules or molecular complexes, or portions of molecules of molecular complexes, described herein.

In one embodiment of the invention, the machine-readable data comprises the relative structural coordinates of amino acid residues Y16, F18, and H65 according to FIG. 2, ± a root mean square deviation from the conserved backbone atoms of said amino acids of not more than 1.5 Å, or preferably, not more than 1.0 Å, or more preferably not more than 0.5 Å. In an alternate preferred embodiment, the machine-readable data further comprises the relative structural coordinates of amino acid residues L17, V58, L59, I72, and D149 according to FIG. 2, ± a root mean square deviation from the conserved backbone atoms of said amino acids of not more than 1.5 Å, or preferably, not more than 1.0 Å, or more preferably not more than 0.5 Å. In a still more preferred embodiment, the machine-readable data still further comprises the relative structural coordinates of amino acid residues K63, I64, D68, Q70, V73, Q74, L75, C78, L118, G121, A122, R124, L125, E150, and L152 according to FIG. 2, ± a root mean square deviation from the conserved backbone atoms of said amino acids of not more than 1.5 Å, or preferably, not more than 1.0 Å, or more preferably not more than 0.5 Å. Finally, in the most preferred embodiment, the machine readable data comprises the complete structural coordinates according to FIG. 2, ± a root mean square deviation of not more than 1.5 Å (or more preferably, not more than 1.0 Å, and most preferably, not more than 0.5 Å).

The structural coordinates of the present invention permit the use of various molecular design and analysis techniques in order to (i) solve the three dimensional structures of related molecules, molecular complexes or N-TRADD analogues, and (ii) to design, select, and synthesize chemical agents capable of favorably associating or interacting with an active site of an N-TRADD molecule, molecular complex or N-TRADD analogue, wherein said chemical agents potentially act as inhibitors of N-TRADD or N-TRADD complex binding to a number of binding proteins, including, but not limited to, C-TRAF2.

More specifically, the present invention provides a method for determining the molecular structure of a molecule or molecular complex whose structure is unknown, comprising the steps of obtaining a solution of the molecule or molecular complex whose structure is unknown, and then generating NMR data from the solution of the molecule or molecular complex. The NMR data from the molecule or molecular complex whose structure is unknown is then compared to the solution structure data obtained from the N-TRADD solutions of the present invention. Then, 2D, 3D and 4D isotope filtering, editing and triple resonance NMR techniques are used to conform the three dimensional structure determined from the N-TRADD solution of the present invention to the NMR data from the solution molecule or molecular complex. Alternatively, molecular replacement analysis may be used to conform the N-TRADD solution structure of the present invention to x-ray diffraction data from crystals of the unknown molecule or molecular complex.

Molecular replacement analysis uses a molecule having a known structure as a starting point to model the structure of an unknown crystalline sample. This technique is based on the principle that two molecules which have similar structures, orientations and positions will diffract x-rays similarly. A corresponding approach to molecular replacement is applicable to modeling an unknown solution structure using NMR technology. The NMR spectra and resulting analysis of the NMR data for two similar structures will be essentially identical for regions of the proteins that are structurally conserved, where the NMR analysis consists of obtaining the NMR resonance assignments and the structural constraint assignments, which may contain hydrogen bond, distance, dihedral angle, coupling constant, chemical shift and dipolar coupling constant constraints. The observed differences in the NMR spectra of the two structures will highlight the differences between the two structures and identify the corresponding differences in the structural constraints. The structure determination process for the unknown structure is then based on modifying the NMR constraints from the known structure to be consistent with the observed spectral differences between the NMR spectra.

Accordingly, in one non-limiting embodiment of the invention, the resonance assignments for the N-TRADD solution provide the starting point for resonance assignments of N-TRADD in a new N-TRADD:"unsolved agent" complex. Chemical shift perturbances in two dimensional $^{15}N/^{1}H$ spectra can be observed and compared between the N-TRADD solution and the new N-TRADD:agent complex. In this way, the affected residues may be correlated with the three dimensional structure of N-TRADD as provided by the relevant structural coordinates of FIG. 2. This effectively identifies the region of the N-TRADD:agent complex that has incurred a structural change relative to the native N-TRADD structure. The $^{1}H$, $^{15}N$, $^{13}C$ and $^{13}CO$ NMR resonance assignments corresponding to both the sequential backbone and side-chain amino acid assignments of N-TRADD may then be obtained and the three dimensional structure of the new N-TRADD:agent complex may be generated using standard 2D, 3D and 4D triple resonance NMR techniques and NMR assignment methodology, using the N-TRADD solution structure, resonance assignments and structural constraints as a reference. Various computer fitting analyses of the new agent with the three dimensional model of N-TRADD may be performed in order to generate an initial three dimensional model of the new agent complexed with N-TRADD, and the resulting three dimensional model may be refined using standard experimental constraints and energy minimization techniques in order to position and orient the new agent in association with the three dimensional structure of N-TRADD.

The present invention further provides that the structural coordinates of the present invention may be used with standard homology modeling techniques in order to determine the unknown three-dimensional structure of a molecule or molecular complex. Homology modeling involves constructing a model of an unknown structure using structural coordinates of one or more related protein molecules, molecular complexes or parts thereof (i.e., active sites). Homology modeling may be conducted by fitting common or homologous portions of the protein whose three dimensional structure is to be solved to the three dimensional structure of homologous structural elements in the known molecule, specifically using the relevant (i.e., homologous) structural coordinates provided by FIG. 2 herein. Homology may be determined using amino acid sequence identity, homologous secondary structure elements, and/or homologous tertiary folds. Homology modeling can include rebuilding part or all of a three dimensional structure with replacement of amino acids (or other components) by those of the related structure to be solved.

Accordingly, a three dimensional structure for the unknown molecule or molecular complex may be generated using the three dimensional structure of the N-TRADD molecule of the present invention, refined using a number of techniques well known in the art, and then used in the same fashion as the structural coordinates of the present invention, for instance, in applications involving molecular replacement analysis, homology modeling, and rational drug design.

Determination of the three dimensional structure of N-TRADD and its C-TRAF2 binding active site as disclosed herein is critical to the rational identification and/or design of agents that may act as inhibitors of C-TRAF2 binding to N-TRADD, and thereby act as inhibitors of JNK/AP1 and NF-κB activation. Alternatively, using conventional drug assay techniques, the only way to identify such an agent is to screen thousands of test compounds until an agent having the desired inhibitory effect on a target compound is identified. Necessarily, such conventional screening methods are expensive, time consuming, and do not elucidate the method of action of the identified agent on the target compound.

However, advancing X-ray, spectroscopic and computer modeling technologies allow researchers to visualize the three dimensional structure of a targeted compound (i.e., of N-TRADD). Using such a three dimensional structure, researchers identify putative binding sites and then identify or design agents to interact with these binding sites. These agents are then screened for an inhibitory effect upon the target molecule. In this manner, not only are the number of agents to be screened for the desired activity greatly reduced, but the mechanism of action on the target compound is better understood.

Accordingly, the present invention further provides a method for identifying a potential inhibitor of N-TRADD, an N-TRADD analogue or of an N-TRADD complex, comprising the steps of using a three dimensional structure of N-TRADD as defined by the relative structural coordinates of FIG. 2 to design or select a potential inhibitor of N-TRADD activity, and synthesizing or obtaining said potential inhibitor. The inhibitor may be selected by screening an appropriate database, may be designed de novo by analyzing the steric configurations and charge potentials of an empty N-TRADD or N-TRADD complex active site in conjunction with the appropriate software programs, or may be designed using characteristics of known inhibitors of protein binding to N-TRADD or N-TRADD complexes in order to create "hybrid" inhibitors.

An agent that interacts or associates with an active site of N-TRADD, an N-TRADD complex or an N-TRADD analogue may be identified by determining an active site from the three dimensional structure of N-TRADD, and performing computer fitting analyses to identify an agent which interacts or associates with said active site. Computer fitting analyses utilize various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. The degree of association may be determined computationally by any number of commercially available software programs, or may be determined experimentally using standard binding assays.

Three dimensional models of the putative active site may be generated using any one of a number of methods known in the art, and include, but are not limited to, homology modeling as well as computer analysis of raw structural coordinate data generated using crystallographic or spectroscopy techniques. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. MO) and LEAPFROG (TRIPOS, Inc., St. Louis, Mo.).

In a preferred method of the present invention, the identified active site of N-TRADD, an N-TRADD complex or of an N-TRADD analogue comprises amino acid residues Y16, F18 and H65 (or conservative substitutions thereof) according to FIG. 1, more preferably further comprises amino acid residues L17, V58, L59, I72, and D149 (or conservative substitutions thereof) according to FIG. 1, and most preferably still further comprises amino acid residues K63, I64, D68, Q70, V73, Q74, L75, C78, L118, G121, A122, R124, L125, E150, and L152 (or conservative substitutions thereof) according to FIG. 1.

The method of the present invention also comprises an identified active site characterized by the three dimensional structure comprising the relative structural coordinates of amino acid residues Y16, F18, and H65 according to FIG. 2, ± a root mean square deviation from the conserved backbone atoms of said amino acids of not more than 1.5 Å, or preferably, not more than 1.0 Å, or more preferably not more than 0.5 Å. Preferably, the identified active site is characterized by three dimensional structure further comprising the relative structural coordinates of amino acid residues L17, V58, L59, I72, and D149 according to FIG. 2, and most preferably still further comprising the relative structural coordinates of amino acid residues K63, I64, D68, Q70, V73, Q74, L75, C78, L118, G121, A122, R124, L125, E150, and L152, in each case, ± a root mean square deviation from the conserved backbone atoms of said amino acids of not more than 1.5 Å, or preferably, not more than 1.0 Å, or more preferably not more than 0.5 Å. It is understood that the method of the present invention includes additional embodiments comprising conservative substitutions of the noted amino acids which result in the same structural coordinates of the corresponding residues in FIG. 2 within the stated root mean square deviation.

The effect of such an agent identified by computer fitting analyses on N-TRADD, an N-TRADD complex or an N-TRADD analogue activity may be further evaluated computationally, or experimentally by competitive binding experiments or by contacting the identified agent with N-TRADD (or an N-TRADD complex or analogue) and measuring the effect of the agent on the target's biological activity. Standard enzymatic assays may be performed and the results analyzed to determine whether the agent is an inhibitor of N-TRADD activity (i.e., the agent may reduce or prevent binding affinity between N-TRADD and the relevant binding protein, such as C-TRAF2, and thereby reduce the level or rate of JNK/AP1 and/or NF-κB activity compared to baseline). Further tests may be performed to evaluate the selectivity of the identified agent to N-TRADD with regard to other N-TRADD analogues or C-TRAF2 binding targets.

Agents designed or selected to interact with N-TRADD or an N-TRADD complex must be capable of both physically and structurally associating with N-TRADD via various covalent and/or non-covalent molecular interactions, and of assuming a three dimensional configuration and orientation that complements the relevant active site of the N-TRADD molecule or of the N-TRADD complex.

Accordingly, using these criteria, the structural coordinates of the N-TRADD molecule as disclosed herein, and/or structural coordinates derived therefrom using molecular replacement analysis or homology modeling, agents may be designed to increase either or both of the potency and selectivity of known inhibitors, either by modifying the structure of known inhibitors or by designing new agents de novo via computational inspection of the three dimensional configuration and electrostatic potential of an N-TRADD or N-TRADD complex active site.

Accordingly, in one embodiment of the invention, the structural coordinates of FIG. 2 of the present invention, or structural coordinates derived therefrom using molecular replacement or homology modeling techniques as discussed above, are used to screen a database for agents that may act as potential inhibitors of N-TRADD or N-TRADD complex activity. Specifically, the obtained structural coordinates of the present invention are read into a software package and the three dimensional structure is analyzed graphically. A number of computational software packages may be used for the analysis of structural coordinates, including, but not limited to, Sybyl (Tripos Associates), QUANTA and XPLOR (Brunger, A. T., (1994) *X-Plor* 3.851: *a system for X-ray Crystallography and NMR. Xplor Version* 3.851 New Haven, Conn.: Yale University Press). Additional software programs check for the correctness of the coordinates with regard to features such as bond and atom types. If necessary, the three dimensional structure is modified and then energy minimized using the appropriate software until all of the structural parameters are at their equilibrium/optimal values. The energy minimized structure is superimposed against the original structure to make sure there are no significant deviations between the original and the energy minimized coordinates.

The energy minimized coordinates of N-TRADD or of an N-TRADD complex bound to a "solved" inhibitor are then analyzed and the interactions between the solved ligand and N-TRADD or the N-TRADD complex are identified. The final N-TRADD or N-TRADD complex structure is modified by graphically removing the solved inhibitor so that only N-TRADD or the N-TRADD complex and a few residues of the solved agent are left for analysis of the binding site cavity. QSAR and SAR analysis and/or conformational analysis may be carried out to determine how other inhibitors compare to the solved inhibitor. The solved agent may be docked into the uncomplexed structure's binding site to be used as a template for data base searching, using software to create excluded volume and distance restrained queries for the searches. Structures qualifying as hits are then screened for activity using standard assays and other methods known in the art.

Further, once the specific interaction is determined between the solved inhibitor, docking studies with different inhibitors allow for the generation of initial models of new inhibitors bound to N-TRADD or to the N-TRADD complex. The integrity of these new models may be evaluated a number of ways, including constrained conformational analysis using molecular dynamics methods (i.e., where both N-TRADD (or the N-TRADD complex) and the bound inhibitor are allowed to sample different three dimensional conformational states until the most favorable state is reached or found to exist between the protein (or protein complex) and the bound agent). The final structure as proposed by the molecular dynamics analysis is analyzed visually to make sure that the model is in accord with known experimental SAR based on measured binding affinities. Once models are obtained of the original solved agent bound to N-TRADD or the N-TRADD complex and computer models of other molecules bound to N-TRADD or the N-TRADD complex, strategies are determined for designing modifications into the inhibitors to improve their activity and/or enhance their selectivity.

Once an N-TRADD or N-TRADD complex binding agent has been optimally selected or designed, as described above, substitutions may then be made in some of its atoms or side groups in order to improve or modify its selectivity and binding properties. Generally, initial substitutions are conservative, i.e., the replacement group will have approximately the same size, shape, hydrophobicity and charge as the original group. Such substituted chemical compounds may then be analyzed for efficiency of fit to the N-TRADD molecule or the N-TRADD complex by the same computer methods described in detail above.

Various molecular analysis and rational drug design techniques are further disclosed in U.S. Pat. Nos. 5,834,228, 5,939,528 and 5,856,116, as well as in PCT Application No. PCT/US98/16879, published as WO 99/09148, the contents of which are hereby incorporated by reference.

The present invention may be better understood by reference to the following non-limiting Example. The following Example is presented in order to more fully illustrate the preferred embodiments of the invention, and should in no way be construed as limiting the scope of the present invention.

EXAMPLE 1

The structure of N-TRADD was determined by NMR spectroscopy. The structure consists of four β strands which form an antiparallel beta sheet, with α helices packing around the sheet. N-TRADD interacts with the C-terminal domain of TRAF2 ("C-TRAF2") to initiate one of the most important TNFR1 activities, NF-κB and JNK activation. N-TRADD residues involved in C-TRAF2 interaction were identified from NMR binding experiments of N-TRADD with C-TRAF2, where several residues important for the binding were determined to be located primarily in the antiparallel beta sheet. The mutation of some N-TRADD residues that were identified from $^1$H-$^{15}$N HSQC perturbations to be involved in C-TRAF2 binding caused a 2-16 fold decrease in the affinity of N-TRADD for C-TRAF2. Interestingly, the interaction between N-TRADD and C-TRAF2 was inhibited by a 13-mer peptide derived from CD40, inferring that the binding site of N-TRADD and CD40 in C-TRAF2 overlap. The knowledge of the N-TRADD NMR structure and the C-TRAF2 crystal structure (McWhirter, *Proc. Natl. Acad. Sci. USA* 96: 8408-8413, 1999; published PDB Accession No. 1QSC), in addition to the characterization of their interaction sites, are critical components in the design of drugs that may inhibit their interactions, therefore allowing intervention of the inflammatory cascade in the TNFR1 pathway.

Experimental Methods

Cloning and site directed mutagenesis: The DNA sequence coding for the first 169 amino acids from N-TRADD was cloned in pRSETB (Invitrogen) after amplification by PCR. The primer at the 5' end introduces an NdeI site upstream from the initiation site, and the primer at the 3' end introduces a His tag after aa169. The sequence was confirmed by sequencing analysis. Single point mutations were introduced using Chameleon double-stranded site directed mutagenesis (Stratagene). The C-TRAF2 sequence (residues 262 to 501 of human TRAF2) was amplified by PCR using a 5' end primer flanking with an XhoI and NdeI site, which introduces a Met before residue 262, and a 3' end primer introducing 6xHis before a stop codon followed by a NcoI site. The C-TRAF2 sequence was cloned into pAcSG2 (Pharmingen) by XhoI and NcoI sites for baculovirus expression.

Protein expression and purification: The polypeptide for N-TRADD (1-169) was overexpressed in BL-21 *E. coli*. [U-$^{15}$N] or [U-$^{13}$C, U-$^{15}$N]. N-TRADD was purified from cells grown at 25° C. on minimal medium containing 2 g/L [U-$^{15}$N]ammonium sulfate or [$^{15}$N]ammonium sulfate and 2 g/L [U-$^{13}$C]glucose. The cells were lysed at 4° C. in 20 mM Tris-HCl (pH=8.0), 20 mM DTT (buffer B) with 200 mM NaCl. The lysate was centrifuged at 21000×g at 4° C. for 60 minutes. All purification steps were performed at room temperature unless noted otherwise. The supernatant containing soluble N-TRADD was diluted four-fold with buffer B and subjected to anion exchange chromatography using a Toyo-Pearl Q 550C column. The resulting unbound fraction was applied to a ToyoPearl AF-Heparin 650M column. The heparin unbound fraction was diluted 2-fold with buffer B and applied to a Pharmacia Blue Sepharose CL-6B column. N-TRADD was recovered using a linear gradient with buffer B from 0-0.5 M NaCl. The N-TRADD containing fraction was concentrated and applied to a ToyoPearl G3000SWx1 size exclusion column equilibrated with 20 mM imidazole (pH=6.6), 200 mM NaCl, 20 mM DTT, and 10% D$_2$O. The resulting N-TRADD sample was judged to be pure (>95%) by SDS-PAGE and monomeric (>95%) by SEC-HPLC. All NMR samples were in 20 mM imidazole, pH 6.6, 200 mM NaCl, 20 mM DTT and 0.05% NaN3, at concentrations between 0.8-1.0 mM with 90% H$_2$O/10% D$_2$O or 100% D$_2$O.

C-TRAF2 protein was expressed in baculovirus in Tini cells. The cell pellet was resuspended in the buffer A (20 mM Tris pH 7.5, 200 mM NaCl, 10% glycerol) containing 2 mM PMSF, 10 ug/ml leupeptin and 5 ug/ml aprotinin. Cells were then lysed by sonication. Extracts were clarified by centrifugation at 18K for 30 min and applied to Ni-NTA agarose (Qiagen). The column was washed with buffer A containing 20 mM imidazole and later, 50 mM imidazole. C-TRAF2 protein was then eluted with buffer A containing 250 mM imidazole and 10 mM DTT. The eluted protein was then diluted with 50 mM Tris pH7.5 and 10 mM DTT and applied to a Toyopearl QAE-550C column. The unbound fraction was collected and applied to a Toyopearl AF Heparin-650M column equilibrated with 50 mM Tris pH 7.5 and 10 mM DTT. The column was then eluted with 0-1 N NaCl gradient. The C-TRAF2 protein was eluted at about 200 mM NaCl. The purity of C-TRAF2 was greater than 90% according to SDS-PAGE analysis. C-TRAF2 that was used in the NMR binding experiment was concentrated to 41 mg/ml in 20 mM Tris, 200 mM NaCl, 10% glycerol, 20 mM DTT and 250 mM imidazole, pH 7.5.

NMR Spectroscopy: All NMR spectra were collected on a 600 MHZ Varian Unity Plus spectrometer. For the backbone assignments, HNCACB and HN(CO)CACB experiments (Clore and Gronenborn, *Methods Enzymol.* 239: 349-363, 1994; Muhandiram, et al., *J. Magn. Reson. B*103: 208-216, 1994) were performed. To confirm the type of amino acid assignment, C(CO)NH-TOCSY (Grzesiek, et al., *J. Magnetic Resonance, B*101: 114-119, 1993) was used. Side chain resonances were assigned from the following experiments: HBHA(CO)NH (Clore and Gronenborn, *Methods Enzymol.* 239: 349-363, 1994), HC(CO)NH-TOCSY (Grzesiek, et al., *J. Magnetic Resonance. B*101: 114-119, 1993) for the $^{15}$N/$^{13}$C sample in 90% H$_2$O, 10% D$_2$O, HCCH-TOCSY for the $^{15}$N/$^{13}$C-labeled sample in D$_2$O, and $^{15}$N-TOCSY-HSQC with the uniformly labeled $^{15}$N protein.

Initial backbone assignments were carried on with the program ASSIGN (Lukin, et al., *J. Biomolecular NMR* 9: 151-166, 1997) with the HNCACB and HN(CO)CACB experiments. Stereospecific assignments for β-methylene protons and chi1 angles were obtained from the HNHB (Archer, et al., *J. Mag. Res.* 95: 636-641, 1991), $^{15}$N-TOCSY-HSQC and $^{15}$N-NOESY-HSQC (Clore and Gronenborn, *Methods Enzymol.* 239: 349-363, 1994) with a mixing time of 40 ms. Stereospecific assignments of methyls in Leu residues were obtained from the 3D $^{13}$C-$^{13}$C long range correlation (Bax, *J. Biom. NMR* 4: 781-797, 1994), together with intra residual NOE intensity.

Distance restraints were obtained from $^{15}$N-Edited NOESY at 50 ms and 100 ms, and $^{13}$C-Edited NOESY at 80 ms experiments. Due to the high overlap of methyl resonances, the methyl-methyl NOE experiment at 90 ms mixing time (Zhwahlen, et al., *J. Am. Chem. Soc.* 120: 7617-7625, 1998) was also performed for the identification of NOEs in the methyl region. Slowly exchanging amide protons were identified from a sample in 50% H$_2$O, 50% D$_2$O by observing the intensity of the amide protons signals, since N-TRADD could not be lyophilized to be redissolved in 100% D$_2$O. Half of an N-TRADD sample in H$_2$O was diluted into D$_2$O, and a series of $^1$H-$^{15}$N HSQCs were taken to monitor the decrease in intensity of the peaks. The other half was diluted into a H$_2$O buffer, and the $^1$H-$^{15}$N HSQC was taken as reference. All peaks (50 amide protons) whose intensities were not decreased by half (maximum decrease) after the first HSQC (after 15 min of dilution in D$_2$O) were used for the hydrogen bond restraint. Phi angle restraints were obtained by measuring the 3J$_{HN,H}$ coupling constant from the HNHA experiment (Vuister and Bax, *J. Am. Chem. Soc.* 115: 7772-7777, 1993).

Structures were calculated with a distance geometry/simulated annealing protocol of XPLOR 3.851 (Brunger, *X-Plor 3.851: a system for X-ray Crystallography and NMR, Xlor Version* 3.851 New Haven, Conn.: Yale University Press, 1994), adapted to incorporate secondary $^{13}$Cα/$^{13}$Cβ chemical shifts (Kuszewski, et al., *J. Magn. Reson B*106: 92-96, 1995)

and a conformational data base potential for the non-bonded contacts derived from high resolution x-ray structures (Kuszewski, et al., *Protein Science* 5: 1067-1080, 1996), with 1873 proton/proton distance restraints, 100 hydrogen bond distance restraints, 125 phi restraints, and 30 chi1 restraints. The NOE distance restraints were categorized as strong (1.8-2.5 Å), medium (1.8-3.3 Å) and weak (1.8-5.0 Å).

C-TRAF2 and N-TRADD binding studies: The affinity of wild-type N-TRADD and C-TRAF2 was measured by surface plasma resonance using a BIAcore 2000 system (Pharmacia Biosensor AB). C-TRAF2 (residues 262-501) was purified and coupled to a sensor chip CM5 by amine coupling at pH=5.0 to get about 800, 1500 and 5500 response units on three different flow cells. A constant flow (20 µL/min) of purified N-TRADD protein in 10 mM Hepes, pH=7.4, 150 mM NaCl, 3.4 mM EDTA and 0.05% P20 surfactant at 8 different concentrations from 650 µM to 84 µM was applied over the protein coupled chip for 2 min to analyze the association. Binding constants were obtained from the BIAevaluation software.

The CD40 peptide (SNTAAPVQETLHG-OH) (SEQ ID NO:2) was synthesized by using fluorenylmethoxycarbonyl (Fmoc) solid-phase methods and purified by reverse-phase HPLC.

Results and Discussion

Structure Determination: The structure of N-TRADD was determined from 2302 NMR derived restraints obtained using uniformly $^{15}$N and $^{15}$N/$^{13}$C labeled protein, with double and triple resonance NMR experiments. N-TRADD was soluble to ~1 mM, but high concentrations of dithiothreitol (20 mM) were required to prevent aggregation of the protein. Under these conditions the sample was stable for 6-8 weeks. The structural statistics and root mean square deviations are shown below in Table 1. The atomic root mean square deviation about the mean coordinate for residues 14-161 is 0.56 Å for the backbone atoms, and 1.01 Å for all atoms. For secondary structure elements only, the rmsd is 0.46 Å for backbone atoms and 0.92 Å for all atoms. The N-terminal residues 1-10 and C-terminal residues 162-169 are disordered. The secondary structure for residues W11, V12 and G13 is not defined, due to lack of assignments for W1 (N, NH, Ca, Ha) and V12 (NH, N). The NH groups of these residues were not observed, possibly due to conformational exchange on the NMR time scale or to higher amide proton chemical exchange rates. S14 is the first residue in β-1, even though the N and the NH assignments are missing. The evidence that S14 is part of the beta strand is the presence of the characteristic interstrand S14 (Hα)-R76 (Hα) NOE. The chemical shifts values for Cα, Cβ and Hα are also indicative of a beta strand structure for S14. This was also observed for R76, where only Cα/Hα and Cβ/Hβ assignments were made.

Structure Description: The structure of N-TRADD consists of 5 alpha helices and four beta strands arranged in a novel fold. N-TRADD has no sequence homology to any known protein based on a BLAST search (Altschul, et al., *Nucl. Acids. Res.* 25: 3389-3402, 1997). Additionally, a structure similarity search was conducted with DALI (Holm and Sander, *Proteins: Structure. Function and Genetics* 33: 88-96, 1998), and the structure of N-TRADD shows no similarity to any of the distinct fold classes in the database.

N-TRADD is ~40 Å in length and ~30 Å in width, where the four beta strands form an antiparallel beta sheet composed of residues S14-E20, Q60-R66, L71-R76 and Q115-R119, respectively, and the five alpha helices correspond to residues L28-Y32, P35-G53, R80-L107, E132-A141 and E150-N161.

The trace of these structural elements is described as follows. The first beta strand and a loop lead to helix 1, which is followed by helix 2 and a three residue turn. β-2, characterized by a beta bulge at L62 and K63 and a beta hairpin (residues 67-70), is followed by β-3 and helix 3. Helix 3 is the longest helix, spanning nearly the length of the protein and contains a slight curvature. The last beta strand follows helix 3 and leads into a beta turn, a three residue helical turn and helix 4. Finally, a stretch of eight unstructured residues precedes the final helix. Helices 2 and 3 pack against the beta sheet, where most interactions are hydrophobic in nature. Helix 4 makes contact with the N-terminus of helix 2 and the N-terminus of N-TRADD, while helix 5 packs against helix 1 and β-2.

The hydrophobic core of the protein is formed primarily by residues derived from all four beta strands (L17, V19, 164, V73, L75, L116, L118) and residues in helix 1 (L28, Y32), helix 2 (V41, L45, L49), and helix 3 (F87, Y90). Most hydrophobic residues are buried in N-TRADD, except for a few residues in helix 3. V39 and Y42 of helix 2 point away from the main core of the protein, making hydrophobic contacts with residues in helix 5 (L152, L155 and L159). Also, residues L62 and K63 in the beta bulge of β-2 are well positioned to make contact with helix 5. Interestingly, the only tryptophan in N-TRADD, W11, is at the edge of the protein, making long range hydrophobic contacts with L136, L139 and L140 in helix 4.

NMR and BIAcore binding studies of N-TRADD with C-TRAF2: The affinity of the interaction between N-TRADD and C-TRAF2 was determined by BIAcore and the $K_d$ was found to be 6 µM. The $^{1}$H-$^{15}$N HSQC of N-TRADD was used as a tool to map the binding interface with C-TRAF2, since the chemical shifts of contact residues will be perturbed upon complex formation. In the case of N-TRADD, the $^{1}$H-$^{15}$N HSQC peaks broadened with the addition of C-TRAF2 due to formation of the large molecular size complex. Differential line broadening was observed, which is consistent with the expectation that the residues at the binding interface would exhibit a larger resonance broadening when compared to other residues in the protein. Equilibrium sedimentation analysis (Park, et al., *Nature* 398: 533-538, 1999) has shown that C-TRAF2 (310-501) is a trimer in solution, and both crystal structures of C-TRAF2 (Park, et al., *Nature* 398: 533-538, 1999; McWhirter, *Proc. Nad. Acad. Sci. USA* 96: 8408-8413, 1999) have revealed a trimeric structure. The C-TRAF2 (residues 262-501) used in the instant HSQC titration experiment (at 120 µM) is also a trimer, as determined by size exclusion chromatography. A surface representation of residues in N-TRADD that exhibit broadened $^{1}$H-$^{15}$N HSQC peaks by a factor of three or more relative to the rest of the protein upon addition of C-TRAF2 indicate that most of these residues are located on or nearby the beta sheet. Many of the NH resonances belong to residues which face the interior of the protein, and comprise part of the hydrophobic core. The perturbed amino acids whose side chains face the surface of the protein correspond to residues Y16 and F18 in β-1, Q70, 172 and Q74 in β-3, K63 and H65 in β-2 and D68 in the hairpin turn. Additionally, the NH of residues D149, E150 and L152 from helix 5 are also significantly perturbed, as well as residues G121, A122, R124 and L125 in the turn region between β-4 and helix 4. The observed line broadening of these NMR resonances in the $^{1}$H-$^{15}$N HSQC are most likely from residues in the binding interface between N-TRADD and C-TRAF2. Additional residues with observed chemical shift differences in their NH side chains include L17, V58, L59, 164, V73, L75, C78, and L118. The side chains for these residues are not facing the C-TRAF2 binding site of N-TRADD, but exhibit significant perturburance when C-TRAF2 is nearby.

N-TRADD Mutagenesis and interactions between C-TRAF2 and N-TRADD: In order to further characterize the amino acids in N-TRADD that are involved in C-TRAF2 recognition, site directed mutants of N-TRADD were prepared and evaluated for their ability to bind C-TRAF2. Based on the NMR structure of N-TRADD and the $^1$H-$^{15}$N HSQC analysis of the N-TRADD/C-TRAF2 interaction described above, residues likely to be involved in the binding interface were selected for mutagenesis studies. Five residues (Y16, F18, H65, I72 and D149) were chosen which are located in β-1, β-2, β-3 and before helix 5. These residues cluster on one side of the protein and therefore are most likely involved in direct interactions with C-TRAF2 during complex formation. In addition, mutations of these residues will be less likely to affect the overall structure of N-TRADD. Indeed, this was evident when the $^1$H-$^{15}$N HSQC spectrum of the mutant Y16A was acquired and compared to the wild-type data. The $^1$H-$^{15}$N HSQC for the mutant protein looks similar to the wild-type protein, with chemical shift differences only for residues near the mutation site (data not shown).

The affinity of N-TRADD mutants to C-TRAF2 was measured by BIAcore. All mutant proteins showed a significant decrease in binding affinity to C-TRAF2 when compared to wild-type N-TRADD. The I72A and D149A mutant proteins show a modest effect, with a ~2-3 fold reduction in binding (FIG. 3), whereas F18A and H65A mutant proteins show a large ~7-10 fold decrease in C-TRAF2 binding. The Y16A mutant protein shows the highest reduction (~16 fold) in C-TRAF2 affinity. The mutagenesis results in conjunction with the $^1$H-$^{15}$N HSQC perturbation data suggests that N-TRADD residues in the beta sheet are essential for C-TRAF2 binding. Residues Y16, F18, H65 in β-1 and β-2 appear to be important in the interaction of N-TRADD with C-TRAF2, leading to speculation that predominantly hydrophobic and to some extent hydrophilic interactions may play a role in the N-TRADD/C-TRAF2 complex formation.

Inhibition of N-TRADD/C-TRAF2 by CD40-derived peptide. Recent reports on a C-TRAF2 binding peptide derived from CD40 receptor (Pullen, et al., *Biochemistry* 37:11836-11845, 1998; Sato, et al., *FEBS Lett* 358:113-118, 1995; Nakano, et al., *J. Biol. Chem.* 271:14661-14664, 1996) led the inventors to study the effect of this peptide on the N-TRADD/C-TRAF2 interaction. CD40 belongs to the TNF receptor family and has been shown to interact with several TRAF family members by yeast two hybrid analysis and co-precipitation assays (Pullen, et al., *J. Biol. Chem.* 274: 14246-14254, 1999; Pullen, et al., *Biochemistry* 37: 11836-11845, 1998; Cheng, et al., *Science* 267: 1494-1498, 1995). In particular, full length TRAF2 has been shown to interact directly with the CD40 cytoplasmic domain (Pullen, et al., *Biochemistry* 37: 11837-11845, 1998). The binding site of CD40 for TRAF2 was defined by peptide mapping where the shortest CD40 sequence that TRAF2 recognized was a five amino acid peptide with the sequence PVQET (amino acid residues 6-10 of SEQ ID NO:2). The crystal structure of C-TRAF2 (311-501) with a peptide derived from CD40 with sequence YPIQET (SEQ ID NO:3) (designated CD40-pl) (McWhirter, et al., *Proc. Nat'l. Acad. Sci. USA* 96:8408-8413, 1999) (Published with Protein Data Bank at Accession No. 1QSC, and expressly incorporated herein by reference) shows that it binds each of the TRAF2 monomers in the C-TRAF2 timer complex. Comparison with the structure of the peptide from TNFR-2 in complex with C-TRAF2 (Park, et al., *Nature* 398: 533-538, 1999), which has a different consensus sequence (QVPFSKEEC) (SEQ ID NO:4), reveals similar affinities and conformations (McWhirter, et al., *Proc. Nat'l. Acad. Sci. USA* 96:8408-8413, 1999). However, despite similar backbone contacts, the two peptides are slightly shifted in the binding site, where CD40 peptide makes many more complementary contacts with C-TRAF2 than does the TNFR-2-derived peptide.

In the instant studies, the interaction between a 13-mer peptide derived from CD40 (a longer version of CD40 -pl, with sequences SNTAAPVQETLHG (SEQ ID NO:2)) with C-TRAF2 was characterized, as well as its effect on the N-TRADD/C-TRAF2 interaction. BIAcore studies show that the peptide binds to C-TRAF2 with an affinity of ~1.0 mM (data not shown). In addition the peptide was also able to compete for the binding of N-TRADD to C-TRAF2, with an IC50 of ~1 mM.

Inhibition by the CD40-derived peptide was also observed in the $^1$H-$^{15}$N HSQC studies of N-TRADD/C-TRAF2 binding. At stoichiometric concentrations of N-TRADD and C-TRAF2 (110 µM each), HSQC peaks for N-TRADD have broadened out due to binding to C-TRAF2 as described above. Addition of the 13-mer CD40 peptide at a concentration of 3 mM restored the $^1$H-$^{15}$N HSQC spectrum of N-TRADD alone (data not shown). These results are consistent with the observed inhibition of N-TRADD/C-TRAF2 binding with the CD40 peptide observed in the BIAcore experiments. The inhibition of N-TRADD/C-TRAF2 by the CD40-derived peptide suggests overlapping C-TRAF2 binding sites for CD40 and N-TRADD. No interaction between N-TRADD and the CD40-derived peptide was observed, since no changes in the $^1$H-$^{15}$N HSQC of N-TRADD were observed with addition of the peptide. The lack of interaction between CD40 peptide and N-TRADD was also observed in a BIAcore experiment, where the final peptide concentration was approximately 15 mM (data not shown).

In addition to this 13-mer peptide, the effect of the CD40-p1 peptide (McWhirter et al, *Proc. Natl. Acad. Sci. USA* 96: 8408-8413, 1999) on the interaction between N-TRADD and C-TRAF2 was also evaluated. An inhibition with an $IC_{50}$ around 200 mM was observed, correlating with the reported $K_d$ for the binding of CD40-p1 with C-TRAF2 (McWhirter, et al., *Proc. Nad. Acad. Sci. USA* 96: 8408-8413, 1999). The instant results suggest that the 13-mer peptide also binds in the same C-TRAF2 groove as the 6-mer peptide, a site also shared by N-TRADD.

Interaction interface between N-TRADD and C-TRAF2: The N-TRADD/C-TRAF2 binding experiments, in conjunction with the CD40 peptide binding and inhibition data, suggest that the binding sites on C-TRAF2 for CD40 and N-TRADD may overlap. The crystal structure of C-TRAF2 complexed with the CD40 peptide (McWhirter, et al., *Proc. Natl. Acad. Sci. USA* 96: 8408-8413, 1999) show that each C-TRAF2 monomer can bind to one peptide. The peptide binding site in C-TRAF2 is located on the bottom and side of the 'mushroom cap', covering roughly 500 Å$^2$ of the C-TRAF2 surface and is composed of hydrophobic and hydrophilic residues. The specific interactions between the CD40 peptide and C-TRAF2 involve hydrophobic contacts and a network of hydrogen bonds. Residues in C-TRAF2 that make contact with the CD40 peptide in the crystal complex (McWhirter, et al., *Proc. Nad. Acad. Sci. USA* 96: 8408-8413, 1999) include R393, Y395, D399, G400, F410, F447, R448, P449, D450, S453, S454, S455, I465, A466, S467, G468, and P470.

Based on previous studies (Arch, et al., *Genes Dev* 12: 2821-2830, 1998; Park, et al., *Nature* 398: 533-538, 1999; McWhirter, et al., *Proc. Nat'l. Acad. Sci. USA* 96: 8408-8413, 1999), C-TRAF2 can recognize at least two different sequence motifs, SXXE (SEQ ID NO:5) in the case of TNFR2 and PXQXT (SEQ IID NO:6) for CD40. Although the two peptides make similar backbone contacts, each peptide makes different additional unique contact with C-TRAF2, suggesting the presence of distinct recognition sites. Neither consensus sequence is present in N-TRADD, implying that there may be another set of residues on C-TRAF2 required for N-TRADD binding. This N-TRADD binding site on C-TRAF2 would overlap with the CD40 binding site.

CONCLUSIONS

Based on the information obtained from these studies, the presumed C-TRAF2 binding site in N-TRADD is comprised of residues in one face of N-TRADD that are perturbed in the $^1$H-$^{15}$N HSQC spectra upon addition of C-TRAF2 (Y16, F18, K63, H65, D68, Q70, I72, G121, A122, R124, L125, D149, E150, and L152). Other residues which are significantly perturbed in the $^1$H-$^{15}$N HSQC spectra upon addition of C-TRAF2 but which have side chains facing away from the presumed C-TRAF2 binding site include L17, V58, V59, I64, V73, Q74, L75, C78, and L118. The N-TRADD binding site in C-TRAF2, on the other hand, is based on the crystal structure of C-TRAF2 with the peptide from CD40 (McWhirter, et al., *Proc. Natl. Acad. Sci. USA* 96: 8408-8413, 1999), and is presumed to comprise residues R393, Y395, D399, G400, F410, F447, R448, P449, D450, S453, S454, S455, I465, A466, S467, G468 and P470. A comparison of the surface properties for the proposed binding sites for N-TRADD and C-TRAF2 indicate that the surface of the binding site for both molecules is not highly charged, suggesting that their binding is based on hydrophobic interactions and is not driven by electrostatic interactions. Consistent with this premise is the observation that the N-TRADD/C-TRAF2 interaction is not sensitive to NaCl (up to 1 mM, data not shown). This is not surprising, since mostly van der Waals contacts and hydrogen bonding are observed for both the TNFR-2 and CD40-derived peptides complexes with C-TRAF2 (Park, et al., *Nature* 398: 533-538, 1999; McWhirter, et al., *Proc. Natl. Acad. Sci. USA* 96: 8408-8413, 1999). The fact that Y16, F18 and H65 mutations in the beta sheet of N-TRADD displayed a large effect on the binding of N-TRADD with C-TRAF2 suggests that these residues are important in the N-TRADD affinity to C-TRAF2, presumably contributing a significant amount of hydrophobic interactions between the two proteins. Several residues on the C-TRAF2 binding site could potentially complement these N-TRADD interactions, such as F410, F447, I465, Y395 and P449. Both N-TRADD and C-TRAF2 binding surfaces are rich in aromatic residues, suggesting that aromatic interactions, such as ring stacking, may also contribute to their binding. These studies provide a basis for further studies on the details of the interaction between TRADD and TRAF2.

TABLE 1

Structural Statistics and rmsds for the 25 NMR derived structures for N-TRADD[1]

| Structural Statistics | <SA> | <SA>r |
|---|---|---|
| R.m.s. deviation from experimental distance restraints (Å) (2) | | |
| All (1883) | 0.022 ± 0.0013 | 0.022 |
| Intraresidual (540) | 0.010 ± 0.002 | 0.010 |
| Sequential (506) | 0.019 ± 0.002 | 0.016 |
| Short range (387) | 0.026 ± 0.003 | 0.026 |
| Long range (450) | 0.029 ± 0.002 | 0.031 |
| R.m.s. deviation from experimental torsional angle restraints (degrees)(3) | | |
| φ(123), X1(31), X2(5) | 0.21 ± 0.04 | 0.20 |
| R.m.s. deviations from experimental 13C shifts (ppm) (4) | | |
| 13Cα (130) | 1.14 ± 0.039 | 1.12 |
| 13Cβ (130) | 0.91 ± 0.019 | 0.96 |
| R.m.s. deviation from idealized covalent geometry | | |
| Bonds (Å) | 0.003 ± 0.00009 | 0.003 |
| Angles (°) | 0.60 ± 0.007 | 0.60 |
| Impropers(°) | 0.40 ± 0.013 | 0.41 |
| Ramachandram plot: (5) | | |
| Most favorable region: | 91.1 ± 0.8 | 89.3 |
| Gfactor | 0.09 ± 0.01 | 0.08 |
| N. bad contacts | 5.3 ± 1.6 | 6 |
| Cartesian coordinate r.m.s. deviation (Å) (6) | | |
| | Secondary structure | Residues(14-161) |
| Backbone | 0.46 | 0.56 |
| Heavy atoms | 0.94 | 1.01 |

Notes to Table 1
[1] <SA> is the ensemble of 25 NMR-derived structures, <SA>r is the mean atomic structure obtained by averaging the individual SA structures (residues 14-161) followed by restrained minimization. The X-PLOR repel function was used to simulate the van der Waals interactions with a force constant of 4.0 kcal mol-1 Å-4, with the atomic radii set to 0.8 times their CHARMM PARAM19/20 parameters (REF).
(2) The distance restraints were used with a square-well potential (Fnoe = 30 kcal mol-1 Å-4). Medium-range NOEs are observed between protons separated by more than one and less than five residues in sequence. Long-range NOEs are observed between protons separated by five or more residues. No distance restraint was violated by more than 0.30 Å in any of the final structures. Hydrogen bonds were included as distance restraints and given the bounds of 1.8-2.3 Å (H-O) and 2.8-3.3 Å (N-O)
(3) The torsional restraints were applied with a force constant of 200 kcal mol-1 rad-2, and no torsional restraint was violated by more than 5° in any of the structures.
(4) The carbon chemical shift restraints were applied with a force constant of 0.5 kcal mol-1 ppm-2. A conformational database potential based on the populations of various combinations of torsion angles observed in a database of 70 high-resolution (1.75 Å or better) X-ray structures was used, with a force constant of 1.0 (Kuszewski, et al, 1996)
(5) The program PROCHECK (Lakoswski, et al, 1993) was used to assess the quality of the structures.
(6) The precision of the atomic coordinates is defined as the average rms difference between the 25 final calculated structures and the mean coordinates. The backbone atoms comprise of N, Cα, C and O atoms.

All publications mentioned herein above, whether to issued patents, pending applications, published articles, protein structure deposits, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for identifying an agent that interacts with N-terminal domain of TNFR-1 associated death domain protein (N-TRADD), the method comprising:

providing a solution comprising N-TRADD;

displaying a three-dimensional model of an active site of N-TRADD, wherein the active site of N-TRADD comprises an N-terminal domain of TRADD that interacts with C-TRAF2 and wherein the three dimensional structure of the active site comprises the relative structural coordinates of amino acid residues Y16, L17, F18, V58, L59, K63, I64, H65, D68, Q70, I72, V73, Q74, L75, C78, L118, G121, A122, R124, L125, D149, E150, and L152 according to FIG. 2, ± a root mean square deviation from the conserved backbone atoms of the amino acids of the active site of not more than 1.5Å;

using the three-dimensional structure of the active site of N-TRADD to design an agent that interacts with the active site of N-TRADD; and obtaining or synthesizing the agent.

2. The method of claim 1, wherein the three-dimensional structure of the active site of N-TRADD is a solution structure of the active site of N-TRADD.

3. The method of claim 1, wherein the three-dimensional structure of the active site of N-TRADD is obtained from NMR data.

4. The method of claim 1, wherein the design of the agent comprises using molecular modeling.

5. The method of claim 1, further comprising contacting the agent with N-TRADD and determining the effect of the agent on N-TRADD activity.

6. The method of claim 5, wherein the agent is an inhibitor of the active site of N-TRADD.

7. The method of claim 1, wherein the three dimensional structure of the active site of N-TRADD comprises the relative structural coordinates of the amino acid residues of N-TRADD according to FIG. 2, ± a root mean square deviation from the conserved backbone atoms of said amino acids of not more than 1.5Å.

8. The method of claim 7, wherein the root mean square deviation from the conserved backbone atoms of said amino acids is not more than 1.0Å.

9. The method of claim 8, wherein the root mean square deviation from the conserved backbone atoms of said amino acids is not more than 0.5Å.

10. A method for identifying an agent that interacts with N-terminal domain of TNFR-1 associated death domain protein (N-TRADD), the method comprising:

displaying a three-dimensional model of an active site of N-TRADD, wherein the active site of N-TRADD comprises an N-terminal domain of TRADD that interacts with C-TRAF2 and wherein the three dimensional model of the active site of N-TRADD comprises the relative structural coordinates of amino acid residues Y16, L17, F18, V58, L59, K63, I64, H65, D68, Q70, I72, V73, Q74, L75, C78, L118, G121, A122, R124, L125, E150, and L152 according to FIG. 2, ± a root mean square deviation from the conserved backbone atoms of said amino acids of not more than 1.5Å;
using the three-dimensional structure of the active site of N-TRADD to design an agent that interacts with the active site of N-TRADD; and
obtaining or synthesizing the agent.

11. A method for identifying an agent that interacts with N-terminal domain of TNFR-1 associated death domain protein (N-TRADD), the method comprising:
providing a solution comprising N-TRADD;
using a three-dimensional structure of an active site of N-TRADD to design an agent that interacts with the active site of N-TRADD,
wherein:
the active site of N-TRADD comprises the relative structural coordinates of amino acid residues Y16, L17, F18, V58, L59, K63, I64, H65, D68, Q70, I72, V73, Q74, L75, C78, L118, G121, A122, R124, L125, E150, and L152 according to FIG. 2, ± a root mean square deviation from the conserved backbone atoms of said amino acids of not more than 1.5Å; and
obtaining the agent.

12. A method for identifying an agent that interacts with N-terminal domain of TNFR-1 associated death domain protein (N-TRADD), the method comprising:
providing a solution comprising N-TRADD;
using a three-dimensional structure of an active site of N-TRADD to design an agent that interacts with the active site of N-TRADD,
wherein:
the active site of N-TRADD comprises the relative structural coordinates of amino acid residues Y16, L17, F18, V58, L59, K63, I64, H65, D68, Q70, I72, V73, Q74, L75, C78, L118, G121, A122, R124, L125, E150, and L152 according to FIG. 2, ± a root mean square deviation from the conserved backbone atoms of said amino acids of not more than 1.5 Å;
obtaining the agent; and
interacting the agent with the active site of N-TRADD to determine the effect the agent has on the activity of the active site of N-TRADD.

13. The method of claim 1 or 10, wherein the design of the agent comprises using computer fitting analysis.

14. A method for identifying an agent that interacts with N-terminal domain of TNFR-1 associated death domain protein (N-TRADD), the method comprising:
displaying a three-dimensional structure of an active site of N-TRADD, wherein the active site of N-TRADD comprises the relative structural coordinates of amino acid residues Y16, L17, F18, V58, L59, K63, I64, H65, D68, Q70, I72, V73, Q74, L75, C78, L118, G121, A122, R124, L125, E150, and L152 according to FIG. 2, ± a root mean square deviation from the conserved backbone atoms of said amino acids of not more than 1.5Å;
evaluating the ability of the agent to associate with the three-dimensional structure of the active site of N-TRADD; and
designing the agent and displaying graphical representing of the designed agent;
wherein the agent is designed de novo or using known inhibitors of N-TRADD.

15. The method of claim 10 or 14, wherein the design of the agent comprises using molecular modeling.

16. The method of claim 1, further comprising storing the three-dimensional structure of the active site of N-TRADD in a machine readable storage medium.

17. The method of claim 1, wherein the root mean square deviation from the conserved backbone atoms of said amino acids is not more than 1.0Å.

18. The method of claim 1, wherein the root mean square deviation from the conserved backbone atoms of said amino acids is not more than 0.5Å.

19. The method of claim 14, wherein the root mean square deviation from the conserved backbone atoms of said amino acids of not more than 1.0Å.

20. The method of claim 11, wherein the three dimensional structure of the active site of N-TRADD comprises the relative structural coordinates of the amino acid residues of N-TRADD according to FIG. 2, ± a root mean square deviation from the conserved backbone atoms of said amino acids of not more than 1.5Å.

21. The method of claim 12, wherein the three dimensional structure of the active site of N-TRADD comprises the relative structural coordinates of the amino acid residues of N-TRADD according to FIG. 2, ± a root mean square deviation from the conserved backbone atoms of said amino acids of not more than 1.5Å.

22. The method of claim 14, wherein the three dimensional structure of the active site of N-TRADD comprises the relative structural coordinates of the amino acid residues of N-TRADD according to FIG. 2, ± a root mean square deviation from the conserved backbone atoms of said amino acids of not more than 1.5Å.

23. The method of claim 1, wherein N-TRADD comprises amino acid residues 1-169 of TRADD as shown in FIG. 1, or one or more conservative substitutions thereof.

24. The method of claim 10, further comprising storing the three-dimensional structure of the active site of N-TRADD in a machine readable storage medium.

25. The method of claim 24, wherein the agent is generated de novo or using known inhibitors of N-TRADD.

26. The method of claim 10, wherein the three-dimensional structure of the active site of N-TRADD is a solution structure of the active site of N-TRADD.

27. The method of claim 10, wherein the root mean square deviation from the conserved backbone atoms of said amino acids is not more than 1.0Å.

28. The method of claim 10, wherein the root mean square deviation from the conserved backbone atoms of said amino acids is not more than 0.5Å.

29. The method of claim 10, further comprising contacting the agent with N-TRADD and determining the effect of the agent on N-TRADD activity.

30. The method of claim 10, wherein N-TRADD comprises amino acid residues 1-169 of TRADD as shown in FIG. 1, or one or more conservative substitutions thereof.

31. The method of claim 11, wherein the root mean square deviation from the conserved backbone atoms of said amino acids is not more than 1.0Å.

32. The method of claim 11, wherein the root mean square deviation from the conserved backbone atoms of said amino acids is not more than 0.5Å.

33. The method of claim 11, further comprising contacting the agent with N-TRADD and determining the effect of the agent on N-TRADD activity.

34. The method of claim 11, wherein N-TRADD comprises amino acid residues 1-169 of TRADD as shown in FIG. 1, or one or more conservative substitutions thereof.

35. The method of claim 12, wherein the agent is designed de novo or using known inhibitors of N-TRADD.

36. The method of claim 12, wherein N-TRADD comprises amino acid residues 1-169 of TRADD as shown in FIG. 1, or one or more conservative substitutions thereof.

37. The method of claim 12, wherein the root mean square deviation from the conserved backbone atoms of said amino acids is not more than 1.0Å.

38. The method of claim 12, wherein the root mean square deviation from the conserved backbone atoms of said amino acids is not more than 0.5Å.

39. The method of claim 14, further comprising storing the three-dimensional structure of the active site of N-TRADD in a machine readable storage medium.

40. The method of claim 14, further comprising contacting the agent with N-TRADD and determining the effect of the agent on N-TRADD activity.

41. The method of claim 14, further comprising obtaining or synthesizing the agent.

42. The method of claim 14, wherein the three-dimensional structure of the active site of N-TRADD is obtained from NMR data.

43. The method of claim 40, wherein the agent is an inhibitor of the active site of N-TRADD.

44. The method of claim 14, wherein N-TRADD comprises amino acid residues 1-169 of TRADD as shown in FIG. 1, or one or more conservative substitutions.

45. The method of claim 14, wherein the design of the agent comprises using molecular modeling or computer fitting analysis.

46. The method of claim 14, wherein the root mean square deviation from the conserved backbone atoms of said amino acids is not more than 0.5Å.

47. The method of claim 10, wherein the three dimensional structure of the active site of N-TRADD further comprises the relative structural coordinates according to FIG. 2, ± a root mean square deviation from the conserved backbone atoms of said amino acids of not more than 1.5Å.

* * * * *

SEQUENCE LISTING

<160> NUMBER OF SEQ ID NOS: 6

<210> SEQ ID NO 1
<211> LENGTH: 168
<212> TYPE: PRT
<213> ORGANISM: Homo sapiens

<400> SEQUENCE: 1

Met Ala Ala Gly Gln Asn Gly His Glu Trp Val Gly Ser Ala Tyr Leu
1               5                   10                  15

Phe Val Glu Ser Ser Leu Asp Lys Val Val Leu Ser Asp Ala Tyr Ala
            20                  25                  30

His Pro Gln Gln Lys Val Ala Val Tyr Arg Ala Leu Gln Ala Ala Leu
        35                  40                  45

Ala Glu Ser Gly Gly Ser Pro Asp Val Leu Gln Met Leu Lys Ile His
    50                  55                  60

Arg Ser Asp Pro Gln Leu Ile Val Gln Leu Arg Phe Cys Gly Arg Gln
65                  70                  75                  80

Pro Cys Gly Arg Phe Leu Arg Ala Tyr Arg Glu Gly Ala Leu Arg Ala
                85                  90                  95

Ala Leu Gln Arg Ser Leu Ala Ala Leu Ala Gln His Ser Val Pro
            100                 105                 110

Leu Gln Leu Glu Leu Arg Ala Gly Ala Glu Arg Leu Asp Ala Leu Leu
        115                 120                 125

Ala Asp Glu Glu Arg Cys Leu Ser Cys Ile Leu Ala Gln Gln Pro Asp
    130                 135                 140

Arg Leu Arg Asp Glu Glu Leu Ala Glu Leu Glu Asp Ala Leu Arg Asn
145                 150                 155                 160

Leu Lys Cys Gly Ser Gly Ala Arg
                165

<210> SEQ ID NO 2
<211> LENGTH: 13
<212> TYPE: PRT
<213> ORGANISM: Artificial Sequence
<220> FEATURE:
<221> NAME/KEY: PEPTIDE
<222> LOCATION: (1)..(13)
<223> OTHER INFORMATION: CD40 peptide synthesized using Fmoc solid-
      phase methods
<400> SEQUENCE: 2

Ser Asn Thr Ala Ala Pro Val Gln Glu Thr Leu His Gly
1               5                   10

<210> SEQ ID NO 3
<211> LENGTH: 6
<212> TYPE: PRT
<213> ORGANISM: Artificial Sequence
<220> FEATURE:
<221> NAME/KEY: peptide
<222> LOCATION: (1)..(6)
<223> OTHER INFORMATION: shortest CD40 sequence recognized by TRAF2

<400> SEQUENCE: 3

Tyr Pro Ile Gln Glu Thr
1               5

<210> SEQ ID NO 4
<211> LENGTH: 9
<212> TYPE: PRT

```
-continued

<213> ORGANISM: Artificial Sequence
<220> FEATURE:
<221> NAME/KEY: peptide
<222> LOCATION: (1)..(9)
<223> OTHER INFORMATION: C-TRAF2 consensus sequence

<400> SEQUENCE: 4

Gln Val Pro Phe Ser Lys Glu Glu Cys
1               5

<210> SEQ ID NO 5
<211> LENGTH: 4
<212> TYPE: PRT
<213> ORGANISM: Artificial Sequence
<220> FEATURE:
<221> NAME/KEY: peptide
<222> LOCATION: (1)..(4)
<223> OTHER INFORMATION: TNFR2 sequence motif; X may be any amino acid

<400> SEQUENCE: 5

Ser Xaa Xaa Glu
1

<210> SEQ ID NO 6
<211> LENGTH: 5
<212> TYPE: PRT
<213> ORGANISM: Artificial Sequence
<220> FEATURE:
<221> NAME/KEY: peptide
<222> LOCATION: (1)..(5)
<223> OTHER INFORMATION: CD40 sequence motif; X may be any amino acid

<400> SEQUENCE: 6

Pro Xaa Gln Xaa Thr
1               5
```